United States Patent
Wong et al.

(10) Patent No.: US 10,927,373 B2
(45) Date of Patent: *Feb. 23, 2021

(54) COMPOSITIONS AND METHODS FOR INHIBITING GENE EXPRESSION OF HIF2ALPHA

(71) Applicant: Arrowhead Pharmaceuticals, Inc., Pasadena, CA (US)

(72) Inventors: So Wong, Oregon, WI (US); David L. Lewis, Madison, WI (US); David B. Rozema, Cross Plains, WI (US); Darren H. Wakefield, Fitchburg, WI (US); Steven B. Kanner, Berkeley, CA (US); Weijun Cheng, Middleton, WI (US); Lauren J. Almeida, Madison, WI (US); Andrei V. Blokhin, Fitchburg, WI (US); Jeffrey C. Carlson, Madison, WI (US); Anthony L. Nicholas, Oregon, WI (US); Aaron Almeida, Madison, WI (US); Jonathan D. Benson, Stoughton, WI (US); Justin Woods, Fitchburg, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/954,316

(22) Filed: Apr. 16, 2018

(65) Prior Publication Data

US 2018/0230470 A1 Aug. 16, 2018

Related U.S. Application Data

(62) Division of application No. 15/166,311, filed on May 27, 2016, now Pat. No. 9,976,141.

(60) Provisional application No. 62/168,244, filed on May 29, 2015.

(51) Int. Cl.
| | | |
|---|---|---|
| *C12N 15/113* | (2010.01) | |
| *A61K 31/713* | (2006.01) | |
| *A61K 45/06* | (2006.01) | |
| *A61K 47/60* | (2017.01) | |
| *A61K 47/64* | (2017.01) | |

(52) U.S. Cl.
CPC .......... *C12N 15/113* (2013.01); *A61K 31/713* (2013.01); *A61K 45/06* (2013.01); *A61K 47/60* (2017.08); *A61K 47/64* (2017.08); *C12N 2310/14* (2013.01); *C12N 2310/315* (2013.01); *C12N 2310/343* (2013.01); *C12N 2310/346* (2013.01); *C12N 2310/351* (2013.01); *C12N 2320/31* (2013.01); *C12N 2320/32* (2013.01)

(58) Field of Classification Search
CPC C12N 15/113; C12N 2310/14; A61K 31/713; A01K 2207/05

See application file for complete search history.

(56) References Cited

U.S. PATENT DOCUMENTS

| | | | |
|---|---|---|---|
| 8,084,599 B2 | 12/2011 | Rossi et al. | |
| 8,349,809 B2 | 1/2013 | Brown | |
| 8,513,207 B2 | 8/2013 | Brown | |
| 8,741,868 B2 | 6/2014 | Chun et al. | |
| 8,802,773 B2 | 8/2014 | Rozema et al. | |
| 9,868,949 B2 * | 1/2018 | Bettencourt | C12N 15/113 |
| 9,976,141 B2 * | 5/2018 | Wong | C12N 15/113 |
| 2004/0204377 A1 | 10/2004 | Rana | |
| 2010/0010071 A1 | 1/2010 | Davis et al. | |
| 2012/0172412 A1 | 7/2012 | Rozema et al. | |
| 2013/0236531 A1 | 9/2013 | Chun et al. | |
| 2015/0045573 A1 | 2/2015 | Cheng et al. | |
| 2016/0272970 A1 * | 9/2016 | Rozema | C12N 15/111 |

FOREIGN PATENT DOCUMENTS

| | | |
|---|---|---|
| WO | 2000053722 A2 | 9/2000 |
| WO | 2008022309 A2 | 2/2008 |
| WO | 2009117531 A1 | 9/2009 |
| WO | 2009123764 A2 | 10/2009 |
| WO | 2011104169 A1 | 9/2011 |
| WO | 2012083046 A2 | 6/2012 |
| WO | 2012083185 A2 | 6/2012 |
| WO | 2012174224 A2 | 12/2012 |
| WO | 2013032829 A2 | 3/2013 |
| WO | 2013158141 A1 | 10/2013 |
| WO | 2014134255 A2 | 9/2014 |
| WO | 2015021092 A1 | 2/2015 |

OTHER PUBLICATIONS

Bertout, et al.; "HIF2alpha inhibition promotes p53 pathway activity, tumor cell death, and radiation responses," Proceedings of the National Academy of Sciences; Aug. 25, 2009; vol. 206, No. 34, pp. 14391-14396.

Gossage et al. "VHL, the story of a tumour suppressor gene" Nature Reviews; vol. 15:55-64; 2015.

Koh et al. "Hypoxia-Induced SUMOylation of E3 Ligase HAF Determines Specific Activation of HIF2 in Clear-Cell Renal Cell Carcinoma" Cancer Research 75(2):316-329; 2015.

Monera et al.; "Relationship of Sidechain Hydrophobicity and α-Helical Propensity on the Stability of the Single-stranded Amphipathic α-Helix"; Journal of Peptide Science; (1995) 1, 319-329.

Riches AG et al.; "Scalable synthesis of an integrin-binding peptide mimetic for biomedical applications"; Tetrahedron (2012) 68, p. 9448-9455.

(Continued)

Primary Examiner — Brian Whiteman
(74) Attorney, Agent, or Firm — Robert M. Teigen; Paul VanderVelde

(57) ABSTRACT

RNA interference (RNAi) triggers and RNAi trigger conjugates for inhibiting the expression of Hif2α (EPAS1) gene are described. Pharmaceutical compositions comprising one or more Hif2α RNAi triggers optionally with one or more additional therapeutics are also described. Delivery of the described Hif2α RNAi triggers to tumor cells in vivo provides for inhibition of Hif2α gene expression and treatment of cancer.

20 Claims, 9 Drawing Sheets

Specification includes a Sequence Listing.

(56) References Cited

OTHER PUBLICATIONS

Rozema DB et al. "Protease-triggered siRNA Delivery Vehicles."; J Control Release; vol. 209:57-66; 2015.
GenBank Accession #NM_001430; 1997.
International Search Report and Written Opinion for corresponding International Application No. PCT/US2016/034512, dated Oct. 14, 2016.
Kamlah, F et al.; "Intravenous injection of 1-12, 15 siRNA directed against hypoxia-inducible factors prolongs survival in a Lewis lung carcinoma cancer model"; Cancer Gene Therapy; vol. 16, No. 3; Mar. 1, 2009; pp. 195-205.
Partial ESR and Written Opinion for corresponding European Patent Application No. 16804086.3 dated Feb. 27, 2019.

\* cited by examiner

RGD-PEG$_n$-FCitFP-TFP (n = 1-50)
RGD-PEG$_8$-FCitFP-TFP (n = 8)
RGD-PEG$_{15}$-FCitFP-TFP (n = 15)
RGD-PEG$_{16}$-FCitFP-TFP (n = 16)
RGD-PEG$_{19}$-FCitFP-TFP (n = 19)
RGD-PEG$_{20}$-FCitFP-TFP (n = 20)

RGD-PEG$_n$-ACit-PABC-PNP (n = 4-30)
RGD-PEG$_8$-ACit-PABC-PNP (n = 8)

aldehyde-PEG$_n$-FCit-PABC-PNP (n = 4-30)
aldehyde-PEG$_{12}$-FCit-PABC-PNP (n = 12)

aldehyde-PEG$_n$-ACit-PABC-PNP (n = 4-30)
aldehyde-PEG$_6$-ACit-PABC-PNP (n = 6)
aldehyde-PEG$_{12}$-ACit-PABC-PNP (n = 12)
aldehyde-PEG$_{24}$-ACit-PABC-PNP (n = 24)

SPDP-PEG$_n$-FCit-PABC-PNP (n = 4-30)
SPDP-PEG$_{24}$-FCit-PABC-PNP (n = 23)

PEG$_n$-ACit-PABC-PNP (n = 4-30)
PEG$_6$-ACit-PABC-PNP (n = 5)
PEG$_{12}$-ACit-PABC-PNP (n = 11)
PEG$_{24}$-ACit-PABC-PNP (n = 23)

PEG$_n$-FCit-PABC-PNP (n=4-30)
PEG$_{12}$-FCit-PABC-PNP (n=11)

SEQUENCE LISTING

<160> NUMBER OF SEQ ID NOS: 1044

<210> SEQ ID NO 1
<211> LENGTH: 21
<212> TYPE: RNA
<213> ORGANISM: artificial sequence
<220> FEATURE:
<223> OTHER INFORMATION: Hif2alpha RNAi agent antisense strand

<400> SEQUENCE: 1
aguaaaacaa uuguguacuu u        21

<210> SEQ ID NO 2
<211> LENGTH: 23
<212> TYPE: RNA
<213> ORGANISM: artificial sequence
<220> FEATURE:
<223> OTHER INFORMATION: Hif2alpha RNAi agent antisense strand

<400> SEQUENCE: 2
aguaaaacaa uuguguacuu uaa        23

<210> SEQ ID NO 3
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-19,21
<223> OTHER INFORMATION: modified base = "2'-hydroxy corresponding
      nucleoside"

<400> SEQUENCE: 3
auucaugaaa ucguuacgut g        21

-continued

<210> SEQ ID NO 4
<211> LENGTH: 21
<212> TYPE: RNA
<213> ORGANISM: artificial sequence
<220> FEATURE:
<223> OTHER INFORMATION: Hif2alpha RNAi agent antisense strand

<400> SEQUENCE: 4
auucaugaaa ucguuacguu g                                              21

<210> SEQ ID NO 5
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-22
<223> OTHER INFORMATION: modified base = "2'-hydroxy corresponding
      nucleoside"

<400> SEQUENCE: 5
auucaugaaa ucguuacguu gat                                            23

<210> SEQ ID NO 6
<211> LENGTH: 23
<212> TYPE: RNA
<213> ORGANISM: artificial sequence
<220> FEATURE:
<223> OTHER INFORMATION: Hif2alpha RNAi agent antisense strand

<400> SEQUENCE: 6
auucaugaaa ucguuacguu ggc                                            23

<210> SEQ ID NO 7
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 7
taaaucguua cguugacagt t                                              21

<210> SEQ ID NO 8
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 8
taaccacaua cguuggagut t                                              21

<210> SEQ ID NO 9
<211> LENGTH: 21

```
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 9
taaguuaagc ucccauacat t                                              21

<210> SEQ ID NO 10
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 10
taaucguuac guugacaggt t                                              21

<210> SEQ ID NO 11
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 11
tacguugaca gguaggguut t                                              21

<210> SEQ ID NO 12
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 12
tagaggagcu uguguguuct t                                              21

<210> SEQ ID NO 13
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 13
```

```
tagcuugugu guucgcaggt t                                              21

<210> SEQ ID NO 14
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 14
taggagcuug uguguucgct t                                              21

<210> SEQ ID NO 15
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 15
taucguuacg uugacaggut t                                              21

<210> SEQ ID NO 16
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 16
tcaugaaauc guuacguugt t                                              21

<210> SEQ ID NO 17
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 17
tcguuacguu gacagguagt t                                              21

<210> SEQ ID NO 18
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
```

```
<221> NAME/KEY: modified_base
<222> LOCATION: 2-19
<223> OTHER INFORMATION: modified base = "2'-hydroxy corresponding
      nucleoside"

<400> SEQUENCE: 18
tcuagcaaca aaaccuuaat t                                              21

<210> SEQ ID NO 19
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 19
tgagcuugug uguucgcagt t                                              21

<210> SEQ ID NO 20
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 20
tgaggagcuu guguguucgt t                                              21

<210> SEQ ID NO 21
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 21
tggagcuugu guguucgcat t                                              21

<210> SEQ ID NO 22
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 22
tgguacuggg uggcguagct t                                              21

<210> SEQ ID NO 23
```

-continued

<210> SEQ ID NO 23
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding nucleoside"

<400> SEQUENCE: 23
tguaaaacaa uuguguacut t                                              21

<210> SEQ ID NO 24
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding nucleoside"

<400> SEQUENCE: 24
tuacguugac agguagggut t                                              21

<210> SEQ ID NO 25
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding nucleoside"

<400> SEQUENCE: 25
tucguuacgu ugacagguat t                                              21

<210> SEQ ID NO 26
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding nucleoside"

<400> SEQUENCE: 26
tugauaaaca cuuaacccat t                                              21

<210> SEQ ID NO 27
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding nucleoside"

```
<400> SEQUENCE: 27
tugucacgau gcggugguut t                                              21

<210> SEQ ID NO 28
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-26
<223> OTHER INFORMATION: modified base = "2'-hydroxy corresponding
      nucleoside"

<400> SEQUENCE: 28
tuucaugaaa ucguuacguc ggcuau                                         26

<210> SEQ ID NO 29
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-26
<223> OTHER INFORMATION: modified base = "2'-hydroxy corresponding
      nucleoside"

<400> SEQUENCE: 29
tuucaugaaa ucguuacguc ggcugu                                         26

<210> SEQ ID NO 30
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-19
<223> OTHER INFORMATION: modified base = "2'-hydroxy corresponding
      nucleoside"

<400> SEQUENCE: 30
tuucaugaaa ucguuacgut t                                              21

<210> SEQ ID NO 31
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-23
<223> OTHER INFORMATION: modified base = "2'-hydroxy corresponding
      nucleoside"

<400> SEQUENCE: 31
tuucaugaaa ucguuacguu ggc                                            23

<210> SEQ ID NO 32
<211> LENGTH: 26
<212> TYPE: DNA
<213> ORGANISM: artificial sequence
<220> FEATURE:
<223> OTHER INFORMATION: Hif2alpha RNAi agent antisense strand
```

```
<220> FEATURE:
<221> NAME/KEY: modified_base
<222> LOCATION: 2-26
<223> OTHER INFORMATION: modified base = "2'-hydroxy corresponding
      nucleoside"

<400> SEQUENCE: 32
tuucaugaaa ucguuacguu ggcuau                                         26

<210> SEQ ID NO 33
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-26
<223> OTHER INFORMATION: modified base = "2'-hydroxy corresponding
      nucleoside"

<400> SEQUENCE: 33
tuucaugaaa ucguuacguu ggcugu                                         26

<210> SEQ ID NO 34
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2-24
<223> OTHER INFORMATION: modified base = "2'-hydroxy corresponding
      nucleoside"

<400> SEQUENCE: 34
tuucaugaaa ucguuacguu ggcutt                                         26

<210> SEQ ID NO 35
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 35
ucaugaaauc guuacguugt t                                              21

<210> SEQ ID NO 36
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 36
ucuagcaaca aaaccuuaat t                                              21
```

```
<210> SEQ ID NO 37
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 37
uguaaaacaa uuguguacut t                                              21

<210> SEQ ID NO 38
<211> LENGTH: 21
<212> TYPE: RNA
<213> ORGANISM: artificial sequence
<220> FEATURE:
<223> OTHER INFORMATION: Hif2alpha RNAi agent antisense strand

<400> SEQUENCE: 38
uguaaaacaa uuguguacuu u                                              21

<210> SEQ ID NO 39
<211> LENGTH: 23
<212> TYPE: RNA
<213> ORGANISM: artificial sequence
<220> FEATURE:
<223> OTHER INFORMATION: Hif2alpha RNAi agent antisense strand

<400> SEQUENCE: 39
uguaaaacaa uuguguacuu uaa                                            23

<210> SEQ ID NO 40
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 40
uuucaugaaa ucguuacgut t                                              21

<210> SEQ ID NO 41
<211> LENGTH: 21
<212> TYPE: RNA
<213> ORGANISM: artificial sequence
<220> FEATURE:
<223> OTHER INFORMATION: Hif2alpha RNAi agent antisense strand

<400> SEQUENCE: 41
uuucaugaaa ucguuacguu g                                              21

<210> SEQ ID NO 42
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 1-22
```

```
<223> OTHER INFORMATION: modified base = "2'-hydroxy corresponding
      nucleoside"

<400> SEQUENCE: 42
uuucaugaaa ucguuacguu gat                                              23

<210> SEQ ID NO 43
<211> LENGTH: 21
<212> TYPE: RNA
<213> ORGANISM: artificial sequence
<220> FEATURE:
<223> OTHER INFORMATION: Hif2alpha RNAi agent sense strand

<400> SEQUENCE: 43
aaaguacaca auuguuuac a                                                 21

<210> SEQ ID NO 44
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-20
<223> OTHER INFORMATION: modified base = "2'-hydroxy corresponding
      nucleoside"

<400> SEQUENCE: 44
aaaguacaca auuguuuac t                                                 21

<210> SEQ ID NO 45
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 45
aacccuaccu gucaacguat                                                  20

<210> SEQ ID NO 46
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-20
<223> OTHER INFORMATION: modified base = "2'-hydroxy corresponding
      nucleoside"

<400> SEQUENCE: 46
aacguaacga uuucaugaaa t                                                21

<210> SEQ ID NO 47
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
```

```
<222> LOCATION: 1-20
<223> OTHER INFORMATION: modified base = "2'-hydroxy corresponding
      nucleoside"

<400> SEQUENCE: 47
aacguaacga uuucaugaau t                                              21

<210> SEQ ID NO 48
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 48
acccuaccug ucaagguaat                                                20

<210> SEQ ID NO 49
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 49
accugucaac guaacguaat                                                20

<210> SEQ ID NO 50
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 50
acguaacgau uucaugaaa                                                 19

<210> SEQ ID NO 51
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 51
acguaacgau uucaugaaat                                                20

<210> SEQ ID NO 52
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
```

```
<221> NAME/KEY: modified_base
<222> LOCATION: 1-18
<223> OTHER INFORMATION: modified base = "2'-hydroxy corresponding
      nucleoside"

<400> SEQUENCE: 52
acguaacgau uucaugaatt                                                   20

<210> SEQ ID NO 53
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 53
acguaacgau uucaugaau                                                    19

<210> SEQ ID NO 54
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 54
acguaacgau uucaugaaut                                                   20

<210> SEQ ID NO 55
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 55
acuccaacgu augugguuat                                                   20

<210> SEQ ID NO 56
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 56
aguacacaau uguuuuacat                                                   20

<210> SEQ ID NO 57
<211> LENGTH: 20
<212> TYPE: DNA
<213> ORGANISM: artificial sequence
<220> FEATURE:
<223> OTHER INFORMATION: Hif2alpha RNAi agent sense strand
```

```
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 57
aguacacaau uguuuuacut                                                    20

<210> SEQ ID NO 58
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 58
caacguaacg auuucauga                                                     19

<210> SEQ ID NO 59
<211> LENGTH: 21
<212> TYPE: RNA
<213> ORGANISM: artificial sequence
<220> FEATURE:
<223> OTHER INFORMATION: Hif2alpha RNAi agent sense strand

<400> SEQUENCE: 59
caacguaacg auuucaugaa a                                                  21

<210> SEQ ID NO 60
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 60
caacguaacg auuucaugat                                                    20

<210> SEQ ID NO 61
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 61
cagugcaacg ccacccagat                                                    20

<210> SEQ ID NO 62
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
``` nucleoside"

<400> SEQUENCE: 62
ccugcgaaca cacaagcuat                                                   20

<210> SEQ ID NO 63
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 63
ccugucaacg uaacgauuat                                                   20

<210> SEQ ID NO 64
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 64
cgaacacaca agcuccucat                                                   20

<210> SEQ ID NO 65
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 65
cuaccuguca acguaacgat                                                   20

<210> SEQ ID NO 66
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 66
cugcgaacac acaagcucat                                                   20

<210> SEQ ID NO 67
<211> LENGTH: 20
<212> TYPE: DNA
<213> ORGANISM: artificial sequence

```
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 67
cugucaacgu aacgauuuat                                                     20

<210> SEQ ID NO 68
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 68
gaacacacaa gcuccucuat                                                     20

<210> SEQ ID NO 69
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 69
gcgaacacac aagcuccuat                                                     20

<210> SEQ ID NO 70
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 70
gcuacgccac ccaguaccat                                                     20

<210> SEQ ID NO 71
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-22
<223> OTHER INFORMATION: modified base = "2'-hydroxy corresponding
      nucleoside"

<400> SEQUENCE: 71
uauaccuguc aacguaacgu aat                                                 23
```

-continued

<210> SEQ ID NO 72
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-22
<223> OTHER INFORMATION: modified base = "2'-hydroxy corresponding
      nucleoside"

<400> SEQUENCE: 72
uauacguaac gauuucauga aat                                         23

<210> SEQ ID NO 73
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-22
<223> OTHER INFORMATION: modified base = "2'-hydroxy corresponding
      nucleoside"

<400> SEQUENCE: 73
uauacguaac gauuucauga aut                                         23

<210> SEQ ID NO 74
<211> LENGTH: 24
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-22
<223> OTHER INFORMATION: modified base = "2'-hydroxy corresponding
      nucleoside"

<400> SEQUENCE: 74
uauacguaac gauuucauga autt                                        24

<210> SEQ ID NO 75
<211> LENGTH: 26
<212> TYPE: RNA
<213> ORGANISM: artificial sequence
<220> FEATURE:
<223> OTHER INFORMATION: Hif2alpha RNAi agent sense strand

<400> SEQUENCE: 75
uauaucaacg uaacgauuuc augaaa                                      26

<210> SEQ ID NO 76
<211> LENGTH: 26
<212> TYPE: RNA
<213> ORGANISM: artificial sequence
<220> FEATURE:
<223> OTHER INFORMATION: Hif2alpha RNAi agent sense strand

<400> SEQUENCE: 76
uauaucgacg uaacgauuuc augaaa                                      26

<210> SEQ ID NO 77
<211> LENGTH: 26

```
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-24
<223> OTHER INFORMATION: modified base = "2'-hydroxy corresponding
      nucleoside"

<400> SEQUENCE: 77
uaucaacgua acgauuucau gaautt                                          26

<210> SEQ ID NO 78
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 78
ucacugucaa cguaacgaat                                                 20

<210> SEQ ID NO 79
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 79
ugcgaacaca caagcuccat                                                 20

<210> SEQ ID NO 80
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 80
uggguuaagu guuuaucaat                                                 20

<210> SEQ ID NO 81
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 81
```

```
uguaugggag cuuaacuuat                                            20

<210> SEQ ID NO 82
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1-19
<223> OTHER INFORMATION: modified base = "2'-hydroxy corresponding
      nucleoside"

<400> SEQUENCE: 82
uuaagguuuu guugcuagat                                            20

<210> SEQ ID NO 83
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,16,17,19,20,21,22,23
<223> OTHER INFORMATION: /mod_base = "2'-O-methyl corresponding
      nucleoside"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 83
aguaaaacaa uuguguacuu uaa                                        23

<210> SEQ ID NO 84
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 84
aguaaaacaa uuguguacuu u                                          21

<210> SEQ ID NO 85
<211> LENGTH: 23
<212> TYPE: DNA
<213> ORGANISM: artificial sequence
```

```
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21,22,23
<223> OTHER INFORMATION: /mod_base = "2'-O-methyl corresponding
      nucleoside"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 85
aguaaaacaa uuguguacuu uaa                                              23

<210> SEQ ID NO 86
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,16,17,18,19,20,21,22,23
<223> OTHER INFORMATION: /mod_base = "2'-O-methyl corresponding
      nucleoside"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 86
aguaaaacaa uuguguacuu uaa                                              23

<210> SEQ ID NO 87
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,9,11,12,13,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20,21
<223> OTHER INFORMATION: /mod_base = "2'-MOE nucleotide"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 87
auucaugaaa ucguuacgut g                                                21
```

```
<210> SEQ ID NO 88
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,9,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 88
auucaugaaa ucguuacguu g                                             21

<210> SEQ ID NO 89
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,9,14,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,8,10,11,12,13,15,17,18,19,20,21,22,23
<223> OTHER INFORMATION: /mod_base = "2'-O-methyl corresponding
      nucleoside"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 89
auucaugaaa ucguuacguu ggc                                           23

<210> SEQ ID NO 90
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 90
```
auucaugaaa ucguuacguu g                                                         21

<210> SEQ ID NO 91
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 91
auucaugaaa ucguuacguu g                                                        21

<210> SEQ ID NO 92
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,16,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 92
auucaugaaa ucguuacguu gat                                                  23

<210> SEQ ID NO 93
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,17,18,19,20,21,22,23
<223> OTHER INFORMATION: /mod_base = "2'-O-methyl corresponding
      nucleoside"
<220> FEATURE:

```
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 93
auucaugaaa ucguuacguu ggc                                              23

<210> SEQ ID NO 94
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 94
taaaucguua cguugacagt t                                                21

<210> SEQ ID NO 95
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 95
taaaucguua cguugacagt t                                                21

<210> SEQ ID NO 96
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
```

```
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 96
taaaucguua cguugacagt t                                              21

<210> SEQ ID NO 97
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 97
taaguuaagc ucccauacat t                                              21

<210> SEQ ID NO 98
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 98
taaguuaagc ucccauacat t                                              21
```

```
<210> SEQ ID NO 99
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 99
taaguuaagc ucccauacat t                                              21

<210> SEQ ID NO 100
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 100
taaucguuac guugacaggt t                                              21

<210> SEQ ID NO 101
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
```

```
<222> LOCATION: 21
<223> OTHER INFORMATION: /mod_base = "5'-phosphorothioate corresponding
      nucleotide"

<400> SEQUENCE: 101
tacguugaca gguagggut t                                                 21

<210> SEQ ID NO 102
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 102
tagaggagcu uguguguuct t                                                21

<210> SEQ ID NO 103
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 103
tagcuugugu guucgcaggt t                                                21

<210> SEQ ID NO 104
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
```

```
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 104
taggagcuug uguguucgct t                                                    21

<210> SEQ ID NO 105
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 105
taucguuacg uugacaggut t                                                    21

<210> SEQ ID NO 106
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 106
tcguuacguu gacagguagt t                                                    21

<210> SEQ ID NO 107
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
```

```
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 107
tcuagcaaca aaaccuuaat t                                              21

<210> SEQ ID NO 108
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 108
tcuagcaaca aaaccuuaat t                                              21

<210> SEQ ID NO 109
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 109
tcuagcaaca aaaccuuaat t                                              21

<210> SEQ ID NO 110
<211> LENGTH: 21
```

```
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 110
tgagcuugug uguucgcagt t                                           21

<210> SEQ ID NO 111
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 111
tgaggagcuu guguguucgt t                                           21

<210> SEQ ID NO 112
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 112
tggagcuugu guguucgcat t                                           21
```

```
<210> SEQ ID NO 113
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 113
tgguacuggg uggcguagct t                                              21

<210> SEQ ID NO 114
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 114
tguaaaacaa uuguguacut t                                              21

<210> SEQ ID NO 115
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
``` nucleotide"

<400> SEQUENCE: 115
tguaaaacaa uuguguacut t                                              21

<210> SEQ ID NO 116
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 116
tguaaaacaa uuguguacut t                                              21

<210> SEQ ID NO 117
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 117
taaccacaua cguuggagut t                                              21

<210> SEQ ID NO 118
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base

```
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 118
tcaugaaauc guuacguugt t                                              21

<210> SEQ ID NO 119
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 119
tugauaaaca cuuacccat t                                               21

<210> SEQ ID NO 120
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 120
tuucaugaaa ucguuacgut t                                              21

<210> SEQ ID NO 121
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,15,18
<223> OTHER INFORMATION: /mod_base = "2'-deoxy-2'-fluoro corresponding
      nucleoside"
```

```
<220> FEATURE:
<221> NAME/KEY: modified_base
<222> LOCATION: 3,5,7,9,11,13,16,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 121
tuucaugaaa ucguuacgut t                                              21

<210> SEQ ID NO 122
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,13,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 122
tuucaugaaa ucguuacgut t                                              21

<210> SEQ ID NO 123
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding
      nucleoside"
<220> FEATURE:
<221> NAME/KEY: modified_base
<222> LOCATION: 2,4,6,8,10,14,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19,21,22,23,24,26
<223> OTHER INFORMATION: /mod_base = "2'-O-methyl corresponding
      nucleoside"
<220> FEATURE:
<221> NAME/KEY: modified_base
<222> LOCATION: 2,3,23,24
<223> OTHER INFORMATION: /mod_base = "5'-phosphorothioate corresponding
      nucleotide"

<400> SEQUENCE: 123
tuucaugaaa ucguuacguc ggcugu                                         26

<210> SEQ ID NO 124
<211> LENGTH: 21
<212> TYPE: DNA
<213> ORGANISM: artificial sequence
```

```
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 124
tuucaugaaa ucguuacgut t                                             21

<210> SEQ ID NO 125
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19,21,22,23,24
<223> OTHER INFORMATION: /mod_base = "2'-O-methyl corresponding
      nucleoside"
<220> FEATURE:
<221> NAME/KEY: modified_base
<222> LOCATION: 2,3,25,26
<223> OTHER INFORMATION: /mod_base = "5'-phosphorothioate corresponding
      nucleotide"

<400> SEQUENCE: 125
tuucaugaaa ucguuacguu ggcutt                                        26

<210> SEQ ID NO 126
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding
      nucleoside"
<220> FEATURE:
<221> NAME/KEY: modified_base
<222> LOCATION: 2,4,6,8,10,14,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19,21,22,23,24,26
<223> OTHER INFORMATION: /mod_base = "2'-O-methyl corresponding
      nucleoside"
<220> FEATURE:
<221> NAME/KEY: modified_base
<222> LOCATION: 2,3,23,24
<223> OTHER INFORMATION: /mod_base = "5'-phosphorothioate corresponding
      nucleotide"

<400> SEQUENCE: 126
```
tuucaugaaa ucguuacguu ggcuau					26

<210> SEQ ID NO 127
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding nucleoside"
<220> FEATURE:
<221> NAME/KEY: modified_base
<222> LOCATION: 2,4,6,8,10,14,16,18,20
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,12,13,15,17,19,21,22,23,24,26
<223> OTHER INFORMATION: /mod_base = "2'-O-methyl corresponding nucleoside"
<220> FEATURE:
<221> NAME/KEY: modified_base
<222> LOCATION: 2,3,23,24
<223> OTHER INFORMATION: /mod_base = "5'-phosphorothioate corresponding nucleotide"

<400> SEQUENCE: 127
tuucaugaaa ucguuacguu ggcugu					26

<210> SEQ ID NO 128
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18,20
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,12,13,15,17,19,21,22,23
<223> OTHER INFORMATION: /mod_base = "2'-O-methyl corresponding nucleoside"
<220> FEATURE:
<221> NAME/KEY: modified_base
<222> LOCATION: 2,3,22,23
<223> OTHER INFORMATION: /mod_base = "5'-phosphorothioate corresponding nucleotide"

<400> SEQUENCE: 128
tuucaugaaa ucguuacguu ggc					23

<210> SEQ ID NO 129
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding nucleoside"
<220> FEATURE:
<221> NAME/KEY: modified_base
<222> LOCATION: 2,4,6,8,10,12,14,16,18,20
<223> OTHER INFORMATION: /mod_base = "2'-deoxy-2'-fluoro corresponding nucleoside"
<220> FEATURE:

```
<221> NAME/KEY: modified_base
<222> LOCATION: 3,5,7,11,13,15,17,19,21,22,23,24,26
<223> OTHER INFORMATION: /mod_base = "2'-O-methyl corresponding
      nucleoside"
<220> FEATURE:
<221> NAME/KEY: modified_base
<222> LOCATION: 9
<223> OTHER INFORMATION: /mod_base = "2'-3' seco corresponding
      nucleotide"
<220> FEATURE:
<221> NAME/KEY: modified_base
<222> LOCATION: 2,3,23,24
<223> OTHER INFORMATION: /mod_base = "5'-phosphorothioate corresponding
      nucleotide"

<400> SEQUENCE: 129
tuucaugaaa ucguuacguc ggcuau                                           26

<210> SEQ ID NO 130
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding
      nucleoside"
<220> FEATURE:
<221> NAME/KEY: modified_base
<222> LOCATION: 2,4,6,10,12,14,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19,21,22,23,24,26
<223> OTHER INFORMATION: /mod_base = "2'-O-methyl corresponding
      nucleoside"
<220> FEATURE:
<221> NAME/KEY: modified_base
<222> LOCATION: 8
<223> OTHER INFORMATION: /mod_base = "2'-3' seco corresponding
      nucleotide"
<220> FEATURE:
<221> NAME/KEY: modified_base
<222> LOCATION: 2,3,23,24
<223> OTHER INFORMATION: /mod_base = "5'-phosphorothioate corresponding
      nucleotide"

<400> SEQUENCE: 130
tuucaugaaa ucguuacguc ggcuau                                           26

<210> SEQ ID NO 131
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,15,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,16,17,19
<223> OTHER INFORMATION: /mod_base = "2'-O-methyl corresponding
      nucleoside"
<220> FEATURE:
<221> NAME/KEY: modified_base
<222> LOCATION: 2,21
<223> OTHER INFORMATION: /mod_base = "5'-phosphorothioate corresponding
      nucleotide"
```

```
<400> SEQUENCE: 131
tuucaugaaa ucguuacgut t                                              21

<210> SEQ ID NO 132
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,13,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,15,17,19
<223> OTHER INFORMATION: /mod_base = "2'-O-methyl corresponding
      nucleoside"
<220> FEATURE:
<221> NAME/KEY: modified_base
<222> LOCATION: 2,21
<223> OTHER INFORMATION: /mod_base = "5'-phosphorothioate corresponding
      nucleotide"

<400> SEQUENCE: 132
tuucaugaaa ucguuacgut t                                              21

<210> SEQ ID NO 133
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding
      nucleoside"
<220> FEATURE:
<221> NAME/KEY: modified_base
<222> LOCATION: 2,4,6,8,10,12,14,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,11,13,15,17,19,21,22,23,24,26
<223> OTHER INFORMATION: /mod_base = "2'-O-methyl corresponding
      nucleoside"
<220> FEATURE:
<221> NAME/KEY: modified_base
<222> LOCATION: 9
<223> OTHER INFORMATION: /mod_base = "2'-3' seco corresponding
      nucleotide"
<220> FEATURE:
<221> NAME/KEY: modified_base
<222> LOCATION: 2,24
<223> OTHER INFORMATION: /mod_base = "5'-phosphorothioate corresponding
      nucleotide"

<400> SEQUENCE: 133
tuucaugaaa ucguuacguc ggcuau                                         26

<210> SEQ ID NO 134
<211> LENGTH: 26
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 25
<223> OTHER INFORMATION: modified base = "2'-hydroxy corresponding
```

```
            nucleoside"
<220> FEATURE:
<221> NAME/KEY: modified_base
<222> LOCATION: 2,4,6,10,12,14,16,18,20
<223> OTHER INFORMATION: /mod_base = "2'-deoxy-2'-fluoro corresponding
            nucleoside"
<220> FEATURE:
<221> NAME/KEY: modified_base
<222> LOCATION: 3,5,7,9,11,13,15,17,19,21,22,23,24,26
<223> OTHER INFORMATION: /mod_base = "2'-O-methyl corresponding
            nucleoside"
<220> FEATURE:
<221> NAME/KEY: modified_base
<222> LOCATION: 8
<223> OTHER INFORMATION: /mod_base = "2'-3' seco corresponding
            nucleotide"
<220> FEATURE:
<221> NAME/KEY: modified_base
<222> LOCATION: 2,24
<223> OTHER INFORMATION: /mod_base = "5'-phosphorothioate corresponding
            nucleotide"

<400> SEQUENCE: 134
tuucaugaaa ucguuacguc ggcuau                                        26

<210> SEQ ID NO 135
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
            nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
            nucleoside"
<220> FEATURE:
<221> NAME/KEY: modified_base
<222> LOCATION: 21
<223> OTHER INFORMATION: /mod_base = "5'-phosphorothioate corresponding
            nucleotide"

<400> SEQUENCE: 135
tuacguugac agguagggut t                                             21

<210> SEQ ID NO 136
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
            nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
            nucleoside"
<220> FEATURE:
<221> NAME/KEY: modified_base
<222> LOCATION: 21
<223> OTHER INFORMATION: /mod_base = "5'-phosphorothioate corresponding
            nucleotide"

<400> SEQUENCE: 136
tucguuacgu ugacagguat t                                             21
```

```
<210> SEQ ID NO 137
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 137
tugucacgau gcggugguut t                                              21

<210> SEQ ID NO 138
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 138
tuucaugaaa ucguuacgut t                                              21

<210> SEQ ID NO 139
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,17,19
<223> OTHER INFORMATION: /mod_base = "2'-O-methyl corresponding
      nucleoside"
<220> FEATURE:
<221> NAME/KEY: modified_base
<222> LOCATION: 15
<223> OTHER INFORMATION: /mod_base = "2'-3' seco corresponding
      nucleotide"
<220> FEATURE:
<221> NAME/KEY: modified_base
```

<222> LOCATION: 21
<223> OTHER INFORMATION: /mod_base = "5'-phosphorothioate corresponding
      nucleotide"

<400> SEQUENCE: 139
tuucaugaaa ucguuacgut t                                              21

<210> SEQ ID NO 140
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,13,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 140
tuucaugaaa ucguuacgut t                                              21

<210> SEQ ID NO 141
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 141
tuucaugaaa ucguuacgut t                                              21

<210> SEQ ID NO 142
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,11,13,15,17,19
<223> OTHER INFORMATION: /mod_base = "2'-O-methyl corresponding
      nucleoside"

```
<220> FEATURE:
<221> NAME/KEY: modified_base
<222> LOCATION: 9
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 142
tuucaugaaa ucguuacgut t                                              21

<210> SEQ ID NO 143
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 8
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 143
tuucaugaaa ucguuacgut t                                              21

<210> SEQ ID NO 144
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 144
tuucaugaaa ucguuacgut t                                              21
```

```
<210> SEQ ID NO 145
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 145
tuucaugaaa ucguuacgut t                                              21

<210> SEQ ID NO 146
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,12,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end phosphate modification"

<400> SEQUENCE: 146
tuucaugaaa ucguuacgut t                                              21

<210> SEQ ID NO 147
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
```

```
            nucleoside"
<220> FEATURE:
<221> NAME/KEY: modified_base
<222> LOCATION: 21
<223> OTHER INFORMATION: /mod_base = "5'-phosphorothioate corresponding
            nucleotide"
<220> FEATURE:
<221> NAME/KEY: modified_base
<222> LOCATION: 1
<223> OTHER INFORMATION: /mod_base = "5' end phosphate modification"

<400> SEQUENCE: 147
tuucaugaaa ucguuacgut t                                              21

<210> SEQ ID NO 148
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
            nucleoside"
<220> FEATURE:
<221> NAME/KEY: modified_base
<222> LOCATION: 1,3,5,7,9,11,13,15,17,19
<223> OTHER INFORMATION: /mod_base = "2'-O-methyl corresponding
            nucleoside"
<220> FEATURE:
<221> NAME/KEY: modified_base
<222> LOCATION: 2,3,21
<223> OTHER INFORMATION: /mod_base = "5'-phosphorothioate corresponding
            nucleotide"

<400> SEQUENCE: 148
ucaugaaauc guuacguugt t                                              21

<210> SEQ ID NO 149
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,9,10,13,14,16,18
<223> OTHER INFORMATION: /mod_base = "2'-deoxy-2'-fluoro corresponding
            nucleoside"
<220> FEATURE:
<221> NAME/KEY: modified_base
<222> LOCATION: 1,3,5,7,8,11,12,15,17,19
<223> OTHER INFORMATION: /mod_base = "2'-O-methyl corresponding
            nucleoside"
<220> FEATURE:
<221> NAME/KEY: modified_base
<222> LOCATION: 2,3,21
<223> OTHER INFORMATION: /mod_base = "5'-phosphorothioate corresponding
            nucleotide"

<400> SEQUENCE: 149
ucuagcaaca aaaccuuaat t                                              21

<210> SEQ ID NO 150
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,9,10,12,14,15,18
```

```
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,8,11,13,16,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 150
ucuagcaaca aaaccuuaat t                                               21

<210> SEQ ID NO 151
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,13,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 151
ucuagcaaca aaaccuuaat t                                               21

<210> SEQ ID NO 152
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,15,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,16,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 152
ucuagcaaca aaaccuuaat t                                               21

<210> SEQ ID NO 153
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
```

```
<221> NAME/KEY: modified_base
<222> LOCATION: 2,4,6,8,10,12,14,15,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,16,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 153
uguaaaacaa uuguguacut t                                              21

<210> SEQ ID NO 154
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,13,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 154
uguaaaacaa uuguguacut t                                              21

<210> SEQ ID NO 155
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 155
uguaaaacaa uuguguacuu u                                              21

<210> SEQ ID NO 156
<211> LENGTH: 23
<212> TYPE: DNA
<213> ORGANISM: artificial sequence
<220> FEATURE:
```

```
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21,22,23
<223> OTHER INFORMATION: /mod_base = "2'-O-methyl corresponding
      nucleoside"
<220> FEATURE:
<221> NAME/KEY: modified_base
<222> LOCATION: 2,3,22,23
<223> OTHER INFORMATION: /mod_base = "5'-phosphorothioate corresponding
      nucleotide"

<400> SEQUENCE: 156
uguaaaacaa uuguguacuu uaa                                            23

<210> SEQ ID NO 157
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,9,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 157
uuucaugaaa ucguuacguu g                                              21

<210> SEQ ID NO 158
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,9,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,8,10,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 158
uuucaugaaa ucguuacguu g                                              21

<210> SEQ ID NO 159
<211> LENGTH: 21
<212> TYPE: DNA
```

```
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 159
uuucaugaaa ucguuacguu g                                              21

<210> SEQ ID NO 160
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19
<223> OTHER INFORMATION: /mod_base = "2'-O-methyl corresponding
      nucleoside"
<220> FEATURE:
<221> NAME/KEY: modified_base
<222> LOCATION: 2,3,21
<223> OTHER INFORMATION: /mod_base = "5'-phosphorothioate corresponding
      nucleotide"

<400> SEQUENCE: 160
uuucaugaaa ucguuacgut t                                              21

<210> SEQ ID NO 161
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 161
uuucaugaaa ucguuacguu g                                              21

<210> SEQ ID NO 162
```

```
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,14,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 162
uuucaugaaa ucguuacguu g                                              21

<210> SEQ ID NO 163
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 163
uuucaugaaa ucguuacguu g                                              21

<210> SEQ ID NO 164
<211> LENGTH: 23
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,15,16,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 2,3,22,23
<223> OTHER INFORMATION: /mod_base = "5'-phosphorothioate corresponding
      nucleotide"
```

-continued

```
<400> SEQUENCE: 164
uuucaugaaa ucguuacguu gat                                              23

<210> SEQ ID NO 165
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,10,11,12,13,14,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 165
uuucaugaaa ucguuacguu g                                                21

<210> SEQ ID NO 166
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,3,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,4,5,6,7,9,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"

<400> SEQUENCE: 166
uuucaugaaa ucguuacguu g                                                21

<210> SEQ ID NO 167
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,3,4,8,10,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,5,6,7,9,11,12,13,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
``` nucleotide"

<400> SEQUENCE: 167
uuucaugaaa ucguuacguu g                                             21

<210> SEQ ID NO 168
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,12,13,15,17,19,20,21
<223> OTHER INFORMATION: /mod_base = "2'-O-methyl corresponding
      nucleoside"
<220> FEATURE:
<221> NAME/KEY: modified_base
<222> LOCATION: 2,3,20,21
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end vinyl phosphonate
      modification"

<400> SEQUENCE: 168
uuucaugaaa ucguuacguu g                                             21

<210> SEQ ID NO 169
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-C6) modification"

<400> SEQUENCE: 169
uauaccuguc aacguaacgu aat                                           23

<210> SEQ ID NO 170
<211> LENGTH: 20
<212> TYPE: DNA
<213> ORGANISM: artificial sequence
<220> FEATURE:

```
<223> OTHER INFORMATION: Hif2alpha RNAi agent sense strand
<220> FEATURE:
<221> NAME/KEY: modified_base
<222> LOCATION: 1,3,5,7,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-C6-C6) modification"

<400> SEQUENCE: 170
acguaacgau uucaugaaat                                                   20

<210> SEQ ID NO 171
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 3,4,5,6,10,11,12,13,14,15,16,17
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1,2,18,19
<223> OTHER INFORMATION: /mod_base = "2'-MOE nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 171
acguaacgau uucaugaatt                                                   20

<210> SEQ ID NO 172
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 8,9,10
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,7,11,12,13,14,15,16,17,18,19,20
```

```
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 172
aacguaacga uuucaugaaa t                                              21

<210> SEQ ID NO 173
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 8,9,10
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,7,11,12,13,14,15,16,17,18,19,20
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 173
aacguaacga uuucaugaau t                                              21

<210> SEQ ID NO 174
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,9,13
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,8,10,11,12,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
```

<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 174
acguaacgau uucaugaaat                                                   20

<210> SEQ ID NO 175
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 175
acguaacgau uucaugaaat                                                   20

<210> SEQ ID NO 176
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 18,19
<223> OTHER INFORMATION: /mod_base = "2'-MOE nucleotide"
<220> FEATURE:
<221> NAME/KEY: modified_base
<222> LOCATION: 2
<223> OTHER INFORMATION: /mod_base = "5'-phosphorothioate corresponding

```
       nucleotide"
<220> FEATURE:
<221> NAME/KEY: modified_base
<222> LOCATION: 1
<223> OTHER INFORMATION: /mod_base = "5' end (Alk-C6-SMPT-C6)
       modification"

<400> SEQUENCE: 176
acguaacgau uucaugaatt                                              20

<210> SEQ ID NO 177
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
       nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding
       nucleoside"
<220> FEATURE:
<221> NAME/KEY: modified_base
<222> LOCATION: 20
<223> OTHER INFORMATION: /mod_base = "3'-3'-linked abasic site"
<220> FEATURE:
<221> NAME/KEY: modified_base
<222> LOCATION: 2,19,20
<223> OTHER INFORMATION: /mod_base = "5'-phosphorothioate corresponding
       nucleotide"
<220> FEATURE:
<221> NAME/KEY: modified_base
<222> LOCATION: 1
<223> OTHER INFORMATION: /mod_base = "5' end (Alk-C6-SMPT-C6)
       modification"

<400> SEQUENCE: 177
acguaacgau uucaugaaun                                              20

<210> SEQ ID NO 178
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
       nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding
       nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2,19,20
<223> OTHER INFORMATION: /mod_base = "5'-phosphorothioate corresponding
       nucleotide"
<220> FEATURE:
<221> NAME/KEY: modified_base
<222> LOCATION: 1
<223> OTHER INFORMATION: /mod_base = "5' end (Alk-C6-SMPT-C6)
       modification"
```

```
<400> SEQUENCE: 178
acguaacgau uucaugaaut                                               20

<210> SEQ ID NO 179
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-C6-SMPT-C6)
      modification"

<400> SEQUENCE: 179
acguaacgau uucaugaaut                                               20

<210> SEQ ID NO 180
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6)(Alk-PEG5-Ser)
      modification"

<400> SEQUENCE: 180
```
uauacguaac gauuucauga aat        23

<210> SEQ ID NO 181
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
    nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding
    nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
    nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 181
acguaacgau uucaugaaat        20

<210> SEQ ID NO 182
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
    nucleoside"
<220> FEATURE:
<221> NAME/KEY: modified_base
<222> LOCATION: 6,8,10,11,12,16,18,20
<223> OTHER INFORMATION: /mod_base = "2'-deoxy-2'-fluoro corresponding
    nucleoside"
<220> FEATURE:
<221> NAME/KEY: modified_base
<222> LOCATION: 1,3,4,5,7,9,13,14,15,17,19,21,22
<223> OTHER INFORMATION: /mod_base = "2'-O-methyl corresponding
    nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
    nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 182
uauacguaac gauuucauga aat        23

<210> SEQ ID NO 183

```
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 6,8,10,11,12,16,18,20
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,7,9,13,14,15,17,19,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 183
uauacguaac gauuucauga aut                                             23

<210> SEQ ID NO 184
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,12,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,11,13,14,15,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 184
uauacguaac gauuucauga aat                                             23
```

```
<210> SEQ ID NO 185
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,16,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 185
uauacguaac gauuucauga aat                                            23

<210> SEQ ID NO 186
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 22
<223> OTHER INFORMATION: /mod_base = "2'-MOE nucleotide"
<220> FEATURE:
<221> NAME/KEY: modified_base
<222> LOCATION: 5,23
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"
```

```
<400> SEQUENCE: 186
uauacguaac gauuucauga aat                                        23

<210> SEQ ID NO 187
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 10,11,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,7,8,9,13,14,15,16,17,18,19,20,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 22
<223> OTHER INFORMATION: /mod_base = "2'-MOE nucleotide"
<220> FEATURE:
<221> NAME/KEY: modified_base
<222> LOCATION: 5,23
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 187
uauacguaac gauuucauga aat                                        23

<210> SEQ ID NO 188
<211> LENGTH: 24
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,16,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 24
<223> OTHER INFORMATION: /mod_base = "3'-3'-linked nucleotide"
<220> FEATURE:
<221> NAME/KEY: modified_base
<222> LOCATION: 5,24
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"
```

-continued

<400> SEQUENCE: 188
uauacguaac gauuucauga autt                                              24

<210> SEQ ID NO 189
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 189
uauacguaac gauuucauga aat                                               23

<210> SEQ ID NO 190
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,11,12,16
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,13,14,15,17,18,19,20,21,22
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
       nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 190
uauacguaac gauuucauga aut        23

<210> SEQ ID NO 191
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,12,13,14,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,11,15,16,17,18,19,20,21,23,24
<223> OTHER INFORMATION: /mod_base = "2'-O-methyl corresponding
      nucleoside"
<220> FEATURE:
<221> NAME/KEY: modified_base
<222> LOCATION: 26
<223> OTHER INFORMATION: /mod_base = "3'-3'-linked nucleotide"
<220> FEATURE:
<221> NAME/KEY: modified_base
<222> LOCATION: 5,26
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-PEG5-C6) modification"

<400> SEQUENCE: 191
uaucaacgua acgauuucau gaautt        26

<210> SEQ ID NO 192
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 10,12,13,14,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,4,5,6,7,8,9,11,15,16,17,18,19,20,21,23,24
<223> OTHER INFORMATION: /mod_base = "2'-O-methyl corresponding
      nucleoside"
<220> FEATURE:
<221> NAME/KEY: modified_base
<222> LOCATION: 26
<223> OTHER INFORMATION: /mod_base = "3'-3'-linked nucleotide"
<220> FEATURE:
<221> NAME/KEY: modified_base
<222> LOCATION: 5,6,26
<223> OTHER INFORMATION: /mod_base = "5'-phosphorothioate corresponding
      nucleotide"
<220> FEATURE:
<221> NAME/KEY: modified_base
<222> LOCATION: 1

```
<223> OTHER INFORMATION: /mod_base = "5' end (Alk-PEG5-C6) modification"

<400> SEQUENCE: 192
uaucaacgua acgauuucau gaauutt                                         26

<210> SEQ ID NO 193
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 193
acguaacgau uucaugaaat                                                 20

<210> SEQ ID NO 194
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,8,9,11,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,10,12,14,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 194
acguaacgau uucaugaaat                                                 20

<210> SEQ ID NO 195
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
```

```
<221> NAME/KEY: modified_base
<222> LOCATION: 3,5,7,9,10,11,13,15,19
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,6,8,12,14,16,17,18,20
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 195
aaaguacaca auuguuuuac a                                              21

<210> SEQ ID NO 196
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,9,10,11,13,15,19
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,6,8,12,14,16,17,18,20
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 196
aaaguacaca auuguuuuac t                                              21

<210> SEQ ID NO 197
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 9,10,11
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,7,8,12,13,14,15,16,17,18,19,20
<223> OTHER INFORMATION: /mod_base = "2'-O-methyl corresponding
      nucleoside"
```

```
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 197
aaaguacaca auuguuuuac t                                               21

<210> SEQ ID NO 198
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,9,10,11
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,8,12,13,14,15,16,17,18,19,20
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 198
aaaguacaca auuguuuuac t                                               21

<210> SEQ ID NO 199
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 5,7,9,10,11,13,15
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,6,8,12,14,16,17,18,19,20
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
```

```
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 199
aaaguacaca auuguuuuac t                                               21

<210> SEQ ID NO 200
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,7,9,13,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,5,6,8,10,11,12,14,15,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 200
acguaacgau uucaugaaat                                                 20

<210> SEQ ID NO 201
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,8,9,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,6,10,11,12,14,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 201
acguaacgau uucaugaaat                                                 20
```

```
<210> SEQ ID NO 202
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,8,9,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,6,10,11,12,14,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 202
acguaacgau uucaugaaut                                               20

<210> SEQ ID NO 203
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,8,10,11,12,13,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 203
acguaacgau uucaugaaat                                               20

<210> SEQ ID NO 204
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
```

```
<222> LOCATION: 7,9,13
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,8,10,11,12,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 204
acguaacgau uucaugaaat                                                 20

<210> SEQ ID NO 205
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17,18,19
<223> OTHER INFORMATION: /mod_base = "2'-O-methyl corresponding nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 205
acguaacgau uucaugaaat                                                 20

<210> SEQ ID NO 206
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17,18
<223> OTHER INFORMATION: /mod_base = "2'-O-methyl corresponding
      nucleoside"
```

```
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 19
<223> OTHER INFORMATION: /mod_base = "2'-MOE nucleotide"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 206
acguaacgau uucaugaaat                                                    20

<210> SEQ ID NO 207
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,8,9
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,10,11,12,13,14,15,16,17,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 19
<223> OTHER INFORMATION: /mod_base = "2'-MOE nucleotide"
<220> FEATURE:
<221> NAME/KEY: modified_base
<222> LOCATION: 2,20
<223> OTHER INFORMATION: /mod_base = "5'-phosphorothioate corresponding
      nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 207
acguaacgau uucaugaaat                                                    20

<210> SEQ ID NO 208
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 5,7,9,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,6,8,10,11,12,14,16,18,19
<223> OTHER INFORMATION: /mod_base = "2'-O-methyl corresponding
      nucleoside"
<220> FEATURE:
```

<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 208
acguaacgau uucaugaaat                    20

<210> SEQ ID NO 209
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,8,9,11,13,17
<223> OTHER INFORMATION: /mod_base = "2'-deoxy-2'-fluoro corresponding nucleoside"
<220> FEATURE:
<221> NAME/KEY: modified_base
<222> LOCATION: 1,2,4,6,10,12,14,15,16,18,19
<223> OTHER INFORMATION: /mod_base = "2'-O-methyl corresponding nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding nucleotide"
<220> FEATURE:
<221> NAME/KEY: modified_base
<222> LOCATION: 1
<223> OTHER INFORMATION: /mod_base = "5' end (Alk-SMPT-C6) modification"

<400> SEQUENCE: 209
aguacacaau uguuuuacat                    20

<210> SEQ ID NO 210
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,8,9,11,13,17
<223> OTHER INFORMATION: /mod_base = "2'-deoxy-2'-fluoro corresponding nucleoside"
<220> FEATURE:
<221> NAME/KEY: modified_base
<222> LOCATION: 1,2,4,6,10,12,14,15,16,18,19
<223> OTHER INFORMATION: /mod_base = "2'-O-methyl corresponding nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 2
<223> OTHER INFORMATION: /mod_base = "5'-phosphorothioate corresponding nucleotide"
<220> FEATURE:

<221> NAME/KEY: modified_base
<222> LOCATION: 1
<223> OTHER INFORMATION: /mod_base = "5' end (Alk-SMPT-C6) modification"

<400> SEQUENCE: 210
aguacacaau uguuuuacut					20

<210> SEQ ID NO 211
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 211
aacccuaccu gucaacguat					20

<210> SEQ ID NO 212
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 212
acccuaccug ucaagguaat					20

<210> SEQ ID NO 213
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding

```
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 213
accugucaac guaacguaat                                               20

<210> SEQ ID NO 214
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,5,6,8,10,12,14,16,18
<223> OTHER INFORMATION: /mod_base = "2'-O-methyl corresponding
        nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 214
acguaacgau uucaugaaat                                               20

<210> SEQ ID NO 215
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 215
acguaacgau uucaugaaat                                               20
```

-continued

```
<210> SEQ ID NO 216
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 216
acguaacgau uucaugaaat                                                 20

<210> SEQ ID NO 217
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,6,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 217
acguaacgau uucaugaaat                                                 20

<210> SEQ ID NO 218
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
```

```
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 218
aguacacaau uguuuuacat                                           20

<210> SEQ ID NO 219
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 219
cuaccuguca acguaacgat                                           20

<210> SEQ ID NO 220
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 220
cugcgaacac acaagcucat                                           20

<210> SEQ ID NO 221
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
```

<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 221
cugucaacgu aacgauuuat                                                    20

<210> SEQ ID NO 222
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 222
gaacacacaa gcuccucuat                                                    20

<210> SEQ ID NO 223
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 223
gcgaacacac aagcuccuat                                                    20

<210> SEQ ID NO 224
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 224
ucacugucaa cguaacgaat                                                    20

<210> SEQ ID NO 225
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 225
uguaugggag cuuaacuuat                                                    20

<210> SEQ ID NO 226
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding

```
                 nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Alk-SS-C6) modification"

<400> SEQUENCE: 226
uuaagguuuu guugcuagat                                                       20

<210> SEQ ID NO 227
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
                 nucleoside"
<220> FEATURE:
<221> NAME/KEY: modified_base
<222> LOCATION: 10,12,16
<223> OTHER INFORMATION: /mod_base = "2'-deoxy-2'-fluoro corresponding
                 nucleoside"
<220> FEATURE:
<221> NAME/KEY: modified_base
<222> LOCATION: 1,3,4,5,6,7,8,9,11,13,14,15,17,18,19,20,21,22
<223> OTHER INFORMATION: /mod_base = "2'-O-methyl corresponding
                 nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 5
<223> OTHER INFORMATION: /mod_base = "5'-phosphorothioate corresponding
                 nucleotide"
<220> FEATURE:
<221> NAME/KEY: modified_base
<222> LOCATION: 1
<223> OTHER INFORMATION: /mod_base = "5' end (Chol-TEG) modification"

<400> SEQUENCE: 227
uauacguaac gauuucauga aat                                                   23

<210> SEQ ID NO 228
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
                 nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
                 nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
                 nucleoside"
<220> FEATURE:
<221> NAME/KEY: modified_base
<222> LOCATION: 23
```

```
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (DBCO-TEG) modification"

<400> SEQUENCE: 228
uauacguaac gauuucauga aat                                          23

<210> SEQ ID NO 229
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,11,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (DBCO-TEG) modification"

<400> SEQUENCE: 229
uauacguaac gauuucauga aat                                          23

<210> SEQ ID NO 230
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2,4
<223> OTHER INFORMATION: modified base = "2'-hydroxy corresponding
      nucleoside"
<220> FEATURE:
<221> NAME/KEY: modified_base
<222> LOCATION: 6,8,10,12,14,16,18,20,22,24
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21,23,25
<223> OTHER INFORMATION: /mod_base = "2'-O-methyl corresponding
      nucleoside"
<220> FEATURE:
<221> NAME/KEY: modified_base
<222> LOCATION: 26
<223> OTHER INFORMATION: /mod_base = "3'-3'-linked nucleotide"
<220> FEATURE:
<221> NAME/KEY: modified_base
<222> LOCATION: 6,7
<223> OTHER INFORMATION: /mod_base = "5'-phosphorothioate corresponding
      nucleotide"
<220> FEATURE:
<221> NAME/KEY: modified_base
<222> LOCATION: 1
```

```
<223> OTHER INFORMATION: /mod_base = "5' end (DBCO-TEG) modification"

<400> SEQUENCE: 230
uauaucgacg uaacgauuuc augaaa                                        26

<210> SEQ ID NO 231
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 231
acguaacgau uucaugaaat                                               20

<210> SEQ ID NO 232
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 232
acguaacgau uucaugaaat                                               20

<210> SEQ ID NO 233
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,8,9,11,13,15,17,19
<223> OTHER INFORMATION: /mod_base = "2'-deoxy-2'-fluoro corresponding
```

```
            nucleoside"
<220> FEATURE:
<221> NAME/KEY: modified_base
<222> LOCATION: 2,4,6,7,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 233
acguaacgau uucaugaaat                                                 20

<210> SEQ ID NO 234
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,4,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,5,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 234
acguaacgau uucaugaaat                                                 20

<210> SEQ ID NO 235
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 235
```
acuccaacgu augugguuat                                                  20

<210> SEQ ID NO 236
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,7,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 236
aguacacaau uguuuuacat                                                  20

<210> SEQ ID NO 237
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,4,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,5,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 237
aguacacaau uguuuuacat                                                  20

<210> SEQ ID NO 238
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,8,9,11,13,17
<223> OTHER INFORMATION: /mod_base = "2'-deoxy-2'-fluoro corresponding
      nucleoside"
<220> FEATURE:
<221> NAME/KEY: modified_base -continued

```
<222> LOCATION: 1,2,4,6,7,10,12,14,15,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 238
aguacacaau uguuuuacat                                                 20

<210> SEQ ID NO 239
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,4,7,9,11,13,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,5,6,8,10,12,14,15,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 239
aguacacaau uguuuuacat                                                 20

<210> SEQ ID NO 240
<211> LENGTH: 19
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 19
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 240
caacguaacg auuucauga                                                  19
```

```
<210> SEQ ID NO 241
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 241
caacguaacg auuucaugat                                                     20

<210> SEQ ID NO 242
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 242
uggguuaagu guuuaucaat                                                     20

<210> SEQ ID NO 243
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,4,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,5,6,8,10,12,14,16,18
<223> OTHER INFORMATION: /mod_base = "2'-O-methyl corresponding
      nucleoside"
```

-continued

```
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 243
uuaagguuuu guugcuagat                                            20

<210> SEQ ID NO 244
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,7,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 244
uuaagguuuu guugcuagat                                            20

<210> SEQ ID NO 245
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,4,7,9,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,5,6,8,10,11,12,14,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 245
uuaagguuuu guugcuagat                                            20

<210> SEQ ID NO 246
<211> LENGTH: 20
```

-continued

```
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,8,9,13,15,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,4,6,7,10,11,12,14,16,18,19
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (Me-Alk-SS-C6)
      modification"

<400> SEQUENCE: 246
uuaagguuuu guugcuagat                                              20

<210> SEQ ID NO 247
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 247
aacccuaccu gucaacguat                                              20

<210> SEQ ID NO 248
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
```

```
<220> FEATURE:
<221> NAME/KEY: modified_base
<222> LOCATION: 1
<223> OTHER INFORMATION: /mod_base = "5' end (NH-C6) modification"

<400> SEQUENCE: 248
acccuaccug ucaagguaat                                              20

<210> SEQ ID NO 249
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 249
accugucaac guaacguaat                                              20

<210> SEQ ID NO 250
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 250
acuccaacgu augugguaat                                              20

<210> SEQ ID NO 251
<211> LENGTH: 19
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17
```

```
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 19
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 251
caacguaacg auuucauga                                               19

<210> SEQ ID NO 252
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 252
caacguaacg auuucaugat                                              20

<210> SEQ ID NO 253
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 253
cagugcaacg ccacccagat                                              20
```

<210> SEQ ID NO 254
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 254
ccugcgaaca cacaagcuat                                           20

<210> SEQ ID NO 255
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 255
ccugucaacg uaacgauuat                                           20

<210> SEQ ID NO 256
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:

```
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 256
cgaacacaca agcuccucat                                                   20

<210> SEQ ID NO 257
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 257
cuaccuguca acguaacgat                                                   20

<210> SEQ ID NO 258
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 258
cugcgaacac acaagcucat                                                   20

<210> SEQ ID NO 259
<211> LENGTH: 20
<212> TYPE: DNA
<213> ORGANISM: artificial sequence
<220> FEATURE:
<223> OTHER INFORMATION: Hif2alpha RNAi agent sense strand
```

```
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 259
gaacacacaa gcuccucuat                                                    20

<210> SEQ ID NO 260
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 260
gcgaacacac aagcuccuat                                                    20

<210> SEQ ID NO 261
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"
```

-continued

```
<400> SEQUENCE: 261
gcuacgccac ccaguaccat                                                20

<210> SEQ ID NO 262
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 262
uauccugcga acacacaagc uat                                            23

<210> SEQ ID NO 263
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 263
uaucuaccug ucaacguaac gat                                            23

<210> SEQ ID NO 264
<211> LENGTH: 23
<212> TYPE: DNA
<213> ORGANISM: artificial sequence
```

```
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 264
uaugcuacgc cacccaguac cat                                           23

<210> SEQ ID NO 265
<211> LENGTH: 23
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2
<223> OTHER INFORMATION: modified base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 265
uauugcgaac acacaagcuc cat                                           23

<210> SEQ ID NO 266
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
```

```
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 266
ucacugucaa cguaacgaat                                                       20

<210> SEQ ID NO 267
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 267
ugcgaacaca caagcuccat                                                       20

<210> SEQ ID NO 268
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"
<220> FEATURE:
<221> NAME/KEY: modified_base
<222> LOCATION: 1
<223> OTHER INFORMATION: /mod_base = "5' end (NH-C6) modification"

<400> SEQUENCE: 268
uggguuaagu guuuaucaat                                                       20

<210> SEQ ID NO 269
<211> LENGTH: 20
```

```
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 269
acguaacgau uucaugaaat                                                    20

<210> SEQ ID NO 270
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 270
acguaacgau uucaugaaat                                                    20

<210> SEQ ID NO 271
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 271
aguacacaau uguuuuacat                                                    20

<210> SEQ ID NO 272
<211> LENGTH: 19
<212> TYPE: DNA
```

```
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,8,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,7,10,12,14,16,18
<223> OTHER INFORMATION: /mod_base = "2'-O-methyl corresponding
      nucleoside"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 19
<223> OTHER INFORMATION: /mod_base = "3' end (C6-SS-Alk-Me)
      modification"

<400> SEQUENCE: 272
acguaacgau uucaugaaa                                                  19

<210> SEQ ID NO 273
<211> LENGTH: 19
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,4,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,5,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 19
<223> OTHER INFORMATION: /mod_base = "3' end (C6-SS-Alk-Me)
      modification"

<400> SEQUENCE: 273
acguaacgau uucaugaaa                                                  19

<210> SEQ ID NO 274
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,4,7,9,11,13,17
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,5,6,8,10,12,14,15,16,18,19
<223> OTHER INFORMATION: /mod_base = "2'-O-methyl corresponding
      nucleoside"
<220> FEATURE:
<221> NAME/KEY: modified_base
```

```
<222> LOCATION: 20
<223> OTHER INFORMATION: /mod_base = "3'-3'-linked nucleotide"

<400> SEQUENCE: 274
aguacacaau uguuuuacat                                           20

<210> SEQ ID NO 275
<211> LENGTH: 19
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 7,9,13
<223> OTHER INFORMATION: /mod_base = "2'-deoxy-2'-fluoro corresponding
      nucleoside"
<220> FEATURE:
<221> NAME/KEY: modified_base
<222> LOCATION: 1,2,3,4,5,6,8,10,11,12,14,15,16,17,18,19
<223> OTHER INFORMATION: /mod_base = "2'-O-methyl corresponding
      nucleoside"
<220> FEATURE:
<221> NAME/KEY: modified_base
<222> LOCATION: 2
<223> OTHER INFORMATION: /mod_base = "5'-phosphorothioate corresponding
      nucleotide"
<220> FEATURE:
<221> NAME/KEY: modified_base
<222> LOCATION: 19
<223> OTHER INFORMATION: /mod_base = "3' end (NAG13) modification"

<400> SEQUENCE: 275
acguaacgau uucaugaaa                                            19

<210> SEQ ID NO 276
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,10,11,13,15,17,19,21
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,12,14,16,18,20
<223> OTHER INFORMATION: /mod_base = "2'-O-methyl corresponding
      nucleoside"
<220> FEATURE:
<221> NAME/KEY: modified_base
<222> LOCATION: 2,3
<223> OTHER INFORMATION: /mod_base = "5'-phosphorothioate corresponding
      nucleotide"
<220> FEATURE:
<221> NAME/KEY: modified_base
<222> LOCATION: 21
<223> OTHER INFORMATION: /mod_base = "3' end (C6-SS-Alk-Me)
      modification"

<400> SEQUENCE: 276
caacguaacg auuucaugaa a                                         21

<210> SEQ ID NO 277
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
```

<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 277
cugucaacgu aacgauuuat                                                     20

<210> SEQ ID NO 278
<211> LENGTH: 21
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 3,5,7,9,10,11,13,15,17,19,21
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,12,14,16,18,20
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "2'-3' seco corresponding
      nucleotide"
<220> FEATURE:
<221> NAME/KEY: modified_base
<222> LOCATION: 2,3
<223> OTHER INFORMATION: /mod_base = "5'-phosphorothioate corresponding
      nucleotide"
<220> FEATURE:
<221> NAME/KEY: modified_base
<222> LOCATION: 21
<223> OTHER INFORMATION: /mod_base = "3' end (C6-SS-Alk-Me)
      modification"

<400> SEQUENCE: 278
caacguaacg auuucaugaa a                                                   21

<210> SEQ ID NO 279
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2,4
<223> OTHER INFORMATION: modified base = "2'-hydroxy corresponding
      nucleoside"
<220> FEATURE:
<221> NAME/KEY: modified_base
<222> LOCATION: 6,8,10,12,14,16,18,20,22,24,26
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21,23,25
<223> OTHER INFORMATION: /mod_base = "2'-O-methyl corresponding
      nucleoside"
<220> FEATURE:
<221> NAME/KEY: modified_base
<222> LOCATION: 6

<223> OTHER INFORMATION: /mod_base = "5'-phosphorothioate corresponding
       nucleotide"
<220> FEATURE:
<221> NAME/KEY: modified_base
<222> LOCATION: 26
<223> OTHER INFORMATION: /mod_base = "3' end (C6-SS-Alk-Me)
       modification"

<400> SEQUENCE: 279
uauaucgacg uaacgauuuc augaaa                                            26

<210> SEQ ID NO 280
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2,4
<223> OTHER INFORMATION: modified base = "2'-hydroxy corresponding
       nucleoside"
<220> FEATURE:
<221> NAME/KEY: modified_base
<222> LOCATION: 6,8,10,12,14,15,16,18,20,22,24,26
<223> OTHER INFORMATION: /mod_base = "2'-deoxy-2'-fluoro corresponding
       nucleoside"
<220> FEATURE:
<221> NAME/KEY: modified_base
<222> LOCATION: 1,3,5,7,9,11,13,17,19,21,23,25
<223> OTHER INFORMATION: /mod_base = "2'-O-methyl corresponding
       nucleoside"
<220> FEATURE:
<221> NAME/KEY: modified_base
<222> LOCATION: 6,7
<223> OTHER INFORMATION: /mod_base = "5'-phosphorothioate corresponding
       nucleotide"
<220> FEATURE:
<221> NAME/KEY: modified_base
<222> LOCATION: 26
<223> OTHER INFORMATION: /mod_base = "3' end (C6-SS-Alk-Me)
       modification"

<400> SEQUENCE: 280
uauaucaacg uaacgauuuc augaaa                                            26

<210> SEQ ID NO 281
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2,4
<223> OTHER INFORMATION: modified base = "2'-hydroxy corresponding
       nucleoside"
<220> FEATURE:
<221> NAME/KEY: modified_base
<222> LOCATION: 6,8,10,12,14,16,18,20,22,24,26
<223> OTHER INFORMATION: /mod_base = "2'-deoxy-2'-fluoro corresponding
       nucleoside"
<220> FEATURE:
<221> NAME/KEY: modified_base
<222> LOCATION: 1,3,5,7,9,11,13,15,17,19,21,23,25
<223> OTHER INFORMATION: /mod_base = "2'-O-methyl corresponding
       nucleoside"
<220> FEATURE:
<221> NAME/KEY: modified_base
<222> LOCATION: 6,7
<223> OTHER INFORMATION: /mod_base = "5'-phosphorothioate corresponding
       nucleotide"
<220> FEATURE:
<221> NAME/KEY: modified_base
<222> LOCATION: 26

```
<223> OTHER INFORMATION: /mod_base = "3' end (C6-SS-Alk-Me)
      modification"

<400> SEQUENCE: 281
uauaucgacg uaacgauuuc augaaa                                             26

<210> SEQ ID NO 282
<211> LENGTH: 26
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 2,4
<223> OTHER INFORMATION: modified base = "2'-hydroxy corresponding
      nucleoside"
<220> FEATURE:
<221> NAME/KEY: modified_base
<222> LOCATION: 6,8,10,12,14,15,16,18,20,22,24,26
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,17,19,21,23,25
<223> OTHER INFORMATION: /mod_base = "2'-O-methyl corresponding
      nucleoside"
<220> FEATURE:
<221> NAME/KEY: modified_base
<222> LOCATION: 6,7
<223> OTHER INFORMATION: /mod_base = "5'-phosphorothioate corresponding
      nucleotide"
<220> FEATURE:
<221> NAME/KEY: modified_base
<222> LOCATION: 26
<223> OTHER INFORMATION: /mod_base = "3' end (C6-SS-Alk-Me)
      modification"

<400> SEQUENCE: 282
uauaucgacg uaacgauuuc augaaa                                             26

<210> SEQ ID NO 283
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 283
uguaugggag cuuaacuuat                                                    20

<210> SEQ ID NO 284
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
```

```
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked nucleotide"

<400> SEQUENCE: 284
uuaagguuuu guugcuagat                                              20

<210> SEQ ID NO 285
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 285
gagacuguau ggucagcuc                                               19

<210> SEQ ID NO 286
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 286
cuccgacucc uuccgacuc                                               19

<210> SEQ ID NO 287
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 287
uccgacuccc agcauucga                                               19

<210> SEQ ID NO 288
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 288
cgacucccag cauucgagc                                               19

<210> SEQ ID NO 289
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 289
gacucccagc auucgagcc                                               19

<210> SEQ ID NO 290
```

```
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 290
caggugcucg gcgucugaa                                              19

<210> SEQ ID NO 291
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 291
gugcucggcg ucugaacgu                                              19

<210> SEQ ID NO 292
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 292
ucggcgucug aacgucuca                                              19

<210> SEQ ID NO 293
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 293
ggcgucugaa cgucucaaa                                              19

<210> SEQ ID NO 294
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 294
cgucugaacg ucucaaagg                                              19

<210> SEQ ID NO 295
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 295
aaaaggagua gcucggaga                                              19

<210> SEQ ID NO 296
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 296
```
ggguuucauu gccguggug                                              19

<210> SEQ ID NO 297
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 297
uucaugggac uuacacagg                                              19

<210> SEQ ID NO 298
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 298
gggacuuaca cagguggag                                              19

<210> SEQ ID NO 299
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 299
acacaggugg agcuaacag                                              19

<210> SEQ ID NO 300
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 300
gagcuaacag gacauagua                                              19

<210> SEQ ID NO 301
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 301
gcuaacagga cauaguauc                                              19

<210> SEQ ID NO 302
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 302
cuaacaggac auaguaucu                                              19

<210> SEQ ID NO 303
<211> LENGTH: 19
<212> TYPE: RNA

```
<213> ORGANISM: artificial sequence
<220> FEATURE:
<223> OTHER INFORMATION: Hif2alpha RNAi agent sense strand

<400> SEQUENCE: 303
ggacauagua ucuuugacu                                              19

<210> SEQ ID NO 304
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 304
ucuuugacuu cacucaucc                                              19

<210> SEQ ID NO 305
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 305
ucacucaucc cugcgacca                                              19

<210> SEQ ID NO 306
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 306
gagauucgug agaaccuga                                              19

<210> SEQ ID NO 307
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 307
uucgugagaa ccugagucu                                              19

<210> SEQ ID NO 308
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 308
ucgugagaac cugagucuc                                              19

<210> SEQ ID NO 309
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 309
gacaugucca cagagcggg                                              19
```

<210> SEQ ID NO 310
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 310
gcgggacuuc uucaugagg                                                    19

<210> SEQ ID NO 311
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 311
ggaugaagug cacggucac                                                    19

<210> SEQ ID NO 312
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 312
cacggucacc aacagaggc                                                    19

<210> SEQ ID NO 313
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 313
ucaccaacag aggccguac                                                    19

<210> SEQ ID NO 314
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 314
caccaacaga ggccguacu                                                    19

<210> SEQ ID NO 315
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 315
aggccguacu gucaaccuc                                                    19

<210> SEQ ID NO 316
<211> LENGTH: 19
<212> TYPE: RNA
<213> ORGANISM: artificial sequence
<220> FEATURE:

```
<223> OTHER INFORMATION: Hif2alpha RNAi agent sense strand

<400> SEQUENCE: 316
uccucacaau agucugugu                                                    19

<210> SEQ ID NO 317
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 317
aauagucugu guggcuaca                                                    19

<210> SEQ ID NO 318
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 318
cagaacugau ugguuacca                                                    19

<210> SEQ ID NO 319
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 319
agaacugauu gguuaccac                                                    19

<210> SEQ ID NO 320
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 320
cugauugguu accacccug                                                    19

<210> SEQ ID NO 321
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 321
uuggccgcuc agccuauga                                                    19

<210> SEQ ID NO 322
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 322
uaugaauucu accaugcgc                                                    19
```

```
<210> SEQ ID NO 323
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 323
augaauucua ccaugcgcu                                                    19

<210> SEQ ID NO 324
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 324
ugaauucuac caugcgcua                                                    19

<210> SEQ ID NO 325
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 325
gaauucuacc augcgcuag                                                    19

<210> SEQ ID NO 326
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 326
aauucuacca ugcgcuaga                                                    19

<210> SEQ ID NO 327
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 327
ucuaccaugc gcuagacuc                                                    19

<210> SEQ ID NO 328
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 328
augcgcuaga cuccgagaa                                                    19

<210> SEQ ID NO 329
<211> LENGTH: 19
<212> TYPE: RNA
<213> ORGANISM: artificial sequence
<220> FEATURE:
<223> OTHER INFORMATION: Hif2alpha RNAi agent sense strand
```

```
<400> SEQUENCE: 329
ugcgcuagac uccgagaac                                                19

<210> SEQ ID NO 330
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 330
guaaguggcc aguaccgga                                                19

<210> SEQ ID NO 331
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 331
uaaguggcca guaccggau                                                19

<210> SEQ ID NO 332
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 332
ccaguaccgg augcucgca                                                19

<210> SEQ ID NO 333
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 333
aguaccggau gcucgcaaa                                                19

<210> SEQ ID NO 334
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 334
uaccggaugc ucgcaaagc                                                19

<210> SEQ ID NO 335
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 335
ugcucgcaaa gcauggggg                                                19

<210> SEQ ID NO 336
<211> LENGTH: 19
```

-continued

<212> TYPE: RNA
<213> ORGANISM: artificial sequence
<220> FEATURE:
<223> OTHER INFORMATION: Hif2alpha RNAi agent sense strand

<400> SEQUENCE: 336
cgcaaagcau gggggcuac                                                   19

<210> SEQ ID NO 337
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 337
agcauggggg cuacgugug                                                   19

<210> SEQ ID NO 338
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 338
gcaugggggc uacgugugg                                                   19

<210> SEQ ID NO 339
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 339
caucuacaac ccucgcaac                                                   19

<210> SEQ ID NO 340
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 340
aucuacaacc cucgcaacc                                                   19

<210> SEQ ID NO 341
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 341
cuacaacccu cgcaaccug                                                   19

<210> SEQ ID NO 342
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 342

```
ucaaacccuc gcaaccugc                                                      19

<210> SEQ ID NO 343
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 343
uuugauagca guggcaagg                                                      19

<210> SEQ ID NO 344
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 344
aguaacuucc uauucacca                                                      19

<210> SEQ ID NO 345
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 345
ucgggaauca gaacuucga                                                      19

<210> SEQ ID NO 346
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 346
cugcuccacg cccaauagc                                                      19

<210> SEQ ID NO 347
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 347
ugcuccacgc ccaauagcc                                                      19

<210> SEQ ID NO 348
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 348
gcuccacgcc caauagccc                                                      19

<210> SEQ ID NO 349
<211> LENGTH: 19
<212> TYPE: RNA
<213> ORGANISM: artificial sequence
```

```
<220> FEATURE:
<223> OTHER INFORMATION: Hif2alpha RNAi agent sense strand

<400> SEQUENCE: 349
acgcccaaua gcccugaag                                              19

<210> SEQ ID NO 350
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 350
caucuuugga uaacgaccu                                              19

<210> SEQ ID NO 351
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 351
caaugcagua cccagacgg                                              19

<210> SEQ ID NO 352
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 352
augcaguacc cagacggau                                              19

<210> SEQ ID NO 353
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 353
aguacccaga cggauuuca                                              19

<210> SEQ ID NO 354
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 354
cuguagcccc gcacagucc                                              19

<210> SEQ ID NO 355
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 355
aucuucuuug augccggaa                                              19
```

```
<210> SEQ ID NO 356
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 356
cuuugaugcc ggaagcaaa                                                   19

<210> SEQ ID NO 357
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 357
gaugccggaa gcaaagcau                                                   19

<210> SEQ ID NO 358
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 358
augccggaag caaagcauc                                                   19

<210> SEQ ID NO 359
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 359
gccggaagca aagcauccc                                                   19

<210> SEQ ID NO 360
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 360
cccccagauc caccauuac                                                   19

<210> SEQ ID NO 361
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 361
agauccacca uuacauuuu                                                   19

<210> SEQ ID NO 362
<211> LENGTH: 19
<212> TYPE: RNA
<213> ORGANISM: artificial sequence
<220> FEATURE:
<223> OTHER INFORMATION: Hif2alpha RNAi agent sense strand
```

-continued

<400> SEQUENCE: 362
auuuugggcc cacaaagug                                          19

<210> SEQ ID NO 363
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 363
uuuugggccc acaaagugg                                          19

<210> SEQ ID NO 364
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 364
uuugggccca caaagugggg                                         19

<210> SEQ ID NO 365
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 365
ccacaaagug ggccgucgg                                          19

<210> SEQ ID NO 366
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 366
cacaaagugg gccgucggg                                          19

<210> SEQ ID NO 367
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 367
agugggccgu cggggauca                                          19

<210> SEQ ID NO 368
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 368
aaaggguuuu ggggcucga                                          19

<210> SEQ ID NO 369

```
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 369
ggcucgaggc ccagacgug                                               19

<210> SEQ ID NO 370
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 370
gcucgaggcc cagacgugc                                               19

<210> SEQ ID NO 371
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 371
cucgaggccc agacgugcu                                               19

<210> SEQ ID NO 372
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 372
gguagcccuc uccaacaag                                               19

<210> SEQ ID NO 373
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 373
cuuugaugcc ggacaagcc                                               19

<210> SEQ ID NO 374
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 374
uuugaugccg gacaagcca                                               19

<210> SEQ ID NO 375
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 375
```

-continued uugaugccgg acaagccac                                                19

<210> SEQ ID NO 376
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 376
ggacaagcca cugagcgca                                                19

<210> SEQ ID NO 377
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 377
acaagccacu gagcgcaaa                                                19

<210> SEQ ID NO 378
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 378
ggacuacagc cugucguca                                                19

<210> SEQ ID NO 379
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 379
gacuacagcc ugucgucag                                                19

<210> SEQ ID NO 380
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 380
cuacagccug ucgucagcc                                                19

<210> SEQ ID NO 381
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 381
ccugucguca gcccacaag                                                19

<210> SEQ ID NO 382
<211> LENGTH: 19
<212> TYPE: RNA

```
<213> ORGANISM: artificial sequence
<220> FEATURE:
<223> OTHER INFORMATION: Hif2alpha RNAi agent sense strand

<400> SEQUENCE: 382
gcauggcaag ccggcugcu                                               19

<210> SEQ ID NO 383
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 383
cugaccagau augacugug                                               19

<210> SEQ ID NO 384
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 384
gauaugacug ugaggugaa                                               19

<210> SEQ ID NO 385
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 385
ggugaacgug cccgugcug                                               19

<210> SEQ ID NO 386
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 386
uacaagaugg acuuaccug                                               19

<210> SEQ ID NO 387
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 387
ggacuuaccu ggcagacuu                                               19

<210> SEQ ID NO 388
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 388
uuuuucugag augcucacu                                               19
```

<210> SEQ ID NO 389
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 389
aguacacaau uguuuuacc                                               19

<210> SEQ ID NO 390
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 390
acaaguuugg ugcaugucu                                               19

<210> SEQ ID NO 391
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 391
acuaaaaaga uuccucguu                                               19

<210> SEQ ID NO 392
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 392
agggucaacu ccaacguau                                               19

<210> SEQ ID NO 393
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 393
gggucaacuc caacguaug                                               19

<210> SEQ ID NO 394
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 394
gucaacucca acguaugug                                               19

<210> SEQ ID NO 395
<211> LENGTH: 19
<212> TYPE: RNA
<213> ORGANISM: artificial sequence
<220> FEATURE:

<223> OTHER INFORMATION: Hif2alpha RNAi agent sense strand

<400> SEQUENCE: 395
ucaacuccaa cguaugugg                                                19

<210> SEQ ID NO 396
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 396
caacuccaac guauguggu                                                19

<210> SEQ ID NO 397
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 397
cuccaacgua uggguuau                                                 19

<210> SEQ ID NO 398
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 398
uccaacguau gugguuauc                                                19

<210> SEQ ID NO 399
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 399
ccaacguaug ugguuaucu                                                19

<210> SEQ ID NO 400
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 400
aacguaugug guuaucugu                                                19

<210> SEQ ID NO 401
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 401
uuauaucugg guuaagugu                                                19

```
<210> SEQ ID NO 402
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 402
ccacggccug uacggacac                                                  19

<210> SEQ ID NO 403
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 403
acggccugua cggacacug                                                  19

<210> SEQ ID NO 404
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 404
ugucggcuuu uugccaucu                                                  19

<210> SEQ ID NO 405
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 405
gucggcuuuu ugccaucug                                                  19

<210> SEQ ID NO 406
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 406
aucugugaua ugccauagg                                                  19

<210> SEQ ID NO 407
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 407
ugccauaggu gugacaauc                                                  19

<210> SEQ ID NO 408
<211> LENGTH: 19
<212> TYPE: RNA
<213> ORGANISM: artificial sequence
<220> FEATURE:
<223> OTHER INFORMATION: Hif2alpha RNAi agent sense strand
```

```
<400> SEQUENCE: 408
ccauaggugu gacaauccg                                                 19

<210> SEQ ID NO 409
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 409
cauaggugug acaauccga                                                 19

<210> SEQ ID NO 410
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 410
auagguguga caauccgag                                                 19

<210> SEQ ID NO 411
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 411
ggugugacaa uccgagcag                                                 19

<210> SEQ ID NO 412
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 412
acaauccgag caguggagu                                                 19

<210> SEQ ID NO 413
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 413
ccgagcagug gagucauuc                                                 19

<210> SEQ ID NO 414
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 414
gggagcacug cgcgcuauc                                                 19

<210> SEQ ID NO 415
<211> LENGTH: 19
```

```
<212> TYPE: RNA
<213> ORGANISM: artificial sequence
<220> FEATURE:
<223> OTHER INFORMATION: Hif2alpha RNAi agent sense strand

<400> SEQUENCE: 415
ggagcacugc gcgcuaucc                                             19

<210> SEQ ID NO 416
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 416
agcacugcgc gcuaucccc                                             19

<210> SEQ ID NO 417
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 417
uauugcugcc aagaggguc                                             19

<210> SEQ ID NO 418
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 418
ggucugaugg cacguugug                                             19

<210> SEQ ID NO 419
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 419
cugauggcac guugugggg                                             19

<210> SEQ ID NO 420
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 420
ggcacguugu ggggucggg                                             19

<210> SEQ ID NO 421
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 421
```
gcacguugug gggucgggg					19

<210> SEQ ID NO 422
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 422
cacguugugg ggucggggg					19

<210> SEQ ID NO 423
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 423
gcggggaagu gcucuaacu					19

<210> SEQ ID NO 424
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 424
cggggaagug cucuaacuu					19

<210> SEQ ID NO 425
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 425
uuaagguuuu guugcuagc					19

<210> SEQ ID NO 426
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 426
guugcuagcc cuucaagug					19

<210> SEQ ID NO 427
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 427
gagcuaugug acucggaug					19

<210> SEQ ID NO 428
<211> LENGTH: 19
<212> TYPE: RNA
<213> ORGANISM: artificial sequence

```
<220> FEATURE:
<223> OTHER INFORMATION: Hif2alpha RNAi agent sense strand

<400> SEQUENCE: 428
gcuaugugac ucggauggu                                                      19

<210> SEQ ID NO 429
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 429
cggauggucu uucacacgg                                                      19

<210> SEQ ID NO 430
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 430
gauggucuuu cacacggca                                                      19

<210> SEQ ID NO 431
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 431
uggucuuuca cacggcaca                                                      19

<210> SEQ ID NO 432
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 432
aacuaccaug agaugguuu                                                      19

<210> SEQ ID NO 433
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 433
uaccaugaga ugguuuaga                                                      19

<210> SEQ ID NO 434
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 434
ccaagcucac gaccuugga                                                      19
```

<210> SEQ ID NO 435
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 435
acgaccuugg agccccgug                                              19

<210> SEQ ID NO 436
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 436
ggguaagagg gacgacacc                                              19

<210> SEQ ID NO 437
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 437
gguaagaggg acgacaccu                                              19

<210> SEQ ID NO 438
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 438
guaagaggga cgacaccuc                                              19

<210> SEQ ID NO 439
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 439
ugguuuuuca auaccaauu                                              19

<210> SEQ ID NO 440
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 440
uucaauacca auuacaugg                                              19

<210> SEQ ID NO 441
<211> LENGTH: 19
<212> TYPE: RNA
<213> ORGANISM: artificial sequence
<220> FEATURE:
<223> OTHER INFORMATION: Hif2alpha RNAi agent sense strand

```
<400> SEQUENCE: 441
auaccaauua cauggaacu                                               19

<210> SEQ ID NO 442
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 442
ccaacuauuu aguaagccc                                               19

<210> SEQ ID NO 443
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 443
aacuauuuag uaagcccgg                                               19

<210> SEQ ID NO 444
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 444
acuauuuagu aagcccgga                                               19

<210> SEQ ID NO 445
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 445
agaaauuccu uagucaugg                                               19

<210> SEQ ID NO 446
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 446
cauuaagggc auuuuaccc                                               19

<210> SEQ ID NO 447
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 447
uaagggcauu uuacccuug                                               19

<210> SEQ ID NO 448
```

```
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 448
agcuucauau uaacccuac                                             19

<210> SEQ ID NO 449
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 449
uauuaacccu accugucaa                                             19

<210> SEQ ID NO 450
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 450
uuaacccuac cugucaacg                                             19

<210> SEQ ID NO 451
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 451
acccuaccug ucaacguaa                                             19

<210> SEQ ID NO 452
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 452
cccuaccugu caacguaac                                             19

<210> SEQ ID NO 453
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 453
ccuaccuguc aacguaacg                                             19

<210> SEQ ID NO 454
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 454
```
cuaccuguca acguaacga                                    19

<210> SEQ ID NO 455
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 455
uaccugucaa cguaacgau                                    19

<210> SEQ ID NO 456
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 456
accugucaac guaacgauu                                    19

<210> SEQ ID NO 457
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 457
ccugucaacg uaacgauuu                                    19

<210> SEQ ID NO 458
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 458
cugucaacgu aacgauuuc                                    19

<210> SEQ ID NO 459
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 459
ugucaacgua acgauuuca                                    19

<210> SEQ ID NO 460
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 460
ucaacguaac gauuucaug                                    19

<210> SEQ ID NO 461
<211> LENGTH: 19
<212> TYPE: RNA

<213> ORGANISM: artificial sequence
<220> FEATURE:
<223> OTHER INFORMATION: Hif2alpha RNAi agent sense strand

<400> SEQUENCE: 461
acguaacgau uucaugaac                                                    19

<210> SEQ ID NO 462
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 462
uauuauauug ucgaauucc                                                    19

<210> SEQ ID NO 463
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 463
uuauauuguc gaauccua                                                     19

<210> SEQ ID NO 464
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 464
uauugucgaa uuccuacug                                                    19

<210> SEQ ID NO 465
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 465 gaauccuac ugacaacau                                                     19

<210> SEQ ID NO 466
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 466
uccuacugac aacauuaua                                                    19

<210> SEQ ID NO 467
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 467
uauaacugua ugggagcuu                                                    19

```
<210> SEQ ID NO 468
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 468
uaacuguaug ggagcuuaa                                           19

<210> SEQ ID NO 469
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 469
uguaugggag cuuaacuuu                                           19

<210> SEQ ID NO 470
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 470
uugacacugg uaucuuauu                                           19

<210> SEQ ID NO 471
<211> LENGTH: 19
<212> TYPE: RNA
<213> ORGANISM: artificial sequence
<220> FEATURE:
<223> OTHER INFORMATION: Hif2alpha RNAi agent sense strand

<400> SEQUENCE: 471
aaguauucug auccuacca                                           19

<210> SEQ ID NO 472
<211> LENGTH: 21
<212> TYPE: RNA
<213> ORGANISM: artificial sequence
<220> FEATURE:
<223> OTHER INFORMATION: Hif2alpha RNAi agent sense strand

<400> SEQUENCE: 472
caacguaacg auuucaugaa a                                        21

<210> SEQ ID NO 473
<211> LENGTH: 26
<212> TYPE: RNA
<213> ORGANISM: artificial sequence
<220> FEATURE:
<223> OTHER INFORMATION: Hif2alpha RNAi agent sense strand

<400> SEQUENCE: 473
uauaucaacg uaacgauuuc augaaa                                   26

<210> SEQ ID NO 474
<211> LENGTH: 26
<212> TYPE: RNA
<213> ORGANISM: artificial sequence
<220> FEATURE:
```

```
<223> OTHER INFORMATION: Hif2alpha RNAi agent sense strand

<400> SEQUENCE: 474
uauaucaacg uaacgauuuc augaaa                                          26

<210> SEQ ID NO 475
<211> LENGTH: 26
<212> TYPE: RNA
<213> ORGANISM: artificial sequence
<220> FEATURE:
<223> OTHER INFORMATION: Hif2alpha RNAi agent sense strand

<400> SEQUENCE: 475
uauaucaacg uaacgauuuc augaaa                                          26

<210> SEQ ID NO 476
<211> LENGTH: 26
<212> TYPE: RNA
<213> ORGANISM: artificial sequence
<220> FEATURE:
<223> OTHER INFORMATION: Hif2alpha RNAi agent sense strand

<400> SEQUENCE: 476
uauaucgacg uaacgauuuc augaaa                                          26

<210> SEQ ID NO 477
<211> LENGTH: 22
<212> TYPE: RNA
<213> ORGANISM: artificial sequence
<220> FEATURE:
<223> OTHER INFORMATION: Hif2alpha RNAi agent sense strand

<400> SEQUENCE: 477
uauacguaac gauuucauga aa                                              22

<210> SEQ ID NO 478
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 478
gagcugacca uacagucuc                                                  19

<210> SEQ ID NO 479
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 479
gagucggaag gagucggag                                                  19

<210> SEQ ID NO 480
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 480
ucgaaugcug ggagucgga                                                  19
```

```
<210> SEQ ID NO 481
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 481
gcucgaaugc ugggagucg                                               19

<210> SEQ ID NO 482
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 482
ggcucgaaug cugggaguc                                               19

<210> SEQ ID NO 483
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 483
uucagacgcc gagcaccug                                               19

<210> SEQ ID NO 484
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 484
acguucagac gccgagcac                                               19

<210> SEQ ID NO 485
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 485
ugagacguuc agacgccga                                               19

<210> SEQ ID NO 486
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 486
uuugagacgu ucagacgcc                                               19

<210> SEQ ID NO 487
<211> LENGTH: 19
<212> TYPE: RNA
<213> ORGANISM: artificial sequence
<220> FEATURE:
<223> OTHER INFORMATION: Hif2alpha RNAi agent antisense strand
```

```
<400> SEQUENCE: 487 ccuugagac guucagacg                                              19

<210> SEQ ID NO 488
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 488
ucuccgagcu acuccuuuu                                             19

<210> SEQ ID NO 489
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 489
caccacggca augaaaccc                                             19

<210> SEQ ID NO 490
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 490
ccuguguaag ucccaugaa                                             19

<210> SEQ ID NO 491
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 491
cuccaccugu guaagucccc                                            19

<210> SEQ ID NO 492
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 492
cuguuagcuc caccugugu                                             19

<210> SEQ ID NO 493
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 493
uacuaugucc uguuagcuc                                             19

<210> SEQ ID NO 494
<211> LENGTH: 19
```

```
<212> TYPE: RNA
<213> ORGANISM: artificial sequence
<220> FEATURE:
<223> OTHER INFORMATION: Hif2alpha RNAi agent antisense strand

<400> SEQUENCE: 494
gauacuaugu ccuguuagc                                              19

<210> SEQ ID NO 495
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 495
agauacuaug uccuguuag                                              19

<210> SEQ ID NO 496
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 496
agucaaagau acuaugucc                                              19

<210> SEQ ID NO 497
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 497
ggaugaguga agucaaaga                                              19

<210> SEQ ID NO 498
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 498
uggucgcagg gaugaguga                                              19

<210> SEQ ID NO 499
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 499
ucagguucuc acgaaucuc                                              19

<210> SEQ ID NO 500
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 500
```
agacucaggu ucucacgaa                                              19

<210> SEQ ID NO 501
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 501
gagacucagg uucucacga                                              19

<210> SEQ ID NO 502
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 502
cccgcucugu ggacauguc                                              19

<210> SEQ ID NO 503
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 503
ccucaugaag aagucccgc                                              19

<210> SEQ ID NO 504
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 504
gugaccgugc acuucaucc                                              19

<210> SEQ ID NO 505
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 505
gccucuguug gugaccgug                                              19

<210> SEQ ID NO 506
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 506
guacggccuc uguugguga                                              19

<210> SEQ ID NO 507
<211> LENGTH: 19
<212> TYPE: RNA
<213> ORGANISM: artificial sequence

```
<220> FEATURE:
<223> OTHER INFORMATION: Hif2alpha RNAi agent antisense strand

<400> SEQUENCE: 507
aguacggccu cguuggug                                                  19

<210> SEQ ID NO 508
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 508
gagguugaca guacggccu                                                 19

<210> SEQ ID NO 509
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 509
acacagacua uugugagga                                                 19

<210> SEQ ID NO 510
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 510
uguagccaca cagacuauu                                                 19

<210> SEQ ID NO 511
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 511
ugguaaccaa ucaguucug                                                 19

<210> SEQ ID NO 512
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 512
gugguaacca aucaguucu                                                 19

<210> SEQ ID NO 513
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 513
caggguggua accaaucag                                                 19
```

```
<210> SEQ ID NO 514
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 514
ucauaggcug agcggccaa                                             19

<210> SEQ ID NO 515
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 515
gcgcauggua gaauucaua                                             19

<210> SEQ ID NO 516
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 516
agcgcauggu agaauucau                                             19

<210> SEQ ID NO 517
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 517
uagcgcaugg uagaauuca                                             19

<210> SEQ ID NO 518
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 518
cuagcgcaug guagaauuc                                             19

<210> SEQ ID NO 519
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 519
ucuagcgcau gguagaauu                                             19

<210> SEQ ID NO 520
<211> LENGTH: 19
<212> TYPE: RNA
<213> ORGANISM: artificial sequence
<220> FEATURE:
<223> OTHER INFORMATION: Hif2alpha RNAi agent antisense strand
```

```
<400> SEQUENCE: 520
gagucuagcg caugguaga                                              19

<210> SEQ ID NO 521
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 521
uucucggagu cuagcgcau                                              19

<210> SEQ ID NO 522
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 522
guucucggag ucuagcgca                                              19

<210> SEQ ID NO 523
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 523
uccgguacug gccacuuac                                              19

<210> SEQ ID NO 524
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 524
auccgguacu ggccacuua                                              19

<210> SEQ ID NO 525
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 525
ugcgagcauc cgguacugg                                              19

<210> SEQ ID NO 526
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 526
uuugcgagca uccgguacu                                              19

<210> SEQ ID NO 527
```

-continued

```
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 527
gcuuugcgag cauccggua                                                    19

<210> SEQ ID NO 528
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 528
cccccaugcu uugcgagca                                                    19

<210> SEQ ID NO 529
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 529
guagccccca ugcuuugcg                                                    19

<210> SEQ ID NO 530
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 530
cacacguagc ccccaugcu                                                    19

<210> SEQ ID NO 531
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 531
ccacacguag cccccaugc                                                    19

<210> SEQ ID NO 532
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 532
guugcgaggg uuguagaug                                                    19

<210> SEQ ID NO 533
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 533
```

-continued

```
gguugcgagg guuguagau                                                19

<210> SEQ ID NO 534
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 534
cagguugcga ggguuguag                                                19

<210> SEQ ID NO 535
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 535
gcagguugcg aggguugua                                                19

<210> SEQ ID NO 536
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 536
ccuugccacu gcuaucaaa                                                19

<210> SEQ ID NO 537
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 537
uggugaauag gaaguuacu                                                19

<210> SEQ ID NO 538
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 538
ucgaaguucu gauucccga                                                19

<210> SEQ ID NO 539
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 539
gcuauugggc guggagcag                                                19

<210> SEQ ID NO 540
<211> LENGTH: 19
<212> TYPE: RNA
```

```
<213> ORGANISM: artificial sequence
<220> FEATURE:
<223> OTHER INFORMATION: Hif2alpha RNAi agent antisense strand

<400> SEQUENCE: 540
ggcuauuggg cguggagca                                              19

<210> SEQ ID NO 541
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 541
gggcuauugg gcguggagc                                              19

<210> SEQ ID NO 542
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 542
cuucagggcu auuggcgu                                               19

<210> SEQ ID NO 543
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 543
aggucguuau ccaaagaug                                              19

<210> SEQ ID NO 544
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 544
ccgucugggu acugcauug                                              19

<210> SEQ ID NO 545
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 545
auccgucugg guacugcau                                              19

<210> SEQ ID NO 546
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 546
ugaaauccgu cuggguacu                                              19
```

<210> SEQ ID NO 547
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 547
ggacugugcg gggcuacag                                                19

<210> SEQ ID NO 548
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 548
uuccggcauc aaagaagau                                                19

<210> SEQ ID NO 549
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 549
uuugcuuccg gcaucaaag                                                19

<210> SEQ ID NO 550
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 550
augcuuugcu uccggcauc                                                19

<210> SEQ ID NO 551
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 551
gaugcuuugc uuccggcau                                                19

<210> SEQ ID NO 552
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 552
gggaugcuuu gcuuccggc                                                19

<210> SEQ ID NO 553
<211> LENGTH: 19
<212> TYPE: RNA
<213> ORGANISM: artificial sequence
<220> FEATURE:

```
<223> OTHER INFORMATION: Hif2alpha RNAi agent antisense strand

<400> SEQUENCE: 553
guaauggugg aucuggggg                                                19

<210> SEQ ID NO 554
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 554
aaaauguaau gguggaucu                                                19

<210> SEQ ID NO 555
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 555 cacuugugg gcccaaaau                                                 19

<210> SEQ ID NO 556
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 556
ccacuuugug ggcccaaaa                                                19

<210> SEQ ID NO 557
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 557
cccacuuugu gggcccaaa                                                19

<210> SEQ ID NO 558
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 558
ccgacggccc acuuugugg                                                19

<210> SEQ ID NO 559
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 559
cccgacggcc cacuugug                                                 19
```

```
<210> SEQ ID NO 560
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 560 ugaucccga cggcccacu                                                   19

<210> SEQ ID NO 561
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 561 ucgagccca aaacccuuu                                                   19

<210> SEQ ID NO 562
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 562
cacgucuggg ccucgagcc                                                  19

<210> SEQ ID NO 563
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 563
gcacgucugg gccucgagc                                                  19

<210> SEQ ID NO 564
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 564
agcacgucug ggccucgag                                                  19

<210> SEQ ID NO 565
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 565
cuuguuggag agggcuacc                                                  19

<210> SEQ ID NO 566
<211> LENGTH: 19
<212> TYPE: RNA
<213> ORGANISM: artificial sequence
<220> FEATURE:
<223> OTHER INFORMATION: Hif2alpha RNAi agent antisense strand
```

```
<400> SEQUENCE: 566
ggcuuguccg gcaucaaag                                                    19

<210> SEQ ID NO 567
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 567 uggcuuqucc ggcaucaaa                                                    19

<210> SEQ ID NO 568
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 568
guggcuuguc cggcaucaa                                                    19

<210> SEQ ID NO 569
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 569
ugcgcucagu ggcuugucc                                                    19

<210> SEQ ID NO 570
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 570
uuugcgcuca guggcuugu                                                    19

<210> SEQ ID NO 571
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 571
ugacgacagg cuguagucc                                                    19

<210> SEQ ID NO 572
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 572
cugacgacag gcuguaguc                                                    19

<210> SEQ ID NO 573
<211> LENGTH: 19
```

```
<212> TYPE: RNA
<213> ORGANISM: artificial sequence
<220> FEATURE:
<223> OTHER INFORMATION: Hif2alpha RNAi agent antisense strand

<400> SEQUENCE: 573
ggcugacgac aggcuguag                                              19

<210> SEQ ID NO 574
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 574
cuugugggcu gacgacagg                                              19

<210> SEQ ID NO 575
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 575
agcagccggc uugccaugc                                              19

<210> SEQ ID NO 576
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 576
cacagucaua ucuggucag                                              19

<210> SEQ ID NO 577
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 577
uucaccucac agucauauc                                              19

<210> SEQ ID NO 578
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 578
cagcacgggc acguucacc                                              19

<210> SEQ ID NO 579
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 579
```
cagguaaguc caucuugua                                                    19

<210> SEQ ID NO 580
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 580
aagucugcca gguaagucc                                                    19

<210> SEQ ID NO 581
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 581
agugagcauc ucagaaaaa                                                    19

<210> SEQ ID NO 582
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 582
gguaaaacaa uuguguacu                                                    19

<210> SEQ ID NO 583
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 583
agacaugcac caaacuugu                                                    19

<210> SEQ ID NO 584
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 584
aacgaggaau cuuuuuagu                                                    19

<210> SEQ ID NO 585
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 585
auacguugga guugacccu                                                    19

<210> SEQ ID NO 586
<211> LENGTH: 19
<212> TYPE: RNA
<213> ORGANISM: artificial sequence

```
<220> FEATURE:
<223> OTHER INFORMATION: Hif2alpha RNAi agent antisense strand

<400> SEQUENCE: 586
cauacguugg aguugaccc                                                 19

<210> SEQ ID NO 587
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 587
cacauacguu ggaguugac                                                 19

<210> SEQ ID NO 588
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 588
ccacauacgu uggaguuga                                                 19

<210> SEQ ID NO 589
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 589
accacauacg uuggaguug                                                 19

<210> SEQ ID NO 590
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 590
auaaccacau acguuggag                                                 19

<210> SEQ ID NO 591
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 591
gauaaccaca uacguugga                                                 19

<210> SEQ ID NO 592
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 592
agauaaccac auacguugg                                                 19
```

```
<210> SEQ ID NO 593
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 593
acagauaacc acauacguu                                                  19

<210> SEQ ID NO 594
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 594
acacuuaacc cagauauaa                                                  19

<210> SEQ ID NO 595
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 595
guguccguac aggccgugg                                                  19

<210> SEQ ID NO 596
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 596
caguguccgu acaggccgu                                                  19

<210> SEQ ID NO 597
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 597
agauggcaaa aagccgaca                                                  19

<210> SEQ ID NO 598
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 598
cagauggcaa aaagccgac                                                  19

<210> SEQ ID NO 599
<211> LENGTH: 19
<212> TYPE: RNA
<213> ORGANISM: artificial sequence
<220> FEATURE:
<223> OTHER INFORMATION: Hif2alpha RNAi agent antisense strand
```

<400> SEQUENCE: 599
ccuauggcau aucacagau                                                    19

<210> SEQ ID NO 600
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 600
gauugucaca ccuauggca                                                    19

<210> SEQ ID NO 601
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 601
cggauuguca caccuaugg                                                    19

<210> SEQ ID NO 602
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 602
ucggauuguc acaccuaug                                                    19

<210> SEQ ID NO 603
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 603
cucggauugu cacaccuau                                                    19

<210> SEQ ID NO 604
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 604
cugcucggau ugucacacc                                                    19

<210> SEQ ID NO 605
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 605
acuccacugc ucggauugu                                                    19

<210> SEQ ID NO 606

```
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 606
gaaugacucc acugcucgg                                                  19

<210> SEQ ID NO 607
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 607
gauagcgcgc agugcuccc                                                  19

<210> SEQ ID NO 608
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 608
ggauagcgcg cagugcucc                                                  19

<210> SEQ ID NO 609
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 609
ggggauagcg cgcagugcu                                                  19

<210> SEQ ID NO 610
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 610
gacccucuug gcagcaaua                                                  19

<210> SEQ ID NO 611
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 611
cacaacgugc caucagacc                                                  19

<210> SEQ ID NO 612
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 612
```
ccccacaacg ugccaucag					19

<210> SEQ ID NO 613
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 613 cccgaccccaa caacgugcc					19

<210> SEQ ID NO 614
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 614
ccccgacccc acaacgugc					19

<210> SEQ ID NO 615
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 615
cccccgaccc cacaacgug					19

<210> SEQ ID NO 616
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 616
aguuagagca cuuccccgc					19

<210> SEQ ID NO 617
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 617
aaguuagagc acuuccccg					19

<210> SEQ ID NO 618
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 618
gcuagcaaca aaaccuuaa					19

<210> SEQ ID NO 619
<211> LENGTH: 19
<212> TYPE: RNA

```
<213> ORGANISM: artificial sequence
<220> FEATURE:
<223> OTHER INFORMATION: Hif2alpha RNAi agent antisense strand

<400> SEQUENCE: 619
cacuugaagg gcuagcaac                                                  19

<210> SEQ ID NO 620
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 620
cauccgaguc acauagcuc                                                  19

<210> SEQ ID NO 621
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 621
accauccgag ucacauagc                                                  19

<210> SEQ ID NO 622
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 622
ccgugugaaa gaccauccg                                                  19

<210> SEQ ID NO 623
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 623
ugccguguga aagaccauc                                                  19

<210> SEQ ID NO 624
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 624
ugugccgugu gaaagacca                                                  19

<210> SEQ ID NO 625
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 625
aaaccaucuc augguaguu                                                  19
```

```
<210> SEQ ID NO 626
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 626
ucuaaaccau cucauggua                                              19

<210> SEQ ID NO 627
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 627
uccaaggucg ugagcuugg                                              19

<210> SEQ ID NO 628
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 628
cacggggcuc caaggucgu                                              19

<210> SEQ ID NO 629
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 629
ggugucgucc cucuuaccc                                              19

<210> SEQ ID NO 630
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 630
aggugucguc ccucuuacc                                              19

<210> SEQ ID NO 631
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 631
gaggugucgu cccucuuac                                              19

<210> SEQ ID NO 632
<211> LENGTH: 19
<212> TYPE: RNA
<213> ORGANISM: artificial sequence
<220> FEATURE:
```

<223> OTHER INFORMATION: Hif2alpha RNAi agent antisense strand

<400> SEQUENCE: 632
aauugguauu gaaaaacca                                                    19

<210> SEQ ID NO 633
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 633
ccauguaauu gguauugaa                                                    19

<210> SEQ ID NO 634
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 634
aguuccaugu aauugguau                                                    19

<210> SEQ ID NO 635
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 635
gggcuuacua aauaguugg                                                    19

<210> SEQ ID NO 636
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 636
ccgggcuuac uaaauaguu                                                    19

<210> SEQ ID NO 637
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 637
uccgggcuua cuaaauagu                                                    19

<210> SEQ ID NO 638
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 638
ccaugacuaa ggaauuucu                                                    19

```
<210> SEQ ID NO 639
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 639
ggguaaaaug cccuuaaug                                                19

<210> SEQ ID NO 640
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 640
caaggguaaa augcccuua                                                19

<210> SEQ ID NO 641
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 641 guaggguaa uaugaagcu                                                 19

<210> SEQ ID NO 642
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 642
uugacaggua ggguuaaua                                                19

<210> SEQ ID NO 643
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 643
cguugacagg uaggguuaa                                                19

<210> SEQ ID NO 644
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 644
uuacguugac agguagggu                                                19

<210> SEQ ID NO 645
<211> LENGTH: 19
<212> TYPE: RNA
<213> ORGANISM: artificial sequence
<220> FEATURE:
<223> OTHER INFORMATION: Hif2alpha RNAi agent antisense strand
```

-continued

```
<400> SEQUENCE: 645
guuacguuga cagguaggg                                                    19

<210> SEQ ID NO 646
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 646
cguuacguug acagguagg                                                    19

<210> SEQ ID NO 647
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 647
ucguuacguu gacagguag                                                    19

<210> SEQ ID NO 648
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 648
aucguuacgu ugacaggua                                                    19

<210> SEQ ID NO 649
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 649
aaucguuacg uugacaggu                                                    19

<210> SEQ ID NO 650
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 650
aaaucguuac guugacagg                                                    19

<210> SEQ ID NO 651
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 651
gaaaucguua cguugacag                                                    19

<210> SEQ ID NO 652
<211> LENGTH: 19
```

```
<212> TYPE: RNA
<213> ORGANISM: artificial sequence
<220> FEATURE:
<223> OTHER INFORMATION: Hif2alpha RNAi agent antisense strand

<400> SEQUENCE: 652
ugaaaucguu acguugaca                                                      19

<210> SEQ ID NO 653
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 653
caugaaaucg uuacguuga                                                      19

<210> SEQ ID NO 654
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 654
guucaugaaa ucguuacgu                                                      19

<210> SEQ ID NO 655
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 655
ggaauucgac aauauaaua                                                      19

<210> SEQ ID NO 656
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 656
uaggaauucg acaauauaa                                                      19

<210> SEQ ID NO 657
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 657
caguaggaau ucgacaaua                                                      19

<210> SEQ ID NO 658
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 658
```
auguugucag uaggaauuc 19

<210> SEQ ID NO 659
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 659
uauaauguug ucaguagga 19

<210> SEQ ID NO 660
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 660
aagcucccau acaguuaua 19

<210> SEQ ID NO 661
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 661
uuaagcuccc auacaguua 19

<210> SEQ ID NO 662
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 662
aaaguuaagc ucccauaca 19

<210> SEQ ID NO 663
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 663
aauaagauac cagugucaa 19

<210> SEQ ID NO 664
<211> LENGTH: 19
<212> TYPE: RNA
<213> ORGANISM: artificial sequence
<220> FEATURE:
<223> OTHER INFORMATION: Hif2alpha RNAi agent antisense strand

<400> SEQUENCE: 664
ugguaggauc agaauacuu 19

<210> SEQ ID NO 665
<211> LENGTH: 22
<212> TYPE: RNA
<213> ORGANISM: artificial sequence
<220> FEATURE:
<223> OTHER INFORMATION: Hif2alpha RNAi agent antisense strand

<400> SEQUENCE: 665
uucaugaaau cguuacguug gc                                              22

<210> SEQ ID NO 666
<211> LENGTH: 23
<212> TYPE: RNA
<213> ORGANISM: artificial sequence
<220> FEATURE:
<223> OTHER INFORMATION: Hif2alpha RNAi agent antisense strand

<400> SEQUENCE: 666
uucaugaaau cguuacguug gcu                                             23

<210> SEQ ID NO 667
<211> LENGTH: 25
<212> TYPE: RNA
<213> ORGANISM: artificial sequence
<220> FEATURE:
<223> OTHER INFORMATION: Hif2alpha RNAi agent antisense strand

<400> SEQUENCE: 667
uucaugaaau cguuacguug gcuau                                           25

<210> SEQ ID NO 668
<211> LENGTH: 25
<212> TYPE: RNA
<213> ORGANISM: artificial sequence
<220> FEATURE:
<223> OTHER INFORMATION: Hif2alpha RNAi agent antisense strand

<400> SEQUENCE: 668
uucaugaaau cguuacguug gcugu                                           25

<210> SEQ ID NO 669
<211> LENGTH: 25
<212> TYPE: RNA
<213> ORGANISM: artificial sequence
<220> FEATURE:
<223> OTHER INFORMATION: Hif2alpha RNAi agent antisense strand

<400> SEQUENCE: 669
uucaugaaau cguuacgucg gcuau                                           25

<210> SEQ ID NO 670
<211> LENGTH: 18
<212> TYPE: RNA
<213> ORGANISM: artificial sequence
<220> FEATURE:
<223> OTHER INFORMATION: Hif2alpha RNAi agent antisense strand

<400> SEQUENCE: 670
uucaugaaau cguuacgu                                                   18

<210> SEQ ID NO 671
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"

```
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 671
gagacuguau ggucagcuat                                                     20

<210> SEQ ID NO 672
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 672
cuccgacucc uuccgacuat                                                     20

<210> SEQ ID NO 673
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 673
uccgacuccc agcauucgat                                                     20

<210> SEQ ID NO 674
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 674
cgacucccag cauucgagat                                                     20

<210> SEQ ID NO 675
<211> LENGTH: 20
```

<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 675
gacucccagc auucgagcat                                           20

<210> SEQ ID NO 676
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 676
caggugcucg gcgucugaat                                           20

<210> SEQ ID NO 677
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 677
gugcucggcg ucugaacgat                                           20

<210> SEQ ID NO 678
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 678
ucggcgucug aacgucucat                                           20

<210> SEQ ID NO 679
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 679
ggcgucugaa cgucucaaat                                           20

<210> SEQ ID NO 680
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 680
cgucugaacg ucucaaagat                                           20

<210> SEQ ID NO 681
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 681
aaaaggagua gcucggagat                                           20

<210> SEQ ID NO 682
<211> LENGTH: 20
<212> TYPE: DNA
<213> ORGANISM: artificial sequence
<220> FEATURE:
<223> OTHER INFORMATION: Hif2alpha RNAi agent sense strand

```
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 682
ggguuucauu gccgugguat                                                  20

<210> SEQ ID NO 683
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 683
uucaugggac uuacacagat                                                  20

<210> SEQ ID NO 684
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 684
gggacuuaca cagugggaat                                                  20

<210> SEQ ID NO 685
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 685
```
acacaggugg agcuaacaat 20

<210> SEQ ID NO 686
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 686
gagcuaacag gacauaguat 20

<210> SEQ ID NO 687
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 687
gcuaacagga cauaguauat 20

<210> SEQ ID NO 688
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 688
cuaacaggac auaguaucat 20

<210> SEQ ID NO 689
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding

```
                nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
                nucleoside"

<400> SEQUENCE: 689
ggacauagua ucuuugacat                                              20

<210> SEQ ID NO 690
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
                nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
                nucleoside"

<400> SEQUENCE: 690
ucuuugacuu cacucaucat                                              20

<210> SEQ ID NO 691
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
                nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
                nucleoside"

<400> SEQUENCE: 691
ucacucaucc cugcgaccat                                              20

<210> SEQ ID NO 692
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
                nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
                nucleoside"

<400> SEQUENCE: 692
gagauucgug agaaccugat                                              20

<210> SEQ ID NO 693
```

```
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 693
uucgugagaa ccugagucat                                             20

<210> SEQ ID NO 694
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 694
ucgugagaac cugagucuat                                             20

<210> SEQ ID NO 695
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 695
gacaugucca cagagcggat                                             20

<210> SEQ ID NO 696
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
```

<223> OTHER INFORMATION: /mod_base = "2'-O-methyl corresponding
       nucleoside"

<400> SEQUENCE: 696
gcgggacuuc uucaugagat                                                     20

<210> SEQ ID NO 697
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
       nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
       nucleoside"

<400> SEQUENCE: 697
ggaugaagug cacggucaat                                                     20

<210> SEQ ID NO 698
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
       nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
       nucleoside"

<400> SEQUENCE: 698
cacggucacc aacagaggat                                                     20

<210> SEQ ID NO 699
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
       nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
       nucleoside"

<400> SEQUENCE: 699
ucaccaacag aggccguaat                                                     20

<210> SEQ ID NO 700
<211> LENGTH: 20
<212> TYPE: DNA
<213> ORGANISM: artificial sequence
<220> FEATURE:

```
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 700
caccaacaga ggccguacat                                                    20

<210> SEQ ID NO 701
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 701
aggccguacu gucaaccuat                                                    20

<210> SEQ ID NO 702
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 702
uccucacaau agucugugat                                                    20

<210> SEQ ID NO 703
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 703
```
aauagucugu guggcuacat                                               20

<210> SEQ ID NO 704
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 704
cagaacugau ugguuaccat                                               20

<210> SEQ ID NO 705
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 705
agaacugauu gguuaccaat                                               20

<210> SEQ ID NO 706
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 706
cugauugguu accaccuat                                                20

<210> SEQ ID NO 707
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19

```
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 707
uuggccgcuc agccuaugat                                              20

<210> SEQ ID NO 708
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 708
uaugaauucu accaugcgat                                              20

<210> SEQ ID NO 709
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 709
augaauucua ccaugcgcat                                              20

<210> SEQ ID NO 710
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 710
ugaauucuac caugcgcuat                                              20
```

-continued

```
<210> SEQ ID NO 711
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 711
gaauucuacc augcgcuaat                                               20

<210> SEQ ID NO 712
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 712
aauucuacca ugcgcuagat                                               20

<210> SEQ ID NO 713
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 713
ucuaccaugc gcuagacuat                                               20

<210> SEQ ID NO 714
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
```

```
<222> LOCATION: 2,4,6,8,10,12,14,16,18
<223> OTHER INFORMATION: /mod_base = "2'-O-methyl corresponding
      nucleoside"

<400> SEQUENCE: 714
augcgcuaga cuccgagaat                                                  20

<210> SEQ ID NO 715
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 715
ugcgcuagac uccgagaaat                                                  20

<210> SEQ ID NO 716
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 716
guaaguggcc aguaccggat                                                  20

<210> SEQ ID NO 717
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 717
uaaguggcca guaccggaat                                                  20

<210> SEQ ID NO 718
<211> LENGTH: 20
<212> TYPE: DNA
<213> ORGANISM: artificial sequence
```

```
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 718
ccaguaccgg augcucgcat                                                     20

<210> SEQ ID NO 719
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 719
aguaccggau gcucgcaaat                                                     20

<210> SEQ ID NO 720
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 720
uaccggaugc ucgcaaagat                                                     20

<210> SEQ ID NO 721
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
```

<400> SEQUENCE: 721
ugcucgcaaa gcaugggdat    20

<210> SEQ ID NO 722
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 722
cgcaaagcau gggggcuaat    20

<210> SEQ ID NO 723
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 723
agcauggggg cuacguguat    20

<210> SEQ ID NO 724
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 724 gcauggggc uacgugugat    20

<210> SEQ ID NO 725
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base

```
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 725
caucuacaac ccucgcaaat                                                 20

<210> SEQ ID NO 726
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 726
aucuacaacc cucgcaacat                                                 20

<210> SEQ ID NO 727
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 727
cuacaacccu cgcaaccuat                                                 20

<210> SEQ ID NO 728
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 728
uacaacccuc gcaaccugat                                                 20
```

<210> SEQ ID NO 729
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 729
uuugauagca guggcaagat                                               20

<210> SEQ ID NO 730
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 730
aguaacuucc uauucaccat                                               20

<210> SEQ ID NO 731
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 731
ucgggaauca gaacuucgat                                               20

<210> SEQ ID NO 732
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:

```
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 732
cugcuccacg cccaauagat                                               20

<210> SEQ ID NO 733
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 733
ugcuccacgc ccaauagcat                                               20

<210> SEQ ID NO 734
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 734
gcuccacgcc caauagccat                                               20

<210> SEQ ID NO 735
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 735
acgcccaaua gcccugaaat                                               20

<210> SEQ ID NO 736
<211> LENGTH: 20
<212> TYPE: DNA
```

<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
    nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
    nucleoside"

<400> SEQUENCE: 736
caucuuugga uaacgaccat             20

<210> SEQ ID NO 737
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
    nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
    nucleoside"

<400> SEQUENCE: 737
caaugcagua cccagacgat             20

<210> SEQ ID NO 738
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
    nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
    nucleoside"

<400> SEQUENCE: 738
augcaguacc cagacggaat             20

<210> SEQ ID NO 739
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
    nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
    nucleoside"

-continued

<400> SEQUENCE: 739
aguacccaga cggauuucat                   20

<210> SEQ ID NO 740
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 740
cuguagcccc gcacagucat                   20

<210> SEQ ID NO 741
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 741
aucuucuuug augccggaat                   20

<210> SEQ ID NO 742
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 742
cuuugaugcc ggaagcaaat                   20

<210> SEQ ID NO 743
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:

```
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 743
gaugccggaa gcaaagcaat                                                    20

<210> SEQ ID NO 744
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 744
augccggaag caaagcauat                                                    20

<210> SEQ ID NO 745
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 745
gccggaagca aagcauccat                                                    20

<210> SEQ ID NO 746
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 746
cccccagauc caccauuaat                                                    20
```

```
<210> SEQ ID NO 747
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 747
agauccacca uuacauuuat                                                  20

<210> SEQ ID NO 748
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 748 auuugggcc cacaaaguat                                                   20

<210> SEQ ID NO 749
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 749 uuugggccc acaaagugat                                                   20

<210> SEQ ID NO 750
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
```

<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 750
uuugggccca caaaguggat                                          20

<210> SEQ ID NO 751
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 751
ccacaaagug ggccgucgat                                          20

<210> SEQ ID NO 752
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 752
cacaaagugg gccgucggat                                          20

<210> SEQ ID NO 753
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 753
agugggccgu cggggaucat                                          20

<210> SEQ ID NO 754
<211> LENGTH: 20

```
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 754
aaaggguuuu ggggcucgat                                              20

<210> SEQ ID NO 755
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 755
ggcucgaggc ccagacguat                                              20

<210> SEQ ID NO 756
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 756
gcucgaggcc cagacgugat                                              20

<210> SEQ ID NO 757
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
``` nucleoside"

<400> SEQUENCE: 757
cucgaggccc agacgugcat                                              20

<210> SEQ ID NO 758
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 758
gguagcccuc uccaacaaat                                              20

<210> SEQ ID NO 759
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 759
cuuugaugcc ggacaagcat                                              20

<210> SEQ ID NO 760
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 760
uuugaugccg gacaagccat                                              20

<210> SEQ ID NO 761
<211> LENGTH: 20
<212> TYPE: DNA
<213> ORGANISM: artificial sequence
<220> FEATURE:
<223> OTHER INFORMATION: Hif2alpha RNAi agent sense strand

```
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 761
uugaugccgg acaagccaat                                              20

<210> SEQ ID NO 762
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 762
ggacaagcca cugagcgcat                                              20

<210> SEQ ID NO 763
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 763
acaagccacu gagcgcaaat                                              20

<210> SEQ ID NO 764
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 764
```
ggacuacagc cugucgucat 20

<210> SEQ ID NO 765
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 765
gacuacagcc ugucgucaat 20

<210> SEQ ID NO 766
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 766
cuacagccug ucgucagcat 20

<210> SEQ ID NO 767
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 767
ccugucguca gcccacaaat 20

<210> SEQ ID NO 768
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 768
gcauggcaag ccggcugcat                                               20

<210> SEQ ID NO 769
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 769
cugaccagau augacuguat                                               20

<210> SEQ ID NO 770
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 770
gauaugacug ugaggugaat                                               20

<210> SEQ ID NO 771
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 771
ggugaacgug cccgugcuat                                               20

<210> SEQ ID NO 772

```
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 772
uacaagaugg acuuaccuat                                               20

<210> SEQ ID NO 773
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 773
ggacuuaccu ggcagacuat                                               20

<210> SEQ ID NO 774
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 774
uuuuucugag augcucacat                                               20

<210> SEQ ID NO 775
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
```

-continued

<223> OTHER INFORMATION: /mod_base = "2'-O-methyl corresponding
      nucleoside"

<400> SEQUENCE: 775
aguacacaau uguuuuacat                                                   20

<210> SEQ ID NO 776
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 776
acaaguuugg ugcaugucat                                                   20

<210> SEQ ID NO 777
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 777
acuaaaaaga uuccucguat                                                   20

<210> SEQ ID NO 778
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 778
agggucaacu ccaacguaat                                                   20

<210> SEQ ID NO 779
<211> LENGTH: 20
<212> TYPE: DNA
<213> ORGANISM: artificial sequence
<220> FEATURE:

```
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 779
gggucaacuc caacguauat                                                    20

<210> SEQ ID NO 780
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 780
gucaacucca acguauguat                                                    20

<210> SEQ ID NO 781
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 781
ucaacuccaa cguaugugat                                                    20

<210> SEQ ID NO 782
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 782
```
caacuccaac guauguggat    20

<210> SEQ ID NO 783
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 783
cuccaacgua ugugguuaat    20

<210> SEQ ID NO 784
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 784
uccaacguau gugguuauat    20

<210> SEQ ID NO 785
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 785
ccaacguaug ugguuaucat    20

<210> SEQ ID NO 786
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19

```
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 786
aacguaugug guuaucugat                                                   20

<210> SEQ ID NO 787
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 787
uuauaucugg guuaagugat                                                   20

<210> SEQ ID NO 788
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 788
ccacggccug uacggacaat                                                   20

<210> SEQ ID NO 789
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 789
acggccugua cggacacuat                                                   20
```

-continued

```
<210> SEQ ID NO 790
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 790
ugucggcuuu uugccaucat                                              20

<210> SEQ ID NO 791
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 791
gucggcuuuu ugccaucuat                                              20

<210> SEQ ID NO 792
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 792
aucugugaua ugccauagat                                              20

<210> SEQ ID NO 793
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
```

<222> LOCATION: 2,4,6,8,10,12,14,16,18
<223> OTHER INFORMATION: /mod_base = "2'-O-methyl corresponding
      nucleoside"

<400> SEQUENCE: 793
ugccauaggu gugacaauat                                               20

<210> SEQ ID NO 794
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 794
ccauaggugu gacaauccat                                               20

<210> SEQ ID NO 795
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 795
cauaggugug acaauccgat                                               20

<210> SEQ ID NO 796
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 796
auagguguga caauccgaat                                               20

<210> SEQ ID NO 797
<211> LENGTH: 20
<212> TYPE: DNA
<213> ORGANISM: artificial sequence

```
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 797
ggugugacaa uccgagcaat                                                   20

<210> SEQ ID NO 798
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 798
acaauccgag caguggagat                                                   20

<210> SEQ ID NO 799
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 799
ccgagcagug gagucauuat                                                   20

<210> SEQ ID NO 800
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
```

```
<400> SEQUENCE: 800
gggagcacug cgcgcuauat                                        20

<210> SEQ ID NO 801
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 801
ggagcacugc gcgcuaucat                                        20

<210> SEQ ID NO 802
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 802
agcacugcgc gcuaucccat                                        20

<210> SEQ ID NO 803
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 803
uauugcugcc aagaggguat                                        20

<210> SEQ ID NO 804
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
```

<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 804
ggucugaugg cacguuguat                                           20

<210> SEQ ID NO 805
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 805
cugauggcac guugugggat                                           20

<210> SEQ ID NO 806
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 806
ggcacguugu ggggucggat                                           20

<210> SEQ ID NO 807
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding nucleoside"

<400> SEQUENCE: 807
gcacguugug gggucgggat                                           20

<210> SEQ ID NO 808
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 808
cacguugugg ggucggggat                                            20

<210> SEQ ID NO 809
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 809
gcggggaagu gcucuaacat                                            20

<210> SEQ ID NO 810
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 810
cggggaagug cucuaacuat                                            20

<210> SEQ ID NO 811
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:

<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 811
uuaagguuuu guugcuagat                                                   20

<210> SEQ ID NO 812
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 812
guugcuagcc cuucaaguat                                                   20

<210> SEQ ID NO 813
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 813
gagcuaugug acucggauat                                                   20

<210> SEQ ID NO 814
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 814
gcuaugugac ucggauggat                                                   20

<210> SEQ ID NO 815
<211> LENGTH: 20
<212> TYPE: DNA

```
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 815
cggauggucu uucacacgat                                              20

<210> SEQ ID NO 816
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 816
gauggucuuu cacacggcat                                              20

<210> SEQ ID NO 817
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 817
uggucuuuca cacggcacat                                              20

<210> SEQ ID NO 818
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
```

-continued

<400> SEQUENCE: 818
aacuaccaug agaugguuat                                              20

<210> SEQ ID NO 819
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 819
uaccaugaga ugguuuagat                                              20

<210> SEQ ID NO 820
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 820
ccaagcucac gaccuuggat                                              20

<210> SEQ ID NO 821
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 821
acgaccuugg agccccguat                                              20

<210> SEQ ID NO 822
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:

```
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 822
ggguaagagg gacgacacat                                              20

<210> SEQ ID NO 823
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 823
gguaagaggg acgacaccat                                              20

<210> SEQ ID NO 824
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 824
guaagaggga cgacaccuat                                              20

<210> SEQ ID NO 825
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 825
ugguuuuuca auaccaauat                                              20
```

```
<210> SEQ ID NO 826
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 826
uucaauacca auuacaugat                                             20

<210> SEQ ID NO 827
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 827
auaccaauua cauggaacat                                             20

<210> SEQ ID NO 828
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 828
ccaacuauuu aguaagccat                                             20

<210> SEQ ID NO 829
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
```

```
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 829
aacuauuuag uaagcccgat                                              20

<210> SEQ ID NO 830
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 830
acuauuuagu aagcccggat                                              20

<210> SEQ ID NO 831
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 831
agaaauuccu uagucaugat                                              20

<210> SEQ ID NO 832
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 832
cauuaagggc auuuuaccat                                              20

<210> SEQ ID NO 833
<211> LENGTH: 20
```

```
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 833
uaagggcauu uuacccuuat                                              20

<210> SEQ ID NO 834
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 834
agcuucauau uaacccuaat                                              20

<210> SEQ ID NO 835
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 835
uauuaacccu accugucaat                                              20

<210> SEQ ID NO 836
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
``` nucleoside"

<400> SEQUENCE: 836
uuaacccuac cugucaacat                    20

<210> SEQ ID NO 837
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 837
acccuaccug ucaacguaat                    20

<210> SEQ ID NO 838
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 838
cccuaccugu caacguaaat                    20

<210> SEQ ID NO 839
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 839
ccuaccuguc aacguaacat                    20

<210> SEQ ID NO 840
<211> LENGTH: 20
<212> TYPE: DNA
<213> ORGANISM: artificial sequence
<220> FEATURE:
<223> OTHER INFORMATION: Hif2alpha RNAi agent sense strand

```
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 840
cuaccuguca acguaacgat                                                  20

<210> SEQ ID NO 841
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 841
uaccugucaa cguaacgaat                                                  20

<210> SEQ ID NO 842
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 842
accugucaac guaacgauat                                                  20

<210> SEQ ID NO 843
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 843
```
ccugucaacg uaacgauuat                                                      20

<210> SEQ ID NO 844
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 844
cugucaacgu aacgauuuat                                                      20

<210> SEQ ID NO 845
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 845
ugucaacgua acgauuucat                                                      20

<210> SEQ ID NO 846
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 846
ucaacguaac gauuucauat                                                      20

<210> SEQ ID NO 847
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding

```
          nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
          nucleoside"

<400> SEQUENCE: 847
acguaacgau uucaugaaat                                                    20

<210> SEQ ID NO 848
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
          nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
          nucleoside"

<400> SEQUENCE: 848
uauuauauug ucgaauucat                                                    20

<210> SEQ ID NO 849
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
          nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
          nucleoside"

<400> SEQUENCE: 849
uuauauuguc gaauuccuat                                                    20

<210> SEQ ID NO 850
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
          nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
          nucleoside"

<400> SEQUENCE: 850
uauugucgaa uuccuacuat                                                    20

<210> SEQ ID NO 851
```

```
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 851
gaauuccuac ugacaacaat                                              20

<210> SEQ ID NO 852
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 852
uccuacugac aacauuauat                                              20

<210> SEQ ID NO 853
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"

<400> SEQUENCE: 853
uauaacugua ugggagcuat                                              20

<210> SEQ ID NO 854
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
```

<223> OTHER INFORMATION: /mod_base = "2'-O-methyl corresponding
        nucleoside"

<400> SEQUENCE: 854
uaacuguaug ggagcuuaat                                                   20

<210> SEQ ID NO 855
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 855 uguauggag cuuaacuuat                                                    20

<210> SEQ ID NO 856
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 856
uugacacugg uaucuuauat                                                   20

<210> SEQ ID NO 857
<211> LENGTH: 20
<212> TYPE: DNA
<213> ORGANISM: artificial sequence
<220> FEATURE:
<223> OTHER INFORMATION: Hif2alpha RNAi agent sense strand
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
        nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
        nucleoside"

<400> SEQUENCE: 857
aaguauucug auccuaccat                                                   20

<210> SEQ ID NO 858
<211> LENGTH: 21
<212> TYPE: DNA
<213> ORGANISM: artificial sequence
<220> FEATURE:

<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 858
tagcugacca uacagucuct t                                              21

<210> SEQ ID NO 859
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 859
tagucggaag gagucggagt t                                              21

<210> SEQ ID NO 860
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 860
tcgaaugcug ggagucggat t                                              21

<210> SEQ ID NO 861
<211> LENGTH: 21
<212> TYPE: DNA

```
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 861
tcucgaaugc ugggagucgt t                                              21

<210> SEQ ID NO 862
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 862
tgcucgaaug cugggaguct t                                              21

<210> SEQ ID NO 863
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 863
tucagacgcc gagcaccugt t                                              21

<210> SEQ ID NO 864
```

```
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 864
tcguucagac gccgagcact t                                              21

<210> SEQ ID NO 865
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 865
tgagacguuc agacgccgat t                                              21

<210> SEQ ID NO 866
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 866
tuugagacgu ucagacgcct t                                              21
```

<210> SEQ ID NO 867
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 867
tcuuugagac guucagacgt t                                              21

<210> SEQ ID NO 868
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 868
tcuccgagcu acuccuuuut t                                              21

<210> SEQ ID NO 869
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 869
taccacggca augaaaccct t                                                 21

<210> SEQ ID NO 870
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 870
tcuguguaag ucccaugaat t                                                 21

<210> SEQ ID NO 871
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 871
tuccaccugu guaaguccct t                                                 21

<210> SEQ ID NO 872
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

-continued

<400> SEQUENCE: 872
tuguuagcuc caccugugut t                                       21

<210> SEQ ID NO 873
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 873
tacuaugucc uguuagcuct t                                       21

<210> SEQ ID NO 874
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 874
tauacuaugu ccuguuagct t                                       21

<210> SEQ ID NO 875
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding -continued nucleotide"

<400> SEQUENCE: 875
tgauacuaug uccuguuagt t                      21

<210> SEQ ID NO 876
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 876
tgucaaagau acuaugucct t                      21

<210> SEQ ID NO 877
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 877
tgaugaguga agucaaagat t                      21

<210> SEQ ID NO 878
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base

```
<222> LOCATION: 21
<223> OTHER INFORMATION: /mod_base = "5'-phosphorothioate corresponding
      nucleotide"

<400> SEQUENCE: 878
tggucgcagg gaugagugat t                                                   21

<210> SEQ ID NO 879
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 879
tcagguucuc acgaaucuct t                                                   21

<210> SEQ ID NO 880
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 880
tgacucaggu ucucacgaat t                                                   21

<210> SEQ ID NO 881
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
```

-continued

```
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 881
tagacucagg uucucacgat t                                              21

<210> SEQ ID NO 882
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 882
tccgcucugu ggacauguct t                                              21

<210> SEQ ID NO 883
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 883
tcucaugaag aagucccgct t                                              21

<210> SEQ ID NO 884
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
```

```
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 884
tugaccgugc acuucaucct t                                              21

<210> SEQ ID NO 885
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 885
tccucuguug gugaccgugt t                                              21

<210> SEQ ID NO 886
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 886
tuacggccuc uguuggugat t                                              21

<210> SEQ ID NO 887
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
```

```
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 887
tguacggccu cuguuggugt t                                              21

<210> SEQ ID NO 888
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 888
tagguugaca guacggccut t                                              21

<210> SEQ ID NO 889
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 889
tcacagacua uugugaggat t                                              21

<210> SEQ ID NO 890
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
```

```
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 890
tguagccaca cagacuauut t                                         21

<210> SEQ ID NO 891
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 891
tgguaaccaa ucaguucugt t                                         21

<210> SEQ ID NO 892
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 892
tugguaacca aucaguucut t                                         21

<210> SEQ ID NO 893
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
```

-continued

```
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 893 tagggugguaa accaaucagt t                                              21

<210> SEQ ID NO 894
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 894
tcauaggcug agcggccaat t                                               21

<210> SEQ ID NO 895
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 895
tcgcauggua gaauucauat t                                               21

<210> SEQ ID NO 896
<211> LENGTH: 21
<212> TYPE: DNA
<213> ORGANISM: artificial sequence
<220> FEATURE:
<223> OTHER INFORMATION: Hif2alpha RNAi agent antisense strand
```

```
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 896
tgcgcauggu agaauucaut t                                              21

<210> SEQ ID NO 897
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 897
tagcgcaugg uagaauucat t                                              21

<210> SEQ ID NO 898
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 898
tuagcgcaug guagaauuct t                                              21

<210> SEQ ID NO 899
<211> LENGTH: 21
<212> TYPE: DNA
<213> ORGANISM: artificial sequence
```

-continued

```
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 899
tcuagcgcau gguagaauut t                                              21

<210> SEQ ID NO 900
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 900
tagucuagcg caugguagat t                                              21

<210> SEQ ID NO 901
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 901
tucucggagu cuagcgcaut t                                              21

<210> SEQ ID NO 902
<211> LENGTH: 21
```

```
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 902
tuucucggag ucuagcgcat t                                        21

<210> SEQ ID NO 903
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 903
tccgguacug gccacuuact t                                        21

<210> SEQ ID NO 904
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 904
tuccgguacu ggccacuuat t                                        21
```

```
<210> SEQ ID NO 905
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 905
tgcgagcauc cgguacuggt t                                              21

<210> SEQ ID NO 906
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 906
tuugcgagca uccgguacut t                                              21

<210> SEQ ID NO 907
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 907
tcuuugcgag cauccgguat t                                              21
```

<210> SEQ ID NO 908
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 908
tccccaugcu uugcgagcat t                                              21

<210> SEQ ID NO 909
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 909
tuagccccca ugcuuugcgt t                                              21

<210> SEQ ID NO 910
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 910

-continued tacacguagc ccccaugcut t                                         21

<210> SEQ ID NO 911
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 911
tcacacguag cccccaugct t                                         21

<210> SEQ ID NO 912
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 912
tuugcgaggg uuguagaugt t                                         21

<210> SEQ ID NO 913
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

-continued

<400> SEQUENCE: 913
tguugcgagg guuguagaut t					21

<210> SEQ ID NO 914
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 914
tagguugcga ggguuguagt t					21

<210> SEQ ID NO 915
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 915
tcagguugcg aggguuguat t					21

<210> SEQ ID NO 916
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21

```
<223> OTHER INFORMATION: /mod_base = "5'-phosphorothioate corresponding
      nucleotide"

<400> SEQUENCE: 916
tcuugccacu gcuaucaaat t                                              21

<210> SEQ ID NO 917
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 917
tggugaauag gaaguuacut t                                              21

<210> SEQ ID NO 918
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 918
tcgaaguucu gauucccgat t                                              21

<210> SEQ ID NO 919
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
```

```
<221> NAME/KEY: modified_base
<222> LOCATION: 21
<223> OTHER INFORMATION: /mod_base = "5'-phosphorothioate corresponding
      nucleotide"

<400> SEQUENCE: 919
tcuauugggc guggagcagt t                                              21

<210> SEQ ID NO 920
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 920
tgcuauuggg cguggagcat t                                              21

<210> SEQ ID NO 921
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 921
tggcuauugg gcguggagct t                                              21

<210> SEQ ID NO 922
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
```

```
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 922
tuucagggcu auugggcgut t                                              21

<210> SEQ ID NO 923
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 923
tggucguuau ccaaagaugt t                                              21

<210> SEQ ID NO 924
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 924
tcgucugggu acugcauugt t                                              21

<210> SEQ ID NO 925
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
```

-continued

```
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 925
tuccgucugg guacugcaut t                                              21

<210> SEQ ID NO 926
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 926
tgaaauccgu cuggguacut t                                              21

<210> SEQ ID NO 927
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 927
tgacugugcg gggcuacagt t                                              21

<210> SEQ ID NO 928
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
```

-continued

```
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 928
tuccggcauc aaagaagaut t                                              21

<210> SEQ ID NO 929
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 929
tuugcuuccg gcaucaaagt t                                              21

<210> SEQ ID NO 930
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 930
tugcuuugcu uccggcauct t                                              21

<210> SEQ ID NO 931
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
```

```
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 931
taugcuuugc uuccggcaut t                                             21

<210> SEQ ID NO 932
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 932
tggaugcuuu gcuuccggct t                                             21

<210> SEQ ID NO 933
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 933
tuaauggugg aucugggggt t                                             21

<210> SEQ ID NO 934
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
```

-continued

```
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 934
taaauguaau ggugaaucut t                                             21

<210> SEQ ID NO 935
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 935
tacuuugugg gcccaaaaut t                                             21

<210> SEQ ID NO 936
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 936
tcacuuugug ggcccaaaat t                                             21

<210> SEQ ID NO 937
<211> LENGTH: 21
<212> TYPE: DNA
<213> ORGANISM: artificial sequence
<220> FEATURE:
```

<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 937
tccacuuugu gggcccaaat t                                              21

<210> SEQ ID NO 938
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 938
tcgacggccc acuuguggt t                                               21

<210> SEQ ID NO 939
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 939
tccgacggcc cacuugugt t                                               21

<210> SEQ ID NO 940
<211> LENGTH: 21
<212> TYPE: DNA

```
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 940 tgaucccga cggcccacut t                                                21

<210> SEQ ID NO 941
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 941
tcgagcccca aaacccuuut t                                               21

<210> SEQ ID NO 942
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 942
tacgucuggg ccucgagcct t                                               21

<210> SEQ ID NO 943
```

-continued

```
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 943
tcacgucugg gccucgagct t                                              21

<210> SEQ ID NO 944
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 944
tgcacgucug ggccucgagt t                                              21

<210> SEQ ID NO 945
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 945
tuuguuggag agggcuacct t                                              21
```

-continued

<210> SEQ ID NO 946
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 946
tgcuuguccg gcaucaaagt t         21

<210> SEQ ID NO 947
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 947
tggcuugucc ggcaucaaat t         21

<210> SEQ ID NO 948
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 948
tuggcuuguc cggcaucaat t                                                    21

<210> SEQ ID NO 949
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 949
tgcgcucagu ggcuugucct t                                                    21

<210> SEQ ID NO 950
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 950
tuugcgcuca guggcuugut t                                                    21

<210> SEQ ID NO 951
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 951
tgacgacagg cuguagucct t                                            21

<210> SEQ ID NO 952
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 952
tugacgacag gcuguaguct t                                            21

<210> SEQ ID NO 953
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 953
tgcugacgac aggcuguagt t                                            21

<210> SEQ ID NO 954
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21

-continued

<223> OTHER INFORMATION: /mod_base = "5'-phosphorothioate corresponding
      nucleotide"

<400> SEQUENCE: 954
tuugugggcu gacgacaggt t                                              21

<210> SEQ ID NO 955
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 955
tgcagccggc uugccaugct t                                              21

<210> SEQ ID NO 956
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 956
tacagucaua ucuggucagt t                                              21

<210> SEQ ID NO 957
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:

-continued

```
<221> NAME/KEY: modified_base
<222> LOCATION: 21
<223> OTHER INFORMATION: /mod_base = "5'-phosphorothioate corresponding
      nucleotide"

<400> SEQUENCE: 957
tucaccucac agucauauct t                                              21

<210> SEQ ID NO 958
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 958
tagcacgggc acguucacct t                                              21

<210> SEQ ID NO 959
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 959
tagguaaguc caucuuguat t                                              21

<210> SEQ ID NO 960
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
```

```
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 960
tagucugcca gguaagucct t                                              21

<210> SEQ ID NO 961
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 961
tgugagcauc ucagaaaaat t                                              21

<210> SEQ ID NO 962
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 962
tguaaaacaa uuguguacut t                                              21

<210> SEQ ID NO 963
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
```

<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 963
tgacaugcac caaacuugut t                                              21

<210> SEQ ID NO 964
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 964
tacgaggaau cuuuuuagut t                                              21

<210> SEQ ID NO 965
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 965
tuacguugga guugacccut t                                              21

<210> SEQ ID NO 966
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"

```
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 966
tauacguugg aguugaccct t                                              21

<210> SEQ ID NO 967
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 967
tacauacguu ggaguugact t                                              21

<210> SEQ ID NO 968
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 968
tcacauacgu uggaguugat t                                              21

<210> SEQ ID NO 969
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
```

```
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 969
tccacauacg uuggaguugt t                                            21

<210> SEQ ID NO 970
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 970
tuaaccacau acguuggagt t                                            21

<210> SEQ ID NO 971
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 971
tauaaccaca uacguuggat t                                            21

<210> SEQ ID NO 972
<211> LENGTH: 21
<212> TYPE: DNA
<213> ORGANISM: artificial sequence
<220> FEATURE:
<223> OTHER INFORMATION: Hif2alpha RNAi agent antisense strand
```

```
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 972
tgauaaccac auacguuggt t                                              21

<210> SEQ ID NO 973
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
       nucleotide"

<400> SEQUENCE: 973
tcagauaacc acauacguut t                                              21

<210> SEQ ID NO 974
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 974
tcacuuaacc cagauauaat t                                              21

<210> SEQ ID NO 975
<211> LENGTH: 21
<212> TYPE: DNA
<213> ORGANISM: artificial sequence
```

```
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 975 tguccguac aggccguggt t                                             21

<210> SEQ ID NO 976
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 976
taguguccgu acaggccgut t                                            21

<210> SEQ ID NO 977
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 977
tgauggcaaa aagccgacat t                                            21

<210> SEQ ID NO 978
<211> LENGTH: 21
```

```
-continued

<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 978
tagauggcaa aaagccgact t                                              21

<210> SEQ ID NO 979
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 979
tcuauggcau aucacagaut t                                              21

<210> SEQ ID NO 980
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 980
tauugucaca ccuauggcat t                                              21
```

```
<210> SEQ ID NO 981
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 981
tggauuguca caccuauggt t                                              21

<210> SEQ ID NO 982
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 982
tcggauuguc acaccuaugt t                                              21

<210> SEQ ID NO 983
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 983
tucggauugu cacaccuaut t                                              21
```

<210> SEQ ID NO 984
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 984
tugcucggau ugucacacct t                                                  21

<210> SEQ ID NO 985
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 985
tcuccacugc ucggauugut t                                                  21

<210> SEQ ID NO 986
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 986
taaugacucc acugcucggt t    21

<210> SEQ ID NO 987
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 987
tauagcgcgc agugcuccct t    21

<210> SEQ ID NO 988
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 988
tgauagcgcg cagugcucct t    21

<210> SEQ ID NO 989
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

-continued

<400> SEQUENCE: 989
tgggauagcg cgcagugcut t                                              21

<210> SEQ ID NO 990
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 990
tacccucuug gcagcaauat t                                              21

<210> SEQ ID NO 991
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 991
tacaacgugc caucagacct t                                              21

<210> SEQ ID NO 992
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21

<223> OTHER INFORMATION: /mod_base = "5'-phosphorothioate corresponding
      nucleotide"

<400> SEQUENCE: 992
tcccacaacg ugccaucagt t                                              21

<210> SEQ ID NO 993
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 993
tccgacccca caacgugcct t                                              21

<210> SEQ ID NO 994
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 994
tcccgacccc acaacgugct t                                              21

<210> SEQ ID NO 995
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"

```
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 995
tccccgaccc cacaacgugt t                                              21

<210> SEQ ID NO 996
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 996
tguuagagca cuuccccgct t                                              21

<210> SEQ ID NO 997
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 997
taguuagagc acuuccccgt t                                              21

<210> SEQ ID NO 998
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
```

<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 998
tcuagcaaca aaccuuaat t                                                     21

<210> SEQ ID NO 999
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 999
tacuugaagg gcuagcaact t                                                    21

<210> SEQ ID NO 1000
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1000
tauccgaguc acauagcuct t                                                    21

<210> SEQ ID NO 1001
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:

<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1001
tccauccgag ucacauagct t                                              21

<210> SEQ ID NO 1002
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1002
tcgugugaaa gaccauccgt t                                              21

<210> SEQ ID NO 1003
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1003
tgccguguga aagaccauct t                                              21

<210> SEQ ID NO 1004
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding

```
                 nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
                 nucleoside"
<220> FEATURE:
<221> NAME/KEY: modified_base
<222> LOCATION: 21
<223> OTHER INFORMATION: /mod_base = "5'-phosphorothioate corresponding
                 nucleotide"

<400> SEQUENCE: 1004
tgugccgugu gaaagaccat t                                             21

<210> SEQ ID NO 1005
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
                 nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
                 nucleoside"
<220> FEATURE:
<221> NAME/KEY: modified_base
<222> LOCATION: 21
<223> OTHER INFORMATION: /mod_base = "5'-phosphorothioate corresponding
                 nucleotide"

<400> SEQUENCE: 1005
taaccaucuc augguaguut t                                             21

<210> SEQ ID NO 1006
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
                 nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
                 nucleoside"
<220> FEATURE:
<221> NAME/KEY: modified_base
<222> LOCATION: 21
<223> OTHER INFORMATION: /mod_base = "5'-phosphorothioate corresponding
                 nucleotide"

<400> SEQUENCE: 1006
tcuaaaccau cucaugguat t                                             21

<210> SEQ ID NO 1007
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
```

-continued

<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1007
tccaaggucg ugagcuuggt t                                              21

<210> SEQ ID NO 1008
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1008
tacggggcuc caaggucgut t                                              21

<210> SEQ ID NO 1009
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1009
tgugucgucc cucuuaccct t                                              21

<210> SEQ ID NO 1010
<211> LENGTH: 21
<212> TYPE: DNA
<213> ORGANISM: artificial sequence
<220> FEATURE:
<223> OTHER INFORMATION: Hif2alpha RNAi agent antisense strand

```
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1010 tgguqucguc ccucuuacct t                                              21

<210> SEQ ID NO 1011
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1011
taggugucgu cccucuuact t                                              21

<210> SEQ ID NO 1012
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1012
tauugguauu gaaaaaccat t                                              21

<210> SEQ ID NO 1013
<211> LENGTH: 21
<212> TYPE: DNA
<213> ORGANISM: artificial sequence
```

-continued

```
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1013
tcauguaauu gguauugaat t                                              21

<210> SEQ ID NO 1014
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
       nucleotide"

<400> SEQUENCE: 1014
tguuccaugu aauugguaut t                                              21

<210> SEQ ID NO 1015
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1015
tggcuuacua aauaguuggt t                                              21

<210> SEQ ID NO 1016
<211> LENGTH: 21
```

-continued

```
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1016
tcgggcuuac uaaauaguut t                                              21

<210> SEQ ID NO 1017
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1017
tccgggcuua cuaaauagut t                                              21

<210> SEQ ID NO 1018
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1018
tcaugacuaa ggaauuucut t                                              21
```

```
<210> SEQ ID NO 1019
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1019
tgguaaaaug cccuuaaugt t                                             21

<210> SEQ ID NO 1020
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1020
taaggguaaa augcccuuat t                                             21

<210> SEQ ID NO 1021
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1021
tuaggguuaa uaugaagcut t                                             21
```

<210> SEQ ID NO 1022
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1022
tugacaggua gggguuaauat t                                    21

<210> SEQ ID NO 1023
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1023
tguugacagg uaggguuaat t                                     21

<210> SEQ ID NO 1024
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1024
tuacguugac agguagggut t                                         21

<210> SEQ ID NO 1025
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1025
tuuacguuga cagguagggt t                                         21

<210> SEQ ID NO 1026
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1026
tguuacguug acagguaggt t                                         21

<210> SEQ ID NO 1027
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1027
tcguuacguu gacagguagt t                                                21

<210> SEQ ID NO 1028
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1028
tucguuacgu ugacagguat t                                                21

<210> SEQ ID NO 1029
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1029
taucguuacg uugacaggut t                                                21

<210> SEQ ID NO 1030
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21

<223> OTHER INFORMATION: /mod_base = "5'-phosphorothioate corresponding
      nucleotide"

<400> SEQUENCE: 1030
taaucguuac guugacaggt t                                              21

<210> SEQ ID NO 1031
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1031
taaaucguua cguugacagt t                                              21

<210> SEQ ID NO 1032
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1032
tgaaaucguu acguugacat t                                              21

<210> SEQ ID NO 1033
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:

<221> NAME/KEY: modified_base
<222> LOCATION: 21
<223> OTHER INFORMATION: /mod_base = "5'-phosphorothioate corresponding
      nucleotide"

<400> SEQUENCE: 1033
taugaaaucg uuacguugat t                                              21

<210> SEQ ID NO 1034
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1034
tuucaugaaa ucguuacgut t                                              21

<210> SEQ ID NO 1035
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1035
tgaauucgac aauauaauat t                                              21

<210> SEQ ID NO 1036
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding

```
        nucleoside"
<220> FEATURE:
<221> NAME/KEY: modified_base
<222> LOCATION: 21
<223> OTHER INFORMATION: /mod_base = "5'-phosphorothioate corresponding
        nucleotide"

<400> SEQUENCE: 1036
taggaauucg acaauauaat t                                             21

<210> SEQ ID NO 1037
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
        nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
        nucleoside"
<220> FEATURE:
<221> NAME/KEY: modified_base
<222> LOCATION: 21
<223> OTHER INFORMATION: /mod_base = "5'-phosphorothioate corresponding
        nucleotide"

<400> SEQUENCE: 1037
taguaggaau ucgacaauat t                                             21

<210> SEQ ID NO 1038
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
        nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
        nucleoside"
<220> FEATURE:
<221> NAME/KEY: modified_base
<222> LOCATION: 21
<223> OTHER INFORMATION: /mod_base = "5'-phosphorothioate corresponding
        nucleotide"

<400> SEQUENCE: 1038
tuguugucag uaggaauuct t                                             21

<210> SEQ ID NO 1039
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
        nucleoside"
<220> FEATURE:
<221> NAME/KEY: modified_base
```

```
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1039
tauaauguug ucaguaggat t                                              21

<210> SEQ ID NO 1040
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1040
tagcucccau acaguuauat t                                              21

<210> SEQ ID NO 1041
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 1041
tuaagcuccc auacaguuat t                                              21

<210> SEQ ID NO 1042
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
```

<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1042
taaguuaagc ucccauacat t          21

<210> SEQ ID NO 1043
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1043
tauaagauac cagugucaat t          21

<210> SEQ ID NO 1044
<211> LENGTH: 21
<212> TYPE: DNA
<213> ORGANISM: artificial sequence
<220> FEATURE:
<223> OTHER INFORMATION: Hif2alpha RNAi agent antisense strand
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 1044
tgguaggauc agaauacuut t          21

COMPOSITIONS AND METHODS FOR INHIBITING GENE EXPRESSION OF HIF2ALPHA

BACKGROUND

EPAS1 is a member of the HIF (hypoxia inducible factor) gene family. Also known as Hif2alpha or Hif2α, EPAS1 encodes half of a transcription factor involved in the induction of genes regulated by oxygen, and which is induced as oxygen levels fall (a condition known as hypoxia).

Certain variants of this gene provide protection for people living at high altitude. However, at low altitude, overexpression of wild-type (WT) EPAS1 is associated with increased hypertension and stroke, and with symptoms similar to mountain sickness. Mutations in this gene are associated with erythrocytosis familial type 4 and pulmonary hypertension. EPAS1 can cause excessive production of red blood cells, leading to inhibited reproductive abilities or even death.

EPAS1 has been shown to be required for expression of, or enhance the expression of, various genes involved in an assortment of diseases, including tumor progression. For example, EPAS1 may play a role in the progression of uveal melanomas, possibly by promoting the autocrine loop VEGF-pVEGFR2/KDR, and by enhancing the expression of LDHA, thus conferring a growth advantage.

EPAS1 has also been shown to be involved in, or upregulates expression of, other factors, including: cMyc (which favors cell proliferation, transformation, neoplasia and tumorigenesis, and which is highly expressed in most cancers); Interleukin 8 (a pro-inflammatory mediator, e.g., in gingivitis and psoriasis); SP-1 (a transcription factor involved in IL-8 regulation and, a coactivator of cMyc); LDH5 (which is linked with tumor necrosis and increased tumor size); and LANA (Latency Associated Nuclear Antigen, which is associated with Kaposi's sarcoma-associated Herpesvirus). In addition, HIF (hypoxia induced factor) activity may play a role in angiogenesis required for cancer tumor growth. EPAS1 may also be involved in several other diseases, including inflammation, chronic inflammation, neovascular diseases, rheumatoid arthritis, renal cancer, clear cell renal cell carcinoma (and metastases of this and other cancers), melanoma, uveal melanoma, chondrosarcoma, and multiple myeloma.

Mutations in EPAS1 gene have been correlated to early onset of neuroendocrine tumors such as paragangliomas, somatostatinomas and/or pheochromocytomas. The mutations are commonly somatic missense mutations located in the primary hydroxylation site of HIF-2α. These mutations are believed to disrupt the protein hydroxylation/degradation mechanism and lead to protein stabilization and pseud.ohypoxic signaling. In addition, neuroendocrine tumors release erythropoietin (EPO) into circulating blood, and lead to polycythemia.

SUMMARY

Described herein are Hif2α (also termed EPAS, or Hif2alpha) gene-specific RNA interference (RNAi) trigger molecules (also termed RNAi agent, RNAi trigger, or trigger) able to selectively and efficiently decrease expression of Hif2α. Each RNAi trigger includes at least a sense strand and an antisense strand. The sense strand and the antisense strand can be partially, substantially, or fully complementary to each other. The length of the RNAi trigger sense and antisense strands described herein each can be 16 to 30 nucleotides in length. In some embodiments, the sense and antisense strands are independently 17 to 26 nucleotides in length. The sense and antisense strands can be either the same length or different lengths. The RNAi triggers described herein, upon delivery to a cell expressing the Hif2α gene, inhibit the expression of the Hif2α gene in vitro or in vivo. Examples of Hif2α RNAi trigger sense strands and antisense strands that can be used in a Hif2α RNAi trigger are provided in Tables 1-2 and 5.

A sense strand of an Hif2α RNAi trigger contains a nucleotide sequence having at least 90% identity over a core stretch of at least 16 consecutive nucleotides to a sequence in an Hif2α mRNA. In some embodiments, the nucleotide sequence having at least 90% identity to a sequence in the Hif2α mRNA is 16, 17, 18, 19, 20, 21, 22, or 23 nucleotides in length. An antisense strand of an Hif2α RNAi trigger contains a nucleotide sequence having at least 90% complementary over a core stretch of at least 16 consecutive nucleotides to a sequence in the Hif2α mRNA and the corresponding sense strand. In some embodiments, the nucleotide sequence having at least 90% complementarity to a sequence in the Hif2α mRNA or the corresponding sense strand is 16, 17, 18, 19, 20, 21, 22, or 23 nucleotides in length.

In some embodiments, one or more Hif2α RNAi triggers are delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors or Dynamic Polyconjugates™ (DPCs). In some embodiments, an Hif2α RNAi trigger is conjugated to a targeting group, such as a integrin-binding compound. In some embodiments, an Hif2α RNAi trigger is conjugated to a delivery polymer or vehicle. The delivery polymer can be a reversibly modified membrane active polyamine. The delivery polymer can also be an integrin-targeted reversibly modified membrane active polyamine.

An integrin-targeted reversibly modified membrane active polyamine comprises a membrane active polyamine conjugated to one or more integrin-binding compounds via reversible physiologically labile covalent linkages. In some embodiments, the integrin targeted reversibly modified membrane active polyamine further comprises the membrane active polyamine conjugated to one or more steric stabilizers via reversible physiologically labile covalent linkages. Integrin-binding compounds can be, but are not limited to, RGD peptides and RGD mimics. Reversible physiologically labile covalent linkages include, but are not limited to, dipeptide amidobenzyl carbamate linkages, tetrapeptide linkages, and disubstituted maleamate linkages.

The Hif2α RNAi triggers are optionally combined with one or more additional (i.e., second, third, etc.) therapeutics. A second therapeutic can be another Hif2α RNAi trigger (e.g., a Hif2α RNAi trigger which targets a different sequence within the Hif2α target). An additional therapeutic can also be a small molecule drug, antibody, antibody fragment, and/or vaccine. The Hif2α RNAi triggers, with or without the one or more additional therapeutics, can be combined with one or more excipients to form pharmaceutical compositions.

The present disclosure also encompasses methods of treating a human subject having a pathological state mediated at least in part by Hif2α expression, the methods comprising the step(s) of administering to the subject a therapeutically effective amount of an Hif2α RNAi trigger or Hif2α RNAi trigger-containing composition. The method of treating a subject with an Hif2α RNAi trigger or Hif2α RNAi trigger-containing composition can optionally be combined with one or more steps of administering one or more additional (i.e., second) therapeutics or treatments. The Hif2α RNAi trigger and additional therapeutics can be administered in a single composition or they made be administered separately. Non-limited examples of additional therapeutics include, but are not limited to, VEGFR inhibitors (such as SUTENT®, NEXAVAR®, VOTRIENT®, AVASTIN®, INLYTA®, CABOZANTINIB®), Cytokines (such as IL-2, IFN-α), mTor inhibitors (such as EVEROLIMUS®, TEMSIROLIMUS®) anti-PD1 drugs (such as OPDIVO® and KEYTRUDA®), anti-CTLA4 (such as YERVOY®), drugs targeting signal transduction pathway components in cancer cells (such as VEGF, PI-3-kinase, MEK, JAK, Akt, MYC, Met, Src-family kinases, Abl, Axl, Mer), anti-PD-L1, anti-PD-L2, anti-TIM3, anti-LAG3, anti-CD28, anti-OX40, anti-OX-40L, anti-CD39, anti-CD40, anti-CD80, anti-CD86, anti-CD137, anti-41BBL, anti-TIGIT, anti-GITR, anti-GIRTL, anti-CD155, anti-Fas, anti-FasL, anti-TRAIL/TRAIL-L, IDO-1 inhibitor, and TDO-2 inhibitor.

The pharmaceutical compositions can be administered in a number of ways depending upon whether local or systemic treatment is desired and upon the area to be treated. Administration can be topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration.

The described Hif2α RNAi triggers and/or compositions can be used in methods for therapeutic treatment of diseases, including but not limited to: cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preemclampsia, inflammation, chronic inflammation, neovascular diseases, and rheumatoid arthritis. Such methods comprise administration of an Hif2α RNAi trigger as described herein to a subject, e.g., a human or animal subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
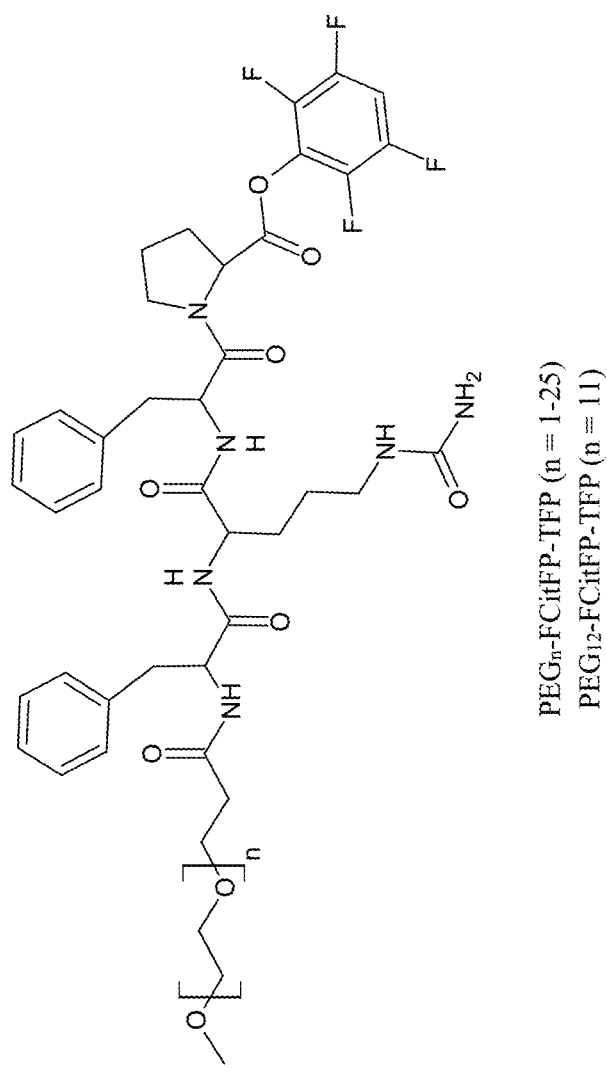
FIG. 1. Chemical structures representing PEG$_n$-FCitFP-TFP modifying agents.

Described herein are RNAi triggers for inhibiting expression of the Hif2α gene (referred to herein as Hif2α RNAi triggers). Each Hif2α RNAi trigger comprises a sense strand and an antisense strand. The sense strand and the antisense strand are partially, substantially, or fully complementary to each other. In some embodiments, the length of the herein described RNAi trigger sense and antisense strands are independently 16 to 30 nucleotides in length. In some embodiments, the length of the herein described RNAi trigger sense and antisense strands are independently 17 to 26 nucleotides in length. In some embodiments, the herein described RNAi trigger sense and antisense strands are independently 17, 18, 19, 20, 21, 22, 23, 24, 25, or 26 nucleotides in length. The sense and antisense strands can be either the same length or they can be different lengths. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In other embodiments, the sense and antisense strands are independently 17-21 nucleotides in length. In some embodiments, both the sense and antisense strands are each 21-26 nucleotides in length. Examples of nucleotide sequences used in forming Hif2α RNAi trigger molecules are provided in Tables 1-2 and 5.

RNAi triggers include, but are not limited to: short interfering RNAs (siRNAs), double-strand RNAs (dsRNA), micro RNAs (miRNAs), short hairpin RNAs (shRNA), and dicer substrates (U.S. Pat. No. 8,084,599 8,349,809 and 8,513,207). The RNAi triggers described herein, upon delivery to a cell expressing the Hif2α gene, inhibit or knockdown expression of Hif2α gene in vitro or in vivo through the biological process of RNA interference (RNAi).

An Hif2α RNAi trigger comprises a sense strand and an antisense strand each containing a core sequence of 16-23 nucleobases in length. An antisense strand core sequence is 100% (perfectly) complementary or at least 90% (substantially) complementary to a nucleotide sequence (sometimes referred to, e.g. as a target sequence) present in the Hif2α mRNA. A sense strand core sequence is 100% (perfectly) complementary or at least 90% (substantially) complementary to a sequence in the antisense strand and thus the sense strand core sequence is perfectly identical or at least 90% identical to a nucleotide sequence (target sequence) present in the Hif2α mRNA. A sense strand core sequence can be the same length as a corresponding antisense core sequence or it can be a different length. In some embodiments, the antisense strand core sequence is 16, 17, 18, 19, 20, 21, 22, or 23 nucleotides in length. In some embodiments, the sense strand core sequence is 16, 17, 18, 19, 20, 21, 22, or 23 nucleotides in length.

The Hif2α RNAi trigger sense and antisense strands typically anneal to form a duplex. Within the complementary duplex region, the sense strand core sequence is at least 90% complementary or 100% complementary to the antisense core sequence. In some embodiments, the sense strand core sequence contains a sequence of at least 16, at least 17, at least 18, at least 19, at least 20, or at least 21 nucleotides that is at least 90% or 100% complementary to a corresponding 16, 17, 18, 19, 20, or 21 nucleotide sequence of the antisense strand core sequence (i.e., the sense strand and antisense core sequences of an Hif2α RNAi trigger have a region of at least 16, at least 17, at least 18, at least 19, at least 20, or at least 21 nucleotides that is at least 90% base paired or 100% base paired.)

As used herein, the term "sequence" or "nucleotide sequence" refers to a succession or order of nucleobases, nucleotides, and/or nucleosides, described with a succession of letters using the standard nucleotide nomenclature and the key for modified nucleotides described herein.

As used herein, and unless otherwise indicated, the term "complementary," when used to describe a first nucleotide sequence (e.g., RNAi trigger sense strand or Hif2α mRNA) in relation to a second nucleotide sequence (e.g., RNAi trigger antisense strand), refers to the ability of an oligonucleotide or polynucleotide comprising the first nucleotide sequence to hybridize (form base pair hydrogen bonds) and form a duplex or double helical structure under certain conditions with an oligonucleotide or polynucleotide comprising the second nucleotide sequence. Complementary sequences include Watson-Crick base pairs or non-Watson-Crick base pairs and include natural or modified nucleotides or nucleotide mimics as long as the above requirements with respect to their ability to hybridize are fulfilled. "Perfectly complementary" or "fully complementary" means that all (100%) of the bases in a contiguous sequence of a first polynucleotide will hybridize with the same number of bases in a contiguous sequence of a second polynucleotide. The contiguous sequence may comprise all or a part of a first or second nucleotide sequence. As used herein, "partial complementary" means that in a hybridized pair of nucleobase sequences, at least 70% of the bases in a contiguous sequence of a first polynucleotide will hybridize with the same number of bases in a contiguous sequence of a second polynucleotide. As used herein, "substantial complementary" means that in a hybridized pair of nucleobase sequences, at least 85% of the bases in a contiguous sequence of a first polynucleotide will hybridize with the same number of bases in a contiguous sequence of a second polynucleotide. The terms "complementary" "fully complementary" and "substantially complementary" as used herein may be used with respect to the base matching between the sense strand and the antisense strand of an RNAi trigger, or between the antisense strand of an RNAi trigger and a sequence of an Hif2α mRNA. Sequence identity or complementarity is independent of modification. For the purposes of determining identity or complementarity, for example, a and Af are complementary to U (or T) and identical to A.

The sense strand and/or the antisense strand may optionally and independently contain an additional 1, 2, 3, 4, 5, or 6 nucleotides (extension) at the 3' end, the 5' end, or both the 3' and 5' ends of the core sequences. The antisense strand additional nucleotides, if present, may or may not be complementary to the corresponding sequence in the Hif2α mRNA. The sense strand additional nucleotides, if present, may or may not be identical to the corresponding sequence in the Hif2α mRNA. The antisense strand additional nucleotides, if present, may or may not be complementary to the corresponding sense strand's additional nucleotides, if present.

As used herein, extension comprises 1, 2, 3, 4, 5, or 6 nucleotides at the 5' and/or 3' end of the sense strand core sequence and/or antisense strand core sequence. The extension nucleotides on a sense strand may or may not be complementary to nucleotides, either core sequence nucleotides or extension nucleotides, in the corresponding antisense strand. Conversely, the extension nucleotides on an antisense strand may or may not be complementary to nucleotides, either core sequence nucleotides or extension nucleotides, in the corresponding sense strand. In some embodiments, both the sense strand and the antisense strand of an RNAi trigger contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an Hif2α RNAi trigger has an antisense strand having a 3' extension and a sense strand having a 5' extension.

In some embodiments an Hif2α RNAi trigger molecule comprises an antisense strand having a 3' extension of 1, 2, 3, 4, 5, or 6 nucleotides in length. In other embodiments, an Hif2α RNAi trigger molecule comprises an antisense strand having a 3' extension of 1, 2, or 3 nucleotides in length. In some embodiments, one or more of the antisense strand extension nucleotides comprise uracil or thymidine nucleotides or nucleotides which are complementary to the corresponding Hif2α mRNA sequence. In some embodiments, the antisense strand extension can be, but is not limited to: uAu, uGu, udTsdT, usdTsdT, UfAu, Aua, Afsusa, UAU, uAfu, uau, udAu, uscu, usgu, uscsu, cAu, AUa, aua, u(invdA)u, cag, agu, gcg, caa, usasu, uAMTM, or usTMsAM (each listed 5' to 3', notation is the same as for Table 2).

In some embodiments, an Hif2α RNAi trigger molecule comprises an antisense strand having a 5' extension of 1, 2, 3, 4, or 5 nucleotides in length. In other embodiments, an Hif2α RNAi trigger molecule comprises an antisense strand having a 5' extension of 1 or 2 nucleotides in length. In some embodiments, one or more of the antisense strand extension nucleotides comprises uracil or thymidine nucleotides or nucleotides which are complementary to the corresponding Hif2α mRNA sequence. In some embodiments, the antisense strand extension includes or consists of dA, dT, pdT, vpdT, or u, wherein dA and dT represent deoxyadenosine and deoxythimidine nucleotides respectively, pdT represents a deoxythimidine nucleotide having a 5' phosphate, vpdT represents a vinylphosphonate deoxythimidine nucleotide, and u represents a 2'-OMe modified uracil nucleotide. An antisense strand may have any of the 3' extensions described above in combination with any of the 5' antisense strand extensions described, if present.

In some embodiments, an Hif2α RNAi trigger molecule comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides which correspond to nucleotides in the Hif2α mRNA sequence. In some embodiments, the 3' sense strand extension includes or consists of Af, invdA, invdT, A(invdT), Af(invdT), U(invdT), U(invdT), AfAbuAu, dTdT, or dTsdT, wherein Af and Uf represent 2'-fluoro adenosine and uracil nucleotides respectively, invdA and invdT represent 3'-3' linked (inverted) deoxyadenosine and deoxythimidine nucleotides respectively, Ab represents an abasic ribose, u represents a 2'-OMe modified uracil nucleotide, dT represents a deoxythimidine nucleotide, sdT represents a deoxythimidine nucleotide having a 5' phosphorothioate, and U and A represent uracil and adenosine ribonucleotides.

In some embodiments, an Hif2α RNAi trigger molecule comprises a sense strand having a 5' extension of 1, 2, 3, 4, 5, or 6 nucleotides in length. In some embodiments, one or more of the sense strand extension nucleotides comprise uracil or adenosine nucleotides or nucleotides which correspond to nucleotides in the Hif2α mRNA sequence. In some embodiments, the sense strand 5' extension can be, but is not limited to: uAuAus, uAuAu, UAUUAGfs, UfaUfaA, uauaA, AUAUU, AfuAfuU, auauU, uaUfau, aAuA($U_{UNA}$), uauau, udAudAu, uuAga, uuAuu, uuGAu, uuaga, uAuga, aUaGas, uauaus, uAuaas, udAuau, adTaga, auaga, u(invdA)uau, gacau, ugaau, gcgau, uauga, uugga, or auaga (each listed 5' to 3', notation is the same as for Table 2). A sense strand may have a 3' extension and/or a 5' extension.

Unmodified Hif2α RNAi trigger sense strand and antisense strand sequences are provided in Tables 1 and Table 5. In forming Hif2α RNAi triggers, each of the nucleotides in each of the sequences listed in Tables 1 and 5 may be a modified nucleotide.

TABLE 1

Unmodified Hif2α RNAi trigger antisense strand and sense strand sequences.

| SEQ ID NO. | Antisense Strand Sequence 5' → 3' | SEQ ID NO. | Sense Strand Sequence 5' → 3' |
|---|---|---|---|
| 1 | AGUAAAACAAUUGUGUACUUU | 57 | AGUACACAAUUGUUUUACUT |
| 2 | AGUAAAACAAUUGUGUACUUUAA | 44 | AAAGUACACAAUUGUUUUACT |
| 3 | AUUCAUGAAAUCGUUACGUTG | 52 | ACGUAACGAUUUCAUGAATT |
| 4 | AUUCAUGAAAUCGUUACGUUG | 52 | ACGUAACGAUUUCAUGAATT |
| 4 | AUUCAUGAAAUCGUUACGUUG | 53 | ACGUAACGAUUUCAUGAAU |
| 4 | AUUCAUGAAAUCGUUACGUUG | 54 | ACGUAACGAUUUCAUGAAUT |
| 4 | AUUCAUGAAAUCGUUACGUUG | 73 | UAUACGUAACGAUUUCAUGAAUT |
| 4 | AUUCAUGAAAUCGUUACGUUG | 74 | UAUACGUAACGAUUUCAUGAAUTT |
| 5 | AUUCAUGAAAUCGUUACGUUGAT | 47 | AACGUAACGAUUUCAUGAAUT |
| 6 | AUUCAUGAAAUCGUUACGUUGGC | 77 | UAUCAACGUAACGAUUUCAUGAAUTT |
| 7 | TAAAUCGUUACGUUGACAGTT | 67 | CUGUCAACGUAACGAUUUAT |
| 8 | TAACCACAUACGUUGGAGUTT | 55 | ACUCCAACGUAUGUGGUUAT |
| 9 | TAAGUUAAGCUCCCAUACATT | 81 | UGUAUGGGAGCUUAACUUAT |
| 10 | TAAUCGUUACGUUGACAGGTT | 63 | CCUGUCAACGUAACGAUUAT |
| 11 | TACGUUGACAGGUAGGGUUTT | 45 | AACCCUACCUGUCAACGUAT |
| 12 | TAGAGGAGCUUGUGUGUUCTT | 68 | GAACACACAAGCUCCUCUAT |
| 13 | TAGCUUGUGUGUUCGCAGGTT | 62 | CCUGCGAACACACAAGCUAT |
| 14 | TAGGAGCUUGUGUGUUCGCTT | 69 | GCGAACACACAAGCUCCUAT |
| 15 | TAUCGUUACGUUGACAGGTT | 49 | ACCUGUCAACGUAACGUAAT |
| 15 | TAUCGUUACGUUGACAGGTT | 71 | UAUACCUGUCAACGUAACGUAAT |
| 16 | TCAUGAAAUCGUUACGUUGTT | 60 | CAACGUAACGAUUUCAUGAT |
| 17 | TCGUUACGUUGACAGGUAGTT | 65 | CUACCUGUCAACGUAACGAT |
| 18 | TCUAGCAACAAAACCUUAATT | 82 | UUAAGGUUUUGUUGCUAGAT |

TABLE 1-continued

Unmodified Hif2α RNAi trigger antisense strand and sense strand sequences.

| SEQ ID NO. | Antisense Strand Sequence 5' → 3' | SEQ ID NO. | Sense Strand Sequence 5' → 3' |
|---|---|---|---|
| 19 | TGAGCUUGUGUGUUCGCAGTT | 66 | CUGCGAACACACAAGCUCAT |
| 19 | TGAGCUUGUGUGUUCGCAGTT | 68 | GAACACACAAGCUCCUCUAT |
| 20 | TGAGGAGCUUGUGUGUUCGTT | 64 | CGAACACACAAGCUCCUCAT |
| 21 | TGGAGCUUGUGUGUUCGCATT | 79 | UGCGAACACACAAGCUCCAT |
| 22 | TGGUACUGGGUGGCGUAGCTT | 70 | GCUACGCCACCCAGUACCAT |
| 23 | TGUAAAACAAUUGUGUACUTT | 56 | AGUACACAAUUGUUUUACAT |
| 24 | TUACGUUGACAGGUAGGGUTT | 48 | ACCCUACCUGUCAAGGUAAT |
| 25 | TUCGUUACGUUGACAGGUATT | 78 | UCACUGUCAACGUAACGAAT |
| 26 | TUGAUAAACACUUAACCCATT | 80 | UGGGUUAAGUGUUUAUCAAT |
| 27 | TUGUCACGAUGCGGUGGUUTT | 61 | CAGUGCAACGCCACCCAGAT |
| 28 | TUUCAUGAAAUCGUUACGUCGGCUAU | 76 | UAUAUCGACGUAACGAUUUCAUGAAA |
| 29 | TUUCAUGAAAUCGUUACGUCGGCUGU | 76 | UAUAUCGACGUAACGAUUUCAUGAAA |
| 30 | TUUCAUGAAAUCGUUACGUTT | 50 | ACGUAACGAUUUCAUGAAA |
| 30 | TUUCAUGAAAUCGUUACGUTT | 51 | ACGUAACGAUUUCAUGAAAT |
| 30 | TUUCAUGAAAUCGUUACGUTT | 72 | UAUACGUAACGAUUUCAUGAAAT |
| 31 | TUUCAUGAAAUCGUUACGUUGGC | 59 | CAACGUAACGAUUUCAUGAAA |
| 32 | TUUCAUGAAAUCGUUACGUUGGCUAU | 75 | UAUAUCAACGUAACGAUUUCAUGAAA |
| 33 | TUUCAUGAAAUCGUUACGUUGGCUGU | 75 | UAUAUCAACGUAACGAUUUCAUGAAA |
| 34 | TUUCAUGAAAUCGUUACGUUGGCUTT | 75 | UAUAUCAACGUAACGAUUUCAUGAAA |
| 35 | UCAUGAAAUCGUUACGUUGTT | 58 | CAACGUAACGAUUUCAUGA |
| 35 | UCAUGAAAUCGUUACGUUGTT | 58 | CAACGUAACGAUUUCAUGA |
| 36 | UCUAGCAACAAAACCUUAATT | 82 | UUAAGGUUUUGUUGCUAGAT |
| 37 | UGUAAAACAAUUGUGUACUTT | 56 | AGUACACAAUUGUUUUACAT |
| 38 | UGUAAAACAAUUGUGUACUUU | 56 | AGUACACAAUUGUUUUACAT |
| 39 | UGUAAAACAAUUGUGUACUUUAA | 43 | AAAGUACACAAUUGUUUUACA |
| 40 | UUUCAUGAAAUCGUUACGUTT | 51 | ACGUAACGAUUUCAUGAAAT |
| 40 | UUUCAUGAAAUCGUUACGUTT | 72 | UAUACGUAACGAUUUCAUGAAAT |
| 41 | UUUCAUGAAAUCGUUACGUUG | 50 | ACGUAACGAUUUCAUGAAA |
| 41 | UUUCAUGAAAUCGUUACGUUG | 51 | ACGUAACGAUUUCAUGAAAT |
| 41 | UUUCAUGAAAUCGUUACGUUG | 72 | UAUACGUAACGAUUUCAUGAAAT |
| 42 | UUUCAUGAAAUCGUUACGUUGAT | 46 | AACGUAACGAUUUCAUGAAAT |

The Hif2α RNAi triggers described herein are formed by annealing an antisense strand with a sense strand. In some embodiments, an Hif2α RNAi trigger antisense strand comprises a nucleotide sequence of any of the sequences in Tables 1 and 5. In some embodiments, an Hif2α RNAi trigger antisense strand comprises the sequence of nucleotides 1-17, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Tables 1 and 5. In some embodiments, an Hif2α RNAi trigger sense strand comprises the nucleotide sequence of any of the sequences in Tables 1 and 5. In some embodiments, an Hif2α RNAi trigger sense strand comprises the sequence of nucleotides 1-17, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Tables 1 and 5.

In some embodiments, the sense and antisense strands of the RNAi triggers described herein contain the same number of nucleotides. In some embodiments the sense and antisense strands of the RNAi triggers described herein contain different numbers of nucleotides. In some embodiments, the sense strand 5' end and the antisense strand 3' end of an RNAi trigger form a blunt end. In some embodiments, the sense strand 3' end and the antisense strand 5' end of an RNAi trigger form a blunt end. In some embodiments, both ends of an RNAi trigger form a blunt end. In some embodiments, neither end of an RNAi trigger is blunt-ended. As used herein a blunt end refers to an end of a double stranded trigger molecule in which the terminal nucleotides of the two annealed strands are complementary (form a complementary base-pair). In some embodiments, the sense strand 5' end and the antisense strand 3' end of an RNAi trigger form a frayed end. In some embodiments, the sense strand 3' end and the antisense strand 5' end of an RNAi trigger form a frayed end. In some embodiments, both ends of an RNAi trigger form a frayed end. In some embodiments, neither end of an RNAi trigger is a frayed end. As used herein a frayed end refers to an end of a double stranded trigger molecule in which the terminal nucleotides of the two annealed strands from a pair (i.e. do not form an overhang) but are not complementary (i.e. form a non-complementary pair). As used herein, an overhang is a stretch of one or more unpaired nucleotides at the end of one strand of a double stranded RNAi trigger molecule. The unpaired nucleotides may be on the sense strand or the antisense strand, creating either 3' or 5' overhangs. In some embodiments the RNAi trigger molecule contains: a blunt end and a frayed end, a blunt end and 5' overhang end, a blunt end and a 3' overhang end, a frayed end and a 5' overhand end, a frayed end and a 3' overhang end, two 5' overhang ends, two 3' overhang ends, a 5' overhang end and a 3' overhand end, two frayed ends, or two blunt ends.

A nucleotide base (or nucleobase) is a heterocyclic pyrimidine or purine compound which is a constituent of all nucleic acids and includes adenine (A), guanine (G), cytosine (C), thymine (T), and uracil (U). As used herein, "G", "g", "C", "c", "A", "a", "U", "u", and "T", each generally stand for a nucleobase, nucleoside, nucleotide or nucleotide mimic that contains guanine, cytosine, adenine, uracil and thymidine as a base. Also as used herein, the term "nucleotide" can include a modified nucleotide or nucleotide mimic, abasic site, or a surrogate replacement moiety.

As used herein, a "modified nucleotide" is a nucleotide other than a ribonucleotide (2'-hydroxyl nucleotide). In some embodiments, an Hif2α RNAi trigger contains one or more modified nucleotides. In some embodiments, at least 50%, at least 60%, at least 70%, at least 80%, at least 90%, at least 95%, or 100% of the nucleotides are modified. Modified nucleotides include, but are not limited to, deoxynucleotides, nucleotide mimics, abasic nucleotides (represented herein as X or Ab), 2'-modified nucleotides, 3' to 3' linkages (inverted) nucleotides (represented herein as invdN, invN, invn, invX), non-natural base-comprising nucleotides, bridged nucleotides, peptide nucleic acids, 2',3'-seco nucleotide mimics (unlocked nucleobase analogues, represented herein as $N_{UNA}$ or NUNA), locked nucleotides (represented herein as $N_{LNA}$ or NLNA), 3'-O-Methoxy (2' internucleotide linked) nucleotides (represented herein as 3'-OMen), 2'-F-Arabino nucleotides (represented herein as NfANA or $Nf_{ANA}$), morpholino nucleotides, vinyl phosphonate deoxyribonucleotides (represented herein as vpdN), and vinyl phosphonate nucleotides. 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxyl ethyl) nucleotides (represented herein as NM or 2'-MOE), 2'-amino nucleotides, 2'-alkyl nucleotides. It is not necessary for all positions in a given compound to be uniformly modified. Conversely, more than one modification may be incorporated in a single Hif2α RNAi trigger or even in a single nucleotide thereof. The Hif2α RNAi trigger sense strands and antisense strands may be synthesized and/or modified by methods known in the art. Modification at one nucleotide is independent of modification of another nucleotide.

Modified nucleotides also include nucleotides having modified nucleobases. Modified nucleobases include, but are not limited to, synthetic and natural nucleobases, 5-substituted pyrimidines, 6-azapyrimidines and N-2, N-6 and O-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

In some embodiments 20% or fewer of the modified nucleotides are 2'-fluoro modified nucleotides. In some embodiments, an Hif2α RNAi trigger sense strand contains a 2'-F nucleotide at position 11 from the 3' end. In some embodiments, an Hif2α RNAi trigger sense strand contains a 2'-F nucleotide at position 12 from the 3' end. In some embodiments, an Hif2α RNAi trigger sense strand contains a 2'-F nucleotide at position 13 from the 3' end. In some embodiments, an Hif2α RNAi trigger sense strand contains at least two 2'-F nucleotides at positions 11, 12, and 13 from the 3' end. In some embodiments, an Hif2α RNAi trigger sense strand contains 2'-F nucleotides at positions 11 and 12, positions 11 and 13, or positions 12 and 13 from the 3' end. In some embodiments, an Hif2α RNAi trigger sense strand contains 2'-F nucleotides at positions 11, 12, and 13 from the 3' end.

In some embodiments, an Hif2α RNAi trigger antisense strand contains a 2'-F nucleotide at position 2 from the 5' end. In some embodiments, an Hif2α RNAi trigger antisense strand contains a 2'-F nucleotide at position 14 from the 5' end. In some embodiments, an Hif2α RNAi trigger antisense strand contains 2'-F nucleotides at positions 2 and 14 from the 5' end. In some embodiments, an Hif2α RNAi trigger contains at least two 2'-F nucleotides at positions 11, 12, and 13 from the 3' end of the sense strand and at positions 2 and 14 from the 5' end of the antisense strand.

In some embodiments, an Hif2α RNAi trigger antisense strand contains a 2'-F nucleotide at position 4 from the 5' end. In some embodiments, an Hif2α RNAi trigger antisense strand contains a 2'-F nucleotide at position 6 from the 5' end. In some embodiments, an Hif2α RNAi trigger antisense strand contains a 2'-F nucleotide at position 8 from the 5' end. In some embodiments, an Hif2α RNAi trigger antisense strand contains a 2'-F nucleotide at position 10 from the 5' end. In some embodiments, an Hif2α RNAi trigger antisense strand contains a 2'-F nucleotide at position 12 from the 5' end. In some embodiments, an Hif2α RNAi trigger antisense strand contains at least two 2'-F nucleotides at positions 4, 6, 8, 10, and 12 from the 5' end. In some embodiments, an Hif2α RNAi trigger antisense strand contains 2'-F nucleotides at positions 4 and 6, positions 4 and 8, positions 4 and 10, positions 4 and 12, positions 6 and 8, positions 6 and 10, positions 6 and 12, positions 8 and 10, positions 8 and 12, or positions 10 and 12 from the 5' end. In some embodiments, an Hif2α RNAi trigger antisense strand contains at three 2'-F nucleotides at positions 4, 6, 8, 10, and 12 from the 5' end. In some embodiments, an Hif2α RNAi trigger antisense strand contains at least four 2'-F nucleotides at positions 4, 6, 8, 10, and 12 from the 5' end. In some embodiments, an Hif2α RNAi trigger antisense strand contains 2'-F nucleotides at positions 4, 6, 8, and 10, positions 4, 6, 8 and 12, positions 4, 6, 10, and 12, positions 4, 8, 10, and 12 or positions 6, 8, 10, and 12 from the 5' end.

In some embodiments, an Hif2α RNAi trigger antisense strand contains a 2'-F nucleotide at position 2 and/or position 14 and one, two, or three 2'-F nucleotides at positions 11, 12, and 13 from the 5' end. In some embodiments, an Hif2α RNAi trigger contains a 2'-F nucleotide at position 2 and/or position 14 and one, two, or three 2'-F nucleotides at positions 11, 12, and 13 from the 5' end of the antisense strand, and at least two 2'-F nucleotides at positions 11, 12, and 13 from the 3' end of the sense strand.

In some embodiments, one or more nucleotides of an Hif2α RNAi trigger are linked by non-standard linkages or backbones (i.e. modified internucleoside linkages or modified backbones). In some embodiments, a modified internucleoside linkage is a non-phosphate-containing covalent internucleoside linkage. Modified internucleoside linkages or backbones include, but are not limited to, phosphorothioates, 5'-phosphorothioate group (represented herein as a lower case 's' before a nucleotide, as in sN, sn, sNf, or sdN), chiral phosphorothioates, thiophosphate, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoratnidates, thionoalkyl-phosphonates, thionoalkylphosphotriesters, morpholino linkages, and boranophosphates having normal 3'-5' linkages, 2'-5' linked analogs of these, and those having inverted polarity wherein the adjacent pairs of nucleoside units are linked 3'-5' to 5'-3' or to 5'-2'. In other embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide, sulfoxide and sulfone backbones; formacetyl and thioformacetyl backbones, methylene formacetyl and thioformacetyl backbones, alkene containing backbones, sulfamate backbones, methyleneimino and methylenehydrazino backbones, sulfonate and sulfonamide backbones, amide backbones; and others having mixed N, O, S, and $CH_2$ component parts.

In some embodiments, an Hif2α RNAi trigger contains one or more modified nucleotides and one or more modified internucleoside linkages. In some embodiments, a 2'-modified nucleotide is combined with modified internucleoside linkage. For example, in some embodiments, a sense strand of an Hif2α RNAi trigger can contain 1, 2, 3, 4 phosphorothioate linkages, an antisense strand of a Hif2α RNAi trigger can contain 1, 2, 3, or 4 phosphorothioate linkages, or both the sense strand and the antisense strand independently can contain 1, 2, 3, or 4 phosphorothioate linkages.

In some embodiments, an Hif2α RNAi trigger sense strand contains two phosphorothioate internucleoside linkages. In some embodiments, the two phosphorothioate internucleoside linkages are between the nucleotides at positions 1-3 from the 3' end of the sense strand. In some embodiments, the two phosphorothioate internucleoside linkages are between the nucleotides at positions 1-3, 2-4, 3-5, 4-6, 4-5, or 6-1 from the 5' end of the sense strand. In some embodiments, an Hif2α RNAi trigger antisense strand contains four phosphorothioate internucleoside linkages. In some embodiments, the four phosphorothioate internucleoside linkages are between the nucleotides at positions 1-3 from the 5' end of the sense strand and between the nucleotides at positions 19-21, 20-22, 21-23, 22-24, 23-25, or 24-26 from the 5' end. In some embodiments, an Hif2α RNAi trigger contains two phosphorothioate internucleoside linkages in the sense strand and four phosphorothioate internucleoside linkages in the antisense strand.

In some embodiments, an Hif2α RNAi trigger is prepared or provided as a salt, mixed salt, or a free-acid.

Examples of antisense strands containing modified nucleotides are provided in Table 2A and Table 5B. Examples of sense strands containing modified nucleotides are provided in Table 29 and Table 5B. In Tables 2A, 2B and 5B, the following notations are used to indicate modified nucleotides:

N=2'-OH (unmodified) ribonucleotide (capital letter without for d indication)
n–2'-OMe modified nucleotide
Nf=2'-fluoro modified nucleotide
dN=2'-deoxy nucleotides
$N_{UNA}$=2',3'-seco nucleotide mimics (unlocked nucleobase analogs)
NM=2'-methoxyethyl nucleotide
(invdN)=inverted deoxyribonucleotide (3'-3' linked nucleotide)
(invAb)=inverted abasic nucleotide
s=phosphorothioate linked nucleotide
p=phosphate
vpdN=vinyl phosphonate deoxyribonucleotide

TABLE 2A

Hif2α RNAi trigger antisense strands having modified nucleotides.

| Antisense Strand ID | Antisense Strand Sequence (5' → 3') | SEQ ID NO. | Unmod. SEQ ID NO. |
|---|---|---|---|
| AM00159-AS | dTGfgAfgCfuUfgUfgUfgUfuCfgCfadTsdT | 112 | 21 |
| AM00160-AS | dTGfgUfaCfuGfgGfuGfgCfgUfaGfcdTsdT | 113 | 22 |

TABLE 2A-continued

Hif2α RNAi trigger antisense strands having modified nucleotides.

| Antisense Strand ID | Antisense Strand Sequence (5' → 3') | SEQ ID NO. | Unmod. SEQ ID NO. |
|---|---|---|---|
| AM00161-AS | dTCfgUfuAfcGfuUfgAfcAfgGfuAfgdTsdT | 106 | 17 |
| AM00162-AS | dTAfgCfuUfgUfgUfgUfuCfgCfaGfgdTsdI | 103 | 13 |
| AM00163-AS | dTGfaGfcUfuGfuGfuGfuUfcGfcAfgdTsdT | 110 | 19 |
| AM00164-AS | dTAfgGfaGfcUfuGfuGfuGfuUfcGfcdTsdT | 104 | 14 |
| AM00165-AS | dTGfaGfgAfgCfuUfgUfgUfgUfuCfgdTsdT | 111 | 20 |
| AM00166-AS | dTAfgAfgGfaGfcUfuGfuGfuGfuUfcdTsdT | 102 | 12 |
| AM00167-AS | dTUfgUfcAfcGfaUfgCfgGfuGfgUfudIsdT | 137 | 27 |
| AM00168-AS | dTAfcGfuUfgAfcAfgGfuAfgGfgUfudTsdT | 101 | 11 |
| AM00169-AS | dTUfaCfgUfuGfaCfaGfgUfaGfgGfudTsdT | 135 | 24 |
| AM00170-AS | dTUfcGfuUfaCfgUfuGfaCfaGfgUfadTsdT | 136 | 25 |
| AM00171-AS | dTAfuCfgUfuAfcGfuUfgAfcAfgGfudTsdT | 105 | 15 |
| AM00172-AS | dTAfaUfcGfuUfaCfgUfuGfaCfaGfgdTsdT | 100 | 10 |
| AM01770-AS | dTGfuAfaAfcCfaAfuUfgUfgUfaCfudTsdT | 114 | 23 |
| AM01772-AS | dTGfuAfaAUNAaCfaAfuUfgUfgUfaCfudTsdT | 116 | 23 |
| AM01773-AS | dTGfuAfaAfAUNACfaAfuUfgUfgUfaCfudTsdT | 115 | 23 |
| AM01775-AS | dTCfuAfgCfaAfcAfaAfaCfcUfuAfadTsdT | 107 | 18 |
| AM01777-AS | dTCfuAfgCUNAaAfcAfaAfaCfcUfuAfadTsdT | 109 | 18 |
| AM01778-AS | dTCfuAfgCfAUNAAfcAfaAfaCfcUfuAfadTsdT | 108 | 18 |
| AM01780-AS | dTAfaAfuCfgUfuAfcGfuUfgAfcAfgdTsdT | 94 | 7 |
| AM01782-AS | dTAfaAfuCUNAgUfuAfcGfuUfgAfcAfgdTsdT | 96 | 7 |
| AM01783-AS | dTAfaAfuCfGUNAUfuAfcGfuUfgAfcAfgdTsdT | 95 | 7 |
| AM01784-AS | dTUfuCfaUfgAfaAfuCfgUfuAfcGfudTsdT | 138 | 30 |
| AM01786-AS | dTUfuCfaUUNAgAfaAfuCfgUfuAfcGfudTsdT | 145 | 30 |
| AM01787-AS | dTUfuCfaUfGUNAAfaAfuCfgUfuAfcGfudTsdT | 144 | 30 |
| AM01789-AS | dTAfaGfuUfaAfgCfuCfcCfaUfaCfadTsdT | 97 | 9 |
| AM01791-AS | dTAfaGfuUUNAaAfgCfuCfcCfaUfaCfadTsdT | 99 | 9 |
| AM01792-AS | dTAfaGfuUfAUNAAfgCfuCfcCfaUfaCfadTsdT | 98 | 9 |
| AM02090-AS | dTUfuCfaUfgAUNAaAfuCfgUfuAfcGfudTsdT | 143 | 30 |
| AM02091-AS | dTUfuCfaUfgAfAUNAAfuCfgUfuAfcGfudTsdT | 142 | 30 |
| AM02092-AS | dTUfuCfaUfgAfaAfuCfgUfUUNAAfcGfudTsdT | 139 | 30 |
| AM02133-AS | dTUfuCfaUfgAfaAfucgUfuAfcGfudTsdT | 141 | 30 |
| AM02140-AS | dTsUfsuCfaUfgAfaAfucgUfuAfcGfuUfgsgsc | 128 | 31 |
| AM02145-AS | dTsUfsuCfaUfgAfaAfucgUfuAfcGfuUfggscsuGu | 127 | 33 |
| AM02146-AS | dTsUfsuCfaUfgAfaAfucgUfuAfcGfuCfggscsuGu | 123 | 29 |
| AM02147-AS | dTsUfsuCfaUfgAfaAfucgUfuAfcGfuUfggscsuAu | 126 | 32 |
| AM02150-AS | dTsUfsuCfaUfgAfaAfucgUfuAfcGfuUfggcusdTsdT | 125 | 34 |

TABLE 2A-continued

Hif2α RNAi trigger antisense strands having modified nucleotides.

| Antisense Strand ID | Antisense Strand Sequence (5' → 3') | SEQ ID NO. | Unmod. SEQ ID NO. |
|---|---|---|---|
| AM02327-AS | pdTUfuCfaUfgAfaAfuCfgUfuAfcGfudTsdT | 147 | 30 |
| AM02341-AS | dTsUfsuCfaUfgAUNAaAfuCfgUfuAfcGfuCfggscsuAu | 130 | 28 |
| AM02342-AS | dTsUfuCfaUfgAUNAaAfuCfgUfuAfcGfuCfggcsuAu | 134 | 28 |
| AM02345-AS | dTsUfsuCfaUfgAfAUNAANCfuUfuAfcGfuCfggscsuAu | 129 | 28 |
| AM02346-AS | dTsUfuCfaUfgAfAUNAAfuCfgUfuAfcGfuCfggscsuAu | 133 | 28 |
| AM02508-AS | dTsUfsuCfaUfgAfaAfuCfgUfuAfcGfudTsdT | 120 | 30 |
| AM02509-AS | dTUfuCfaUfgAfaAfucGfUfuAfcGfudTsdT | 140 | 30 |
| AM02523-AS | dTsAfsaCfcAfcAfuAfcGfuUfgGfaGfudTsdT | 117 | 8 |
| AM02525-AS | dTsUfsgAfuAfaAfcAfcUfuAfaCfcCfadTsdT | 119 | 26 |
| AM02527-AS | dTsCfsaUfgAfaAfuCtUfuAfcGfuUfgdTsdT | 118 | 16 |
| AM02529-AS | usCfsaUfgAfaAfuCtUfuAfcGfuUfgdTsdT | 148 | 35 |
| AM02604-AS | dTsUfsuCfaUfgAfaAfucGfUfuAfcGfudTsdT | 122 | 30 |
| AM02605-AS | dTsUfsuCfaUfgAfaAfucgUfuAfcGfudTsdT | 124 | 30 |
| AM02848-AS | dTsUfuCfaUfgAfaAfucGfUfuAfcGfudTsdT | 132 | 30 |
| AM02849-AS | dTsUfuCfaUfgAfaAfuCtUfUfacGfudTsdT | 131 | 30 |
| AM02850-AS | dTsUfsuCfaUfgAfaAfuCtUfUfacGfudTsdT | 121 | 30 |
| AM02998-AS | usUfsuCfaUfgAfaAfucgUfuAfcGfudTsdT | 160 | 40 |
| AM03000-AS | usCfsuAfgCfaAfcAfaaAfCfcUfuAfadTsdT | 151 | 36 |
| AM03001-AS | usasuAfgCfaaCfAfaaAfCfcUfuAfadTsdT | 149 | 36 |
| AM03002-AS | usCfsuAfgCfAfcAfaAfaCfCfuuAfadTsdT | 152 | 36 |
| AM03003-AS | usCfsuAtCfaaCfAfaAfaCfCfuuAfadTsdT | 150 | 36 |
| AM03008-AS | usGfsuAfaAfaCfaAfuuGfUtUfaCfudTsdT | 154 | 37 |
| AM03009-AS | usGfsuAfaAfaCfaAfuUfgUfGfuaCfudTsdT | 153 | 37 |
| AM03059-AS | pdTsUfsuCfaUfgAfaAfucgUfuAfcGfudTsdT | 146 | 30 |
| AM03465-AS | usUfsuCfaUfgAfaAfucgUfuAfcGfsusg | 161 | 41 |
| AM03513-AS | usUfsuCfaUfgAfaAfucguuacgsusg | 162 | 41 |
| AM03514-AS | usUfsuCfaUfgAfaaucguuacgsusg | 165 | 41 |
| AM03517-AS | asUfsuCfaUfgAfaAfucgUfuAfcGfsusg | 90 | 4 |
| AM03685-AS | usUfsuCfaUfgAfaAfucgUfuacgsusg | 159 | 41 |
| AM03688-AS | usUfsUfCfaugAfaAfucgUfuacgsusg | 167 | 41 |
| AM03689-AS | usUfsuCfaUfgAfaaucgUfuacgsusg | 163 | 41 |
| AM03690-AS | usUfsUfcaugAfaAfucgUfuacgsusg | 166 | 41 |
| AM04001-AS | usGfsuAfaAfaCfaAfuugUfgUfaCfsusu | 155 | 38 |
| AM04004-AS | asGfsuAfaAfaCfaAfuugUfgUfaCfsusu | 84 | 1 |
| AM04007-AS | usGfsuAfaAfaCfaAfuugUfgUfaCfuuusasa | 156 | 39 |
| AM04010-AS | asGfsuAfaAfaCfaAfuugUfgUfaCfuuusasa | 85 | 2 |
| AM04015-AS | asGfsuAfaAfaCfaAfuugUfguaCfuuusasa | 83 | 2 |

TABLE 2A-continued

Hif2α RNAi trigger antisense strands having modified nucleotides.

| Antisense Strand ID | Antisense Strand Sequence (5' → 3') | SEQ ID NO. | Unmod. SEQ ID NO. |
|---|---|---|---|
| AM04018-AS | asGfsuAfaAfaCfaauugUfguacuuusasa | 86 | 2 |
| AM04040-AS | vpusUfsuCfaUfgAfaAfucgUfuAfcGfususg | 168 | 41 |
| AM04101-AS | asUfsuCfaUfgAfaaucgUfuacgususg | 91 | 4 |
| AM04102-AS | usUfsuCfaUfgAfaaucgUfuacguugsas(invdT) | 164 | 42 |
| AM04103-AS | asUfsuCfaUfgAfaaucgUfuacugsas(invdT) | 92 | 5 |
| AM04104-AS | usUfsucaugAfaAfucgUfuacgususg | 157 | 41 |
| AM04105-AS | asUfsucaugAfaAfucgUfuacgususg | 88 | 4 |
| AM04106-AS | asUfsucaugAfaAfucgUfuacgusTMsGM | 87 | 3 |
| AM04244-AS | usUfsuCfaUfgaAfaucgUfuacgususg | 158 | 41 |
| AM04452-AS | asUfsuCfaUfgAfaaucgUfuAfcguugsgsc | 93 | 6 |
| AM04455-AS | asUfsuCfaUfgaAfaucgUfuAfcguugsgsc | 89 | 6 |

TABLE 2B

Hif2α RNAi trigger sense strands having modified nucleotides.

| Sense Strand ID | SS Sequence 5' → 3' | SEQ ID NO. | Unmod. SEQ ID NO. |
|---|---|---|---|
| AM00158-SS | CfuGfuCfaAfcGfuAfaCfgAfuUfuAf(invdT) | 277 | 67 |
| AM00188-SS | (NH2-C6)uAuUfgCfgAfaCfaCfaCfaAfgCfuCfcAf(invdT) | 265 | 79 |
| AM00189-SS | (NH2-C6)uAuGfcUfaCfgCfcAfcCfcAfgUfaCfcAf(invdT) | 264 | 70 |
| AM00190-SS | (NH2-C6)uAuCfuAfcCfuGfuCfaAfcGfuAfaCfgAf(invdT) | 263 | 65 |
| AM00191-SS | (NH2-C6)uAuCfcUfgCfgAfaCfaCfaCfaAfgCfuAf(invdT) | 262 | 62 |
| AM00207-SS | (NH2-C6)CfuGfcGfaAfcAfcAfcAfaGfcUfcAf(invdT) | 258 | 66 |
| AM00208-SS | (NH2-C6)GfcGfaAfcAfcAfcAfaGfcUfcCfuAf(invdT) | 260 | 69 |
| AM00209-SS | (NH2-C6)CfgAfaCfaCfaCfaAfgCfuCfcUfcAf(invdT) | 256 | 64 |
| AM00210-SS | (NH2-C6)GfaAfcAfcAfcAfaGfcUfcCfuCfuAf(invdT) | 259 | 68 |
| AM00211-SS | (NH2-C6)CfaGfuGfcAfaCfgCfcAfcCfcAfgAf(invdT) | 253 | 61 |
| AM00212-SS | (NH2-C6)AfaCfcCfuAfcCfuGfuCfaAfcGfuAf(invdT) | 247 | 45 |
| AM00213-SS | (NH2-C6)AfcCfcUfaCfcUfgUfcAfaGfgUfaAf(invdT) | 248 | 48 |
| AM00214-SS | (NH2-C6)UfcAfcUfgUfcAfaCfgUfaAfcGfaAf(invdT) | 266 | 78 |
| AM00219-SS | (NH2-C6)AfcCfuGfuCfaAfcGfuAfaCfgUfaAf(invdT) | 249 | 49 |
| AM00220-SS | (NH2-C6)CfcUfgUfcAfaCfgUfaAfcGfaUfuAf(invdT) | 255 | 63 |
| AM00221-SS | (NH2-C6)UfgCfgAfaCfaCfaCfaAfgCfuCfcAf(invdT) | 267 | 79 |
| AM00222-SS | (NH2-C6)GfcUfaCfgCfcAfcCfcAfgUfaCfcAf(invdT) | 261 | 70 |
| AM00223-SS | (NH2-C6)CfuAfcCfuGfuCfaAfcGfuAfaCfgAf(invdT) | 257 | 65 |
| AM00224-SS | (NH2-C6)CfcUfgCfgAfaCfaCfaCfaAfgCfuAf(invdT) | 254 | 62 |
| AM00366-SS | (Alk-SS-C6)CfuGfcGfaAfcAfcAfcAfaGfcUfcAf(invdT) | 220 | 66 |

TABLE 2B-continued

Hif2α RNAi trigger sense strands having modified nucleotides.

| Sense Strand ID | SS Sequence 5' → 3' | SEQ ID NO. | Unmod. SEQ ID NO. |
|---|---|---|---|
| AM00367-SS | (Alk-SS-C6)GfcGfaAfcAfcAfcAfaGfcUfcCfuAf(invdT) | 223 | 69 |
| AM00369-SS | (Alk-SS-C6)GfaAfcAfcAfcAfaGfcUfcCfuCfuAf(invdT) | 222 | 68 |
| AM00530-SS | (Alk-SS-C6)AfcCfcUfaCfcUfgUfcAfaGfgUfaAf(invdT) | 212 | 48 |
| AM00531-SS | (Alk-SS-C6)UfcAfcUfgUfcAfaCfgUfaAfcGfaAf(invdT) | 224 | 78 |
| AM00543-SS | (Alk-SS-C6)AfaCfcCfuAfcCfuGfuCfaAfcGfuAf(invdT) | 211 | 45 |
| AM00544-SS | (Alk-SS-C6)AfcCfuGfuCfaAfcGfuAfaCfgUfaAf(invdT) | 213 | 49 |
| AM00545-SS | (Alk-SS-C6)CfuAfcCfuGfuCfaAfcGfuAfaCfgAf(invdT) | 219 | 65 |
| AM01771-SS | AfgUfaCfaCfaAfuUfgUfuUfuAfcAf(invdT) | 271 | 56 |
| AM01776-SS | UfuAfaGfgUfuUfuGfuUfgCfuAfgAf(invdT) | 284 | 82 |
| AM01785-SS | AfcGfuAfaCfgAfuUfuCfaUfgAfaAf(invdT) | 269 | 51 |
| AM01790-SS | UfgUfaUfgGfgAfgCfuAfaAfcUfuAf(invdT) | 283 | 81 |
| AM01859-SS | (Alk-SS-C6)AfgUfaCfaCfaAfuUfgUfuUfuAfcAf(invdT) | 218 | 56 |
| AM01860-SS | (Alk-SS-C6)UfuAfaGfgUfuUfuGfuUfgCfuAfgAf(invdT) | 226 | 82 |
| AM01861-SS | (Alk-SS-C6)CfuGfuCfaAfcGfuAfaCfgAfuUfuAf(invdT) | 221 | 67 |
| AM01862-SS | (Alk-SS-C6)AfcGfuAfaCfgAfuUfuCfaUfgAfaAf(invdT) | 215 | 51 |
| AM01863-SS | (Alk-SS-C6)UfgUfaUfgGfgAfgCfuAfaAfcUfuAf(invdT) | 225 | 81 |
| AM01994-SS | (Alk-C6)uAuAfcCfuGfuCfaAfcGfuAfaCfgUfaAf(invdT) | 169 | 71 |
| AM02043-SS | (Me-Alk-SS-C6)AfcGfuAfaCfgAfuUfuCfaUfgAfaAf(invdT) | 231 | 51 |
| AM02093-SS | (DBCO-TEG)uAuAfcGfuAfaCfgAfuUfuCfaUfgAfaAf(invdT) | 228 | 72 |
| AM02135-SS | (Alk-SS-C6)AfcGfuAfaCfGfAfuUfuCfaUfgAfaAf(invdT) | 216 | 51 |
| AM02137-SS | (Alk-SS-C6)AfcGfuAfAfCfgAfuUfuCfaUfgAfaAf(invdT) | 217 | 51 |
| AM02139-SS | (Alk-SS-C6)AfcGfuaaCfgAfuUfuCfaUfgAfaAf(invdT) | 214 | 51 |
| AM02142-SS | CfsasAfcGfuAfaCfGfAfuUfuCfaUfgAfaAf(C6-SS-Alk-Me) | 276 | 59 |
| AM02144-SS | CUNAsasAfcGfuAfaCfGfAfuUfuCfaUfgAfaAf(C6-SS-Alk-Me) | 278 | 59 |
| AM02149-SS | uAuAusCfsaAfcGfuAfaCfGfAfuUfuCfaUfgAfaAf(C6-SS-Alk-Me) | 280 | 75 |
| AM02163-SS | uAuAusCfsgAfcGfuAfaCfGfAfuUfuCfaUfgAfaAf(C6-SS-Alk-Me) | 282 | 76 |
| AM02363-SS | (DBCO-TEG)uAuAusCfsgAfcGfuAfaCfgAfuUfuCfaUfgAfa(invdA) | 230 | 76 |
| AM02364-SS | uAuAusCfsgAfcGfuAfaCfgAfuUfuCfaUfgAfaAf(C6-SS-Alk-Me) | 281 | 76 |
| AM02365-SS | uAuAusCfgAfcGfuAfaCfgAfuUfuCfaUfgAfaAf(C6-SS-Alk-Me) | 279 | 76 |
| AM02456-SS | (Alk-SMPT-C6)AfcGfuAfaCfgAfuUfuCfaUfgAfaAf(invdT) | 193 | 51 |
| AM02510-SS | (Me-Alk-SS-C6)AfcGfuAfaCfGfAfuUfuCfaUfgAfaAf(invdT) | 232 | 51 |
| AM02512-SS | (Me-Alk-SS-C6)AfcGfuAfacgfAfuUfuCfaUfgAfaAf(invdT) | 233 | 51 |
| AM02522-SS | (NH2-C6)AfcUfcCfaAfcGfuAfuGfuGfgUfuAf(invdT) | 250 | 55 |
| AM02524-SS | (NH2-C6)UfgGfgUfuAfaGfuGfuUfuAfcCfaAf(invdT) | 268 | 80 |
| AM02526-SS | (NH2-C6)CfaAfcGfuAfaCfgAfuUfuCfaUfgAf(invdT) | 252 | 60 |
| AM02528-SS | (NH2-C6)CfaAfcGfuAfaCfgAfuUfuCfaUfg(invdA) | 251 | 58 |
| AM02546-SS | (Me-Alk-SS-C6)AfcUfcCfaAfcGfuAfuGfuGfgUfuAf(invdT) | 235 | 55 |

TABLE 2B-continued

Hif2α RNAi trigger sense strands having modified nucleotides.

| Sense Strand ID | SS Sequence 5' → 3' | SEQ ID NO. | Unmod. SEQ ID NO. |
|---|---|---|---|
| AM02547-SS | (Me-Alk-SS-C6)UfgGfgUfuAfaGfuGfuUfuAfuCfaAf(invdT) | 242 | 80 |
| AM02548-SS | (Me-Alk-SS-C6)CfaAfcGfuAfaCfgAfuUfuCfaUfgAf(invdT) | 241 | 60 |
| AM02549-SS | (Me-Alk-SS-C6)CfaAfcGfuAfaCfgAfuUfuCfaUfg(invdA) | 240 | 58 |
| AM02852-SS | AfscGfuAfacGfAfuUfuCfaUfgAfaAf(C6-SS-Alk-Me) | 272 | 50 |
| AM02853-SS | AfscGfUfaaCfgAfuUfuCfaUfgAfaAf(C6-SS-Alk-Me) | 273 | 50 |
| AM02856-SS | (Me-Alk-SS-C6)AfcGfUfaaCfgAfuUfuCfaUfgAfaAf(invdT) | 234 | 51 |
| AM02959-SS | (DBCO-TEG)uAuAfcGfuAfaCfGfAfuUfuCfaUfgAfaAf(invdT) | 229 | 72 |
| AM03004-SS | (Me-Alk-SS-C6)UfuAfaGfguUfUfuGfuUfgCfuAfgAf(invdT) | 244 | 82 |
| AM03005-SS | (Me-Alk-SS-C6)uuAfaGfguUfUfuguUfgCfuAfga(invdT) | 246 | 82 |
| AM03006-SS | (Me-Alk-SS-C6)UfuAfAfggUfUfuGfuUfgCfuAfgAf(invdT) | 243 | 82 |
| AM03007-SS | (Me-Alk-SS-C6)uuAfAfggUfuUfuguUfgCfuAfga(invdT) | 245 | 82 |
| AM03010-SS | (Me-Alk-SS-C6)AfgUfaCfacAfAfuUfgUfuUfuAfcAf(invdT) | 236 | 56 |
| AM03011-SS | (Me-Alk-SS-C6)agUfaCfacAfAfuUfgUfuuuAfca(invdT) | 238 | 56 |
| AM03012-SS | (Me-Alk-SS-C6)AfgUfAfcaCfaAfuUfgUfuUfuAfcAf(invdT) | 237 | 56 |
| AM03013-SS | (Me-Alk-SS-C6)agUfAfcaCfaAfuUfgUfuuuAfca(invdT) | 239 | 56 |
| AM03058-SS | AfcGfuAfaCfgFAfuUfuCfaUfgAfaAf(invdT) | 270 | 51 |
| AM03307-SS | agUfAfcaCfaAfuUfgUfuuuAfca(invdT) | 274 | 56 |
| AM03308-SS | (Alk-C6-C6)AfcGfuAfaCfgFAfuUfuCfaUfgAfaAf(invdT) | 170 | 51 |
| AM03467-SS | (Alk-SMPT-C6)AfscGfuAfaCfgFAfuUfuCfaUfgAfaa(invdT) | 194 | 51 |
| AM03469-SS | (Alk-SMPT-C6)ascGfuAfaCfgFAfuUcCfaUfgAfaa(invdT) | 201 | 51 |
| AM03471-SS | (Alk-SMPT-C6)ascguAfaCfgAfuuuCfaUfgAfaa(invdT) | 208 | 51 |
| AM03473-SS | (Alk-SMPT-C6)ascGfuaaCfgAfuuuCfaugAfaa(invdT) | 200 | 51 |
| AM03475-SS | (Alk-SMPT-C6)ascguaaCfgAfuuuCfaugaaa(invdT) | 204 | 51 |
| AM03516-SS | (Alk-SMPT-C6)ascguaaCfgAfuuucaugaaa(invdT) | 203 | 51 |
| AM03519-SS | (Alk-SMPT-C6)ascGfuAfaCfgFAfuUfuCfaUfgAfau(invdT) | 202 | 54 |
| AM03687-SS | (Alk-SMPT-C6)ascguaaCfgFAfuuucaugaaa(invdT) | 205 | 51 |
| AM03692-SS | (Alk-PEG5-C6)uAuascguaaCfgFAfuuucaugaaa(invdT) | 185 | 72 |
| AM03694-SS | (Alk-PEG5-C6)uAuascGfuAfaCfgFAfuuuCfaUfgAfau(invdT) | 183 | 73 |
| AM03708-SS | (Alk-PEG5-C6)uAuaScGfuAfaCfgFAfuuuCfaUfgAfaa(invdT) | 182 | 72 |
| AM03710-SS | (Alk-PEG5-C6)uAuascguaaCfgFAfuuuCfaugaaa(invdT) | 189 | 72 |
| AM03712-SS | (Alk-PEG5-C6)uAuascguaaCfgFAfuuuCfaugaau(invdT) | 190 | 73 |
| AM03714-SS | (Alk-PEG5-C6)(Alk-PEG5-Ser)-uAuascguaaCfgFAfuuuCfaugaaa(invdT) | 180 | 72 |
| AM03774-SS | (Alk-C6-SMPT-C6)ascguaaCfgAfuuuCfaugaaa(invdT) | 174 | 51 |
| AM03829-SS | (Alk-PEG5-C6)uAuascguaaCfgAfuuuCfaugaaa(invdT) | 184 | 72 |
| AM03830-SS | (Chol-TEG)uAuascguaaCfgAfuuuCfaugaaa(invdT) | 227 | 72 |
| AM03831-SS | ascguaaCfgAfuuuCfaugaaa(NAG13) | 275 | 50 |
| AM04003-SS | (Alk-SMPT-C6)asgUfaCfaCfAfAfuUfgUfuuuAfca(invdT) | 209 | 56 |

TABLE 2B-continued

Hif2α RNAi trigger sense strands having modified nucleotides.

| Sense Strand ID | SS Sequence 5' → 3' | SEQ ID NO. | Unmod. SEQ ID NO. |
|---|---|---|---|
| AM04G06-SS | (Alk-SMPT-C6)asgUfaCfaCfAfAfuUfgUfuuuAfcu(invdT) | 210 | 57 |
| AM04009-SS | (Alk-SMPT-C6)asaAfgUfaCfaCfAfAfuUfgUfuuuAfc(invdA) | 195 | 43 |
| AM04012-SS | (Alk-SMPT-C6)asaAfgUfaCfaCfAfAfuUfgUfuuuAfc(invdT) | 196 | 44 |
| AM04014-SS | (Alk-SMPT-C6)asaaguaCfaCfAfAfuuguuuuac(invdT) | 198 | 44 |
| AM04017-SS | (Alk-SMPT-C6)asaagUfaCfaCfAfAfuUfgUfuuuac(invdT) | 199 | 44 |
| AM04020-SS | (Alk-SMPT-C6)asaaguacaCfAfAfuuguuuuac(invdT) | 197 | 44 |
| AM04107-SS | (Alk-C6-SMPT-C6)ascguaaCfGfAfuuucaugaaa(invdT) | 175 | 51 |
| AM04107-SS | (Alk-C6-SMPT-C6)ascguaaCfGfAfuuucaugaaa(invdT) | 175 | 51 |
| AM04109-SS | (Alk-C6-SMPT-C6)ascguaaCfGfAfuuucaugaAMTM(invdT) | 176 | 52 |
| AM04111-SS | (Alk-C6-SMPT-C6)AMsCMguaaCfGfAfuuucaugaAMTM(invdT) | 171 | 52 |
| AM04113-SS | (Alk-C6-SMPT-C6)ascguaaCfGfAfuuucaugaasus(invdT) | 178 | 54 |
| AM04115-SS | (Alk-C6-SMPT-C6)ascguaaCfGfAfuuucaugaasus(invAb) | 177 | 53 |
| AM04117-SS | (Alk-C6-SMPT-C6)ascguaaCfGfAfuuucaugaau(invdT) | 179 | 54 |
| AM04119-SS | (Alk-C6-SMPT-C6)asacguaaCfGfAfuuucaugaau(invdT) | 173 | 47 |
| AM04121-SS | (Alk-C6-SMPT-C6)asacguaaCfGfAfuuucaugaaa(invdT) | 172 | 46 |
| AM04122-SS | (Alk-PEG5-C6)ascguaaCfGfAfuuucaugaaa(invdT) | 181 | 51 |
| AM04241-SS | (Alk-SMPT-C6)ascguaaCfGfAfuuucaugaaAM(invdT) | 206 | 51 |
| AM04243-SS | (Alk-SMPT-C6)ascguaaCfGfAfuuucaugaaAMs(invdT) | 207 | 51 |
| AM04246-SS | (Alk-PEG5-C6)uAuascguaaCfGfAfuuucaugaaAMs(invdT) | 186 | 72 |
| AM04248-SS | (Alk-PEG5-C6)uauascguaaCfGfAfuuucaugaaAMs(invdT) | 187 | 72 |
| AM04451-SS | (Alk-PEG5-C6)uAuascguaaCfGfAfuuucaugaaudTs(invdT) | 188 | 74 |
| AM04454-SS | (Alk-PEG5-C6)uAucsasacguAfaCfGfAfuuucaugAfaudTs(invdT) | 192 | 77 |
| AM04457-SS | (Alk-PEG5-C6)uAucsaacguAfaCfGfAfuuucaugAfaudTs(invdT) | 191 | 77 |
| AM03710-SS | (Alk-PEG5-C6)uAuascguaaCfGfAfuuuCfaugaaa(invdT) | 189 | 72 |

TABLE 3

Hif2α RNAi trigger duplexes with Duplex ID numbers.

| Duplex ID | Antisense Strand ID | SEQ ID NO. | Unmod. SEQ ID NO. | Sense Strand ID | SEQ ID NO. | Unmod. SEQ ID NO. |
|---|---|---|---|---|---|---|
| AD00086 | AM00159-AS | 112 | 21 | AM00188-SS | 265 | 79 |
| AD00087 | AM00160-AS | 113 | 22 | AM00189-SS | 264 | 70 |
| AD00088 | AM00161-AS | 106 | 17 | AM00190-SS | 263 | 65 |
| AD00089 | AM00162-AS | 103 | 13 | AM00191-SS | 262 | 62 |
| AD00102 | AM00163-AS | 110 | 19 | AM00207-SS | 258 | 66 |
| AD00103 | AM00164-AS | 104 | 14 | AM00208-SS | 260 | 69 |
| AD00104 | AM00165-AS | 111 | 20 | AM00209-SS | 256 | 64 |
| AD00105 | AM00166-AS | 102 | 12 | AM00210-SS | 259 | 68 |
| AD00106 | AM00167-AS | 137 | 27 | AM00211-SS | 253 | 61 |
| AD00107 | AM00168-AS | 101 | 11 | AM00212-SS | 247 | 45 |
| AD00108 | AM00169-AS | 135 | 24 | AM00213-SS | 248 | 48 |
| AD00109 | AM00170-AS | 136 | 25 | AM00214-SS | 266 | 78 |
| AD00110 | AM00171-AS | 105 | 15 | AM00219-SS | 249 | 49 |
| AD00111 | AM00172-AS | 100 | 10 | AM00220-SS | 255 | 63 |

TABLE 3-continued

Hif2α RNAi trigger duplexes with Duplex ID numbers.

| Duplex ID | Antisense Strand ID | SEQ ID NO. | Unmod. SEQ ID NO. | Sense Strand ID | SEQ ID NO. | Unmod. SEQ ID NO. |
|---|---|---|---|---|---|---|
| AD00112 | AM00159-AS | 112 | 21 | AM00221-SS | 267 | 79 |
| AD00113 | AM00160-AS | 113 | 22 | AM00222-SS | 261 | 70 |
| AD00114 | AM00161-AS | 106 | 17 | AM00223-SS | 257 | 65 |
| AD00115 | AM00162-AS | 103 | 13 | AM00224-SS | 254 | 62 |
| AD00215 | AM00163-AS | 110 | 19 | AM00369-SS | 222 | 68 |
| AD00268 | AM00166-AS | 102 | 12 | AM00369-SS | 222 | 68 |
| AD00269 | AM00169-AS | 135 | 24 | AM00530-SS | 212 | 48 |
| AD00270 | AM00170-AS | 136 | 25 | AM00531-SS | 224 | 78 |
| AD00274 | AM00168-AS | 101 | 11 | AM00543-SS | 211 | 45 |
| AD00275 | AM00171-AS | 105 | 15 | AM00544-SS | 213 | 49 |
| AD00276 | AM00161-AS | 106 | 17 | AM00545-SS | 219 | 65 |
| AD00285 | AM00163-AS | 110 | 19 | AM00366-SS | 220 | 66 |
| AD00286 | AM00164-AS | 104 | 14 | AM00367-SS | 223 | 69 |
| AD00373 | AM00169-AS | 135 | 24 | AM00659-SS | 212 | 48 |
| AD00374 | AM00170-AS | 136 | 25 | AM00660-SS | 224 | 78 |
| AD00375 | AM00168-AS | 101 | 11 | AM00679-SS | 211 | 45 |
| AD00376 | AM00171-AS | 105 | 15 | AM00661-SS | 213 | 49 |
| AD00377 | AM00161-AS | 106 | 17 | AM00662-SS | 219 | 65 |
| AD00988 | AM01772-AS | 116 | 23 | AM01771-SS | 271 | 56 |
| AD00989 | AM01777-AS | 109 | 18 | AM01776-SS | 284 | 82 |
| AD00990 | AM01782-AS | 96 | 7 | AM00158-SS | 277 | 67 |
| AD00991 | AM01786-AS | 145 | 30 | AM01785-SS | 269 | 51 |
| AD00992 | AM01791-AS | 99 | 9 | AM01790-SS | 283 | 81 |
| AD00993 | AM01773-AS | 115 | 23 | AM01771-SS | 271 | 56 |
| AD00994 | AM01778-AS | 108 | 18 | AM01776-SS | 284 | 82 |
| AD00995 | AM01783-AS | 95 | 7 | AM00158-SS | 277 | 67 |
| AD00996 | AM01787-AS | 144 | 30 | AM01785-SS | 269 | 51 |
| AD00997 | AM01792-AS | 98 | 9 | AM01790-SS | 283 | 81 |
| AD01020 | AM01772-AS | 116 | 23 | AM01859-SS | 218 | 56 |
| AD01021 | AM01773-AS | 115 | 23 | AM01859-SS | 218 | 56 |
| AD01022 | AM01770-AS | 114 | 23 | AM01859-SS | 218 | 56 |
| AD01023 | AM01777-AS | 109 | 18 | AM01860-SS | 226 | 82 |
| AD01024 | AM01778-AS | 108 | 18 | AM01860-SS | 226 | 82 |
| AD01025 | AM01775-AS | 107 | 18 | AM01860-SS | 226 | 82 |
| AD01026 | AM01782-AS | 96 | 7 | AM01861-SS | 221 | 67 |
| AD01027 | AM01783-AS | 95 | 7 | AM01861-SS | 221 | 67 |
| AD01028 | AM01780-AS | 94 | 7 | AM01861-SS | 221 | 67 |
| AD01029 | AM01786-AS | 145 | 30 | AM01862-SS | 215 | 51 |
| AD01030 | AM01787-AS | 144 | 30 | AM01862-SS | 215 | 51 |
| AD01031 | AM01784-AS | 138 | 30 | AM01862-SS | 215 | 51 |
| AD01032 | AM01791-AS | 99 | 9 | AM01863-SS | 225 | 81 |
| AD01033 | AM01792-AS | 98 | 9 | AM01863-SS | 225 | 81 |
| AD01034 | AM01789-AS | 97 | 9 | AM01863-SS | 225 | 81 |
| AD01180 | AM00171-AS | 105 | 15 | AM01994-SS | 169 | 71 |
| AD01214 | AM01784-AS | 138 | 30 | AM02043-SS | 231 | 51 |
| AD01255 | AM01784-AS | 138 | 30 | AM02093-SS | 228 | 72 |
| AD01256 | AM02090-AS | 143 | 30 | AM01862-SS | 215 | 51 |
| AD01257 | AM02091-AS | 142 | 30 | AM01862-SS | 215 | 51 |
| AD01258 | AM02092-AS | 139 | 30 | AM01862-SS | 215 | 51 |
| AD01288 | AM02133-AS | 141 | 30 | AM02135-SS | 216 | 51 |
| AD01289 | AM01784-AS | 138 | 30 | AM02137-SS | 217 | 51 |
| AD01290 | AM01784-AS | 138 | 30 | AM02139-SS | 214 | 51 |
| AD01291 | AM02140-AS | 128 | 31 | AM02142-SS | 276 | 59 |
| AD01292 | AM02140-AS | 128 | 31 | AM02144-SS | 278 | 59 |
| AD01293 | AM02145-AS | 127 | 33 | AM02149-SS | 280 | 75 |
| AD01294 | AM02146-AS | 123 | 29 | AM02163-SS | 282 | 76 |
| AD01295 | AM02147-AS | 126 | 32 | AM02149-SS | 280 | 75 |
| AD01296 | AM02150-AS | 125 | 34 | AM02149-SS | 280 | 75 |
| AD01391 | AM01784-AS | 138 | 30 | AM01785-SS | 269 | 51 |
| AD01392 | AM02327-AS | 147 | 30 | AM01785-SS | 269 | 51 |
| AD01404 | AM02341-AS | 130 | 28 | AM02364-SS | 281 | 76 |
| AD01405 | AM02341-AS | 130 | 28 | AM02365-SS | 279 | 76 |
| AD01406 | AM02342-AS | 134 | 28 | AM02364-SS | 281 | 76 |
| AD01407 | AM02342-AS | 134 | 28 | AM02365-SS | 279 | 76 |
| AD01408 | AM02345-AS | 129 | 28 | AM02364-SS | 281 | 76 |
| AD01409 | AM02345-AS | 129 | 28 | AM02365-SS | 279 | 76 |
| AD01410 | AM02346-AS | 133 | 28 | AM02364-SS | 281 | 76 |
| AD01411 | AM02346-AS | 133 | 28 | AM02365-SS | 279 | 76 |
| AD01424 | AM02345-AS | 129 | 28 | AM02363-SS | 230 | 76 |
| AD01476 | AM01784-AS | 138 | 30 | AM02456-SS | 193 | 51 |
| AD01522 | AM02133-AS | 141 | 30 | AM02510-SS | 232 | 51 |
| AD01523 | AM02509-AS | 140 | 30 | AM02512-SS | 233 | 51 |
| AD01524 | AM02508-AS | 120 | 30 | AM02043-SS | 231 | 51 |
| AD01525 | AM02523-AS | 117 | 8 | AM02522-SS | 250 | 55 |

TABLE 3-continued

Hif2α RNAi trigger duplexes with Duplex ID numbers.

| Duplex ID | Antisense Strand ID | SEQ ID NO. | Unmod. SEQ ID NO. | Sense Strand ID | SEQ ID NO. | Unmod. SEQ ID NO. |
|---|---|---|---|---|---|---|
| AD01526 | AM02525-AS | 119 | 26 | AM02524-SS | 268 | 80 |
| AD01527 | AM02527-AS | 118 | 16 | AM02526-SS | 252 | 60 |
| AD01528 | AM02529-AS | 148 | 35 | AM02528-SS | 251 | 58 |
| AD01546 | AM02523-AS | 117 | 8 | AM02546-SS | 235 | 55 |
| AD01547 | AM02525-AS | 119 | 26 | AM02547-SS | 242 | 80 |
| AD01548 | AM02527-AS | 118 | 16 | AM02548-SS | 241 | 60 |
| AD01549 | AM02529-AS | 148 | 35 | AM02549-SS | 240 | 58 |
| AD01554 | AM02604-AS | 122 | 30 | AM02512-SS | 233 | 51 |
| AD01555 | AM02605-AS | 124 | 30 | AM02510-SS | 232 | 51 |
| AD01654 | AM02848-AS | 132 | 30 | AM02852-SS | 272 | 50 |
| AD01655 | AM02848-AS | 132 | 30 | AM02512-SS | 233 | 51 |
| AD01656 | AM02849-AS | 131 | 30 | AM02853-SS | 273 | 50 |
| AD01657 | AM02849-AS | 131 | 30 | AM02856-SS | 234 | 51 |
| AD01658 | AM02850-AS | 121 | 30 | AM02853-SS | 273 | 50 |
| AD01659 | AM02850-AS | 121 | 30 | AM02856-SS | 234 | 51 |
| AD01884 | AM02998-AS | 160 | 40 | AM02510-SS | 232 | 51 |
| AD01885 | AM02998-AS | 160 | 40 | AM02999-SS | 229 | 72 |
| AD01886 | AM03000-AS | 151 | 36 | AM03004-SS | 244 | 82 |
| AD01887 | AM03001-AS | 149 | 36 | AM03005-SS | 246 | 82 |
| AD01888 | AM03002-AS | 152 | 36 | AM03006-SS | 243 | 82 |
| AD01889 | AM03003-AS | 150 | 36 | AM03007-SS | 245 | 82 |
| AD01890 | AM03008-AS | 154 | 37 | AM03010-SS | 236 | 56 |
| AD01891 | AM03008-AS | 154 | 37 | AM03011-SS | 238 | 56 |
| AD01892 | AM03009-AS | 153 | 37 | AM03012-SS | 237 | 56 |
| AD01893 | AM03009-AS | 153 | 37 | AM03013-SS | 239 | 56 |
| AD01910 | AM02605-AS | 124 | 30 | AM03058-SS | 270 | 51 |
| AD01911 | AM03059-AS | 146 | 30 | AM03058-SS | 270 | 51 |
| AD02073 | AM03009-AS | 153 | 37 | AM03307-SS | 274 | 56 |
| AD02074 | AM02605-AS | 124 | 30 | AM03308-SS | 170 | 51 |
| AD02691 | AM03465-AS | 161 | 41 | AM03467-SS | 194 | 51 |
| AD02692 | AM03465-AS | 161 | 41 | AM03469-SS | 201 | 51 |
| AD02693 | AM03465-AS | 161 | 41 | AM03471-SS | 208 | 51 |
| AD02694 | AM03465-AS | 161 | 41 | AM03473-SS | 200 | 51 |
| AD02695 | AM03465-AS | 161 | 41 | AM03475-SS | 204 | 51 |
| AD02733 | AM03513-AS | 162 | 41 | AM03516-SS | 203 | 51 |
| AD02734 | AM03514-AS | 165 | 41 | AM03516-SS | 203 | 51 |
| AD02735 | AM03517-AS | 90 | 4 | AM03519-SS | 202 | 54 |
| AD02857 | AM03685-AS | 159 | 41 | AM03687-SS | 205 | 51 |
| AD02858 | AM03688-AS | 167 | 41 | AM03687-SS | 205 | 51 |
| AD02859 | AM03689-AS | 163 | 41 | AM03687-SS | 205 | 51 |
| AD02860 | AM03690-AS | 166 | 41 | AM03687-SS | 205 | 51 |
| AD02861 | AM03685-AS | 159 | 41 | AM03692-SS | 185 | 72 |
| AD02862 | AM03517-AS | 90 | 4 | AM03694-SS | 183 | 73 |
| AD02873 | AM03465-AS | 161 | 41 | AM03708-SS | 182 | 72 |
| AD02874 | AM03465-AS | 161 | 41 | AM03710-SS | 189 | 72 |
| AD02875 | AM03517-AS | 90 | 4 | AM03712-SS | 190 | 73 |
| AD02876 | AM03465-AS | 161 | 41 | AM03714-SS | 180 | 72 |
| AD02949 | AM03465-AS | 161 | 41 | AM03774-SS | 174 | 51 |
| AD03011 | AM03465-AS | 161 | 41 | AM03829-SS | 184 | 72 |
| AD03012 | AM03465-AS | 161 | 41 | AM03830-SS | 227 | 72 |
| AD03013 | AM03465-AS | 161 | 41 | AM03831-SS | 275 | 50 |
| AD03187 | AM04001-AS | 155 | 38 | AM04003-SS | 209 | 56 |
| AD03188 | AM04004-AS | 84 | 1 | AM04006-SS | 210 | 57 |
| AD03189 | AM04007-AS | 156 | 39 | AM04009-SS | 195 | 43 |
| AD03190 | AM04010-AS | 85 | 2 | AM04012-SS | 196 | 44 |
| AD03191 | AM04010-AS | 85 | 2 | AM04014-SS | 198 | 44 |
| AD03192 | AM04015-AS | 83 | 2 | AM04017-SS | 199 | 44 |
| AD03193 | AM04018-AS | 86 | 2 | AM04020-SS | 197 | 44 |
| AD03215 | AM04040-AS | 168 | 41 | AM03469-SS | 201 | 51 |
| AD03216 | AM04040-AS | 168 | 41 | AM03475-SS | 204 | 51 |
| AD03253 | AM03689-AS | 163 | 41 | AM04107-SS | 175 | 51 |
| AD03254 | AM04101-AS | 91 | 4 | AM04117-SS | 179 | 54 |
| AD03255 | AM04102-AS | 164 | 42 | AM04121-SS | 172 | 46 |
| AD03256 | AM04103-AS | 92 | 5 | AM04119-SS | 173 | 47 |
| AD03257 | AM04104-AS | 157 | 41 | AM04107-SS | 175 | 51 |
| AD03258 | AM04105-AS | 88 | 4 | AM04117-SS | 179 | 54 |
| AD03259 | AM04106-AS | 87 | 3 | AM04109-SS | 176 | 52 |
| AD03260 | AM04105-AS | 88 | 4 | AM04109-SS | 176 | 52 |
| AD03261 | AM04105-AS | 88 | 4 | AM04111-SS | 171 | 52 |
| AD03262 | AM04105-AS | 88 | 4 | AM04113-SS | 178 | 54 |
| AD03263 | AM04105-AS | 88 | 4 | AM04115-SS | 177 | 53 |
| AD03264 | AM03690-AS | 166 | 41 | AM04107-SS | 175 | 51 |
| AD03265 | AM03689-AS | 163 | 41 | AM03692-SS | 185 | 72 |
| AD03266 | AM03689-AS | 163 | 41 | AM04122-SS | 181 | 51 |

TABLE 3-continued

Hif2α RNAi trigger duplexes with Duplex ID numbers.

| Duplex ID | Antisense Strand ID | SEQ ID NO. | Unmod. SEQ ID NO. | Sense Strand ID | SEQ ID NO. | Unmod. SEQ ID NO. |
|---|---|---|---|---|---|---|
| AD03345 | AM03689-AS | 163 | 41 | AM04241-SS | 206 | 51 |
| AD03346 | AM03689-AS | 163 | 41 | AM04243-SS | 207 | 51 |
| AD03347 | AM04244-AS | 158 | 41 | AM04243-SS | 207 | 51 |
| AD03348 | AM03689-AS | 163 | 41 | AM04246-SS | 186 | 72 |
| AD03349 | AM03689-AS | 163 | 41 | AM04248-SS | 187 | 72 |
| AD03505 | AM04101-AS | 91 | 4 | AM04451-SS | 188 | 74 |
| AD03506 | AM04452-AS | 93 | 6 | AM04454-SS | 192 | 77 |
| AD03507 | AM04455-AS | 89 | 6 | AM04454-SS | 192 | 77 |
| AD03508 | AM04452-AS | 93 | 6 | AM04457-SS | 191 | 77 |

A sense strand containing a sequence listed in Table 2B can be hybridized to any antisense strand containing a sequence listed in Table 2A provided the two sequences have a region of at least 90% complementarity over a contiguous 16, 17, 18, 19, 20, or 21 nucleotide sequence. Representative Hif2α RNA triggers are represented by the Duplex ID Nos. shown in Table 3. In some embodiments an Hif2α RNAi trigger consists of any of the Duplex ID Nos. presented herein. In some embodiments an Hif2α RNAi trigger comprises of any of the Duplex ID Nos. presented herein. In some embodiments, an Hif2α RNAi trigger comprises the sense strand and antisense strand nucleotide sequences of any of the Duplex ID Nos. presented herein. In some embodiments, an Hif2α RNAi trigger comprises the sense strand and antisense strand nucleotide sequences of any of the Duplex ID Nos. presented herein and a targeting group and/or linking group wherein the targeting group and/or linking group is covalently linked to the sense strand or the antisense strand. In some embodiments, an Hif2α RNAi trigger comprises the sense strand and antisense strand modified nucleotide sequences of any of the Duplex ID Nos. presented herein. In some embodiments, an Hif2α RNAi trigger comprises the sense strand and antisense strand modified nucleotide sequences of any of the Duplex ID Nos. presented herein and a targeting group and/or linking group wherein the targeting group and/or linking group is covalently linked to the sense strand or the antisense strand.

In some embodiments, a Hif2α RNAi trigger comprises an antisense strand comprising a nucleotide base sequence of nucleotides 2-21 of SEQ ID NO. 4. In some embodiments, a Hif2α RNAi trigger comprises an antisense strand comprising a nucleotide base sequence of nucleotides 2-21 of SEQ ID NO, 4 and a sense strand comprising a nucleotide base sequence of SEQ ID NO. 53.

In some embodiments, a Hif2α RNAi trigger comprises an antisense strand comprising a nucleotide base sequence of SEQ ID NO. 88, SEQ ID NO. 157, SEQ ID NO, 159, or SEQ NO. 163. In some embodiments, a Hif2α RNAi trigger comprises an antisense strand comprising a nucleotide base sequence of SEQ ID NO. 88 and a sense strand comprising a nucleotide base sequence of SEQ ID NO. 179. In some embodiments, a Hif2α RNAi trigger comprises an antisense strand comprising a nucleotide base sequence of SEQ ID NO, 88 and a sense strand comprising a nucleotide base sequence of SEQ ID NO. 177. In some embodiments, a Hif2α RNAi trigger comprises an antisense strand comprising a nucleotide base sequence of SEQ ID NO. 157 and a sense strand comprising a nucleotide base sequence of SEQ ID NO. 175. In some embodiments, a Hif2α RNAi trigger comprises an antisense strand comprising a nucleotide base sequence of SEQ ID NO. 159 and a sense strand comprising a nucleotide base sequence of SEQ ID NO. 185. In some embodiments, a Hif2α RNAi trigger comprises an antisense strand comprising a nucleotide base sequence of SEQ ID NO. 163 and a sense strand comprising a nucleotide base sequence of SEQ ID NO. 185.

In some embodiments, a Hif2α RNAi trigger comprises an antisense strand comprising SEQ ID NO. 88, SEQ ID NO. 157, SEQ ID NO. 159, or SEQ ID NO. 163. In some embodiments, a Hif2α RNAi trigger comprises an antisense strand comprising SEQ ID NO. 88 and a sense strand comprising SEQ ID NO. 179. In some embodiments, a Hif2α RNAi trigger comprises an antisense strand comprising SEQ ID NO. 88 and a sense strand comprising SEQ ID NO. 177. In some embodiments, a Hif2α RNAi trigger comprises an antisense strand comprising SEQ ID NO. 157 and a sense strand comprising SEQ NO. 175. In some embodiments, a Hif2α RNAi trigger comprises an antisense strand comprising SEQ ID NO. 159 and a sense strand comprising SEQ ID NO. 185. In some embodiments, a Hif2α RNAi trigger comprises an antisense strand comprising SEQ ID NO. 163 and a sense strand comprising SEQ ID NO. 185.

In some embodiments, a Hif2α RNAi trigger comprises an antisense strand comprising a nucleotide base sequence of nucleotides 2-21 of SEQ ID NO. 38. In some embodiments, a Hif2α RNAi trigger comprises an antisense strand comprising a nucleotide base sequence of nucleotides 2-21 of SEQ ID NO. 38 and a sense strand comprising a nucleotide base sequence of nucleotides 1-19 of SEQ ID NO. 56.

In some embodiments, a Hif2α RNAi trigger comprises an antisense strand comprising a nucleotide base sequence of SEQ ID NO. 86, SEQ NO, 155. SEQ ID NO. 156. In some embodiments, a Hif2α RNAi trigger comprises an antisense strand comprising a nucleotide base sequence of SEQ ID NO. 156 and a sense strand comprising a nucleotide base sequence of SEQ ID NO. 195. In some embodiments, a Hif2α RNAi trigger comprises an antisense strand comprising a nucleotide base sequence of SEQ ID NO, 86 and a sense strand comprising a nucleotide base sequence of SEQ ID NO. 197. In some embodiments, a Hif2α RNAi trigger comprises an antisense strand comprising a nucleotide base sequence of SEQ ID NO. 155 and a sense strand comprising a nucleotide base sequence of SEQ ID NO. 209.

In some embodiments, a Hif2α RNAi trigger comprises an antisense strand comprising SEQ ID NO. 86, SEQ ID NO. 155, SEQ ID NO. 156. In some embodiments, a Hif2α RNAi trigger comprises an antisense strand comprising SEQ ID NO. 156 and a sense strand comprising SEQ ID NO. 195. In some embodiments, a Hif2α RNAi trigger comprises an antisense strand comprising SEQ ID NO. 86 and a sense strand comprising SEQ ID NO. 197. In some embodiments, a Hif2α RNAi trigger comprises an antisense strand comprising SEQ ID NO. 155 and a sense strand comprising SEQ ID NO. 209.

In some embodiments, an Hif2α RNAi trigger contains or is conjugated to a targeting group, linking group, delivery polymer, delivery vehicle, and/or other non-nucleotide group. The targeting group, linking group, delivery polymer, delivery vehicle, and/or other non-nucleotide group can be covalently linked to the 3' and/or 5' end of either the sense strand and/or the antisense strand. In some embodiments, an Hif2α RNAi trigger can contains a targeting group, linking group, delivery polymer, delivery vehicle, or other non-nucleotide group linked to the 3' and/or 5' end of the sense strand. In some embodiments a targeting group, linking group, delivery polymer, delivery vehicle, or other non-nucleotide group is linked to the 5' end of an Hif2α RNAi trigger sense strand. In some embodiments, the targeting group, linking group, delivery polymer, delivery vehicle, and/or other non-nucleotide group is linked directly or indirectly to the trigger via a linker/linking group. In some embodiments, targeting group, linking group, delivery polymer, delivery vehicle, and/or other non-nucleotide group is linked to the trigger via a labile, cleavable, or reversible bond or linker.

A targeting group can enhance the pharmacokinetic or biodistribution properties of an RNAi trigger or conjugate to which it is attached to improve cell- or tissue-specific distribution and cell-specific uptake of the conjugate. In some instances, binding of a targeting group to a cell or cell receptor may initiate endocytosis. A targeting group can be monovalent, divalent, trivalent, tetravalent, or have higher valency. Representative targeting groups include, without limitation, compounds with affinity to cell surface molecule, cell receptor ligands, hapten, antibodies, monoclonal antibodies, antibody fragments, and antibody mimics with affinity to cell surface molecules.

The RNAi trigger molecules described herein may be synthesized having a reactive group, such as an amine group, at the 5'-terminus. The reactive group may be used to subsequently attach a targeting moiety using methods typical in the art.

In some embodiments, an Hif2α RNAi trigger includes a linking group conjugated to the trigger. The linking group facilitates covalent linkage of the trigger to a targeting group or delivery polymer or delivery vehicle. The linking group can be linked to the 3' or the 5' end of the RNAi trigger sense strand or antisense strand. In some embodiments, the linking group is linked to the RNAi trigger sense strand. In some embodiments, the linking group is conjugated to the 5' or 3' end of an RNAi trigger sense strand. In some embodiments a linking group is conjugated to the 5' end of an RNAi trigger sense strand. Examples of linking groups, include, but are not limited to: Alk-SMPT-C6, Alk-SS-C6, DBCO-TEG, Me-Alk-SS-C6, and C6-SS-Alk-Me, reactive groups such a primary amines and alkynes, alkyl groups, abasic ribose, ribitol, and/or PEG groups.

A linker or linking group is a connection between two atoms that links one chemical group (such as an RNAi trigger) or segment of interest to another chemical group (such as a targeting group or delivery polymer) or segment of interest via one or more covalent bonds. A labile linkage contains a labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

Targeting groups and linking groups include, but are not limited to, (Alk-C6), (Alk-C6-C6), (Alk-C6-SMPT-C6), (Alk-PEG5-C6), (Alk-PEG5-C6)(Alk-PEG5-Ser), (Alk-SMPT-C6), (Alk-SS-C6), (C6-SS-Alk-Me), (Chol-TEG), (DBCO-TEG), (Me-Alk-SS-C6), (NAG13), (NH2-C6). In some embodiments, any of the Hif2α RNAi trigger sense strands listed in Table 2B which contains a 3' or 5' targeting group or linking group, may alternatively contain no 3' or 5' targeting group or linking group, or may contain a different 3' or 5' targeting group or linking group including, but not limited to, those depicted in Table 4.

In some of the targeting group and linking group structures shown in Table 4, the RNAi trigger is shown and denoted by Trigger, RNA, R, or R1 or R2 (i.e. Trigger, RNA or R1 or R2 each comprises the RNAi trigger). For example, with respect to (Alk-C6-Ser), (Alk-PEG5-Ser), and (Alk-PEG13-Ser), one of R1 and R2 comprises the RNAi trigger and the other can be a hydrogen.

TABLE 4

Structures representing targeting groups and linking groups.

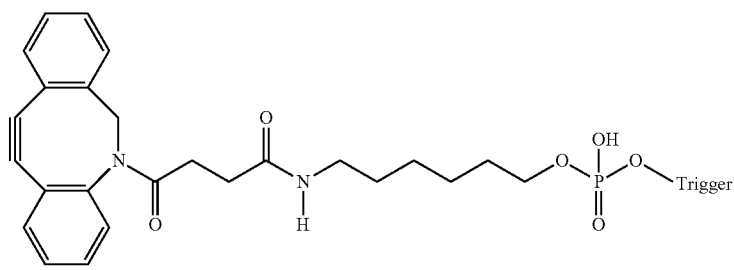

(Alk-C6)-Trigger

TABLE 4-continued
Structures representing targeting groups and linking groups.
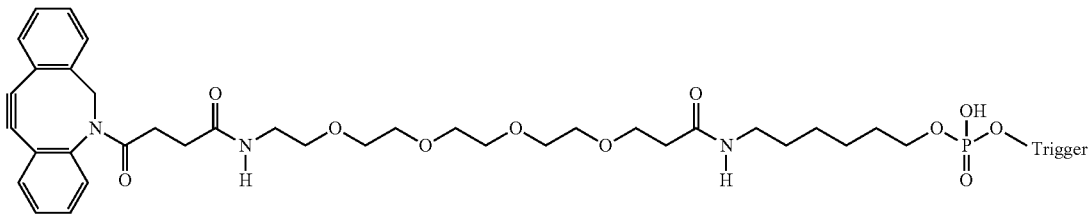
(Alk-PEG4-C6)-Trigger
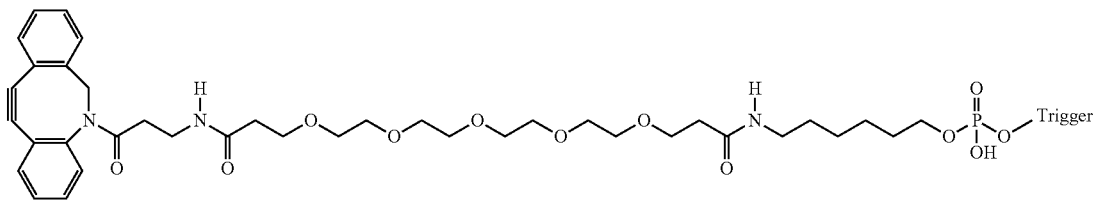
(Alk-PEG5-C6)-Trigger or Trigger-(C6-PEG5-Alk)
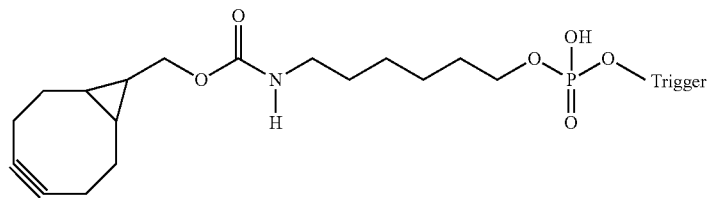
(Alk-BC9-C6)-Trigger
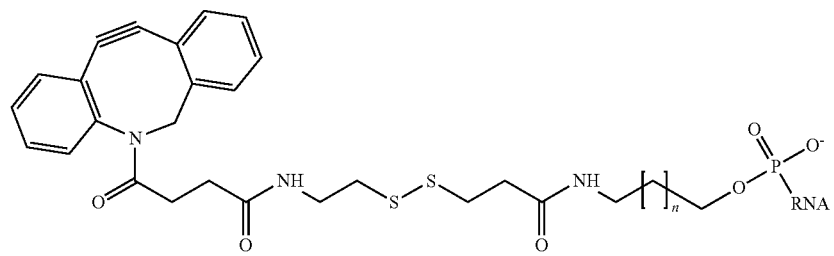
(Alk-SS-C6)-RNA or RNA-(C6-SS-Alk); (n = 1-10), In some embodiments, n = 4
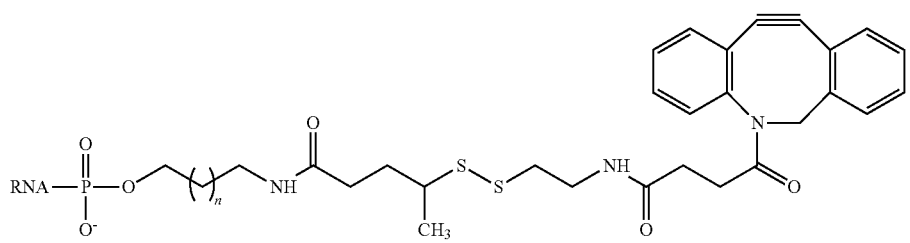
RNA-(C6-SS-Alk-Me) or ((Me-Alk-SS-C6)-RNA; (n = 1-10), In some embodiments, n = 4.

TABLE 4-continued
Structures representing targeting groups and linking groups.
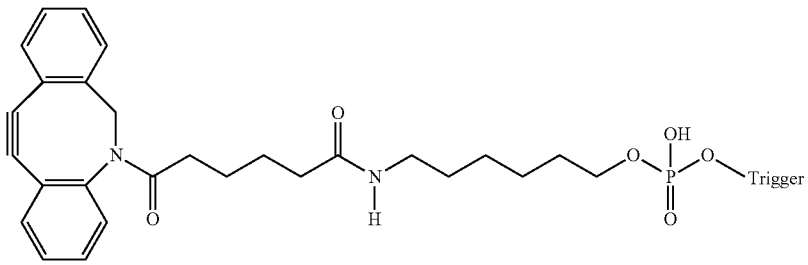
(Alk-C6-C6)-Trigger or Trigger-(C6-C6-Alk)
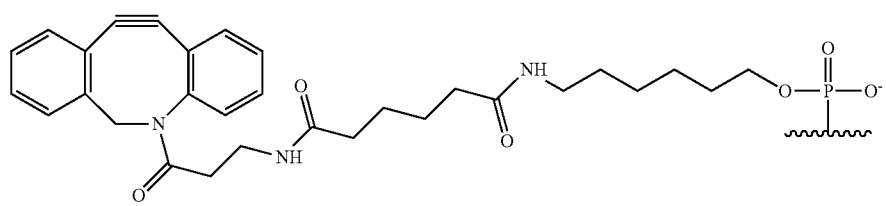
(Alk-NHCO-C6)
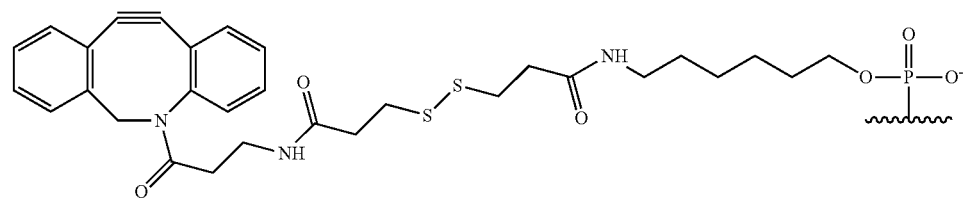
(Alk-NHCO-SS-C6)
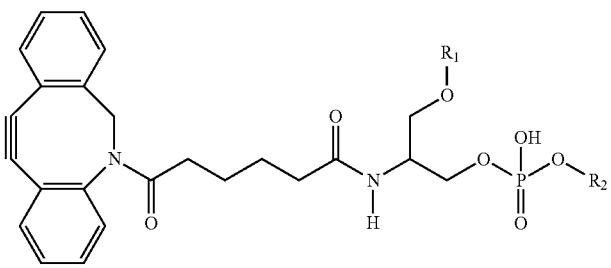
(Alk-C6-Ser)-RNA or RNA-(Ser-C6-Alk), RNA is R1 or R2
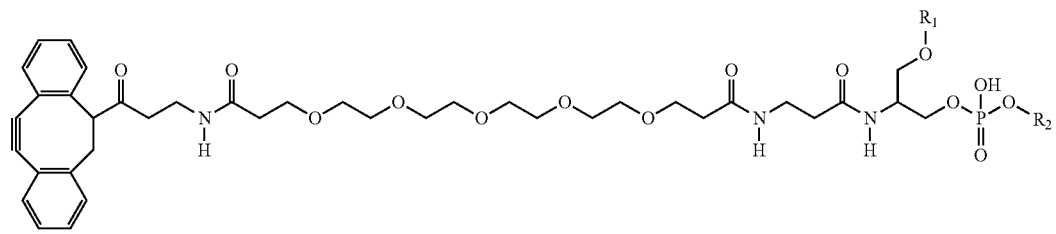
(Alk-PEG5-Ser)-RNA, RNA is R1 or R2

TABLE 4-continued
Structures representing targeting groups and linking groups.
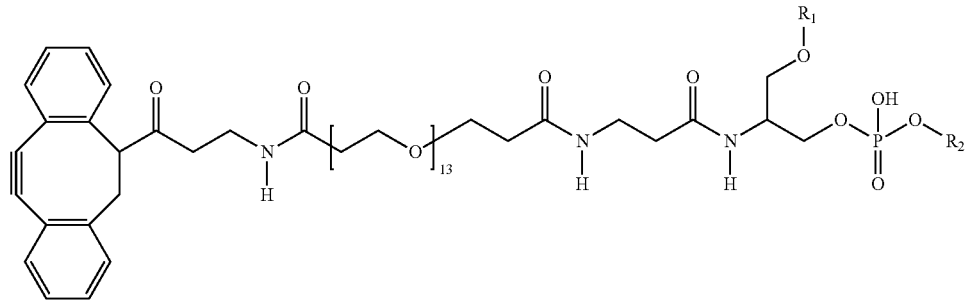
(Alk-PEG13-Ser)-RNA, RNA is R1 or R2
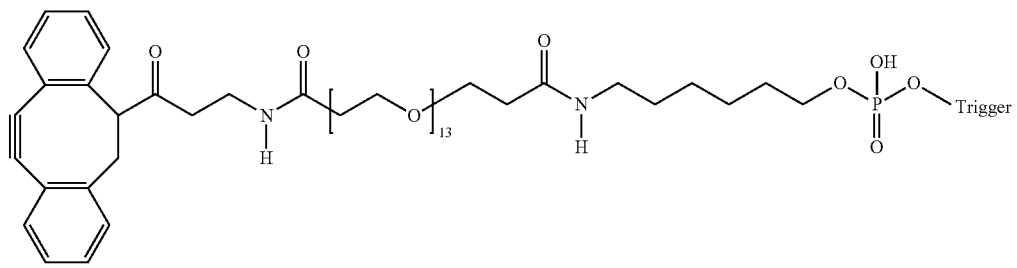
(Alk-PEG13-C6)-Trigger
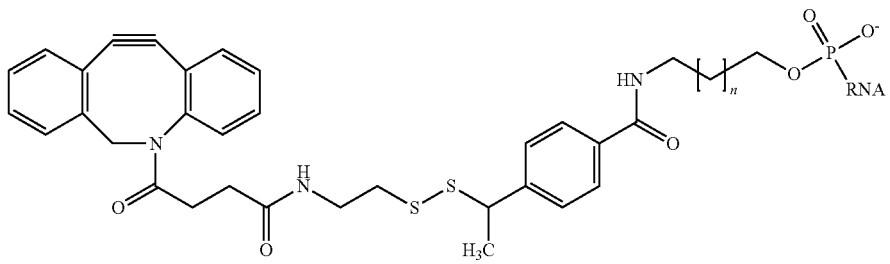
RNA-(C6-SMPT-Alk) or (Alk-SMPT-C6)-RNA, n = 1-10, In some embodiments, n = 4
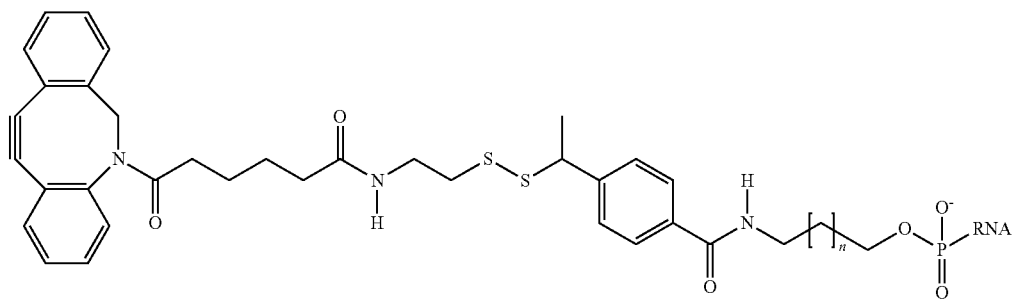
(Alk-C6-SMPT-C6)-RNA or RNA-(C6-SMPT-C6-Alk), n = 1-10, In some embodiments, n = 4

TABLE 4-continued
Structures representing targeting groups and linking groups.
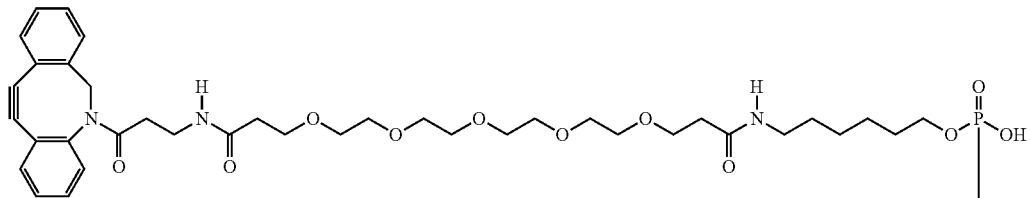
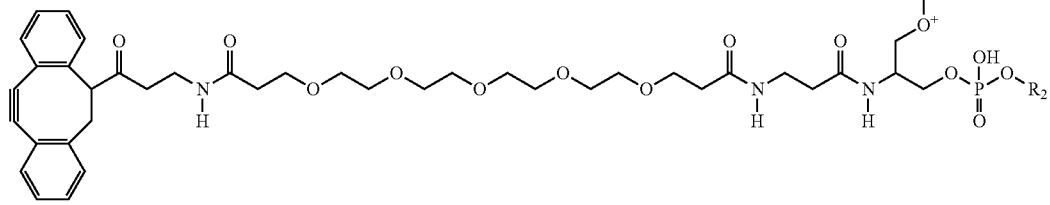
(Alk-PEG5-C6)(Alk-PEG5-Ser)-RNA
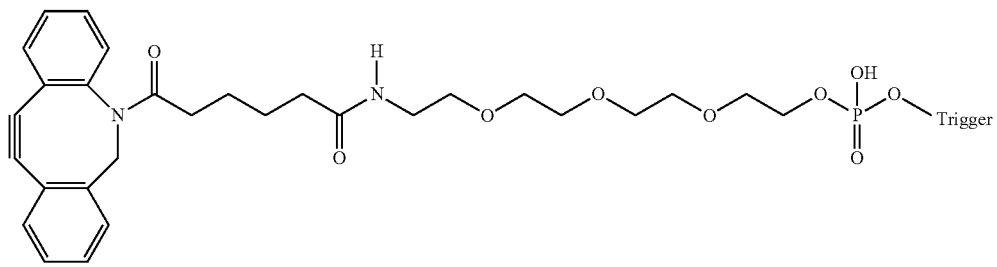
(DBCO-TEG)-Trigger
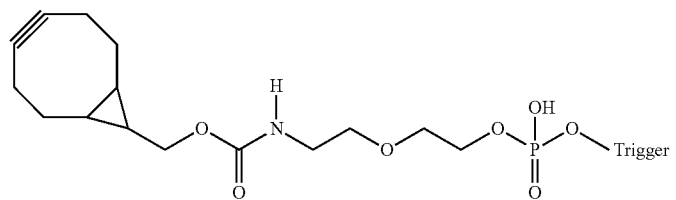
(BCN)-Trigger
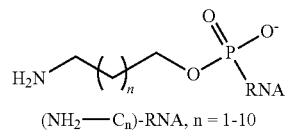
(NH$_2$—C$_n$)-RNA, n = 1-10
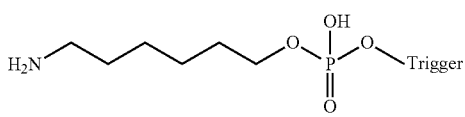
(NH2-C6)-Trigger or Trigger-(C6-NH2)
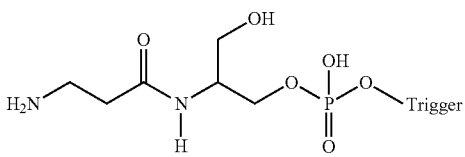
(NH2-Ser)-Trigger or Trigger-(Ser-NH2)

TABLE 4-continued

Structures representing targeting groups and linking groups.

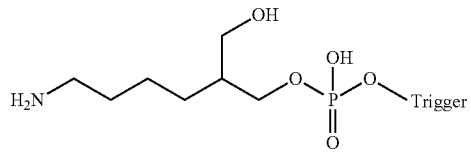

(NH2-C7)-Trigger

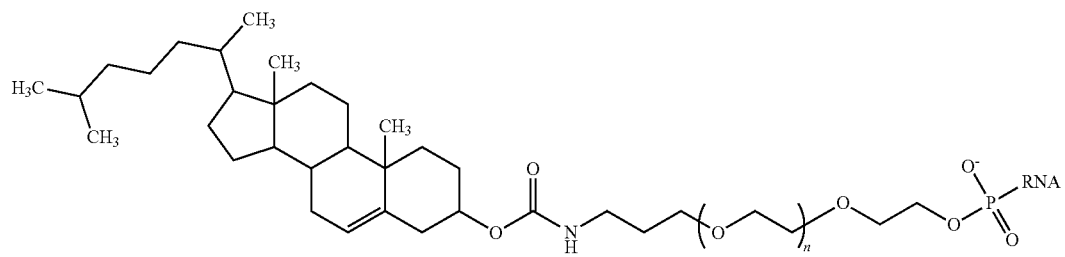

(Chol-TEG)-RNA, n = 1-10, In some embodiments, n = 2.

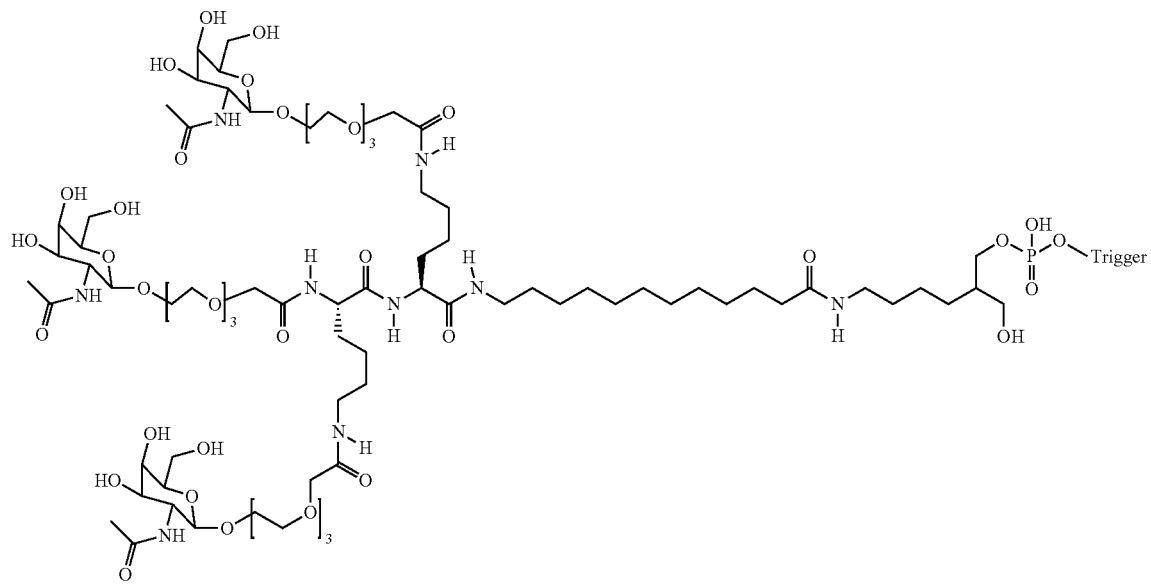

(NAG13)-Trigger

In some embodiments, a delivery vehicle may be used to deliver an RNAi trigger to a cell or tissue. A delivery vehicle is a compound that improves delivery of the RNAi trigger to a cell or tissue. A delivery vehicle can include, or consist of, but is not limited to: a polymer, such as an amphipathic polymer, a membrane active polymer, a peptide, a melittin peptide, a melittin-like peptide, a lipid, a reversibly modified polymer or peptide, or a reversibly modified membrane active polyamine.

In some embodiments, the RNAi triggers can be combined with lipids, nanoparticles, polymers, liposomes, micelles, DPCs or other delivery systems available in the art. The RNAi triggers can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

In some embodiments, pharmaceutical compositions for delivering an Hif2α RNAi trigger to a tumor cell in vivo are described. Such pharmaceutical compositions can include, but are not limited to, an Hif2α RNAi trigger conjugated to delivery polymer to form an RNAi trigger-delivery polymer conjugate. In some embodiments, the delivery polymer is a membrane active polyamine. In some embodiments, the delivery polymer is a reversibly modified membrane active polyamine.

Hif2α RNAi Trigger-Deliver Polymer Conjugates

In some embodiments, we describe compositions represented by the formula:

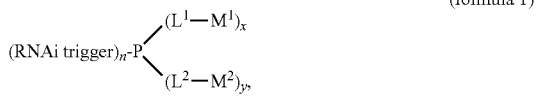

(formula 1)

wherein RNAi trigger is an Hif2α RNAi trigger as described herein, P is a membrane active polyamine, $M^1$ comprises a targeting group linked to P via reversible physiologically labile linkage $L^1$, and $M^2$ comprises a steric stabilizer linked to P via reversible physiologically labile linkage $L^2$, x is greater than 1, y is greater than or equal to 0. $(M^2-L^2)_y$-P-$(L^1-M^1)_x$ is not membrane active. As used herein, $(M^2-L^2)_y$-P-$(L^1-M^1)_x$ refers to a delivery polymer. Cleavage of $(L^1-M^1)$ and $(M^2-L^2)$ restores P to a membrane active state. In some embodiments, the value of x+y is greater than 80%, greater than 90%, or greater than 95% of the number of primary amines of P. In some embodiments, the value of x+y is greater than 80%, greater than 90%, or greater than 95% of the number of primary amines on a population of P. The value of n can be from 0.2.5 to 5 (one (1) RNAi trigger per every 4 polymers to 5 RNAi triggers per polymer). In some embodiments, the value of n is 0.5 to 5. In some embodiments, n is 0.5-2. In some embodiments, n is 0.8-1.6. In some embodiments, x is 1-20, 2-20, 3-20, 4-20, 5-20, 6-20, 7-20, 8-20, 9-20, 10-20, 11-20, 12-20, 13-20, 14-20, or 15-20.

In some embodiments, $M^1$ comprises an integrin-binding compound. In some embodiments, the integrin-binding compound comprises an $α_vβ_3$-binding compound. In some embodiments, the integrin-binding compound comprises an RGD ligand. In some embodiments, the $α_vβ_3$-binding compound comprises an RGD ligand. In some embodiments the RGD ligand comprises an RGD mimic. In some embodiments, the steric stabilizer comprises a polyethylene glycol (PEG). In some embodiments, cleavage of $L^1$ and/or $L^2$ restores an unmodified amine on P. In some embodiments, $(L^1-M^1)$ and $(L^2-M^2)$ are independently tetrapeptide modifying agents and/or dipeptide modifying agents. In some embodiments, $L^1$ and $L^2$ are independently tetrapeptide linkages or dipeptide-PABC (p-amidobenzyl-carbamate) linkages. In some embodiments, $L^1$ and $L^2$ are tetrapeptide linkages. In other embodiments, $L^1$ and $L^2$ are dipeptide-PABC linkages. In some embodiments, $L^1$ is a dipeptide-PABC linkage and $L^2$ is a tetrapeptide linkage. In other embodiments, $L^1$ is a tetrapeptide linkage and $L^2$ is a dipeptide-PABC linkage. In some embodiments, a tetrapeptide linkage is an FCitFP (Phenylalanine-Citrulline-Phenylalanine-Proline) tetrapeptide linkage. In some embodiments, a dipeptide-PABC linkage is an ACit-PABC linkage. For x=2 or more, $L^1$ can be all tetrapeptide linkages, all dipeptide-PABC linkages, or a combination tetrapeptide linkages and dipeptide-PABC linkages. For y=2 or more, $L^2$ and be all tetrapeptide linkages, all dipeptide-PABC linkages, or a combination tetrapeptide linkages and dipeptide-PABC linkages.

In some embodiments, a described Hif2α RNAi trigger is conjugated to a reversibly modified membrane active polyamine to form an RNAi trigger-delivery polymer conjugate. In some embodiments, the RNAi trigger-delivery polymer conjugate comprises the formula represented by:

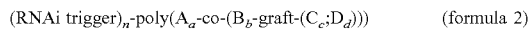

(formula 2)

wherein
A is a hydrophobic group-containing monomeric unit,
B is a primary amine-containing monomeric unit,
C comprises an integrin-binding ligand linked (i.e., grafted) to a primary amine-containing monomeric unit via a reversible physiologically labile linkage,
D comprises a steric stabilizer linked (i.e., grafted) to a primary amine-containing monomeric unit via a reversible physiologically labile linkage,
a is an integer greater than zero,
b is an integer greater than or equal to two,
c is an integer greater than or equal to one,
d is an integer greater than or equal to one,
the value of c+d is greater than 80%, greater than 85%, greater than 90%, or greater than 95% of the value of b,
poly($A_a$-co-$B_b$) is a membrane active polyamine copolymer having A and B monomeric units
RNAi trigger comprises a Hif2α RNAi trigger described herein, and
n has a value from 0.2.5 (i.e., conjugated to only one out of every four delivery polymers) to 5.0.

Poly($A_a$-co-($B_b$-graft-($C_c$; $D_d$))) is not membrane active. In some embodiments, the integrin-binding compound comprises an $α_vβ_3$-binding compound. In some embodiments, the integrin-binding compound comprises an RGD ligand, such as an RGD mimic. In some embodiments, the $α_vβ_3$-binding compound comprises an RGD ligand, such as an RGD mimic. In some embodiments, the steric stabilizer comprises a polyethylene glycol (PEG). In some embodiments, the PEG contains 2 to 25 ethylene glycol units. In some embodiments, c is any integer from 1-75, 1-50, 5-50, 5-40, 5-30, 5-25, 5-20, 5-15, 10-35, 10-30, 10-25, 10-20, or 15-20. In some embodiments, n has a value from 0.5 to 2. In some embodiments, the ratio A:B (i.e., a:b) is 30:70 to 60:40. In some embodiments, the ratio A:B is 60:40 to 40:60. In some embodiments, the ratio A:B is about 45±5:55±5. In some embodiments, the ratio A:B is about 44:56. In some embodiments, the ratio A:B is about 46:54. In some embodiments, the molecular weight (Mw) of the polymer is 30 kDa-70 kDa. In other embodiments, the Mw of the polymer is 40 kDa-60 kDa. In other embodiments, the Mw of the polymer is 40 kDa-50 kDa. In yet other embodiments, the Mw of the polymer about 43 kDa to about 48 kDa. In some embodiments, the polymer has a polydispersity index (PDI) less than 1.4, less than 1.3, 1.25, less than 1.2, less than 1.15, or less than 1.1. In some embodiments, the polymer contains a terminal azide group for attachment of an RNAi trigger. In some embodiments, n is 0.8-1.6. In some embodiments, n is 1±0.5. In some embodiments, c is 1-20, 2-20, 3-20, 4-20, 5-20, 6-20, 7-20, 8-20, 9-20, 10-20, 11-20, 12-20, 13-20, 14-20, or 15-20. In some embodiments, the value of c+d is greater than 80%, greater than 90%, or greater than 95% of the value of b. In some embodiments, C is RGD-$PEO_x$-FcitFPro and D is $PEG_y$-ACit-PABC, wherein x is 1-50, y is 4-30. In some embodiments, x is greater than y.

In some embodiments, polyamine poly($A_a$-co-$B_b$) is a poly(acrylate) random copolymer wherein A is a hydrophobic group-containing acrylate monomer and B is a primary amine-containing acrylate monomer. In some embodiments A is a propyl acrylate monomer and B is an ethoxyethylamine acrylate monomer.

Membrane active polyamines are membrane active and therefore capable of disrupting plasma membranes or lysosomal/endocytic membranes. As used herein, membrane active polyamines are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the peptide's activity in at least one the following assays: red blood cell lysis (hemolysis), liposome leakage, liposome fusion, cell fusion, cell lysis, and endosomal release. Peptides, or modified peptides that preferentially cause disruption of endosomes or lysosomes over plasma membranes are considered endosomolytic. A reversibly modified membrane active polyamine is an example of an endosomolytic peptide. The effect of membrane active polymers on a cell membrane may be transient. Membrane active polymers possess affinity for the membrane and cause a denaturation or deformation of bilayer structures. Delivery of a RNAi trigger to a cell is mediated by the membrane active polyamine disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm. A preferred polymer is an amphipathic poly (acrylate) random copolymer.

Integrin-Binding Compound

An integrin-binding compound has affinity for one or more integrins expressed on a cell surface. A non-limiting example of an integrin includes an $\alpha_v\beta_3$ integrin. Examples of integrin-binding compounds include, but are not limited to: $\alpha_v\beta_3$-binding compounds, RGD ligand. RGD ligands include RGD peptide-containing compounds and RGD mimic-containing compounds. As used herein, an RGD peptide comprises an arginine-glycine-aspartate tripeptide. An RGD peptide may be conformationally constrained. An RGD peptide may have non-peptide components linked to the RGD amino acid sequence.

As used herein, an RGD ligand comprises an RGD peptide or RGD mimic <1500 kDa in size that binds to (has affinity for) an integrin, such as an alpha v/beta 3 ($\alpha v\beta 3$ or $\alpha_v\beta_3$) integrin.

As used herein, an RGD mimic is a non-peptide synthetic molecule other than an RDG peptide that biologically mimics the active determinants of an RGD peptide, an integrin-binding RGD portion of an integrin-binding protein, or an $\alpha_v\beta_3$ integrin-binding RGD motif. An RGD mimic may contain one or two naturally occurring amino acids linked via amide bonds. An RGD mimetic may be a modified peptide, contain non-standard amino acids or non-standard amino acid side chains.

In one embodiment, an RGD ligand comprises a guanidinium group linked to a glycine-aspartate dipeptide via an amide bond. Guanidinium groups of the invention have the structure represented by:

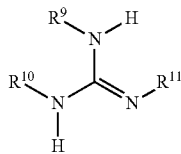

wherein $R^9$ and $R^{10}$ are independently hydrogen or alkyl and may by connected to form a ring, and $R^{11}$ is a linker connecting the guanidinium group to the glycine-aspartate dipeptide. The guanidinium group includes both the structure represented above and its resonance structures. A preferred linker is: —(CRR')—(CRR')—(CRR')— or —(CRR')—(CRR')—(CRR')—(CRR')—, wherein: a) each R is independently optional and if present is independently hydrogen, alkyl, or aryl, b) R' is independently hydrogen, alkyl, aryl, or $NH_2$, and c) each carbon (C) may be linked by single bonds, a single bond and a double bond, or aromatic bonds.

In some embodiments, an RGD mimic contains a phenoxy group attached to the aspartate amino acid. In some embodiments, an RGD mimic comprises a quanidinium-glycine-aspartate-4-aminophenoxy compound. In some embodiments, a quanidinium-glycine-aspartate-4-aminophenoxy compound comprises the structure represented by:

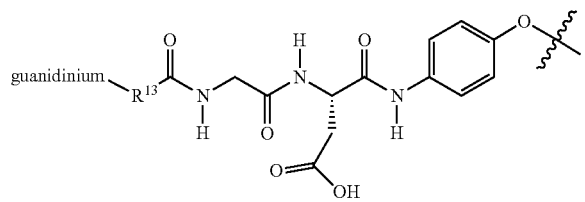

wherein $R^{13}$ is:

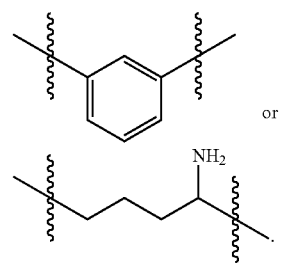

In some embodiments, a guanidinium is

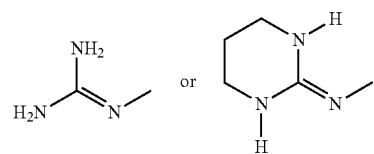

and their resonance structures.

In some embodiments, an RGD mimic comprises the structure represented by:

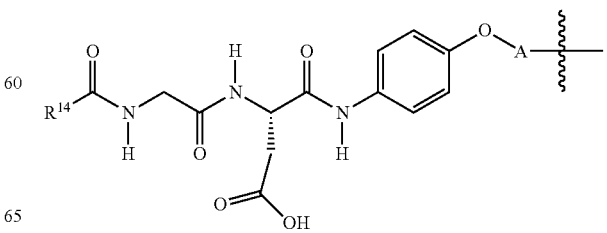

wherein:

R$^{14}$ is

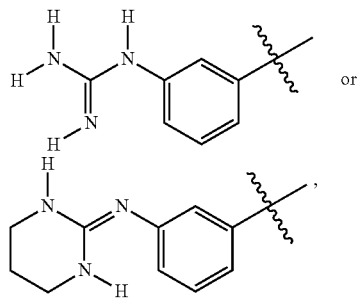

and

A comprises a linker. The linker connects the RGD mimic to another molecule such as a dipeptide amidobenzyl-carbonate or tetrapeptide, provides for increased solubility, or provides a means for covalent linkage to another molecule.

Steric Stabilizer

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. In some embodiments, a steric stabilizer is a polyethylene glycol (PEG) or PEG derivative. In some embodiments, a PEG can have about 1-500 ethylene monomers or units. In some embodiments, the PEG contains 2-25 ethylene units. In some embodiments, the PEG contains 4-30 ethylene units. In some embodiments, PEG contains 5-24 ethylene units. In some embodiments, a PEG has a molecular weight average of about 85-20,000 Daltons (Da). In some embodiments a PEG has a molecular weight of about 85-1000 Da. As used herein, steric stabilizers prevent or inhibit intramolecular or intermolecular interactions of a polymer to which it is attached relative to the polymer containing no steric stabilizer in aqueous solution.

Reversible Physiologically Labile Linkages/Modifying Agents

A membrane active polyamine may be reversibly modified. Reversible modification can be accomplished through reversible attachment of modifying agents to primary amines of the membrane active polyamine.

In some embodiments, a reversible physiologically labile linkage comprises a tetrapeptide linkage. In some embodiments, P-(L$^1$-M$^1$)$_x$ and/or P-(L$^2$-M$^2$)$_y$ (of formula 1) comprises:

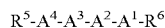

wherein

R$^5$ comprises a targeting group (M$^1$) or a steric stabilizer (M$^2$),

A$^4$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^3$ is an uncharged hydrophilic L amino acid wherein the hydrophobicity index (Monera et al, J. Protein Sci. 1995, 1, 319) at pH 7 is 28 or less, normalized to glycine, as it relates to the composition of amino acid side chain (R-group), A$^2$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^1$ is L-proline, L-leucine, or L-N-methyl alanine, and R$^6$ is P, wherein P is a membrane active polyamine of formula 1.

In some embodiments, A$^1$ is prolific, A$^2$ and A$^4$ are independently alanine, valine, leucine, isoleucine or phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_6$, respectively), and A$^3$ is citrulline or asparagine (side chains or —(CH$_2$)$_3$NHCONH$_2$ or —CH$_2$CONH$_2$, respectively).

In some embodiments, A$^1$ is proline, A$^2$ and A$^4$ are phenylalanine, and A$^3$ is citrulline (FCitFPro). In some embodiments, A$^1$ is proline, A$^2$ is phenylalanine, and A$^3$ is citrulline, and A$^4$ is alanine (ACitFPro).

In some embodiments, a tetrapeptide modifying agent has the structure represented by:

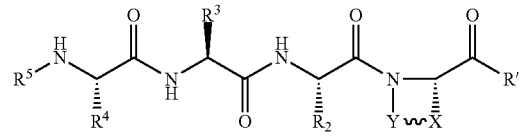

wherein,

R$^5$ comprises a targeting group (M$^1$) or a steric stabilizer (M$^2$),

R$^4$ is a side chain of a natural, non-natural isomeric, or synthetic hydrophobic amino acid, R$^3$ is a side chain of an uncharged hydrophilic amino acid, preferably citrulline, R$^2$ is a side chain of a natural, non-natural isomeric, or synthetic hydrophobic amino acid, preferably phenylalanine, X and Y are:
 a) (CH$_2$)$_2$(CH$_3$)$_2$ and H, respectively (tetrapeptide A$^1$ is Leucine),
 b) CH$_3$— and CH$_3$—, respectively (tetrapeptide A$^1$ is N-methyl alanine), or
 c) CH$_2$— and CH$_2$—CH$_2$—, respectively (tetrapeptide A$^1$ is proline); and R' is

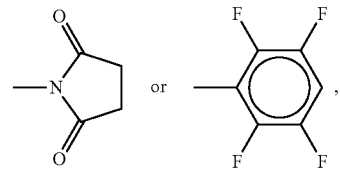

Reaction of the tetrapeptide modifying agent a polyamine yields P-(L-M).

In some embodiments, R⁴ is a side chain of phenylalanine or alanine. In some embodiments, R³ is a side chain of citrulline. In some embodiments, R² is a side chain of phenylalanine.

In some embodiments, the membrane active polyamine is modified with dipeptide modifying agents (dipeptide-PABC-PNP modifying agent) having the general form:

R-A¹A²-amidobenzyl-carbonate wherein R comprises a steric stabilizer or targeting group, A¹ is a hydrophobic amino acid, and A² is a hydrophilic uncharged amino acid. Reaction of the modifying agent carbonate with a polymer amine yields a carbamate linkage. In some embodiments, the amidobenzyl group is a p-amidobenzyl group. In some embodiments, the carbonate is an activated amine reactive carbonate. In some embodiments, dipeptide-PABC cleavable linkers have the general structure:

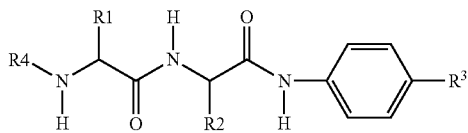

wherein R4 comprises a targeting group or steric stabilizer, R3 comprises an amine reactive carbonate moiety, such as a para-nitrophenyl group, R1 is the side chain of a hydrophobic amino acid, such as Phenylalanine or Alanine and R2 is the side chain of a hydrophilic uncharged are amino acid, such as citrulline (Cit). In some embodiments, R1 is the side chain of Phenylalanine or Alanine. In some embodiments, R2 is the side chain of citrulline (Cit).

In some embodiments, an RGD modifying agent comprises the structure represented by:

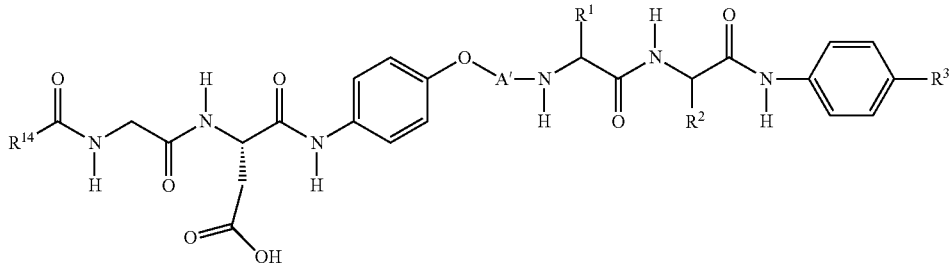

wherein R¹⁴ is a guanidinium-containing group as defined above, A' comprises a PEG-containing linker, R¹ is a side chain of a Phenylalanine or Alanine, R² is a side chain of citrulline, and R³ is an amine-reactive carbonate.

A delivery polymer can include a polyamine reversibly modified by reaction of primary amines on the polymer with a disubstituted alkylmaleic anhydride:

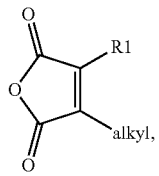

wherein R1 comprises a targeting group or a steric stabilizer.

In some embodiments, the disubstituted alkylmaleic anhydride has the structure represented by:

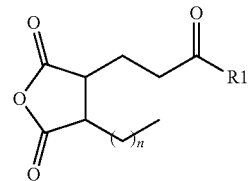

wherein R1 comprises an targeting group or a steric stabilizer.

In some embodiments, a targeting group (e.g., RGD ligand) is linked to a modifying agent via a linker, such as a PEG linker. The PEG linker can have 1-50 ethylene units.

RGD and PEG modifying agents are shown in FIGS. 1-7.

In some embodiments, we describe compositions represented by the formula:

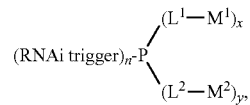

wherein: RNAi trigger is an Hif2α RNAi trigger, n is 0.5-5, P is a membrane active polyamine, $L^1$-$M^1$ comprises RGD-$PEG_a$-FCitFPro, a is 1-50, x is 1-20, $L^2$-$M^2$ comprises $PEG_b$-ACit-PABC-, b is 4-30, and y is greater than or equal to 0, and $(M^2-L^2)_y$-P-$(L^1-M^1)_x$ is not membrane active. In some embodiments, the value of x+y is greater than 80%, greater than 90%, or greater than 95% of the number of primary amines of P. In some embodiments, n is 0.5-2. In some embodiments, n is 0.8-1.6. In some embodiments, x is 2-20, 3-20, 4-20, 5-20, 6-20, 7-20, 8-20, 9-20, 10-20, 11-20, 12-20, 13-20, 14-20, or 15-20. In some embodiments, the value of a is greater than the value of b.

Pharmaceutical Compositions

In some embodiments, at least one of the described Hif2α RNAi triggers is used in the preparation of a pharmaceutical composition (i.e., medicament) for treatment of a subject that would benefit from reduction or inhibition in Hif2α expression. These pharmaceutical compositions are useful in the inhibition of the expression of the Hif2α gene in a cell, a tissue, or an organism. In some embodiments, the described pharmaceutical compositions are used to treat a subject having a disease or disorder that would benefit from reduction or inhibition in Hif2α expression.

As used herein, a pharmaceutical composition or medicament comprises a pharmacologically effective amount of at least one of the described Hif2α RNAi triggers or Hif2α RNAi trigger-containing conjugates and one or more pharmaceutically acceptable excipients. Pharmaceutically acceptable excipients (excipients) are substances other than the Active Pharmaceutical ingredient (API, therapeutic product, e.g., RNAi trigger) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi triggers may be used as "pharmaceutical compositions". As used herein, "pharmacologically effective amount," "therapeutically effective amount," or simply "effective amount" refers to that amount of an RNAi trigger to produce the intended pharmacological, therapeutic or preventive result.

In some embodiments, a described Hif2α RNAi trigger s combined one or more additional therapeutics or treatments including, but not limited to: a second Hif2α RNAi trigger or other RNAi agent, a small molecule drug, an antibody, an antibody fragment, and/or a vaccine.

The described RNAi triggers and pharmaceutical compositions comprising Hif2α RNAi triggers disclosed herein may be packaged or included in a kit, container, pack, or dispenser. The Hif2α RNAi triggers and pharmaceutical compositions comprising said Hif2α RNAi triggers may be packaged in pre-filled syringes or vials.

Cells, tissues, and non-human organisms that include at least one of the Hif2α RNAi triggers described herein is contemplated. The cell, tissue, or non-human organism is made by delivering the RNAi trigger to the cell, tissue, or non-human organism by any means available in the art. In some embodiments, the cell is a mammalian cell, including, but no limited to, a human cell. The cell, tissue, or non-human organisms are useful for research or as research tools (e.g., drug testing or diagnoses).

Method of Treatment

In some embodiments, the Hif2α RNAi triggers described herein are used to treat a subject having a disease or disorder that would benefit from reduction or inhibition in Hif2α expression. In some embodiments, the described Hif2α RNAi triggers are used to treat or prevent at least one symptom in a subject having a disease or disorder that would benefit from reduction or inhibition in Hif2α expression. The subject is administered a therapeutically effective amount of any one or more of the described RNAi triggers thereby treating the symptom.

In some embodiments, the Hif2α RNAi triggers are used to treat or manage a clinical presentation wherein a subject in need of such treatment, prevention or management is administered a therapeutically or prophylactically effective amount of one or more of the Hif2α RNAi triggers or Hif2α RNAi trigger-containing compositions described herein. In some embodiments, the method comprises administering a composition comprising an Hif2α RNAi trigger molecule described herein to a mammal to be treated.

Representative diseases that would benefit from a reduction and/or inhibition of Hif2α gene expression include, but are not limited to, cancer, renal cancer, clear cell renal cell carcinoma, non-small cell lung cancer, astrocytoma (brain cancer), bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, melanoma, multiple myeloma, ovarian cancer, rectal cancer, metastases, gingivitis, psoriasis, Kaposi's sarcoma-associated herpesvirus, preeclampsia, inflammation, chronic inflammation, neovascular diseases, and rheumatoid arthritis.

In some embodiments, an Hif2α RNAi trigger can be used to inhibit expression of Hif2α in a cell, group of cells, or a tissue, e.g., in a subject. In some embodiments, an Hif2α RNAi trigger can be used to formulate a composition for inhibiting expression of Hif2α in a cell, group of cells, or a tissue, e.g., in a subject. In some embodiments, a therapeutically effective amount of one type (or several different types) of Hif2α RNAi triggers as described herein is administered to a subject, thereby inhibiting expression of Hif2α in the subject (e.g., an amount effective to inhibit expression of Hif2α in the subject).

As used herein, the terms "silence," "reduce," "inhibit," "down-regulate," or "knockdown gene expression," when referring to an Hif2α gene, mean that the expression of the gene, as measured by the level of RNA transcribed from the gene or the level of polypeptide, protein, or protein subunit translated from the mRNA in a cell, group of cells, or tissue, in which the Hif2α gene is transcribed, is reduced when the cell, group of cells, or tissue, is treated with the described Hif2α RNAi triggers as compared to a second cell, group of cells, or tissue that has or has not been so treated or compared to the same cell, group of cells, or tissue, prior to administration of the Hif2α RNAi trigger.

In some embodiments, the gene expression level and/or mRNA level of Hif2α in a subject to whom a described Hif2α RNAi trigger is administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject prior to being administered the Hif2α RNAi trigger or to a subject not receiving the Hif2α RNAi trigger. The gene expression level and/or mRNA level in the subject may be reduced in a cell, group of cells, and/or tissue of the subject. In some embodiments, the protein level of Hif2α in a subject to whom a described Hif2α RNAi trigger has been administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject prior to being administered the Hif2α

RNAi trigger or to a subject not receiving the Hif2α RNAi trigger. The protein level in the subject may be reduced in a cell, group of cells, tissue, blood, and/or other fluid of the subject. A reduction in gene expression, mRNA, or protein levels can be assessed by any methods known in the art. Reduction or decrease in Hif2α mRNA level and/or protein level are collectively referred to herein as a reduction or decrease in Hif2α or inhibiting or reducing the expression of Hif2α.

"Introducing into a cell", when referring to an RNAi trigger, means functionally delivering the RNAi trigger into a cell. By functional delivery, it is meant that the RNAi trigger is delivered to the cell and has the expected biological activity, (e.g., sequence-specific inhibition of gene expression).

The route of administration is the path by which an RNAi trigger is brought into contact with the body. In general, methods of administering drugs and nucleic acids for treatment of a subject are well known in the art and can be applied to administration of the compositions described herein. The compounds described herein can be administered via any suitable route in a preparation appropriately tailored to the particular route. Thus, the compounds described herein can be administered by injection, for example, intravenously, intramuscularly, intracutaneously, subcutaneously, or intraperitoneally.

In some embodiments, the Hif2α RNAi trigger molecules or compositions described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with an Hif2α RNAi trigger described herein. For example, delivery can be by local administration, (e.g., direct injection, implantation, or topical administering), systemic administration, or subcutaneous, intravenous, oral, intraperitoneal, or parenteral routes, including intracranial (e.g., intraventricular, intraparenchymal and intrathecal), intramuscular, transdermal, airway (aerosol), nasal, rectal, or topical (including buccal and sublingual) administration. In certain embodiments, the compositions are administered by subcutaneous or intravenous infusion or injection.

The above provided embodiments and items are now illustrated with the following, non-limiting examples.

EXAMPLES

Example 1. RNAi Trigger Synthesis

A) Synthesis.

RNAi trigger molecules were synthesized according to phosphoramidite technology on solid phase used in oligonucleotide synthesis. Depending on the scale either a MerMade96E (Bioautomation) or a MerMade12 (Bioautomation) was used. Syntheses were performed on a solid support made of controlled pore glass (CPG, 500 Å or 600 Å, obtained from Prime Synthesis, Aston, Pa., USA). All DNA, 2'-modified RNA, and UNA phosphoramidites were purchased from Thermo Fisher Scientific (Milwaukee, Wis., USA). Specifically, the following 2'-O-Methyl phosphoramidites were used: (5'-O-dimethoxytrityl-N$^6$-(benzoyl)-2'-O-methyl-adenosine-3'-O-(2-cyanoethyl-N,N-diisopropylamino) phosphoramidite, 5'-O-dimethoxy-trityl-N$^4$-(acetyl)-2'-O-methyl-cytidine-3'-O-(2-cyanoethyl-N,N-diisopropyl-amino) phosphoramidite, (5'-O-dimethoxytrityl-N$^2$-(isobutyryl)-2'-O-methyl-guanosine-3'-O-(2-cyano-ethyl-N,N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-Deoxy-2'-fluoro-phosphor-amidites carried the same protecting groups as the 2'-O-methyl RNA amidites. The following UNA phosphoramidites were used: 5'-(4,4'-Dimethoxytrityl)-N-benzoyl-2',3'-seco-adenosine, 2'-benzoyl-3'-[(2-cyanoethyl)-(N,N-diisopropyl)]-phosphor-amidite, 5'-(4,4'-Dimethoxytrityl)-N-acetyl-2',3'-seco-cytosine, 2'-benzoyl-3'-[(2-cyanoethyl)-(N,N-diisopropyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diisopropyl)]-phosphoramidite. All amidites were dissolved in anhydrous acetonitrile (50 mM) and molecular sieves (3 Å) were added. In order to introduce the TEG-Cholesterol at the 5'-end of the oligomers, the 1-Dimethoxytrityloxy-3-O—(N-cholesteryl-3-aminopropyl)-triethyleneglycol-glyceryl-2-O-(2-cyanoethyl)-(N,N,-diisopropyl)-phosphoramidite from Glen Research (Sterling, Va., USA) was employed. The 5'-modifications were introduced without any modification of the synthesis cycle. 5-Benzylthio-1H-tetrazole (BTT, 250 mM in acetonitrile) was used as activator solution. Coupling times were 10 min (RNA), 180 sec (Cholesterol), 90 sec (2'OMe and UNA), and 60 sec (2'F and DNA). In order to introduce phosphorothioate linkages, a 100 mM solution of 3-phenyl 1,2,4-dithiazoline-5-one (POS, obtained from PolyOrg. Inc., Leominster, Mass., USA) in anhydrous Acetonitrile was employed. See Tables 1-2 and 5 for specific sequences.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for two hours at 30° C. The solution was evaporated and the solid residue was reconstituted in water (see below).

C. Purification.

Crude Cholesterol containing oligomers were purified by reverse phase HPLC using a Waters XBridge BEH 300 C4 5 u Prep column and a Shimadzu LC-8 system. Buffer A was 100 mM TEAA, pH 7.5 and contained 5% Acetonitrile and buffer B was 100 mM TEAA and contained 95% Acetonitrile. UV traces at 260 nm were recorded. Appropriate fractions were then run on size exclusion HPLC using a GE Healthcare XK 16/40 column packed with Sephadex G-25 medium with a running buffer of 100 mM ammonium bicarbonate, pH 6.7 and 20% Acetonitrile. Other crude oligomers were purified by anionic exchange HPLC using a TKSgel SuperQ-5PW 13 u column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC as described for cholesterol containing oligomers.

D. Annealing.

Complementary strands were mixed by combining equimolar solutions (sense and antisense) in 0.2×PBS (Phosphate-Buffered Saline, 1×, Corning, Cellgro) to form the RNAi triggers. This solution was placed into a thermomixer at 70° C. heated to 95° C., held at 95° C. for 5 mM, and cooled to room temperature slowly. Some RNAi triggers were lyophilized and stored at 15 to 25° C. Duplex concentration was determined by measuring the solution absorbance on a UV-Vis spectrometer in 0.2×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

Example 2. Synthesis of APN 1170-400A (100A), APN 1203-006 (006), APN 1203-064 (064) Amphipathic Membrane Active Polyamines

| Polymer | MW (protected) | Theoretical MW (deprotected) | PDI | % Amine Incorp. | % Alkyl Incorp. | % End Group Removal | Azides/Polymer |
|---|---|---|---|---|---|---|---|
| APN 1170-100A | 64,430 | 45,765 | 1.22 | 56 | 44 | 0 | 1.25 |
| APN 1203-006 | 60,330 | 43,578 | 1.05 | 56 | 44 | 99 | 1.14 |
| APN 1203-062 | 65,170 | 46,736 | 1.05 | 54 | 46 | 99 | 0.96 |

A. Materials. 2,2'-Azobis(2,4-dimethyl valeronitrile) (V-65, radical initiator) was purchased from Wako Pure Chemical Industries, Propyl acrylate was purchased from Polysciences Inc. N-Boc-ethoxy-ethylamine acrylate was obtained from WuXi Inc. 2-(Dodecylthio-carbonothioyl-thio)-2-methylpropionic acid (DDMAT, RAFT Agent), 1,1'-Azobis-(cyclo-hexanecarbonitrile) (ACHN), 1-Ethyl piperidine hypophosphite (EPHP), Pentafluorophenol, N,N'-Dicyclohexylcarbodiimide and N,N-diisopropyl-ethylamine were purchased from Sigma Aldrich. O-(2-Aminoethyl)-O'-(2-azidoethyl)triethylene Glycol (azido-PEG$_4$-amine) was purchased from Biomatrik Inc.

B. RAFT copolymer of N-Boc-ethoxyethylamine acrylate and propyl acrylate (EAP). Solutions of V-65 (2 mg/mL) and RAFT agent DDMAT (10 mg/mL) in butyl acetate were prepared. Monomer molar feed was 52% N-Boc-ethoxyethylamine acrylate, 48% propyl acrylate. Theoretical Mw was 75,000. RAFT agent (DDMAT) to initiator (V-65) molar ratio was 6.67:1.

N-Boc-ethoxyethylamine acrylate (1.778 g, 6.86 mmol), propyl acrylate (0.794 mL, 0.722 g, 6.33 mmol), DDMAT solution (1.215 mL, 0.0333 mmol). V-65 solution (0.621 mL, 0.005 mmol), and butyl acetate (10.2 mL) were added to a 20 mL glass vial with a stir bar. The vial was sealed with a septa cap and the solution bubbled with nitrogen using a long needle with a second needle as the outlet for 1 h. The needles were removed and the vial was heated to 50° C. for 24 h with stirring. The solution was allowed to cool to room temperature and transferred equally between two 50 mL centrifuge tube before hexane (35 mL) was added to both tubes. The solution was centrifuged for 2 min at 4400 rpm. The supernatant layer was carefully decanted and the bottom layer rinsed with hexane. The bottom layer of each tube was then re-dissolved in dichloromethane (7 mL), precipitated in hexane (40 mL) and centrifuged once more. The supernatant was decanted and the bottom layer rinsed with hexane before the layers were combined to one 50 mL centrifuge tube and the polymer was dried under reduced pressure for several hours. The yield of crude EAP copolymer was 2.1 g. Samples of the copolymer were taken for multi-angle light scattering (MALS), and $^1$H-NMR.

Polymer 006: The composition determined by $^1$H-NMR was 55% N-Boc-ethoxyethylamine acrylate and 45% propyl acrylate. The Mw for 006 determined by MALS was 58,600 g/mol with a polydispersity index (PDI) of 1.04.

Polymer 100A: Composition by 1H-NMR: 56% N-Boc-ethoxyethylamine acrylate and 44% propyl acrylate. MW by MALS: 65,150, PDI of 1.122.

Polymer 064: Composition by 1H-NMR: 54% N-Boc-ethoxyethylamine acrylate and 46% propyl acrylate. The Mw for 064 determined by MALS was 57,957 g/mol with a polydispersity index (PDI) of 1.07.

C. Radical induced ω-end group removal (polymers 006 and 064). Solutions of 1,1'-Azobis-(cyclohexanecarbonitrile) (ACHN, 20 mg/mL) and 1-Ethyl piperidine hypophosphite (EPHP, 100 mg/mL) were prepared in toluene. EAP (2 g, 0.035 mmol), ACHN (0.213 mL, 0.5 eq, 0.0174 mmol), EPHP (1.25 mL, 20 eq, 0.697 mmol), and toluene (25.2 mL) were added to a 40 mL glass vial with a stir bar. The vial was sealed with a septa cap and the solution bubbled with nitrogen using a long needle with a second needle as the outlet for 1 h. The needles were removed and the vial was heated to 100° C. for 2 h. The solution was allowed to cool to room temperature and ~20 mL toluene was removed by rotary evaporation. The remaining solution was transferred to a 50 mL centrifuge vial, and hexane (35 mL) was added. The solution was centrifuged for 2 min at 4400 rpm. The supernatant layer was carefully decanted and the bottom layer rinsed with hexane. The bottom layer was then re-dissolved in dichloromethane (7 mL), precipitated in hexane (40 mL) and centrifuged once more. The supernatant was decanted and the bottom layer rinsed with hexane before the polymer was dried under reduced pressure for ~1 h. The polymer was dissolved in methyl tert-butyl ether (80 mL) and transferred to a separatory funnel. The solution was then washed with 3×30 mL volumes of $H_2O$ followed by 3×30 mL volumes of saturated NaCl. The polymer solution was then dried over sodium sulfate, and vacuum filtered through 0.45 μm GHP filters. MTBE was removed via rotary evaporation and high vacuum. A sample was taken for monitoring of end group removal using a UV spectrophotometer. End group removal was calculated to be 99%. Samples were taken for MALS, GC-FID, and $^1$H-NMR. The composition of 006 by $^1$H-NMR was 55% N-Boc-eth oxyethylamine acrylate and 45% propyl acrylate. The conversion of 006 determined by GC-FID was 81.4% for the N-Hoc-ethoxyethylamine acrylate and 77.3% for the propyl acrylate. The conversion of 100A determined by GC-FID conversion was 87% for N-Boc-ethoxyethylamine acrylate and 83% for propyl acrylate. The Mw for polymer 006 determined by MALS was 57,700 g/mol with a polydispersity index (PDI) of 1.06.

D. Pentafluorophenol activation of α-end group. EAP polymer (2 g, 0.0347 mmol), pentafluorophenol (63.8 mg, 0.3466 mmol), N,N'-Dicyclohexylcarbodiimide (71.5 mg, 0.3466 mmol), and dichloromethane (40 mL) were added to a 100 mL round bottom flask with a stir bar. The flask was stoppered with a rubber septum and the system was purged with nitrogen for 15 min. The solution was stirred for 16 h at room temperature. Additional Pentafluorophenol (63.8 mg, 0.3466 mmol) and N,N'-Dicyclohexylcarbodiimide (71.5 mg, 0.3466 mmol) were added, the flask stoppered with a rubber septum, and the system was purged with nitrogen for 1.5 min. The solution was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer was dissolved in minimal ethyl acetate, precipitated with hexane (~10× volume), centrifuged, and the solvent was decanted. The polymer precipitate was dried under high vacuum until the solid reached a constant weight.

E. Azide α-end group. In a 100 ml round bottom flask equipped with a rubber septum and stir bar, polymer from the previous step (1.9 g, 0.0329 mmol) was dissolved in dichloromethane (38 mL). Azido-PEG4-Amine (86.4 mg, 0.3293 mmol) and N,N-Diisopropylethylamine (46.8 mg, 63.1 µL, 0.3622 mmol) were added to the flask with stirring. The system was purged with nitrogen for 15 min, and the reaction was left to stir at room temperature overnight. Additional Azido PEG$_4$ Amine (86.4 mg, 0.3293 mmol) and N,N-Diisopropylethylamine (46.8 mg, 63.1 µL, 0.3622 mmol) were added to the flask, the system was purged with N$_2$ gas, and the reaction was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer precipitate was dried under high vacuum until the solid reached a constant weight. The yield of Azide functionalized EAP was 1.77 g. Samples of the copolymer were taken for multi-angle light scattering (MALS), and $^1$H-NMR.

Polymer 006: The composition determined by was 56% N-Boc-ethoxyethylamine acrylate and 44% propyl acrylate. Mw determined by MALS was 60,330 g/mol with a polydispersity index (PDI) of 1.05.

Polymer 100A: The composition by $^1$H-NMR was 56% N-Boc-ethoxyethylamine acrylate and 44% propyl acrylate. The Mw determined by MALS: 64,430 with PDI of 1.217.

Polymer 064: The composition by 1H-NMR was 54% N-Boc-ethoxyethylamine acrylate and 46% propyl acrylate. The Mw determined by MALS: 65,170 with PDI of 1.05

Mono-Azide: The term "mono-azide" or "mono-azide polymer" indicates that steps D and E of the procedures above were done and an azide group was coupled to the α-end group of the polymer.

F. Boc Deprotection and Tangential Flow Filtration. In a 100 mL round bottom flask, 2M HCl in acetic acid (28 mL) was added to Azide functionalized EAP copolymer (1.67 g, 0.0277 mmol). The reaction was stirred at room temperature for 1 h. De-ionized H$_2$O (56 mL) was added, and stirred for 10 min. The solution was then immediately exchanged with 10 equivalent volumes of 5 mM Phosphate-Citrate buffer (pH 5) using a mPES 30 kD 115 cm$^2$ filter module equipped with a tangential flow filtration system (KrosFlo Research). The solution was then concentrated using the apparatus to 55 mL final volume. A pH value of 5.1 was recorded. Samples were taken for concentration determination by headspace gas chromatography. An aliquot was lyophilized and then reconstituted in 33.3% Acetonitrile-d in Deuterium Oxide at a concentration of 10 mg/mL for $^1$H-NMR analysis. Theoretical MW was calculated to be 43,026 g/mol 45,765 g/mol for 006 and 100A respectively.

G. Using similar techniques, similar amphipathic membrane active polyamines can be readily formed. Particularly, amphipathic membrane active polyamines with molecular weight (Mw) 40-120 k protected (25 k to 85 k deprotected), PDI ranges of 1.03 to 1.2, and monomer ratios of 35% amine monomer/65% hydrophobic group monomer to 70% amine monomer/30% hydrophobic group monomer.

Example 3. Synthesis of APN 1095-126 (126)

| MW (protected) | Theoretical MW (deprotected) | PDI | % Amine Incorporation | % Alkyl Incorporation | % End Group Removal | Azides Per Polymer |
|---|---|---|---|---|---|---|
| 66,670 | 47,606 | 1.11 | 56 | 44 | 0 | 4.1 |

Synthesis of APN 1095-126 used dithiobenzoate moiety RAFT agent and AIBN RAFT initiator, compared to the trithiocarbonate moiety RAFT agent and V-65 RAFT initiator used for synthesis of 100A and 006. The conditions for this polymerization required different heating temperatures and times. In addition, this polymer required fractional precipitation. The polymer was not end capped, but the method of azide addition was the same as 100A and 006.

A. Materials. Propyl acrylate was purchased from Polysciences Inc. N-Hoc-ethoxyethylamine acrylate was obtained from WuXi Inc. 4-Cyano-4-(phenylcarbonothioylthio) pentanoic acid (CPCPA, RAFT Agent), 2,2'-Azobis(2-methylpropionitrile) (AIBN, radical initiator), Pentafluorophenol, N,N'-Dicyclohexylcarbodiimide and N,N-diisopropylethylamine were purchased from Sigma Aldrich. O-(2-Aminoethyl)-O'-(2-azidoethyl)triethylene Glycol (azido-PEG$_4$-amine) was purchased from Biomatrik Inc.

B. RAFT copolymer of N-Boc-ethoxyethylamine acrylate and propyl acrylate (EAP). The following procedure was repeated 8 times to yield a total of 4.5513 g fractionated EAP copolymer. Solutions of AIBN (1.035 mg/mL) and RAFT agent CPCPA (50.54 mg/mL) in butyl acetate were prepared. Monomer molar feed was 52% N-Boc-ethoxyethylamine acrylate, 48% propyl acrylate. Theoretical Mw was 75,000. RAFT agent (CPCPA) to initiator (AIBN) molar ratio was 6.67:1.

N-Boc-ethoxyethylamine acrylate (1.7879 g, 6.9 mmol), propyl acrylate (0.774 mL, 0.7121 g, 6.24 mmol), CPCPA solution (0.184 mL, 0.0333 mmol), AIBN solution (0.793 mL, 0.005 mmol), and butyl acetate (11.02 mL) were added to a 20 mL glass vial with a stir bar. The vial was sealed with a septa cap and the solution bubbled with nitrogen using a long needle with a second needle as the outlet for 1 h. The needles were removed and the vial was heated to 50° C. for 24 h with stirring. The solution was allowed to cool to room temperature and transferred to a 50 mL centrifuge tube before hexane (35 mL) was added. The solution was centrifuged for 2 min at 4400 rpm. The supernatant layer was carefully decanted and the bottom layer rinsed with hexane. The bottom layer of each tube was then re-dissolved in dichloromethane (7 mL), precipitated in hexane (40 mL) and centrifuged once more. The supernatant was decanted and the bottom layer rinsed with Hexane before the polymer was dried under reduced pressure for several hours. The yield of crude EAP copolymer was 1.734 g. Samples of the crude copolymer were taken for multi-angle light scattering (MALS), and $^1$H-NMR. The dried, crude copolymer was dissolved in DCM (100 mg/mL). Hexane was added until just after the cloud point was reached. The resulting milky solution was centrifuged. The bottom layer was extracted and fully precipitated into hexane. The fraction was centrifuged, after which the copolymer was isolated and dried under vacuum. The yield of isolated fraction of EAP copolymer was 0.602 g. Samples of the fractionated copolymer were taken for $^1$H-NMR and MALS. The composition determined by $^1$H-NMR was 56% N-Boc-ethoxyethylamine acrylate and 44% propyl acrylate. The Mw determined by MALS was 62,010 g/mol with a polydispersity index (PDI) of 1.14.

C. Pentafluorophenol activation of α-end group. EAP polymer (2 g, 0.0347 mmol), pentafluorophenol (63.8 mg, 0.3466 mmol), N,N'-Dicyclohexylcarbodiimide (71.5 mg, 0.3466 mmol), and dichloromethane (40 mL) were added to a 100 mL round bottom flask with a stir bar. The flask was stoppered with a rubber septum and the system was purged with nitrogen for 15 min. The solution was stirred for 16 h at room temperature. Additional Pentafluorophenol (63.8 mg, 0.3466 mmol) and N,N'-Dicyclohexylcarbodiimide (71.5 mg, 0.3466 mmol) were added, the flask stoppered with a rubber septum, and the system was purged with nitrogen for 15 min. The solution was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer was dissolved in minimal ethyl acetate, precipitated with hexane (~10× volume), centrifuged, and the solvent was decanted. The polymer precipitate was dried under high vacuum until the solid reached a constant weight.

D. Azide functionalization of α-end group. In a 100 ml round bottom flask equipped with a rubber septum and stir bar, polymer from the previous step (1.9 g, 0.0329 mmol) was dissolved in dichloromethane (38 mL). Azido-PEG4-Amine (86.4 mg, 0.3293 mmol) and N,N-Diisopropyl-ethylamine (46.8 mg, 63.1 µL, 0.3622 mmol) were added to the flask with stirring. The system was purged with nitrogen for 15 min, and the reaction was left to stir at room temperature overnight. Additional Azido PEG$_4$ Amine (86.4 mg, 0.3293 mmol) and N,N-Diisopropyl-ethylamine (46.8 mg, 63.1 µL, 0.3622 mmol) were added to the flask, the system was purged with N$_2$ gas, and the reaction was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer precipitate was dried under high vacuum until the solid reached a constant weight. The yield of Azide functionalized EAP was 1.77 g. Samples of the copolymer were taken for multi-angle light scattering (MALS), and $^1$H-NMR. The composition determined by $^1$H-NMR was 56% N-Boc-ethoxyethylamine acrylate and 44% propyl acrylate. The Mw determined by MALS was 66,670 g/mol with a polydispersity index (PDI) of 1.11.

E. Boc Deprotection and Tangential Flow Filtration. In a 100 mL round bottom flask, 2M HCl in acetic acid (28 mL) was added to Azide functionalized EAP copolymer (1.67 g, 0.0277 mmol). The reaction was stirred at room temperature for 1 hour. De-ionized H$_2$O (56 mL) was added, and stirred for 10 min. The solution was then immediately exchanged with 10 equivalent volumes of 5 mM Phosphate-Citrate buffer (pH 5) using a mPES 30 kD 115 cm$^2$ filter module equipped with a tangential flow filtration system (KrosFlo Research). The solution was then concentrated using the apparatus to 55 mL final volume. A pH value of 5.1 was recorded. Samples were taken for concentration determination by headspace gas chromatography. An aliquot was lyophilized and then reconstituted in 33.3% Acetonitrile-d in Deuterium Oxide at a concentration of 10 mg/mL for $^1$H-NMR analysis. Theoretical MW was calculated to be 43,026 g/mol.

Example 4. Polymer Analytics (i) MALS analysis. Approximately 10 mg of the copolymer was dissolved in 0.5 mL 75% dichloromethane, 20% tetrahydrofuran, and 5% acetonitrile. The molecular weight and polydispersity (PDI) were measured using a Wyatt Heleos II multiangle light scattering detector attached to a Shimadzu Prominence HPLC using a Jordi 5 µm 7.8×300 Mixed Bed LS DVB column. Molecular weight (polymer 006) before de-protection: 60,330 (PDI 1.05).

(ii) Monomer conversion by Gas Chromatography. Approximately 40 µL of copolymer solution (section B) was taken after mixing (pre-N$_2$ bubbling), after N$_2$ bubbling, and after reaction completion. Samples were diluted 100 fold into ethyl acetate. The samples were analyzed with a Shimadzu GC-2010 plus equipped with a flame ionization detector using a Phenomenex Zebron capillary column (ZB-5, 30 m, 0.25 mm ID, 0.5 µm film thickness). Using the pre-N$_2$ bubbled sample as a single point calibration, monomer conversion was measured by comparing post reaction monomer concentrations with pre reaction/post N$_2$ bubbling monomer concentrations.

(iii) Polymer concentration by propanol content using headspace gas chromatography (HS-GC). Deprotected polymer solution (~20 mg/mL) was diluted 50 fold into 3M NaOH using 1-Butanol as an internal standard. The reaction tube was sealed and shaken for 1 h. The reaction was then incubated for at least 6 h at room temperature. In a 10 mL headspace vial, hydrolyzed test article (250 µL) was added to saturated NaCl (500 µL) and HCl (4M, 250 µL) and the system was sealed. Test articles were analyzed using a Shimadzu GC-2010 plus with HS-20 headspace sampler using a Phenomenex ZB-WAX plus gc column (30.0 m, 0.25 mm ID, 0.25 µm film thickness). Propanol concentration was then quantitated using an external standard curve or propanol containing the same NaCl/HCl/NaOH matrix. Polymer concentration was then calculated by dividing propanol concentration by the amount of propanol per polymer as determined by monomer incorporation.

(iv) Azide quantitation using UV Spectroscopy. Deprotected polymer solution (~20 mg/mL) was diluted to 5 mg/mL in 60 mM MES, pH 6. The polymer was then reacted with DBCO-amine (2.5 molar eq.) at room temperature for at least 6 h. The difference in absorbance at 310 nm was calculated and azide content per polymer was determined.

Example 5. Tangential Flow Filtration and Analysis of Conjugate

Following conjugate formation, i.e., modification of polymer by addition of RGD and PEG modifying agents and attachment of RNAi trigger (see example 9 below) the conjugate solution (2 mg/mL, 10 mL) was exchanged with 10 equivalent volumes of 10 mM Phosphate-Citrate buffer (pH 5) using a mPES 30 kD 20 cm$^2$ filter module equipped with a tangential flow filtration system (KrosFlo Research). A pH value of 5.1 was recorded.

A. Conjugate Characterization and Analysis.
  (i) Polymer concentration throughout conjugation. The same method as section G(iii) was used throughout the assembly of the conjugate to monitor polymer concentration.
  (ii) Impurity quantitation by HPLC-reverse-phase chromatography. Polymer conjugate (after TFF purification) was diluted to 1 mg/mL with $H_2O$ and injected onto a Shimadzu Prominence HPLC with a SPD-20A UV detector and a Waters Xbridge C18 5 μm 4.6×250 mm column. The method used a binary gradient consisting of $H_2O$/Acetonitrile/0.1% formic acid with detection set to 247 nm. Concentrations of $PEG_n$-ACit-PABOH, RGD-$PEG_n$-FCFP-COOH, and PNP were calculated using external standard quantitation.
  (iii) RGD-$PEG_n$-FCitFP-1TFP and $PEG_n$-ACit-PABC-PNP modification through amino acid analysis. Polymer conjugate (after TFF purification) with NorValine as an internal standard was hydrolyzed for 16 h in HCl (6 M) at 110° C. in a sealed hydrolysis tube. The hydrolysis solution was then neutralized with NaOH, diluted with borate buffer (pH 10.1), and derivatized with phthaldialdehyde/3-mercaptopropionic acid. The sample was then injected onto a Shimadzu Nexera HPLC system with SIL-30A autosampler, SPD-20A photo diode array detector, and a Waters Xbridge C18 5 μm 4.6×250 mm column. Sample was eluted using a 10 mM Sodium tetraborate decahydrate/10 mM dibasic sodium phosphate/5 mM Sodium azide and 45% Methanol 45% Acetonitrile/10% $H_2O$ binary gradient. UV detection was set to 338 nm. Alanine and Phenylalanine concentrations were calculated using external standard curves. Alanine and Phenylalanine concentrations along with polymer concentration and monomer incorporations were used to calculate total amine group modification, as well as the ratio between both ligands.
  (iv) RNA trigger quantitation and conjugate purity by size exclusion chromatography. A Shimadzu Prominence HPLC equipped with SPD-20A UV detector and Acclaim SEC-300 4.6 mm×300 mm, 5 μm, 300 Å size exclusion column (1$^{st}$ in series) connected to Acclaim SEC-1000 4.6 mm×300 mm, 7 μm, 1000 Å (2$^{nd}$ in series) size exclusion column was assembled. The method used was isocratic, with 200 mM NaBr, 10 mM Tris 8, 1 mM EDTA, and 20% Acetonitrile as mobile phase and detection at 260 nm. A sample of polymer conjugate (after RNA trigger addition) was diluted into mobile phase and injected onto the system. Another sample of conjugate followed the same dilution scheme but was treated with 200 mM dithiothreitol for 2 h before injection onto the system. RNA trigger concentration for both samples was calculated using an external standard curve. Amount of conjugated RNA trigger was calculated by subtracting DTT treated RNA levels from untreated RNA levels. Post-TFF purity of the conjugate was also determined using this method.

Example 6. RGD Ligands (RGD Mimic)

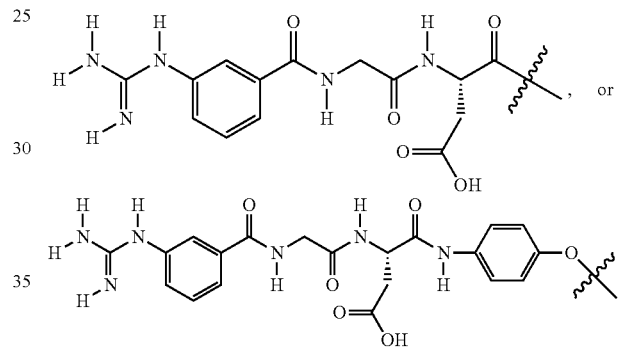

A. RGD Mimic #1-$PEG_n$-HyNic, MW 1272.

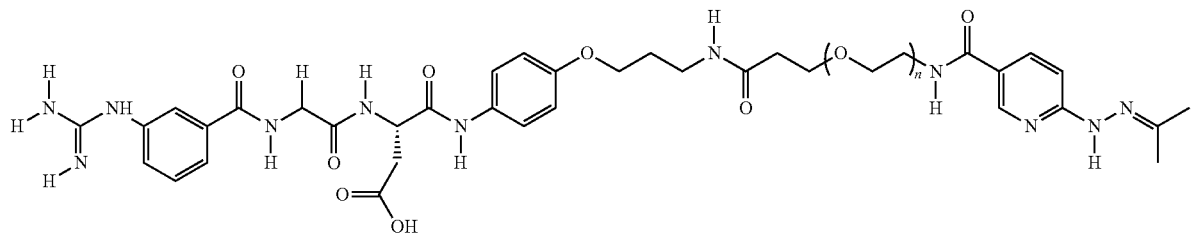

n=4-24 (preferably 8-12)
B. RGD Mimic 41a-HyNic, MW 802.8.

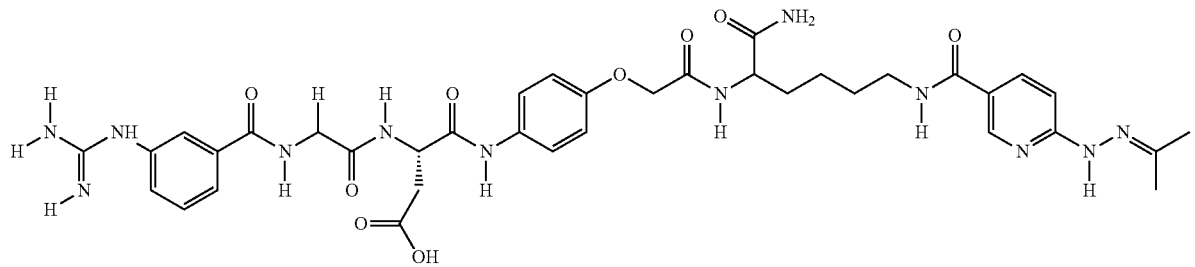 [SMILES: [H]/N=C(\N)Nc1cccc(C(=O)NCC(=O)N[C@@H](CC(=O)O)C(=O)Nc2ccc(OCC(=O)NC(CCCCNC(=O)c3ccc(NN=C(C)C)nc3)C(N)=O)cc2)c1]

C. RGD Mimic #1b-HyNic, MW 830.9 (RGD).

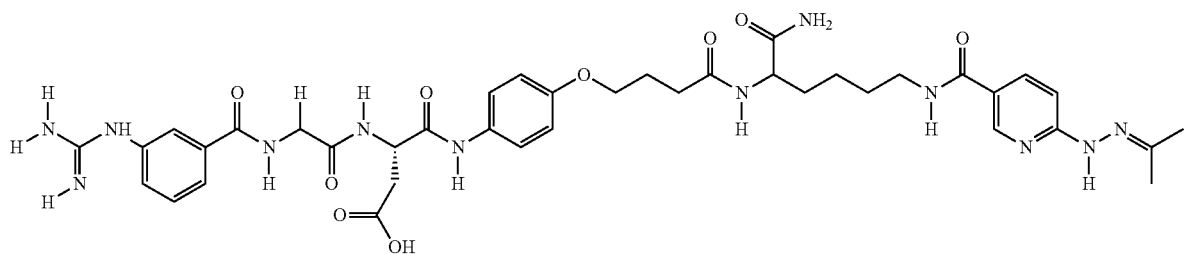 [SMILES: [H]/N=C(\N)Nc1cccc(C(=O)NCC(=O)N[C@@H](CC(=O)O)C(=O)Nc2ccc(OCCCC(=O)NC(CCCCNC(=O)c3ccc(NN=C(C)C)nc3)C(N)=O)cc2)c1]

Example 7. RGD and PEG Modifying Agents

A. Dipeptide RGD-dipeptide and PEG-dipeptide modifying agents were made as described in US-2012-0172412-A1 (WO 2012/092373) and US 2015-0045573 A1 (WO 2015/021092) (both of which are incorporated herein by reference). FIG. 3-7.

B. RGD-PEG$_n$-FCitFP-TFP and PEG$_n$-FCitFP-TFP modifying agent synthesis. The modifying agent precursor (di-Boc)RGD(OtBu)-APBA-PEG$_n$-FCitFPro-COOH was prepared using general Fmoc chemistry solid phase synthesis using 2-Cl-Trt resin preloaded with Fmoc-Proline-OH. To Resin-Pro-Fmoc was added sequentially (following Fmoc deprotection at each step): FMoc-Phe-OH, Fmoc-Cit-OH, Fmoc-Phe-OH, Fmoc-NH-PEG$_n$-COOH, 4-(N-Fmoc-p-aminophenoxy)-butyric acid (APBA), Fmoc-Asp(OtBu)-OH, Fmoc-Gly-OH, and diboc-m-guanidino benzoic acid.

(diboc)RGD(OtBu)-APBA-PEG$_n$-FCitFPro-COOH (458 mg, 0.200 mmols) and TFP (66.5 mg, 0.400 mmols) were dissolved in anhydrous DCM (5.0 mL) and cooled to 0° C. in an ice/water bath while stirring under Argon. EDC (77 mg, 0.400 mmols) was added and the reaction mixture stirred in an ice/water bath at 0° C. for 30 min. Reaction progress was monitored by TLC (8.5:1.5 CHCl$_3$:MeOH) and was complete after 90 min with no starting material observed by TLC. The reaction mixture was diluted to 100 mL total volume with DCM, washed 3×40 mL with DI H$_2$O (pH=5), and washed 1×40 mL aqueous saturated NaCl solution. The organics were then dried over Na$_2$SO$_4$, and concentrated on a rotovap to yield 448 mg (92% yield) of a tan/orange foam. The structure was confirmed by $^1$H NMR, and ESI MS (Reaction shown above for PEG$_{20}$ (n=20)).

(diboc)RGD(OtBu)-PEGn-FCitFPro-TFP (497 mg, 0.204 mmols) was dissolved in [9.25:0.75:0.50] TFA:H$_2$O:Thioanisole (5.0 mL) and stirred at room temperature in a closed flask for 45 min. Reaction completion was confirmed by MS (ESI, scan neg, 300-3000) with no masses related to starting material or partially deprotected intermediates observed. The reaction mixture was then precipitated into 45 mL diethyl ether, spun down, the supernatant poured off, and washed 2×10 mL diethyl ether and dried on high vacuum overnight. The final product was purified on prep HPLC using a Thermo Aquasil C18 5 um semi prep column, with mobile phases 0.1% TFA in H$_2$O and ACN. Each injection was 50 mg of crude material dissolved in 3.0 mL of 0.1% TFA in [61:39] H$_2$O:ACN run on a gradient of (indicated in % B) 39-(5)-39-(35)-43-(5)-95-(10)-95-(2)-39-(5)-39. Each sample for injection was prepared (dissolved) within 15 minutes of being injected and positive fractions were pooled in one flask and kept cold in the freezer until the last injection of the day had finished. The positive fractions were then concentrated on the rotovap with a bath temperature of 32° C. to dryness, then chased 2× with ACN/Toluene, then 3× with ACN and then dried on high vacuum overnight. Out of 257 mg injected crude, 180 mg (70%) was isolated as pure material (Reaction shown above for PEG$_{20}$ (n=20)).

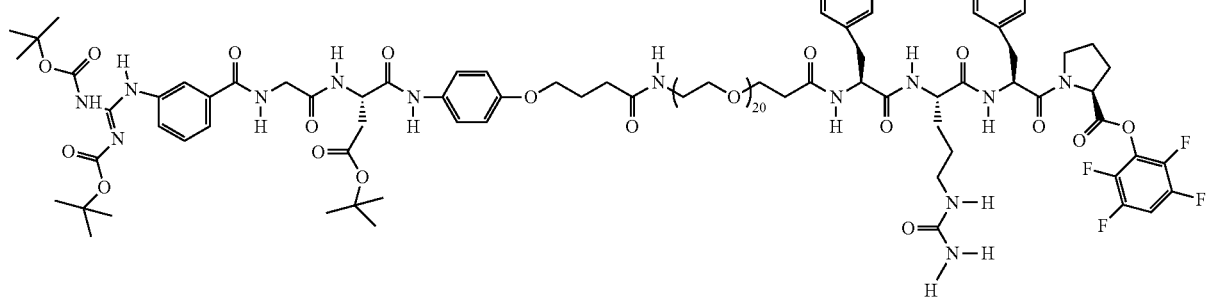

(diboc)RGD(OtBu)—APBA—PEG$_n$—FCitFPro—TFP (shown for n = 20)

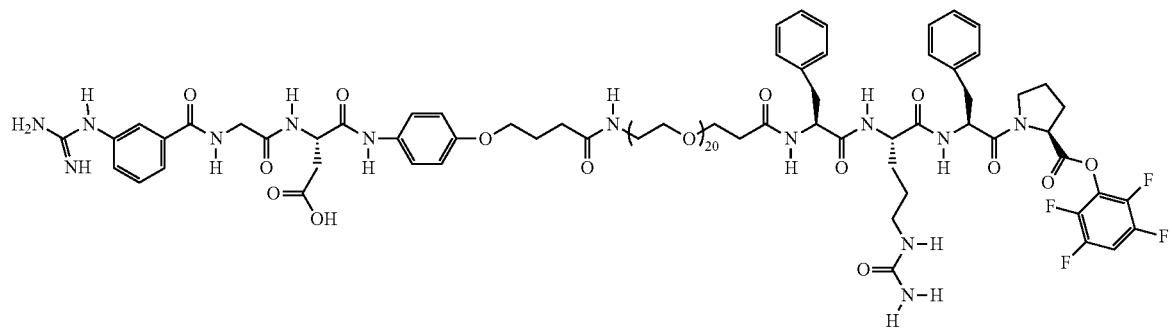

RGD-PEG$_n$FCitFPro-TFP (shown for n = 20)

4-(N-Fmoc-p-aminophenoxy)-butyric acid 1 synthesis. p-Nitro-phenol (2) (7.5 g, 53.9 mmole) was combined with ethyl 4-bromobutyrate (8.45 ml, 59 mmol) and K$_2$CO$_3$ (7.5 g, 54 mmole) in DMF (75 mL). The mixture was stirred for 2 h at 100° C. DMF was removed and the crude product was diluted in a mixture of 3:1 mixture of 2 N NaOH and methanol and stirred 4 h at RT. The reaction mixture was acidified with 6 M HCl. The white precipitate was collected to yield 4-(p-Nitrophenyloxy)-butyric acid 3: (10.9 g, 90% yield).

4-(p-Nitrophenyloxy)-butyric acid 3 (37.1 g, 165 mmole) was dissolved in MeOH (1 L) with ammonium formate (35 g, 555 mmole) and 10% Pd/C (Degussa Type) (3.5 g) was added. The mixture was refluxed at 65° C. overnight. The reaction was filtered with celite to yield a reddish brown solid of product 4-(p-Aminophenyloxy)-butyric acid 4 (30.5 g, 95% yield).

4-(p-Aminophenyloxy)-butyric acid 4 (5.1 g, 26 mmole) was dissolved in 6:4 a mixture of an aqueous saturated NaHCO$_3$ (3.36 g, 40 mmol) in H$_2$O (450 mL) and THF (300 ml) to make a white slurry. Fmoc-OSu (8.82 g, 26.1 mmole) was added and the reaction was stirred for 4 h. The acetone was removed, the reaction was acidified (HCl), and the off-white precipitate was collected and triturated in 1N HCl to yield 9.6 g of product 4-(N-Fmoc-p-aminophenoxy)-butyric acid 1 (88% yield).

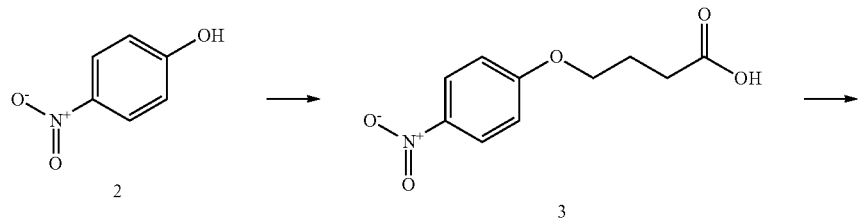

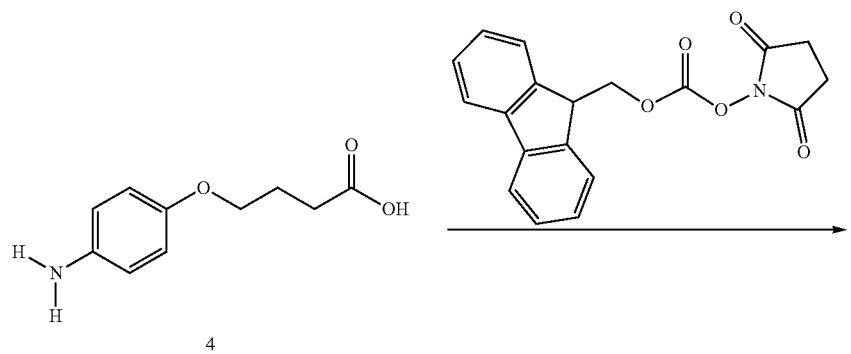

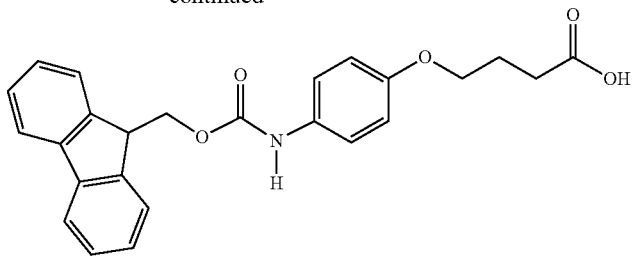

diBoc-m-guanidino-benzoic acid 5 was synthesized according to Riches A G et al. Tetrahedron (2012) 68, p. 9448-9455.

Figure 2:
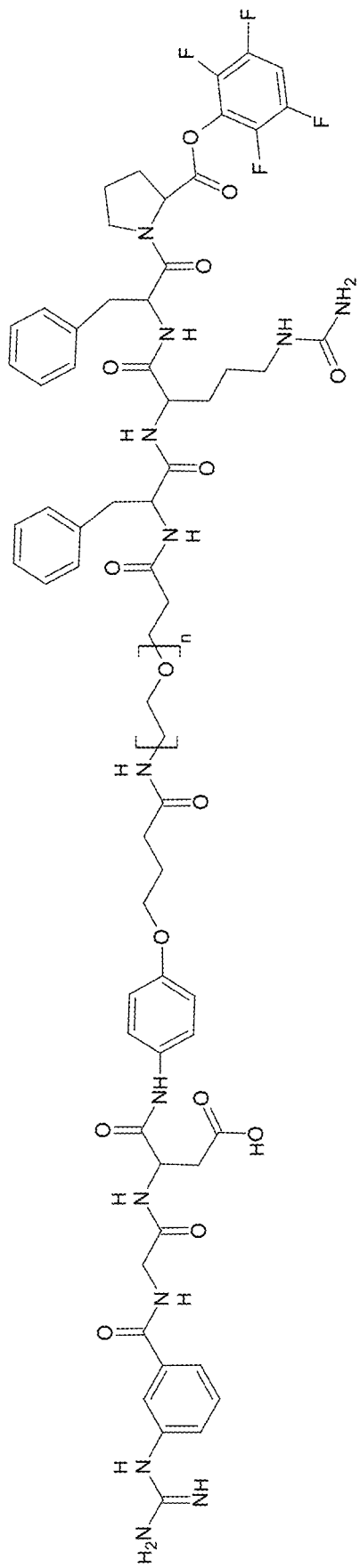
FIG. 2. Chemical structures representing RGD-PEG$_n$-FCitFP-TFP modifying agents.
Figure 3:
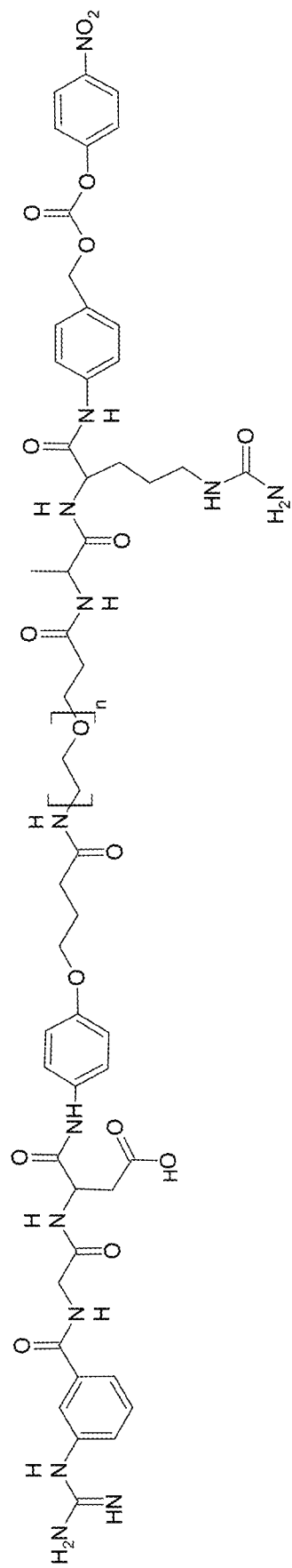
FIG. 3. Chemical structures representing RGD-PEG$_n$-ACit-PABC-PNP modifying agents.
Figure 4:
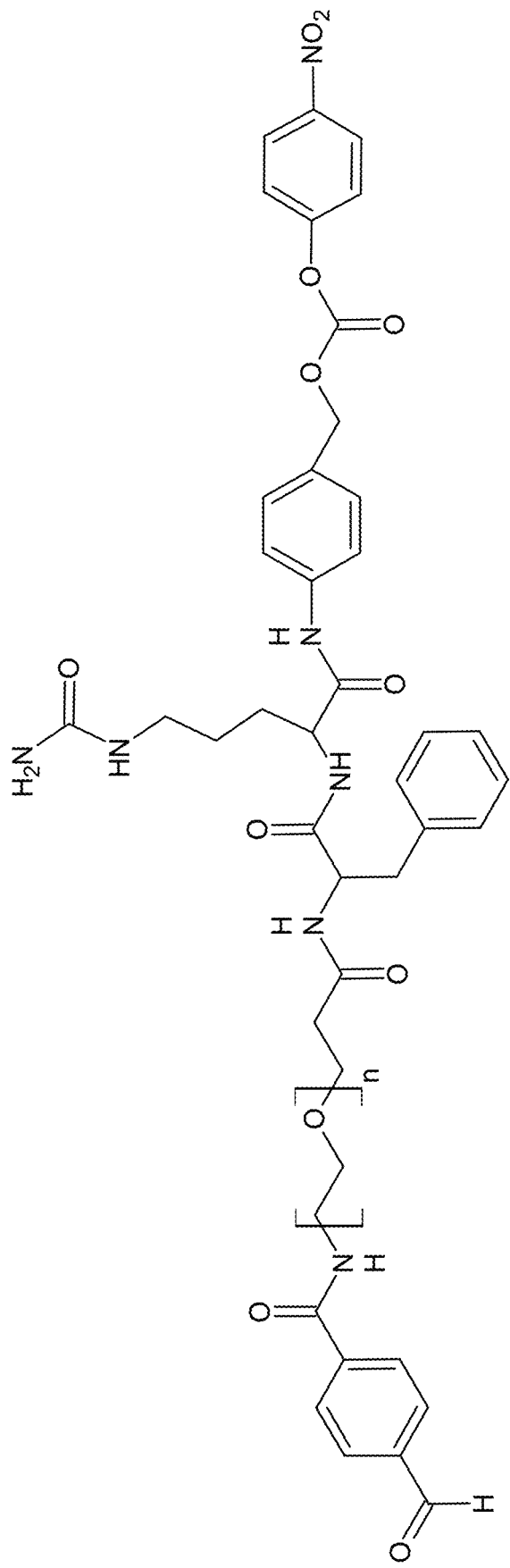
FIG. 4. Chemical structures representing aldehyde-PEG$_n$-FCit-PABC-PNP modifying agents.
Figure 5:
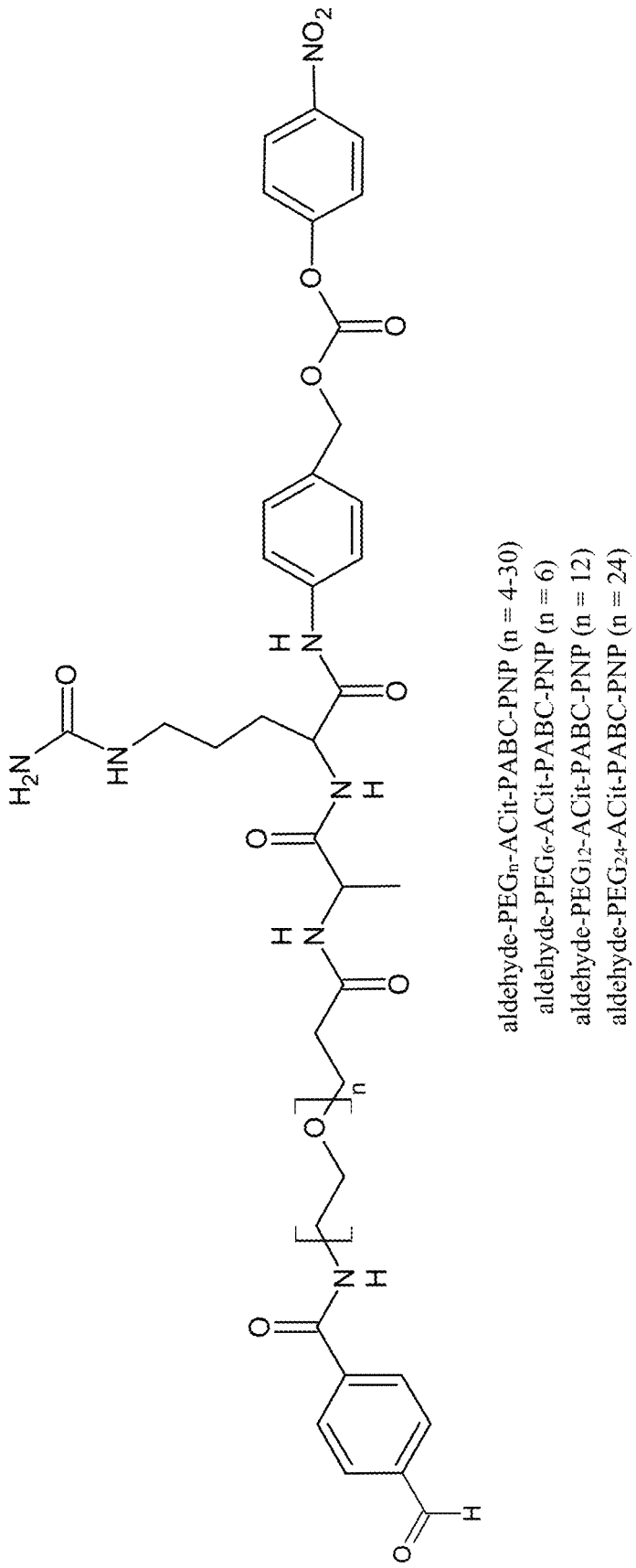
FIG. 5. Chemical structures representing aldehyde-PEG$_n$-ACit-PABC-PNP modifying agents.
Figure 6:
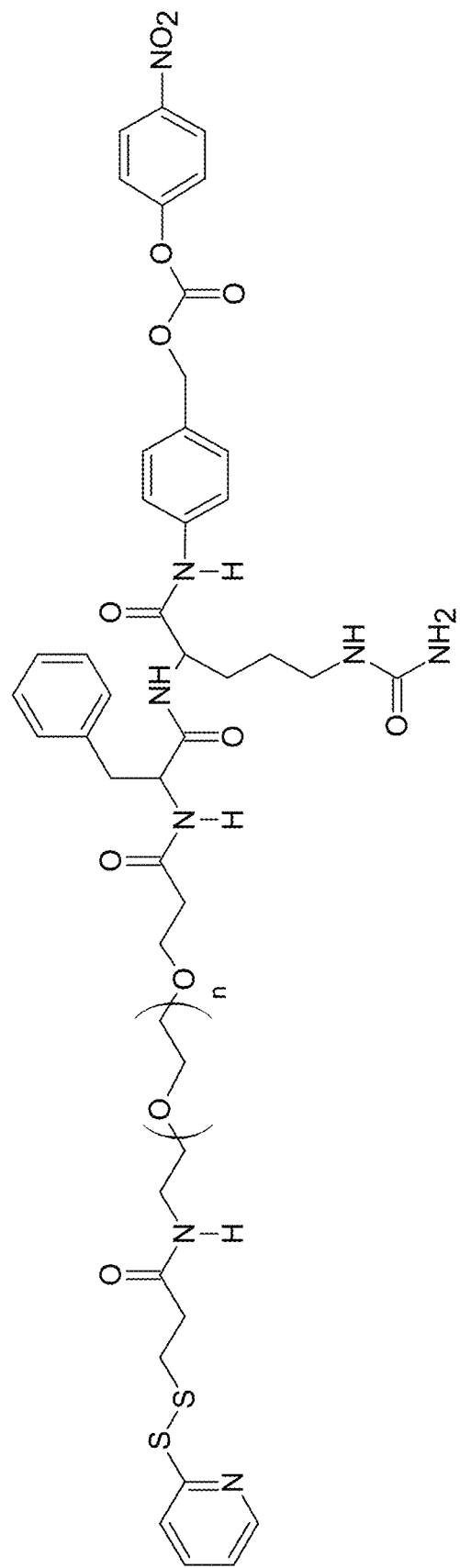
FIG. 6. Chemical structures representing SPDP-PEG$_n$-FCit-PABC-PNP modifying agents.
Figure 7:
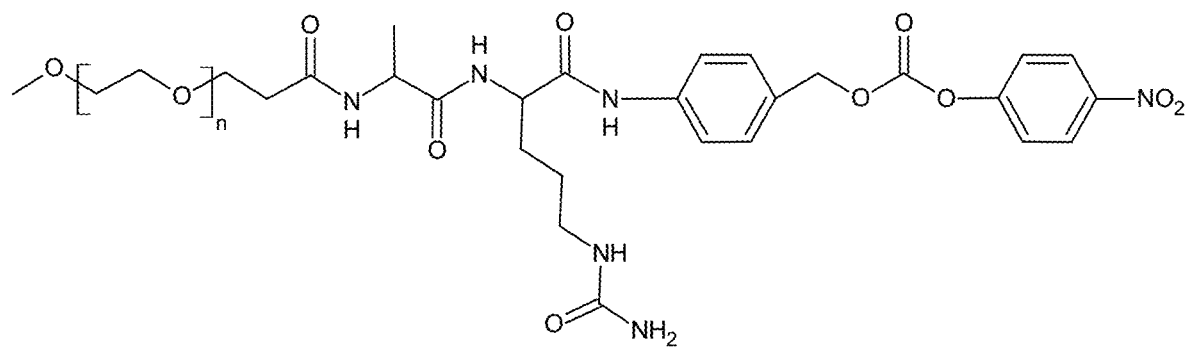
FIG. 7. Chemical structures representing PEG$_n$-ACit-PABC-PNP and PEG$_n$-FCit-PABC-PNP modifying agents.
Figure 7:
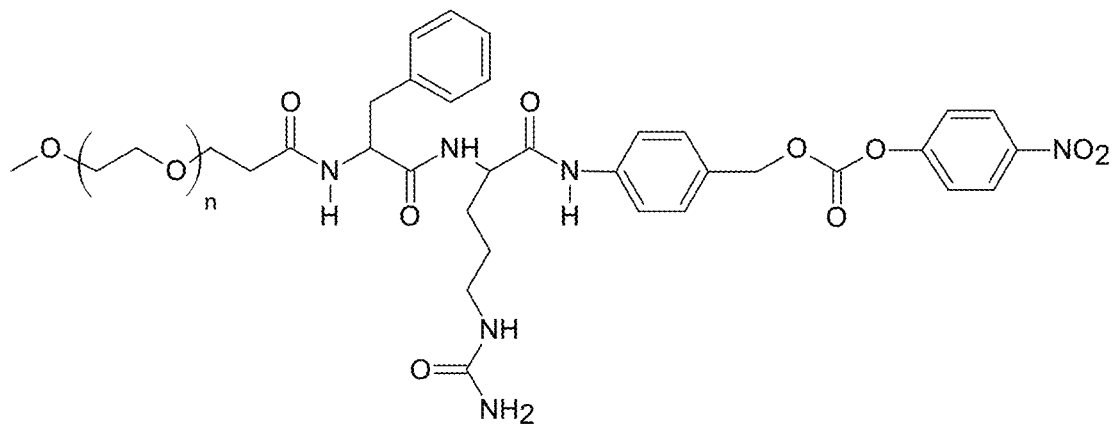

$PEG_n$-FCitFP modifying agents were made using similar chemistry FIG. 1-2.

Example 8. Tetrapeptide Peptide Linkages

A. Tetrapeptide Syntheses. All tetrapeptides were synthesized in the same manner using standard solid phase Fmoc procedures. Some peptides were synthesized from commercially available 2-Cl-Trt resin (EMD Millipore, Billerica, Mass.) containing either proline, leucine, or alanine. For other peptides, 2-Cl-Trt resin was loaded with either FMOC-$PEG_n$-$CO_2H$ or FMOC-N-methyl-Ala-$CO_2H$ by adding a solution of DMF containing the amino acid or PEG (1 eq) and DIEA (2 eq) to 2-Cl-Trt resin for 16 h. Upon completion, resins were capped with MeOH. Stepwise addition was performed using PYBOP (4 eq), amino acid (4 eq), and DIEA (8 eq) for coupling and 20% piperdine in DMF for Fmoc de-protection.

After peptide syntheses, the tetrapeptides were reacted with 2 eq of N-Hydroxysuccinimide (NHS) activated esters of either protected N-Acetyl-galactosamine, $NAG(OAc)_3$ (Rozema D B et al. "Protease-triggered siRNA Delivery Vehicles." J Control Release. 2015 Vol. 209:57-66 and U.S. Pat. No. 8,802,773) or $PEG_n$ in DMF containing 4 eq DIEA. Following attachment of $NAG(OAc)_3$ or PEG, the peptides were removed from resin using HFIP (30%) in DCM for 0.5 h. After solvent removal the residue was triturated with $Et_2O$.

Tetrapeptides were either purified and conjugated to activated esters to form modifying agents or conjugated to chromophore N-(p-Nitrophenyl)ethylenediamine (pNA) without purification to form substrates for physiological lability testing. Prior to purification, $NAG(OAc)_3$-containing substrates were de-acetylated by treatment with TEA (35%) in water (45%) and MeOH (20%) and stirred at room temp. For purification, tetrapeptide substrates were separated by HPLC using a Thermo Scientific Aquasil C18 reverse-phase column (250×21.2, Waltham, Mass.), eluting a gradient of acetonitrile and water buffered with 0.1% formic acid. Following purification, the substrates were lyophilized.

Attachment of amine-reactive groups to tetrapeptides. 1 eq HPLC purified peptide with N-terminal NAG ($R_5$=$NAG(OH)_3$ or PEG ($R_5$=$PEG_n$) in DMF or DCM was added to a flame dried flask at 0° C. to give a 0.2 M concentration of peptide. NHS (3 eq) and N,N'-Dicyclohexylcarbodiimide (DCC) (3 eq) were added and allowed to stir at room temp. under argon overnight to yield the modifying agents. The mixture was partially concentrated, chilled to −20° C., and filtered. All solvents were then removed in vacuo. The residue was dissolved in a minimum of DCM and MeOH, precipitated into cold $Et_2O$ and collected by decantation of the solvent after centrifugation. Precipitation into $Et_2O$ was repeated until no residual DCU (dicyclohexylurea) was detectable. All prepared compounds were subsequently used without further purification.

Example 9. Polymer Modification

Formation of siRNA delivery conjugate using RGD-PEG-HyNic, RGD-PEG-ACit-PNP, or RDG-PEG-FCitFP-TFP and PEG-dipeptide modifying agents.

1) Protocol 1. The indicated polymer was reacted with SMPT at a weight ratio of 1:0.015 (polymer:SMPT) in 5 mM HEPES, pH 8.0 buffer for 1 h at RT. The SMPT-modified polymer was then reacted with aldehyde-PEG-dipeptide modifying agent (aldehyde-$PEG_{12}$-FCit or aldehyde-$PEG_{24}$-ACit) at desired ratios for 1 h at RT. The modified polymer was then reacted with $PEG_{12}$-dipeptide modifying agent ($PEG_{12}$-FCit, $PEG_{12}$-ACit or $PEG_{24}$-ACit) at a weight ratio of 1:2 (polymer:PEG) in 100 mM HEPES, pH 9.0 buffer for 1 h at RT. The modified polymer was then reacted overnight with SATA-RNAi trigger at a weight ratio of 1:0.2 (polymer:SATA-RNAi trigger) in 100 mM HEPES, pH 9.0 buffer at RT to attach the RNAi trigger. Next, the modified polymer was reacted with protease cleavable PEG ($PEG_{12}$-FCit or $PEG_{12}$-ACit or $PEG_{24}$-ACit) at a weight ratio of 1:6 (polymer:PEG) in 100 mM HEPES, pH 9.0 buffer for 1 h at RT. The resultant conjugate was purified using a sephadex G-50 spin column.

RGD-HyNic (Example 6B) was attached to the modified polymer to form the full delivery conjugate by reaction with the modified polymer at a weight ratio of 1:0.7 (polymer:RGD-HyNic mimic) in 50 mM MES, pH 5.0 buffer for a minimum of 4 h at RT. The conjugate was purified using a sephadex G-50 spin column. RGD ligand attachment efficiency was determined as described above.

2) Protocol 2. The indicated polymer was reacted with SMPT at a weight ratio of 1:0.015 (polymer:SMPT) in 5 mM HEPES, pH 8.0 buffer for 1 h at RT. The SMPT-modified polymer was then reacted with aldehyde-PEG-dipeptide modifying agent (aldehyde-$PEG_{24}$-ACit) at a weight ratio of 1:0.5 (polymer:PEG) and with PEG-dipeptide modifying agent ($PEG_{12}$-FCit, $PEG_{12}$-ACit or $PEG_{24}$-ACit) at a weight ratio of 1:2 (polymer:PEG) in 100 mM HEPES, pH 9.0 buffer for 1 h at RT. The modified polymer was then reacted overnight with SATA-RNAi trigger at a weight ratio of 1:0.2 (polymer:SATA-RNAi trigger) in 100 mM HEPES, pH 9.0 buffer at RT to attach the RNAi trigger. Next, the modified polymer was reacted with protease cleavable-PEG (PEG$_{12}$-FCit or PEG$_{12}$-ACit or PEG$_{24}$-ACit) at a weight ratio of 1:6 (polymer:PEG) in 100 mM HEPES, pH 9.0 buffer for 1 h at RT. RGD-HyNic (Example 6) was attached to the modified polymer to form the full conjugate by reaction with the modified polymer at a weight ratio of 1:0.7 (polymer:RGD-HyNic) in 69 mM hydrogen chloride solution (HCl) overnight at RT. RGD ligand attachment efficiency was determined as described above.

3) Protocol 3. The indicated polymer was reacted with SMPT at a weight ratio of 1:0.015 (polymer:SMPT) in 5 mM HEPES, pH 8.0 buffer for 1 h at RT. The SMPT-modified polymer was then reacted with aldehyde-PEG-dipeptide modifying agent (aldehyde-PEG$_{24}$-ACit) at a weight ratio of 1:0.5 (polymer:PEG) and with PEG-dipeptide modifying agent (PEG$_{12}$-FCit, PEG$_{12}$-ACit or PEG$_{24}$-ACit) at a weight ratio of 1:2 (polymer:PEG) in 50 mM HEPES, pH 9.0 buffer for 1 h at RT. The modified polymer was then reacted overnight with SATA-RNAi trigger at a weight ratio of 1:0.2 (polymer:SATA-RNAi trigger) in 50 mM. HEPES, pH 9.0 buffer at RT to attach the RNAi trigger. Next, the modified polymer was reacted with protease cleavable-PEG (PEG$_{12}$-FCit or PEG$_{12}$-ACit or PEG$_{24}$-ACit) at a weight ratio of 1:6 (polymer:PEG) in 50 mM HEPES, pH 9.0 buffer for 1 h at RT. RGD-HyNic (Example 6) was attached to the modified polymer to form the full delivery conjugate by reaction with the modified polymer at a weight ratio of 1:0.7 (polymer:RGD-HyNic mimic) in 100 mM MES free acid solution overnight at RT. RGD targeting ligand conjugation efficiency was determined as described above.

4) Protocol 4. The indicated polymer was reacted with Azido-PEG4-NHS at a weight ratio of 1:0.015 (polymer:Azido) in 5 mM HEPES, pH 8.0 buffer for 1 h at RT. The Azido-modified polymer was then reacted with aldehyde-PEG-dipeptide modifying agent (aldehyde-PEG$_{24}$-ACit) at a weight ratio of 1:0.5 (polymer:PEG) and with PEG-dipeptide modifying agent (PEG$_{12}$-ACit) at a weight ratio of 1:2 (polymer:PEG) in 50 mM HEPES, pH 9.0 buffer for 1 h at RT. The modified polymer was then reacted overnight with Alkyne-RNAi trigger at a weight ratio of 1:0.2 (polymer:Alkyne-RNAi trigger) in 50 mM HEPES, pH 9.0 buffer at RT to attach the RNAi trigger. Next, the modified polymer was reacted with protease cleavable-PEG (PEG$_{12}$-ACit) at a weight ratio of 1:6 (polymer:PEG) in 50 mM HEPES, pH 9.0 buffer for 1 h at RT. RGD-HyNic (Example 6) was attached to the modified polymer to form the full delivery conjugate by reaction with the modified polymer at a weight ratio of 1:0.7 (polymer:RGD-HyNic mimic) in 100 mM sodium acetate-acetic acid buffer solution, pH 5.0 overnight at RT. RGD targeting ligand conjugation efficiency was determined as described above.

5) Protocol 5. The mono azide-polymer was reacted with aldehyde-PEG-dipeptide modifying agent (aldehyde-PEG$_{24}$-ACit) at a weight ratio of 1:0.5 (polymer:PEG) and with PEG-dipeptide modifying agent (PEG$_{12}$-ACit) at a weight ratio of 1:2 (polymer:PEG) in 50 mM HEPES, pH 9.0 buffer for 1 h at RT. The modified polymer was then reacted overnight with Alkyne-RNAi trigger at a weight ratio of 1:0.2 (polymer:Alkyne-RNAi trigger) in 50 mM HEPES, pH 9.0 buffer at RT to attach the RNAi trigger.

Next, the modified polymer was reacted with protease cleavable-PEG (PEG$_{12}$-ACit) at a weight ratio of 1:6 (polymer:PEG) in 50 mM HEPES, pH 9.0 buffer for 1 h at RT. RGD4-HyNic (Example 6) was attached to the modified polymer to form the full delivery conjugate by reaction with the modified polymer at a weight ratio of 1:0.7 (polymer:RGD-HyNic mimic) in 100 mM sodium acetate-acetic acid buffer solution, pH 5.0 overnight at RT. RGD targeting ligand conjugation efficiency was determined as described above.

6) Protocol 6. The mono azide-polymer was reacted with protease cleavable-RGD agent (RGD-PEG$_8$-ACit-PNP, RDG-PEG$_8$-FCitFP-TFP, RGD-PEG$_{15}$-FCitFP-TFP, RGD-PEG$_{19}$-FCitFP-TFP, or RGD-PEG$_{20}$-FCitFP-TFP) at weight ratios of 1:0125, 1:0.25, 1:0.5, 1:1, 1:1.5, 1:2 (polymer:RGD) in 50 mM HEPES, pH 8.5 buffer for 4 h at RT. The modified polymer was then reacted with protease cleavable-PEG agent (PEG$_6$-ACit-PABC-PNP, PEG$_{12}$-ACit-PABC-PNP, PEG$_{12}$-FCit-PABC-PNP, PEG$_{12}$-FCitFP-TFP) at a weight ratio of 1:8 (polymer:PEG) in 50 mM HEPES, pH 8.5 buffer for 2 h at RT. Alkyne-RNAi trigger at a weight ratio of 1:0.3 (polymer:Alkyne-RNAi trigger) was added to the modified polymer in 100 mM sodium acetate-acetic acid buffer solution, pH 5.0 for 5 days at RT. The completed conjugate was TFF purified and conjugation efficiency determined.

7) Protocol 7. The mono azide-polymer was reacted with protease cleavable-RGD agent (RGD-PEG$_{20}$-FCitFP-TFP) at weight ratio of 1:1 (polymer:RGD) in 50 mM. HEPES, pH 8.5 buffer for 2 h at RT. The modified polymer was then reacted with protease cleavable-PEG agent (PEG$_{12}$-ACit-PABC-PNP) at a weight ratio of 1:8 (polymer:PEG) in 50 mM HEPES, pH 8.5 buffer for 2 h at RT. The modified polymer was then TFF purified. Alkyne-RNAi trigger at a weight ratio of 1:0.4 (polymer:Alkyne-RNAi trigger) was added to the TFF purified polymer for 3 days at 37° C.

Example 10. In Vitro Analysis of Hif2α RNAi Triggers

Candidate sequences were identified by in silico analysis and screened as chemically modified canonical siRNAs in vitro. For screening purposes, the human EPAS1 (Hif2α) cDNA sequence (accession #NM_001430) was synthesized and cloned (DNA 2.0, Menlo Park, Calif.) into a commercially-available reporter-based screening plasmid, psiCHECK2 (Promega, Madison, Wis.) which generated a Renilla luciferase/EPAS1 fusion mRNA. For RNAi trigger efficacy evaluation, Hep3B cells, a human hepatocellular carcinoma line, were plated at ~10,000 cells per well in 96-well format. Each of the 187 EPAS1 RNAi triggers, in two subsets, was co-transfected at two concentrations, 1 nM and 0.1 nM, with 25 ng EPAS1-psiCHECK2 plasmid DNA per well and 0.2 μL LipoFectamine 2000 (Life Technologies) per well. Gene knockdown was determined by measuring Renilla luciferase levels normalized to the levels of constitutively-expressed firefly luciferase, also present on the psiCHECK-2 plasmid, using the Dual Luciferase Reporter Assay (Promega, Madison, Wis.) Table 5.

TABLE 5A

Unmodified Hif2α RNAi trigger
antisense strand and sense strand sequences.

| SEQ ID NO. | Sense Strand Sequence (5' → 3') | SEQ ID NO. | Antisense Strand Sequence (5' → 3') |
|---|---|---|---|
| 285 | GAGACUGUAUGGUCAGCUC | 478 | GAGCUGACCAUACAGUCUC |
| 286 | CUCCGACUCCUUCCGACUC | 479 | GAGUCGGAAGGAGUCGGAG |
| 287 | UCCGACUCCCAGCAUUCGA | 480 | UCGAAUGCUGGGAGUCGGA |
| 288 | CGACUCCCAGCAUUCGAGC | 481 | GCUCGAAUGCUGGGAGUCG |
| 289 | GACUCCCAGCAUUCGAGCC | 482 | GGCUCGAAUGCUGGGAGUC |
| 290 | CAGGUGCUCGGCGUCUGAA | 483 | UUCAGACGCCGAGCACCUG |
| 291 | GUGCUCGGCGUCUGAACGU | 484 | ACGUUCAGACGCCGAGCAC |
| 292 | UCGGCGUCUGAACGUCUCA | 485 | UGAGACGUUCAGACGCCGA |
| 293 | GGCGUCUGAACGUCUCAAA | 486 | UUUGAGACGUUCAGACGCC |
| 294 | CGUCUGAACGUCUCAAAGG | 487 | CCUUUGAGACGUUCAGACG |
| 295 | AAAAGGAGUAGCUCGGAGA | 488 | UCUCCGAGCUACUCCUUUU |
| 296 | GGGUUUCAUUGCCGUGGUG | 489 | CACCACGGCAAUGAAACCC |
| 297 | UUCAUGGGACUUACACAGG | 490 | CCUGUGUAAGUCCCAUGAA |
| 298 | GGGACUUACACAGGUGGAG | 491 | CUCCACCUGUGUAAGUCCC |
| 299 | ACACAGGUGGAGCUAACAG | 492 | CUGUUAGCUCCACCUGUGU |
| 300 | GAGCUAACAGGACAUAGUA | 493 | UACUAUGUCCUGUUAGCUC |
| 301 | GCUAACAGGACAUAGUAUC | 494 | GAUACUAUGUCCUGUUAGC |
| 302 | CUAACAGGACAUAGUAUCU | 495 | AGAUACUAUGUCCUGUUAG |
| 303 | GGACAUAGUAUCUUUGACU | 496 | AGUCAAAGAUACUAUGUCC |
| 304 | UCUUUGACUUCACUCAUCC | 497 | GGAUGAGUGAAGUCAAAGA |
| 305 | UCACUCAUCCCUGCGACCA | 498 | UGGUCGCAGGGAUGAGUGA |
| 306 | GAGAUUCGUGAGAACCUGA | 499 | UCAGGUUCUCACGAAUCUC |
| 307 | UUCGUGAGAACCUGAGUCU | 500 | AGACUCAGGUUCUCACGAA |
| 308 | UCGUGAGAACCUGAGUCUC | 501 | GAGACUCAGGUUCUCACGA |
| 309 | GACAUGUCCACAGAGCGGG | 502 | CCCGCUCUGUGGACAUGUC |
| 310 | GCGGGACUUCUUCAUGAGG | 503 | CCUCAUGAAGAAGUCCCGC |
| 311 | GGAUGAAGUGCACGGUCAC | 504 | GUGACCGUGCACUUCAUCC |
| 312 | CACGGUCACCAACAGAGGC | 505 | GCCUCUGUUGGUGACCGUG |
| 313 | UCACCAACAGAGGCCGUAC | 506 | GUACGGCCUCUGUUGGUGA |
| 314 | CACCAACAGAGGCCGUACU | 507 | AGUACGGCCUCUGUUGGUG |
| 315 | AGGCCGUACUGUCAACCUC | 508 | GAGGUUGACAGUACGGCCU |
| 316 | UCCUCACAAUAGUCUGUGU | 509 | ACACAGACUAUUGUGAGGA |
| 317 | AAUAGUCUGUGUGGCUACA | 510 | UGUAGCCACACAGACUAUU |
| 318 | CAGAACUGAUUGGUUACCA | 511 | UGGUAACCAAUCAGUUCUG |
| 319 | AGAACUGAUUGGUUACCAC | 512 | GUGGUAACCAAUCAGUUCU |
| 320 | CUGAUUGGUUACCACCCUG | 513 | CAGGGUGGUAACCAAUCAG |
| 321 | UUGGCCGCUCAGCCUAUGA | 514 | UCAUAGGCUGAGCGGCCAA |

TABLE 5A-continued

Unmodified Hif2α RNAi trigger
antisense strand and sense strand sequences.

| SEQ ID NO. | Sense Strand Sequence (5' → 3') | SEQ ID NO. | Antisense Strand Sequence (5' → 3') |
|---|---|---|---|
| 322 | UAUGAAUUCUACCAUGCGC | 515 | GCGCAUGGUAGAAUUCAUA |
| 323 | AUGAAUUCUACCAUGCGCU | 516 | AGCGCAUGGUAGAAUUCAU |
| 324 | UGAAUUCUACCAUGCGCUA | 517 | UAGCGCAUGGUAGAAUUCA |
| 325 | GAAUUCUACCAUGCGCUAG | 518 | CUAGCGCAUGGUAGAAUUC |
| 326 | AAUUCUACCAUGCGCUAGA | 519 | UCUAGCGCAUGGUAGAAUU |
| 327 | UCUACCAUGCGCUAGACUC | 520 | GAGUCUAGCGCAUGGUAGA |
| 328 | AUGCGCUAGACUCCGAGAA | 521 | UUCUCGGAGUCUAGCGCAU |
| 329 | UGCGCUAGACUCCGAGAAC | 522 | GUUCUCGGAGUCUAGCGCA |
| 330 | GUAAGUGGCCAGUACCGGA | 523 | UCCGGUACUGGCCACUUAC |
| 331 | UAAGUGGCCAGUACCGGAU | 524 | AUCCGGUACUGGCCACUUA |
| 332 | CCAGUACCGGAUGCUCGCA | 525 | UGCGAGCAUCCGGUACUGG |
| 333 | AGUACCGGAUGCUCGCAAA | 526 | UUUGCGAGCAUCCGGUACU |
| 334 | UACCGGAUGCUCGCAAAGC | 527 | GCUUUGCGAGCAUCCGGUA |
| 335 | UGCUCGCAAAGCAUGGGGG | 528 | CCCCCAUGCUUUGCGAGCA |
| 336 | CGCAAAGCAUGGGGGCUAC | 529 | GUAGCCCCCAUGCUUUGCG |
| 337 | AGCAUGGGGGCUACGUGUG | 530 | CACACGUAGCCCCCAUGCU |
| 338 | GCAUGGGGGCUACGUGUGG | 531 | CCACACGUAGCCCCCAUGC |
| 339 | CAUCUACAACCCUCGCAAC | 532 | GUUGCGAGGGUUGUAGAUG |
| 340 | AUCUACAACCCUCGCAACC | 533 | GGUUGCGAGGGUUGUAGAU |
| 341 | CUACAACCCUCGCAACCUG | 534 | CAGGUUGCGAGGGUUGUAG |
| 342 | UACAACCCUCGCAACCUGC | 535 | GCAGGUUGCGAGGGUUGUA |
| 343 | UUUGAUAGCAGUGGCAAGG | 536 | CCUUGCCACUGCUAUCAAA |
| 344 | AGUAACUUCCUAUUCACCA | 537 | UGGUGAAUAGGAAGUUACU |
| 345 | UCGGGAAUCAGAACUUCGA | 538 | UCGAAGUUCUGAUUCCCGA |
| 346 | CUGCUCCACGCCCAAUAGC | 539 | GCUAUUGGGCGUGGAGCAG |
| 347 | UGCUCCACGCCCAAUAGCC | 540 | GGCUAUUGGGCGUGGAGCA |
| 348 | GCUCCACGCCCAAUAGCCC | 541 | GGGCUAUUGGGCGUGGAGC |
| 349 | ACGCCCAAUAGCCCUGAAG | 542 | CUUCAGGGCUAUUGGGCGU |
| 350 | CAUCUUUGGAUAACGACCU | 543 | AGGUCGUUAUCCAAAGAUG |
| 351 | CAAUGCAGUACCCAGACGG | 544 | CCGUCUGGGUACUGCAUUG |
| 352 | AUGCAGUACCCAGACGGAU | 545 | AUCCGUCUGGGUACUGCAU |
| 353 | AGUACCCAGACGGAUUUCA | 546 | UGAAAUCCGUCUGGGUACU |
| 354 | CUGUAGCCCCGCACAGUCC | 547 | GGACUGUGCGGGGCUACAG |
| 355 | AUCUUCUUUGAUGCCGGAA | 548 | UUCCGGCAUCAAAGAAGAU |
| 356 | CUUUGAUGCCGGAAGCAAA | 549 | UUUGCUUCCGGCAUCAAAG |
| 357 | GAUGCCGGAAGCAAAGCAU | 550 | AUGCUUUGCUUCCGGCAUC |

TABLE 5A-continued

Unmodified Hif2α RNAi trigger
antisense strand and sense strand sequences.

| SEQ ID NO. | Sense Strand Sequence (5' → 3') | SEQ ID NO. | Antisense Strand Sequence (5' → 3') |
| --- | --- | --- | --- |
| 358 | AUGCCGGAAGCAAAGCAUC | 551 | GAUGCUUUGCUUCCGGCAU |
| 359 | GCCGGAAGCAAAGCAUCCC | 552 | GGGAUGCUUUGCUUCCGGC |
| 360 | CCCCCAGAUCCACCAUUAC | 553 | GUAAUGGUGGAUCUGGGGG |
| 361 | AGAUCCACCAUUACAUUUU | 554 | AAAAUGUAAUGGUGGAUCU |
| 362 | AUUUUGGGCCCACAAAGUG | 555 | CACUUUGUGGGCCCAAAAU |
| 363 | UUUUGGGCCCACAAAGUGG | 556 | CCACUUUGUGGGCCCAAAA |
| 364 | UUUGGGCCCACAAAGUGGG | 557 | CCCACUUUGUGGGCCCAAA |
| 365 | CCACAAAGUGGGCCGUCGG | 558 | CCGACGGCCCACUUUGUGG |
| 366 | CACAAAGUGGGCCGUCGGG | 559 | CCCGACGGCCCACUUUGUG |
| 367 | AGUGGGCCGUCGGGGAUCA | 560 | UGAUCCCCGACGGCCCACU |
| 368 | AAAGGGUUUUGGGGCUCGA | 561 | UCGAGCCCCAAAACCCUUU |
| 369 | GGCUCGAGGCCCAGACGUG | 562 | CACGUCUGGGCCUCGAGCC |
| 370 | GCUCGAGGCCCAGACGUGC | 563 | GCACGUCUGGGCCUCGAGC |
| 371 | CUCGAGGCCCAGACGUGCU | 564 | AGCACGUCUGGGCCUCGAG |
| 372 | GGUAGCCCUCUCCAACAAG | 565 | CUUGUUGGAGAGGGCUACC |
| 373 | CUUUGAUGCCGGACAAGCC | 566 | GGCUUGUCCGGCAUCAAAG |
| 374 | UUUGAUGCCGGACAAGCCA | 567 | UGGCUUGUCCGGCAUCAAA |
| 375 | UUGAUGCCGGACAAGCCAC | 568 | GUGGCUUGUCCGGCAUCAA |
| 376 | GGACAAGCCACUGAGCGCA | 569 | UGCGCUCAGUGGCUUGUCC |
| 377 | ACAAGCCACUGAGCGCAAA | 570 | UUUGCGCUCAGUGGCUUGU |
| 378 | GGACUACAGCCUGUCGUCA | 571 | UGACGACAGGCUGUAGUCC |
| 379 | GACUACAGCCUGUCGUCAG | 572 | CUGACGACAGGCUGUAGUC |
| 380 | CUACAGCCUGUCGUCAGCC | 573 | GGCUGACGACAGGCUGUAG |
| 381 | CCUGUCGUCAGCCCACAAG | 574 | CUUGUGGGCUGACGACAGG |
| 382 | GCAUGGCAAGCCGGCUGCU | 575 | AGCAGCCGGCUUGCCAUGC |
| 383 | CUGACCAGAUAUGACUGUG | 576 | CACAGUCAUAUCUGGUCAG |
| 384 | GAUAUGACUGUGAGGUGAA | 577 | UUCACCUCACAGUCAUAUC |
| 385 | GGUGAACGUGCCCGUGCUG | 578 | CAGCACGGGCACGUUCACC |
| 386 | UACAAGAUGGACUUACCUG | 579 | CAGGUAAGUCCAUCUUGUA |
| 387 | GGACUUACCUGGCAGACUU | 580 | AAGUCUGCCAGGUAAGUCC |
| 388 | UUUUUCUGAGAUGCUCACU | 581 | AGUGAGCAUCUCAGAAAAA |
| 389 | AGUACACAAUUGUUUUACC | 582 | GGUAAAACAAUUGUGUACU |
| 390 | ACAAGUUUGGUGCAUGUCU | 583 | AGACAUGCACCAAACUUGU |
| 391 | ACUAAAAAGAUUCCUCGUU | 584 | AACGAGGAAUCUUUUUAGU |
| 392 | AGGGUCAACUCCAACGUAU | 585 | AUACGUUGGAGUUGACCCU |
| 393 | GGGUCAACUCCAACGUAUG | 586 | CAUACGUUGGAGUUGACCC |
| 394 | GUCAACUCCAACGUAUGUG | 587 | CACAUACGUUGGAGUUGAC |

TABLE 5A-continued

Unmodified Hif2α RNAi trigger antisense strand and sense strand sequences.

| SEQ ID NO. | Sense Strand Sequence (5' → 3') | SEQ ID NO. | Antisense Strand Sequence (5' → 3') |
|---|---|---|---|
| 395 | UCAACUCCAACGUAUGUGG | 588 | CCACAUACGUUGGAGUUGA |
| 396 | CAACUCCAACGUAUGUGGU | 589 | ACCACAUACGUUGGAGUUG |
| 397 | CUCCAACGUAUGUGGUUAU | 590 | AUAACCACAUACGUUGGAG |
| 398 | UCCAACGUAUGUGGUUAUC | 591 | GAUAACCACAUACGUUGGA |
| 399 | CCAACGUAUGUGGUUAUCU | 592 | AGAUAACCACAUACGUUGG |
| 400 | AACGUAUGUGGUUAUCUGU | 593 | ACAGAUAACCACAUACGUU |
| 401 | UUAUAUCUGGGUUAAGUGU | 594 | ACACUUAACCCAGAUAUAA |
| 402 | CCACGGCCUGUACGGACAC | 595 | GUGUCCGUACAGGCCGUGG |
| 403 | ACGGCCUGUACGGACACUG | 596 | CAGUGUCCGUACAGGCCGU |
| 404 | UGUCGGCUUUUUGCCAUCU | 597 | AGAUGGCAAAAAGCCGACA |
| 405 | GUCGGCUUUUUGCCAUCUG | 598 | CAGAUGGCAAAAAGCCGAC |
| 406 | AUCUGUGAUAUGCCAUAGG | 599 | CCUAUGGCAUAUCACAGAU |
| 407 | UGCCAUAGGUGUGACAAUC | 600 | GAUUGUCACACCUAUGGCA |
| 408 | CCAUAGGUGUGACAAUCCG | 601 | CGGAUUGUCACACCUAUGG |
| 409 | CAUAGGUGUGACAAUCCGA | 602 | UCGGAUUGUCACACCUAUG |
| 410 | AUAGGUGUGACAAUCCGAG | 603 | CUCGGAUUGUCACACCUAU |
| 411 | GGUGUGACAAUCCGAGCAG | 604 | CUGCUCGGAUUGUCACACC |
| 412 | ACAAUCCGAGCAGUGGAGU | 605 | ACUCCACUGCUCGGAUUGU |
| 413 | CCGAGCAGUGGAGUCAUUC | 606 | GAAUGACUCCACUGCUCGG |
| 414 | GGGAGCACUGCGCGCUAUC | 607 | GAUAGCGCGCAGUGCUCCC |
| 415 | GGAGCACUGCGCGCUAUCC | 608 | GGAUAGCGCGCAGUGCUCC |
| 416 | AGCACUGCGCGCUAUCCCC | 609 | GGGGAUAGCGCGCAGUGCU |
| 417 | UAUUGCUGCCAAGAGGGUC | 610 | GACCCUCUUGGCAGCAAUA |
| 418 | GGUCUGAUGGCACGUUGUG | 611 | CACAACGUGCCAUCAGACC |
| 419 | CUGAUGGCACGUUGUGGGG | 612 | CCCCACAACGUGCCAUCAG |
| 420 | GGCACGUUGUGGGGUCGGG | 613 | CCCGACCCCACAACGUGCC |
| 421 | GCACGUUGUGGGGUCGGGG | 614 | CCCCGACCCCACAAGGUGC |
| 422 | CACGUUGUGGGGUCGGGGG | 615 | CCCCCGACCCCACAACGUG |
| 423 | GCGGGGAAGUGCUCUAACU | 616 | AGUUAGAGCACUUCCCCGC |
| 424 | CGGGGAAGUGCUCUAACUU | 617 | AAGUUAGAGCACUUCCCCG |
| 425 | UUAAGGUUUUGUUGCUAGC | 618 | GCUAGCAACAAAACCUUAA |
| 426 | GUUGCUAGCCCUUCAAGUG | 619 | CACUUGAAGGGCUAGCAAC |
| 427 | GAGCUAUGUGACUCGGAUG | 620 | CAUCCGAGUCACAUAGCUC |
| 428 | GCUAUGUGACUCGGAUGGU | 621 | ACCAUCCGAGUCACAUAGC |
| 429 | CGGAUGGUCUUUCACACGG | 622 | CCGUGUGAAAGACCAUCCG |
| 430 | GAUGGUCUUUCACACGGCA | 623 | UGCCGUGUGAAAGACCAUC |

TABLE 5A-continued

Unmodified Hif2α RNAi trigger
antisense strand and sense strand sequences.

| SEQ ID NO. | Sense Strand Sequence (5' → 3') | SEQ ID NO. | Antisense Strand Sequence (5' → 3') |
|---|---|---|---|
| 431 | UGGUCUUUCACACGGCACA | 624 | UGUGCCGUGUGAAAGACCA |
| 432 | AACUACCAUGAGAUGGUUU | 625 | AAACCAUCUCAUGGUAGUU |
| 433 | UACCAUGAGAUGGUUUAGA | 626 | UCUAAACCAUCUCAUGGUA |
| 434 | CCAAGCUCACGACCUUGGA | 627 | UCCAAGGUCGUGAGCUUGG |
| 435 | ACGACCUUGGAGCCCCGUG | 628 | CACGGGGCUCCAAGGUCGU |
| 436 | GGGUAAGAGGGACGACACC | 629 | GGUGUCGUCGCUGUUACCC |
| 437 | GGUAAGAGGGACGACACCU | 630 | AGGUGUCGUCCCUCUUACC |
| 438 | GUAAGAGGGACGACACCUC | 631 | GAGGUGUCGUCCCUCUUAC |
| 439 | UGGUUUUUCAAUACCAAUU | 632 | AAUUGGUAUUGAAAAACCA |
| 440 | UUCAAUACCAAUUACAUGG | 633 | CCAUGUAAUUGGUAUUGAA |
| 441 | AUACCAAUUACAUGGAACU | 634 | AGUUCCAUGUAAUUGGUAU |
| 442 | CCAACUAUUUAGUAAGCCC | 635 | GGGCUUACUAAAUAGUUGG |
| 443 | AACUAUUUAGUAAGCCCGG | 636 | CCGGGCUUACUAAAUAGUU |
| 444 | ACUAUUUAGUAAGCCCGGA | 637 | UCCGGGCUUACUAAAUAGU |
| 445 | AGAAAUUCCUUAGUCAUGG | 638 | CCAUGACUAAGGAAUUUCU |
| 446 | CAUUAAGGGCAUUUUACCC | 639 | GGGUAAAAUGCCCUUAAUG |
| 447 | UAAGGGCAUUUUACCCUUG | 640 | CAAGGGUAAAAUGCCCUUA |
| 448 | AGCUUCAUAUUAACCCUAC | 641 | GUAGGGUUAAUAUGAAGCU |
| 449 | UAUUAACCCUACCUGUCAA | 642 | UUGACAGGUAGGGUUAAUA |
| 450 | UUAACCCUACCUGUCAACG | 643 | CGUUGACAGGUAGGGUUAA |
| 451 | ACCCUACCUGUCAACGUAA | 644 | UUACGUUGACAGGUAGGGU |
| 452 | CCCUACCUGUCAACGUAAC | 645 | GUUACGUUGACAGGUAGGG |
| 453 | CCUACCUGUCAACGUAACG | 646 | CGUUACGUUGACAGGUAGG |
| 454 | CUACCUGUCAACGUAACGA | 647 | UCGUUACGUUGACAGGUAG |
| 455 | UACCUGUCAACGUAACGAU | 648 | AUCGUUACGUUGACAGGUA |
| 456 | ACCUGUCAACGUAACGAUU | 649 | AAUCGUUACGUUGACAGGU |
| 457 | CCUGUCAACGUAACGAUUU | 650 | AAAUCGUUACGUUGACAGG |
| 458 | CUGUCAACGUAACGAUUUC | 651 | GAAAUCGUUACGUUGACAG |
| 459 | UGUCAACGUAACGAUUUCA | 652 | UGAAAUCGUUACGUUGACA |
| 460 | UCAACGUAACGAUUUCAUG | 653 | CAUGAAAUCGUUACGUUGA |
| 461 | ACGUAACGAUUUCAUGAAC | 654 | GUUCAUGAAAUCGUUACGU |
| 462 | UAUUAUAUUGUCGAAUUCC | 655 | GGAAUUCGACAAUAUAAUA |
| 463 | UUAUAUUGUCGAAUUCCUA | 656 | UAGGAAUUCGACAAUAUAA |
| 464 | UAUUGUCGAAUUCCUACUG | 657 | CAGUAGGAAUUCGACAAUA |
| 465 | GAAUUCCUACUGACAACAU | 658 | AUGUUGUCAGUAGGAAUUC |
| 466 | UCCUACUGACAACAUUAUA | 659 | UAUAAUGUUGUCAGUAGGA |
| 467 | UAUAACUGUAUGGGAGCUU | 660 | AAGCUCCCAUACAGUUAUA |

TABLE 5A-continued

Unmodified Hif2α RNAi trigger antisense strand and sense strand sequences.

| SEQ ID NO. | Sense Strand Sequence (5' → 3') | SEQ ID NO. | Antisense Strand Sequence (5' → 3') |
|---|---|---|---|
| 468 | UAACUGUAUGGGAGCUUAA | 661 | UUAAGCUCCCAUACAGUUA |
| 469 | UGUAUGGGAGCUUAACUUU | 662 | AAAGUUAAGCUCCCAUACA |
| 470 | UUGACACUGGUAUCUUAUU | 663 | AAUAAGAUACCAGUGUCAA |
| 471 | AAGUAUUCUGAUCCUACCA | 664 | UGGUAGGAUCAGAAUACUU |
| 472 | CAACGUAACGAUUUCAUGAAA | 665 | UUCAUGAAAUCGUUACGUUGGC |
| 473 | UAUAUCAACGUAACGAUUUCAUGAAA | 666 | UUCAUGAAAUCGUUACGUUGGCU |
| 474 | UAUAUCAACGUAACGAUUUCAUGAAA | 667 | UUCAUGAAAUCGUUACGUUGGCUAU |
| 475 | UAUAUCAACGUAACGAUUUCAUGAAA | 668 | UUCAUGAAAUCGUUACGUUGGCUGU |
| 476 | UAUAUCGACGUAACGAUUUCAUGAAA | 669 | UUCAUGAAAUCGUUACGUCGGCUAU |
| 477 | UAUACGUAACGAUUUCAUGAAA | 670 | UUCAUGAAAUCGUUACGU |

TABLE 5B

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2231 | 671 | GfaGfaCfuGfuAfuGfgUfcAfgCfuAfdT | 858 | dTAfgCfuGfaCfcAfuAfcAfgUfcUfcdTsdT |
| 2232 | 672 | CfuCfcGfaCfuCfcUfuCfcGfaCfuAfdT | 859 | dTAfgUfcGfgAfaGfgAfgUfcGfgAfgdTsdT |
| 2233 | 673 | UfcCfgAfcUfcCfcAfgCfaUfcCfgAfdT | 860 | dTCfgAfaUfgCfuGfgGfaGfuCfgGfadTsdT |
| 2234 | 674 | CfgAfcUfcCfcAfgCfaUfcCfgAfgAfdT | 861 | dTCfuCfgAfaUfgCfuGfgGfaGfuCfgdTsdT |
| 2235 | 675 | GfaCfuCfcCfaGfcAfuUfcGfaGfcAfdT | 862 | dTGfcUfcGfaAfuGfcUfgGfgAfgUfcdTsdT |
| 2236 | 676 | CfaGfgUfgCfuCfgGfcGfuCfuGfaAfdT | 863 | dTUfcAfgAfcGfcCfgAfgCfaCfcUfgdTsdT |
| 2237 | 677 | GfuGfcUfcGfgCfgUfcUfgAfaCfgAfdT | 864 | dTCfgUfuCfaGfaCfgCfcGfaGfcAfcdTsdT |
| 2238 | 678 | UfcGfgCfgUfcUfgAfaCfgUfcUfcAfdT | 865 | dTGfaGfaCfgUfuCfaGfaCfgCfcGfadTsdT |
| 2239 | 679 | GfgCfgUfcUfgAfaCfgUfcUfcAfaAfdT | 866 | dTUfuGfaGfaCfgUfuCfaGfaCfgCfcdTsdT |
| 2240 | 680 | CfgUfcUfgAfaCfgUfcUfcAfaAfgAfdT | 867 | dTCfuUfuGfaGfaCfgUfuCfaGfaCfgdTsdT |
| 2241 | 681 | AfaAfaGfgAfgUfaGfcUfcCfgGfaGfdT | 868 | dTCfuCfcGfaGfcUfaCfuCfcUfuUfudTsdT |
| 2242 | 682 | GfgGfuUfuCfaUfuGfcCfgUfgGfuUfdT | 869 | dTAfcCfaCfgGfcAfaUfgAfaAfcCfcdTsdT |
| 2243 | 683 | UfuCfaUfgGfgAfcUfuAfcAfcAfgAfdT | 870 | dTCfuGfuGfuAfaGfuCfcCfaUfgAfadTsdT |
| 2244 | 684 | GfgGfaCfuUfaCfaCfaGfuGfgAfaAfdT | 871 | dTUfcCfaCfcUfgUfgUfaAfgUfcCfcdTsdT |
| 2245 | 685 | AfcAfcAfgGfuGfgAfgCfuAfaCfaAfdT | 872 | dTUfgUfuAfgCfuCfcAfcCfuGfuGfudTsdT |
| 2246 | 686 | GfaGfcUfaAfcAfgGfaCfaUfaGfuAfdT | 873 | dTAfcUfaUfgUfcCfuGfuUfaGfcUfcdTsdT |
| 2247 | 687 | GfcUfaAfcAfgGfaCfaUfaGfuAfuAfdT | 874 | dTAfuAfcUfaUfgUfcCfuGfuUfaGfcdTsdT |
| 2248 | 688 | CfuAfaCfaGfgAfcAfuAfgUfaUfcAfdT | 875 | dTGfaUfaCfuAfuGfuCfcUfgUfuAfgdTsdT |
| 2249 | 689 | GfgAfcAfuAfgUfaUfcUfuUfgAfcAfdT | 876 | dTGfuCfaAfaGfaUfaCfuAfuGfuCfcdTsdT |
| 2250 | 690 | UfcUfuUfgAfcUfuCfaCfuCfaUfcAfdT | 877 | dTGfaUfgAfgUfgAfaGfuCfaAfaGfadTsdT |
| 2251 | 691 | UfcAfcUfcAfuCfcCfuUfcGfaCfcAfdT | 878 | dTGfgUfcGfcAfgGfgAfuGfaGfuGfadTsdT |

TABLE 5B-continued

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2252 | 692 | GfaGfaUfcCfgUfgAfgAfaCfcUfgAfdT | 879 | dTCfaGfgUfUfcCfuCfaCfgAfaUfcUfcdTsdT |
| 2253 | 693 | UfuCfgUfgAfgAfaCfcUfgAfgUfcAfdT | 880 | dTGfaCfuCfaGfgUfuCfuCfaCfgAfadTsdT |
| 2254 | 694 | UfcGfuGfaGfaAfcCfuGfaGfuCfuAfdT | 881 | dTAfgAfcUfcAfgGfuUfcUfcAfcGfadTsdT |
| 2255 | 695 | GfaCfaUfgUfcCfaCfaGfaGfcGfgAfdT | 882 | dTCfcGfcUfcUfgUfgGfaCfaUfgUfcdTsdT |
| 2256 | 696 | GfcGfgGfaCfuUfcUfcAfuGfaGfaAfdT | 883 | dTCfuCfaUfgAfgAfaGfuCfcCfgCfcdTsdT |
| 2257 | 697 | GfgAfuGfaAfgUfgCfaCfgUfuCfaAfdT | 884 | dTUfgAfcCfgUfgCfaCfuUfcAfuCfcdTsdT |
| 2258 | 698 | CfaCfgGfuCfaCfcAfaCfaGfaGfdT | 885 | dTCfcUfcUfgUfuGfgUfgAfcCfgUfgdTsdT |
| 2259 | 699 | UfcAfcCfaAfcAfgAfgGfcCfgUfaAfdT | 886 | dTUfaCfgGfcCfuCfuGfuUfgGfuGfadTsdT |
| 2260 | 700 | CfaCfcAfaCfaGfaGfcGfcGfuAfcAfdT | 887 | dTGfuAfcGfgCfcUfcUfgUfuGfgUfgdTsdT |
| 2261 | 701 | AfgGfcCfgUfaCfuGfuCfaAfcCfuAfdT | 888 | dTAfgGfuUfgAfcAfgUfaCfgGfcCfudTsdT |
| 2262 | 702 | UfcCfuCfaCfaAfuAfgUfcUfgUfgAfdT | 889 | dTCfaCfaGfaCfuAfuUfgUfgAfgGfadTsdT |
| 2263 | 703 | AfaUfaGfuCfuGfuGfuUgCfuAfcAfdT | 890 | dTGfuAfgCfaAfcAfcAfgAfcUfaUfudTsdT |
| 2264 | 704 | CfaGfaAfcUfgAfuUfgGfuUfaCfcAfdT | 891 | dTGfgUfaAfcCfaAfuCfaGfuUfcUfgdTsdT |
| 2265 | 705 | AfgAfaCfuGfaUfuGfgUfuAfcCfaAfdT | 892 | dTUfgGfuAfaCfcAfaUfcAfgUfuCfudTsdT |
| 2266 | 706 | CfuGfaUfuGfgUfuAfcCfaCfcUfuAfdT | 893 | dTAfgGfuGfgUfaAfcCfaAfuCfAfgdTsdT |
| 2267 | 707 | UfuGfgCfcGfcUfcAfgCfcUfaUfgAfdT | 894 | dTCfaUfaGfgCfuGfaGfcGfcCfaAfdTsdT |
| 2268 | 708 | UfaUfgAfaUfuCfuAfcCfaUfgCfgAfdT | 895 | dTCfgCfaUfgGfuAfgAfaUfuCfaUfadTsdT |
| 2269 | 709 | AfuGfaAfuUfcUfaCfcAfuGfcGfcAfdT | 896 | dTGfcGfcAfuGfgUfaGfaAfuUfcAfudTsdT |
| 2270 | 710 | UfgAfaUfuCfuAfcCfaUfgCfgCfuAfdT | 897 | dTAfgCfgCfaUfgGfuAfgAfaUfuCfadTsdT |
| 2271 | 711 | GfaAfuUfcUfaCfcAfuGfcGfcUfaAfdT | 898 | dTUfaGfcGfcAfuGfgUfaGfaAfuUfcdTsdT |
| 2272 | 712 | AfaUfuCfuAfcCfaUfgCfgCfuAfgAfdT | 899 | dTCfuAfgCfgCfaUfgGfuAfgAfaUfudTsdT |
| 2273 | 713 | UfcUfaCfcAfuGfcGfcUfaGfaCfuAfdT | 900 | dTAfgUfcUfaGfcGfcAfuGfgUfaGfadTsdT |
| 2274 | 714 | AfuGfcGfcUfaGfaCfuCfcGfaGfaAfdT | 901 | dTUfcUfcGfgAfgUfcUfaGfcGfcAfudTsdT |
| 2275 | 715 | UfgCfgCfuAfgAfcUfcCfgAfgAfaAfdT | 902 | dTUfuCfuCfgGfaGfuCfuAfgCfgCfadTsdT |
| 2276 | 716 | GfuAfaGfuGfgCfcAfgUfaCfcGfgAfdT | 903 | dTCfcGfgUfaCfuGfgCfcAfcUfuAfcdTsdT |
| 2277 | 717 | UfsAfgUfgGfcCfaGfuAfcCfgGfaAfdT | 904 | dTUfcCfgGfuAfcUfgGfcCfaCfuUfadTsdT |
| 2278 | 718 | CfcAfgUfaCfcGfgAfuGfcUfcGfcAfdT | 905 | dTGfcGfaGfcAfuCfcGfgUfaCfuGfgdTsdT |
| 2279 | 719 | AfgUfaCfcGfgAfuGfcUfcGfcAfaAfdT | 906 | dTUfuGfcGfaGfcAfuCfcGfgUfaCfudTsdT |
| 2280 | 720 | UfaCfcGfgAfuGfcUfcGfcAfaAfgAfdT | 907 | dTCfuUfuGfcGfaGfcAfuCfcGfgUfadTsdT |
| 2281 | 721 | UfgCfuCfgCfaAfaGfcAfuGfgGfgAfdT | 908 | dTCfcCfcAfuGfcUfuUfgCfgAfgCfadTsdT |
| 2282 | 722 | CfgCfaAfaGfcAfuGfgGfgCfuAfdT | 909 | dTUfaGfcCfcCfaUfgCfuUfuGfcGfdTsdT |
| 2283 | 723 | AfgCfaUfgGfgGfcUfaCfcGfuGfuAfdT | 910 | dTAfcAfcGfuAfgCfcCfcAfuGfcUfudTsdT |
| 2284 | 724 | GfcAfuGfgGfgGfcUfaCfgUfgUfgAfdT | 911 | dTCfaCfaCfgUfaGfcCfcCfaUfgCfdTsdT |
| 2285 | 725 | CfaUfcUfaCfaAfcCfcUfcGfcAfaAfdT | 912 | dTUfuGfcGfaGfgGfuUfgUfaGfaUfgdTsdT |
| 2286 | 726 | AfuCfuAfcAfaCfcCfuCfgCfaAfcAfdT | 913 | dTGfuUfgCfgAfgGfgUfuGfuAfgAfudTsdT |
| 2287 | 727 | CfuAfcAfaCfcCfuCfgCfaAfcCfuAfdT | 914 | dTAfgGfuUfgCfgAfgGfgUfuGfuAfgdTsdT |
| 2288 | 728 | UfaCfaAfcCfcUfcGfcAfaAfcCfuGfdT | 915 | dTCfaGfgUfuGfcGfaGfgGfuUfgUfadTsdT |
| 2289 | 729 | UfuUfgAfuAfgCfaGfuGfgCfaAfgAfdT | 916 | dTCfuUfgCfcAfcUfgCfuAfuCfaAfadTsdT |

TABLE 5B-continued

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2290 | 730 | AfgUfaAfcUfuCfcUfaUfuCfaCfcAfdT | 917 | dTGfgUfgAfaUfaGfgAfaGfuUfaCfudTsdT |
| 2291 | 731 | UfcGfgGfaAfuCfaGfaAfcUfuCfgAfdT | 918 | dTCfgAfaGfuUfcUfgAfuUfcCfcGfadTsdT |
| 2292 | 732 | CfuGfcUfcCfaCfgCfcCfaAfuAfgAfdT | 919 | dTCfuAfuUfgGfgCfgUfgGfaGfcAfgdTsdT |
| 2293 | 733 | UfgCfuCfcAfcGfcCfcAfaUfaGfcAfdT | 920 | dTGfcUfaUfuGfgGfcGfuGfgAfgCfadTsdT |
| 2294 | 734 | GfcUfcCfaCfgCfcCfaAfuAfgCfcAfdT | 921 | dTGfgCfuAfuUfgGfgCfgUfgGfaGfcdTsdT |
| 2295 | 735 | AfcGfcCfcAfaUfaGfcCfcUfgAfaAfdT | 922 | dTUfuCfaGfgGfcUfaUfuGfgGfcGfudTsdT |
| 2296 | 736 | CfaUfcUfuUfgGfaUfaAfcGfaCfcAfdT | 923 | dTGfgUfcGfuUfaUfcCfaAfaGfaUfgdTsdT |
| 2297 | 737 | CfaAfuGfcAfgUfaCfcCfaGfaCfgAfdT | 924 | dTCfgUfcUfgGfgUfaCfuGfcAfuUfgdTsdT |
| 2298 | 738 | AfuGfcAfgUfaCfcCfaGfaCfgGfaAfdT | 925 | dTUfcCfgUfcUfgGfgUfaCfuGfcAfudTsdT |
| 2299 | 739 | AfgUfaCfcCfaGfaCfgGfaUfuUfcAfdT | 926 | dTGfaAfaUfcCfgUfcUfgGfgUfaCfudTsdT |
| 2300 | 740 | CfuGfuAfgCfcCfcGfcAfcAfgUfcAfdT | 927 | dTGfaCfuGfuGfcGfgGfcUfaCfaGfdTsdT |
| 2301 | 741 | AfuCfuUfcUfuUfgAfuGfcCfgGfaAfdT | 928 | dTUfcCfgGfcAfuCfaAfaGfaAfgAfudTsdT |
| 2302 | 742 | CfuUfuGfaUfgCfcGfgAfaGfcAfaAfdT | 929 | dTUfuGfcUfuCfcGfgCfaUfcAfaAfgdTsdT |
| 2303 | 743 | GfaUfgCfcGfgAfaGfcAfaAfgCfaAfdT | 930 | dTUfgCfuUfuGfcUfuCfcGfgCfaUfcdTsdT |
| 2304 | 744 | AfuGfcCfgGfaAfgCfaAfaGfcAfuAfdT | 931 | dTAfuGfcUfuUfgCfuUfcCfgGfcAfudTsdT |
| 2305 | 745 | GfcCfgGfaAfgCfaAfaGfcAfuCfcAfdT | 932 | dTGfgAfuGfcUfuUfgCfuUfcCfgGfcdTsdT |
| 2306 | 746 | CfcCfcCfaGfaUfcCfaCfcAfuUfaAfdT | 933 | dTUfaAfuGfgUfgGfaUfcUfgGfgGfgdTsdT |
| 2307 | 747 | AfgAfuCfcAfcCfaUfuAfcAfuUfuAfdT | 934 | dTAfaAfuGfuAfaUfgGfuGfgAfuCfudTsdT |
| 2308 | 748 | AfuUfuUfgGfgCfcCfaCfaAfaGfuAfdT | 935 | dTAfcUfuUfgUfgGfgCfcCfaAfaAfudTsdT |
| 2309 | 749 | UfuUfuGfgGfcCfcAfcAfaAfgUfgAfdT | 936 | dTCfaCfuUfuGfuGfgGfcCfcAfaAfadTsdT |
| 2310 | 750 | UfuUfgGfgCfcCfaCfaAfaGfuGfgAfdT | 937 | dTCfcAfcUfuUfgUfgGfgCfcCfaAfadTsdT |
| 2311 | 751 | CfcAfcAfaAfgUfgGfgCfcGfuCfgAfdT | 938 | dTCfgAfcGfgCfcCfaCfuUfuGfuGfgdTsdT |
| 2312 | 752 | CfaCfaAfaGfuGfgGfcCfgUfcGfgAfdT | 939 | dTCfcGfaCfgGfcCfcAfcUfuUfgUfgdTsdT |
| 2313 | 753 | AfgUfgGfgCfcGfuCfgGfgGfaUfcAfdT | 940 | dTGfaUfcCfcCfgAfcGfgCfcCfaCfudTsdT |
| 2314 | 754 | AfaAfgGfgUfuUfuGfgGfcUfcGfaAfdT | 941 | dTCfgAfgCfcCfcAfaAfaCfcCfuUfudTsdT |
| 2315 | 755 | GfgCfuCfgAfgGfcCfcAfgAfcGfuAfdT | 942 | dTAfcGfuCfuGfgGfcCfuCfgAfgCfcdTsdT |
| 2316 | 756 | GfcUfcGfaGfgCfcCfaGfaCfgUfgAfdT | 943 | dTCfaCfgUfcUfgGfgCfcUfcGfaGfcdTsdT |
| 2317 | 757 | CfuCfgAfgGfcCfcAfgAfcGfuGfcAfdT | 944 | dTGfcAfcGfuCfuGfgGfcCfuCfgAfgdTsdT |
| 2318 | 758 | GfgUfaGfcCfcUfcUfcCfaAfcAfaAfdT | 945 | dTUfuGfuUfgGfaGfaGfgGfcUfaCfcdTsdT |
| 2319 | 759 | CfuUfuGfaUfgCfcGfgAfcAfaGfcAfdT | 946 | dTGfcUfuGfuCfcGfgCfaUfcAfaAfgdTsdT |
| 2320 | 760 | UfuUfgAfuGfcCfgGfaCfaAfgCfcAfdT | 947 | dTGfgCfuUfgUfcCfgGfcAfuCfaAfadTsdT |
| 2321 | 761 | UfuGfaUfgCfcGfgAfcAfaGfcCfaAfdT | 948 | dTUfgGfcUfuGfuCfcGfgCfaUfcAfadTsdT |
| 2322 | 762 | GfgAfcAfaGfcCfaCfuGfaGfcGfcAfdT | 949 | dTGfcGfcUfcAfgUfgGfcUfuGfuCfcdTsdT |
| 2323 | 763 | AfcAfaGfcCfaCfuGfaGfcGfcAfaAfdT | 950 | dTUfuGfcGfcUfcAfgUfgGfcUfuGfudTsdT |
| 2324 | 764 | GfgAfcUfaCfaGfcCfuGfuCfgUfcAfdT | 951 | dTGfaCfgAfcAfgGfcUfgUfaGfuCfcdTsdT |
| 2325 | 765 | GfaCfuAfcAfgGfcUfgUfcGfuCfaAfdT | 952 | dTUfgAfcGfaCfaGfcCfuGfuAfgUfcdTsdT |
| 2326 | 766 | CfuAfcAfgGfcUfgUfcGfuCfaGfcAfdT | 953 | dTGfcUfgAfcGfaCfaGfcCfuGfuAfgdTsdT |

TABLE 5B-continued

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2327 | 767 | CfcUfgUfcGfuCfaGfcCfcAfcAfaAfdT | 954 | dTUfuGfuGfgGfcUfgAfcGfaCfaGfgdTsdT |
| 2328 | 768 | GfcAfuGfgCfaAfgCfcGfgCfuGfcAfdT | 955 | dTGfcAfgCfcGfgCfuUfgCfcAfuGfcdTsdT |
| 2329 | 769 | CfuGfaCfcAfgAfuAfuGfaCfuGfuAfdT | 956 | dTAfcAfgUfcAfuAfuCfuGfgUfcAfgdTsdT |
| 2330 | 770 | GfaUfaUfgAfcUfgUfgAfgGfuGfaAfdT | 957 | dTUfcAfcCfuCfaCfaGfuCfaUfaUfcdTsdT |
| 2331 | 771 | GfgUfgAfaCfgUfgCfcCfgUfgCfuAfdT | 958 | dTAfgCfaCfgGfgCfaCfgUfuCfaCfcdTsdT |
| 2332 | 772 | UfaCfaAfgAfuGfaCfuUfaCfcfuAfdT | 959 | dTAfgGfuAfaGfuCfcAfuCfuUfgUfadTsdT |
| 2333 | 773 | GfgAfcUfuAfcCfuGfgCfaGfaCfuAfdT | 960 | dTAfgUfcUfgCfcAfgGfuAfaGfuCfcdTsdT |
| 2334 | 774 | UfuUfuUfcUfgAfgAfuGfcUfcAfcAfdT | 961 | dTGfuGfaGfcAfuCfuCfaGfaAfaAfadTsdT |
| 2335 | 775 | AfgUfaCfaCfaAfuUfgUfuUfaCfAfdT | 962 | dTGfuAfaAfaCfaAfuUfgUfgUfaCfudTsdT |
| 2336 | 776 | AfcAfaGfuUfuGfgUfgCfaUfgUfcAfdT | 963 | dTGfaCfaUfgCfaCfcAfaAfcUfuGfudTsdT |
| 2337 | 777 | AfcUfaAfaAfgAfuUfcUfcGfuAfdT | 964 | dTAfcGfaGfaAfuUfcUfuUfuAfgUfudTsdT |
| 2338 | 778 | AfgGfgUfcAfaCfuCfcAfaCfgUfaAfdT | 965 | dTUfaCfgUfuGfgAfgUfuGfaCfcCfudTsdT |
| 2339 | 779 | GfgGfuCfaAfcUfcCfaAfcGfuAfuAfdT | 966 | dTAfuAfcGfuUfgGfaGfuUfgAfcCfcdTsdT |
| 2340 | 780 | GfuCfaAfcUfcCfaAfcGfuAfuGfuAfdT | 967 | dTAfcAfuAfcGfuUfgGfaGfuUfgAfcdTsdT |
| 2341 | 781 | UfcAfaCfuCfcAfaCfgUfaUfgUfgAfdT | 968 | dTCfaCfaUfaCfgUfuGfgAfgUfuGfadTsdT |
| 2342 | 782 | CfaAfcUfcCfaAfcGfuAfuGfuGfgAfdT | 969 | dTCfcAfcAfuAfcGfuUfgGfaGfuUfgdTsdT |
| 2343 | 783 | CfuCfcAfaCfgUfaUfgUfgGfuUfaAfdT | 970 | dTUfaAfcCfaCfaUfaCfgUfuGfaGfgdTsdT |
| 2344 | 784 | UfcCfaAfcGfuAfuGfuGfgUfuAfuAfdT | 971 | dTAfuAfaCfcAfcAfuAfcGfuUfgGfadTsdT |
| 2345 | 785 | CfcAfaCfgUfaUfgUfgGfuUfaUfcAfdT | 972 | dTGfaUfaAfcCfaCfaUfaCfgUfuGfgdTsdT |
| 2346 | 786 | AfaCfgUfaUfgUfgGfuUfaUfcUfgAfdT | 973 | dTCfaGfaUfaAfcCfaCfaUfaCfgUfudTsdT |
| 2347 | 787 | UfuAfuAfuCfuGfgGfuUfaAfgUfgAfdT | 974 | dTCfaCfuUfaAfcCfcAfgAfuAfuAfadTsdT |
| 2348 | 788 | CfcAfcGfgCfcUfgUfaCfgGfaCfaAfdT | 975 | dTUfgUfcCfgUfaCfaGfgCfcGfuGfgdTsdT |
| 2349 | 789 | AfcGfgCfcUfgUfaCfgGfaCfaCfuAfdT | 976 | dTAfgUfgUfcCfgUfaCfaGfgCfcGfudTsdT |
| 2350 | 790 | UfgUfcGfgCfuUfuUfuGfcCfaUfcAfdT | 977 | dTGfaUfgGfcAfaAfaAfgCfcGfaCfadTsdT |
| 2351 | 791 | GfuCfgGfcUfuUfuUfgCfcAfuCfuAfdT | 978 | dTAfgAfuGfgCfaAfaAfaGfcCfgAfcdTsdT |
| 2352 | 792 | AfuCfuGfuGfaUfaUfgCfcAfuAfgAfdT | 979 | dTCfuAfuGfgCfaUfaUfcAfcAfgAfudTsdT |
| 2353 | 793 | UfgCfcAfuAfgGfuUfgUfgAfcAfuAfdT | 980 | dTAfuGfuCfaAfcAfcCfuAfuGfgCfadTsdT |
| 2354 | 794 | CfcAfuAfgGfuUfgUfgAfcAfuCfcAfdT | 981 | dTGfgAfuGfuCfaCfaCfcUfaUfgGfcdTsdT |
| 2355 | 795 | CfaUfaGfgUfgUfgAfcAfuCfgAfdT | 982 | dTCfgAfuUfgUfuCfaCfaCfcUfaUfgdTsdT |
| 2356 | 796 | AfuAfgGfuGfuGfaCfaAfuCfcGfaAfdT | 983 | dTUfcGfgAfuUfgUfcAfcAfcCfuAfudTsdT |
| 2357 | 797 | GfgUfgUfgAfcAfaUfcCfgAfgCfaAfdT | 984 | dTUfgCfuCfgGfaUfuGfuCfaCfaCfcdTsdT |
| 2358 | 798 | AfcAfaUfcCfgAfgCfaGfuGfgAfgAfdT | 985 | dTCfuCfcAfcUfgCfuCfgGfaUfuGfudTsdT |
| 2359 | 799 | CfcGfaGfcAfgUfgGfaGfuCfaUfuAfdT | 986 | dTAfaUfgAfcUfcCfaCfuGfcUfcGfgdTsdT |
| 2360 | 800 | GfgGfaGfcAfcUfgCfgCfgCfuAfuAfdT | 987 | dTAfuAfgCfgCfgCfaGfuGfcUfcCfcdTsdT |
| 2361 | 801 | GfgAfgCfaCfuGfcGfcGfcUfaUfcAfdT | 988 | dTGfaUfaGfcGfcGfcAfgUfgCfuCfcdTsdT |
| 2362 | 802 | AfgCfaCfuGfcGfcGfcUfaUfcCfcAfdT | 989 | dTGfgGfaUfaGfcGfcGfcAfgUfgCfudTsdT |
| 2363 | 803 | UfaUfuGfcUfgCfcAfaAfgAfgGfuAfdT | 990 | dTAfcCfcUfcUfuGfgCfaGfcAfaUfadTsdT |
| 2364 | 804 | GfgUfcUfgAfuGfgCfaCfgUfuGfuAfdT | 991 | dTAfcAfaCfgUfgCfcAfuCfaGfaCfcdTsdT |

TABLE 5B-continued

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2365 | 805 | CfuGfaUfgGfcAfcGfuUfgUfgGfgAfdT | 992 | dTCfcCfaCfaAfcGfuGfcCfaUfcAfgdTsdT |
| 2366 | 806 | GfgCfaCfgUfuGfuGfgGfgUfcGfgAfdT | 993 | dTCfcGfaCfcCfcAfcAfaCfgUfgCfcdTsdT |
| 2367 | 807 | GfcAfcGfuUfgUfgGfgGfuCfgGfgAfdT | 994 | dTCfcCfgAfcCfcCfaCfaAfcGfuGfcdTsdT |
| 2368 | 808 | CfaCfgUfuGfuGfgGfgUfcGfgGfgAfdT | 995 | dTCfcCfcGfaCfcCfcAfcAfaCfgUfgdTsdT |
| 2369 | 809 | GfcGfgGfgAfaGfuGfcUfcUfaAfcAfdT | 996 | dTGfuUfaGfaGfcAfcUfuCfcCfcGfcdTsdT |
| 2370 | 810 | CfgGfgGfaAfgUfgCfuCfuUfaAfcUfAfdT | 997 | dTAfgUfuAfgAfgCfaCfuUfcCfcCfgdTsdT |
| 2371 | 811 | UfuAfaGfgUfuUfuGfuUfgCfuAfgAfdT | 998 | dTCfuAfgCfaAfcAfaAfaCfcUfuAfadTsdT |
| 2372 | 812 | GfuUfgCfuAfgCfcCfuUfcAfaGfuAfdT | 999 | dTAfcUfuGfaAfgGfgCfuAfgCfaAfcdTsdT |
| 2373 | 813 | GfaGfcUfaUfgUfgAfcUfcGfgAfuAfdT | 1000 | dTAfuCfcGfaGfuCfaCfaUfaGfcUfcdTsdT |
| 2374 | 814 | GfcUfaUfgUfgAfcUfcGfgAfuUfgAfdT | 1001 | dTCfcAfuCfcGfaGfuCfaCfaUfaGfcdTsdT |
| 2375 | 815 | CfgGfaUfgGfuCfuUfcCfaCfaCfgAfdT | 1002 | dTCfgUfgUfgGfaAfgAfcCfaUfcCfgdTsdT |
| 2376 | 816 | GfaUfgGfuCfuUfuCfaCfaCfgGfcAfdT | 1003 | dTGfcCfgUfgUfgAfaAfgAfcCfaUfcdTsdT |
| 2377 | 817 | UfgGfuCfuUfuCfaCfaCfgGfcAfcAfdT | 1004 | dTGfuGfcCfgUfgUfgAfaAfgAfcCfadTsdT |
| 2378 | 818 | AfaCfuAfcCfaUfgAfgAfuGfgUfuAfdT | 1005 | dTAfaCfcAfuCfuCfaUfgGfuAfgUfudTsdT |
| 2379 | 819 | UfaCfcAfuGfaGfaUfgGfuUfuAfgAfdT | 1006 | dTCfuAfaAfcCfaUfcUfcAfuGfgUfadTsdT |
| 2380 | 820 | CfcAfaGfcUfcAfcGfaCfcUfuGfgAfdT | 1007 | dTCfcAfaGfgUfcGfuGfaGfcUfuGfgdTsdT |
| 2381 | 821 | AfcGfaCfcUfuGfgAfgCfcCfgUfaAfdT | 1008 | dTAfcGfgGfcUfcCfaAfgGfuCfgUfdTsdT |
| 2382 | 822 | GfgGfuAfaGfaGfgGfaCfgAfcAfcAfdT | 1009 | dTGfuGfuCfgUfcCfcUfcUfaCfcCfcdTsdT |
| 2383 | 823 | GfgUfaAfgAfgGfgAfcGfaCfaCfcAfdT | 1010 | dTGfgUfgUfcGfuCfcCfuCfuUfaCfcdTsdT |
| 2384 | 824 | GfuAfaGfaGfgGfaCfgAfcAfcCfuAfdT | 1011 | dTAfgGfuGfuCfgUfcCfcUfcUfuAfcdTsdT |
| 2385 | 825 | UfgGfuUfuUfuCfaAfuAfcCfaAfuAfdT | 1012 | dTAfuUfgGfuAfuUfgAfaAfaAfcCfadTsdT |
| 2386 | 826 | UfuCfaAfuAfcCfaAfuUfaCfaUfgAfdT | 1013 | dTCfaUfgUfaAfuUfgGfuAfuUfgAfadTsdT |
| 2387 | 827 | AfuAfcCfaAfuUfaCfaUfgGfaAfcAfdT | 1014 | dTGfuUfcCfaUfgUfaAfuUfgGfuAfudTsdT |
| 2388 | 828 | CfcAfaCfuAfuUfuAfgUfgaAfgCfcAfdT | 1015 | dTGfgCfuUfaCfuAfaAfuAfgUfuGfgdTsdT |
| 2389 | 829 | AfaCfuAfuUfuAfgUfaAfgCfcCfgAfdT | 1016 | dTCfgGfgCfuUfaCfuAfaAfuAfgUfudTsdT |
| 2390 | 830 | AfcUfaUfuUfaGfuAfaGfcCfcGfgAfdT | 1017 | dTCfcGfgGfcUfuAfcUfaAfaUfaGfudTsdT |
| 2391 | 831 | AfgAfaAfuUfcCfuUfaGfuOfaUfgAfdT | 1018 | dTCfaUfgAfcUfaAfgGfaAfuUfuCfudTsdT |
| 2392 | 832 | CfaUfuAfaGfgGfcAfuUfuUfaCfcAfdT | 1019 | dTGfgUfaAfaAfuGfcCfcUfuAfaUfgdTsdT |
| 2393 | 833 | UfaAfgGfgCfaUfuUfuAfcCfcUfaAfdT | 1020 | dTAfaGfgGfuAfaAfaUfgCfcCfuUfadTsdT |
| 2394 | 834 | AfgCfuUfcAfuAfuUfaAfcCfcUfaAfdT | 1021 | dTUfaGfgGfuUfaAfuAfuGfaAfgCfudTsdT |
| 2395 | 835 | UfaUfaAfcCfcCfuAfcCfuGfuCfaAfdT | 1022 | dTUfgAfcAfgGfuAfgGfgUfuAfuAfdTsdT |
| 2396 | 836 | UfuAfcCfcCfuAfcCfuGfuCfaAfcAfdT | 1023 | dTGfuUfgAfcAfgGfuAfgGfgUfuAfadTsdT |
| 2397 | 837 | AfcCfcUfaCfcUfgUfcAfaCfgUfaAfdT | 1024 | dTUfaCfgUfuGfaCfaGfgUfaGfgGfudTsdT |
| 2398 | 838 | CfcCfuAfcCfuGfuCfaAfcGfuAfaAfdT | 1025 | dTUfuAfcGfuUfgAfcAfgGfuAfgGfgdTsdT |
| 2399 | 839 | CfcUfaCfcUfgUfcAfaCfgUfaAfcAfdT | 1026 | dTGfuUfaCfgUfuGfaCfaGfgUfaGfgdTsdT |
| 2400 | 840 | CfuAfcCfuGfuCfaAfcGfuAfaCfgAfdT | 1027 | dTCfgUfuAfcGfuUfgAfcAfgGfuAfgdTsdT |
| 2401 | 841 | UfaCfcUfgUfcAfaCfgUfaAfcGfaAfdT | 1028 | dTUfcGfuUfaCfgUfuGfaCfaGfgUfadTsdT |

TABLE 5B-continued

Hif2α RNAi trigger sequences having modified nucleotides.

| Duplex ID No. | SEQ ID No. | Sense Strand Sequence (5' → 3') | SEQ ID No. | Antisense Strand Sequence (5' → 3') |
|---|---|---|---|---|
| 2402 | 842 | AfcCfuGfuCfaAfcGfuAfaCfgAfuAfdT | 1029 | dTAfuCfgUfuAfcGfuUfgAfcAfgGfudTsdT |
| 2403 | 843 | CfcUfgUfcAfaCfgUfaAfcGfaUfuAfdT | 1030 | dTAfaUfcGfuUfaCfgUfuGfaCfaGfgdTsdT |
| 2404 | 844 | CfuGfuCfaAfcGfuAfaCfgAfuUfuAfdT | 1031 | dTAfaAfuCfgUfuAfcGfuUfgAfcAfgdTsdT |
| 2405 | 845 | UfgUfcAfaCfgUfaAfcGfaUfuUfcAfdT | 1032 | dTGfaAfaUfcGfuUfaCfgUfuGfaCfadTsdT |
| 2406 | 846 | UfcAfaCfgUfaAfcGfaUfuUfcAfuAfdT | 1033 | dTAfuGfaAfaUfcGfuUfaCfgUfuGfadTsdT |
| 2407 | 847 | AfcGfuAfaCfgAfuUfuCfaUfgAfaAfdT | 1034 | dTUfuCfaUfgAfaAfuCfgUfuAfcGfudTsdT |
| 2408 | 848 | UfaUfuAfuAfuUfgUfcGfaAfuUfcAfdT | 1035 | dTGfaAfuUfcGfaCfaAfuAfuAfaUfadTsdT |
| 2409 | 849 | UfuAfuAfuUfgUfcGfaAfuUfcCfuAfdT | 1036 | dTAfgGfaAfuUfcGfaCfaAfuAfuAfadTsdT |
| 2410 | 850 | UfaUfuGfuCfgAfaUfuCfcUfaCfuAfdT | 1037 | dTAfgUfaGfgAfaUfuCfgAfcAfaUfadTsdT |
| 2411 | 851 | GfaAfuUfcCfuAfcUfgAfcAfaCfaAfdT | 1038 | dTUfgUfuGfuCfaGfuAfgGfaAfuUfcdTsdT |
| 2412 | 852 | UfcCfuAfcUfgAfcAfaCfaUfuAfuAfdT | 1039 | dTAfuAfaUfgUfuGfuCfaGfuAfgGfadTsdT |
| 2413 | 853 | UfaUfaAfcUfgUfaUfgGfgAfgCfuAfdT | 1040 | dTAfgCfuCfcCfaUfaCfaGfuUfaUfadTsdT |
| 2414 | 854 | UfaAfcUfgUfaUfgGfgAfgCfuUfaAfdT | 1041 | dTUfaAfgCfuCfcCfaUfaCfaGfuUfadTsdT |
| 2415 | 855 | UfgUfaUfgGfgAfgCfuUfaAfcUfuAfdT | 1042 | dTAfaGfuUfaAfgCfuCfcCfaUfaCfadTsdT |
| 2416 | 856 | UfuGfaCfaCfuGfgUfaUfcUfuAfuAfdT | 1043 | dTAfuAfaGfaUfaCfcAfgUfgUfcAfadTsdT |
| 2417 | 857 | AfaGfuAfuUfcUfgAfuCfcUfaCfcAfdT | 1044 | dTGfgUfaGfgAfuCfaGfaAfuAfcUfudTsdT |

TABLE 5C

Efficacy screen results of Hif2α RNAi triggers in vitro, as determined by dual-luciferase reporter assay.

| duplex number | Relative $R_{luc}$-Hif2α 1 nM | Relative $R_{luc}$-Hif2α 0.1 nM | AD number | Relative $R_{luc}$-Hif2α 1 nM | Relative $R_{luc}$-Hif2α 0.1 nM |
|---|---|---|---|---|---|
| 2231 | 0.491 ± 0.198 | 0.544 ± 0.368 | 2325 | 1.379 ± 0.275 | 1.304 ± 0.134 |
| 2232 | 0.468 ± 0.032 | 0.684 ± 0.061 | 2326 | 0.546 ± 0.083 | 0.660 ± 0.114 |
| 2233 | 0.862 ± 0.125 | 0.913 ± 0.019 | 2327 | 1.073 ± 0.089 | 1.339 ± 0.179 |
| 2234 | 0.388 ± 0.046 | 0.508 ± 0.148 | 2328 | 1.192 ± 0.144 | 1.291 ± 0.109 |
| 2235 | 0.857 ± 0.090 | 0.743 ± 0.129 | 2329 | 0.456 ± 0.064 | 0.807 ± 0.117 |
| 2236 | 0.761 ± 0.042 | 0.693 ± 0.071 | 2330 | 0.464 ± 0.035 | 1.097 ± 0.416 |
| 2237 | 0.978 ± 0.083 | 0.746 ± 0.029 | 2331 | 0.783 ± 0.080 | 1.002 ± 0.321 |
| 2238 | 0.148 ± 0.024 | 0.208 ± 0.023 | 2332 | 0.871 ± 0.235 | 1.174 ± 0.027 |
| 2239 | 0.157 ± 0.017 | 0.225 ± 0.022 | 2333 | 0.291 ± 0.019 | 0.684 ± 0.147 |
| 2240 | 0.845 ± 0.052 | 0.841 ± 0.048 | 2334 | 0.389 ± 0.044 | 0.672 ± 0.082 |
| 2241 | 0.270 ± 0.068 | 0.385 ± 0.028 | 2335 | 0.104 ± 0.013 | 0.311 ± 0.032 |
| 2242 | 0.222 ± 0.064 | 0.411 ± 0.019 | 2336 | 0.299 ± 0.034 | 0.783 ± 0.037 |
| 2243 | 0.694 ± 0.107 | 0.688 ± 0.059 | 2337 | 0.131 ± 0.033 | 0.334 ± 0.066 |
| 2244 | 0.915 ± 0.115 | 0.760 ± 0.050 | 2338 | 0.334 ± 0.091 | 0.743 ± 0.070 |
| 2245 | 0.727 ± 0.066 | 0.761 ± 0.039 | 2339 | 0.189 ± 0.028 | 0.523 ± 0.134 |
| 2246 | 0.327 ± 0.042 | 0.509 ± 0.044 | 2340 | 0.444 ± 0.039 | 0.920 ± 0.114 |
| 2247 | 0.231 ± 0.048 | 0.439 ± 0.082 | 2341 | 0.202 ± 0.018 | 0.378 ± 0.116 |
| 2248 | 0.148 ± 0.036 | 0.215 ± 0.007 | 2342 | 0.549 ± 0.041 | 1.058 ± 0.064 |
| 2249 | 0.190 ± 0.028 | 0.303 ± 0.042 | 2343 | 0.254 ± 0.009 | 0.620 ± 0.208 |
| 2250 | 0.139 ± 0.046 | 0.255 ± 0.020 | 2344 | 0.276 ± 0.033 | 0.570 ± 0.071 |
| 2251 | 0.872 ± 0.121 | 0.857 ± 0.087 | 2345 | 0.129 ± 0.026 | 0.296 ± 0.096 |
| 2252 | 0.592 ± 0.061 | 0.696 ± 0.096 | 2346 | 0.273 ± 0.012 | 0.523 ± 0.133 |
| 2253 | 0.564 ± 0.043 | 0.646 ± 0.144 | 2347 | 0.530 ± 0.040 | 0.753 ± 0.092 |
| 2254 | 0.641 ± 0.054 | 0.756 ± 0.080 | 2348 | 0.454 ± 0.096 | 0.840 ± 0.270 |
| 2255 | 0.721 ± 0.055 | 0.653 ± 0.130 | 2349 | 0.504 ± 0.062 | 0.674 ± 0.172 |
| 2256 | 0.765 ± 0.124 | 0.796 ± 0.028 | 2350 | 0.678 ± 0.105 | 0.755 ± 0.085 |
| 2257 | 0.802 ± 0.044 | 0.647 ± 0.127 | 2351 | 1.306 ± 0.216 | 1.216 ± 0.415 |
| 2258 | 0.972 ± 0.168 | 0.882 ± 0.098 | 2352 | 0.749 ± 0.049 | 1.012 ± 0.048 |
| 2259 | 0.836 ± 0.110 | 0.743 ± 0.086 | 2353 | 0.324 ± 0.075 | 0.635 ± 0.156 |
| 2260 | 1.030 ± 0.187 | 0.861 ± 0.031 | 2354 | 0.741 ± 0.189 | 1.043 ± 0.239 |
| 2261 | 0.657 ± 0.067 | 0.568 ± 0.065 | 2355 | 0.248 ± 0.063 | 0.457 ± 0.066 |

TABLE 5C-continued

Efficacy screen results of Hif2α RNAi triggers
in vitro, as determined by dual-luciferase reporter assay.

| duplex number | Relative $R_{luc}$-Hif2α 1 nM | Relative $R_{luc}$-Hif2α 0.1 nM | AD number | Relative $R_{luc}$-Hif2α 1 nM | Relative $R_{luc}$-Hif2α 0.1 nM |
|---|---|---|---|---|---|
| 2262 | 0.277 ± 0.071 | 0.755 ± 0.031 | 2356 | 0.210 ± 0.023 | 0.574 ± 0.006 |
| 2263 | 0.875 ± 0.059 | 1.126 ± 0.083 | 2357 | 0.435 ± 0.062 | 0.737 ± 0.082 |
| 2264 | 0.183 ± 0.019 | 0.381 ± 0.023 | 2358 | 0.731 ± 0.123 | 0.647 ± 0.113 |
| 2265 | 0.186 ± 0.045 | 0.448 ± 0.042 | 2359 | 0.354 ± 0.022 | 0.576 ± 0.208 |
| 2266 | 0.368 ± 0.046 | 0.808 ± 0.062 | 2360 | 0.962 ± 0.167 | 1.102 ± 0.119 |
| 2267 | 0.651 ± 0.049 | 1.029 ± 0.104 | 2361 | 0.603 ± 0.133 | 0.800 ± 0.198 |
| 2268 | 0.210 ± 0.037 | 0.409 ± 0.023 | 2362 | 0.454 ± 0.069 | 0.673 ± 0.089 |
| 2269 | 0.302 ± 0.080 | 0.530 ± 0.097 | 2363 | 0.452 ± 0.091 | 0.653 ± 0.199 |
| 2270 | 0.613 ± 0.147 | 0.658 ± 0.149 | 2364 | 0.855 ± 0.282 | 1.070 ± 0.042 |
| 2271 | 0.930 ± 0.094 | 1.056 ± 0.291 | 2365 | 1.259 ± 0.247 | 1.132 ± 0.107 |
| 2272 | 0.864 ± 0.197 | 1.028 ± 0.281 | 2366 | 0.695 ± 0.115 | 0.879 ± 0.223 |
| 2273 | 0.588 ± 0.057 | 0.574 ± 0.033 | 2367 | 0.376 ± 0.039 | 0.665 ± 0.064 |
| 2274 | 0.506 ± 0.074 | 0.870 ± 0.108 | 2368 | 1.140 ± 0.221 | 1.036 ± 0.063 |
| 2275 | 0.464 ± 0.048 | 0.515 ± 0.264 | 2369 | 0.338 ± 0.055 | 0.464 ± 0.032 |
| 2276 | 0.330 ± 0.080 | 0.543 ± 0.029 | 2370 | 0.294 ± 0.026 | 0.498 ± 0.128 |
| 2277 | 0.702 ± 0.091 | 0.625 ± 0.384 | 2371 | 0.166 ± 0.037 | 0.193 ± 0.030 |
| 2278 | 0.564 ± 0.070 | 0.947 ± 0.044 | 2372 | 0.514 ± 0.044 | 0.831 ± 0.103 |
| 2279 | 0.280 ± 0.042 | 0.506 ± 0.086 | 2373 | 0.162 ± 0.032 | 0.369 ± 0.082 |
| 2280 | 0.911 ± 0.086 | 0.871 ± 0.147 | 2374 | 0.192 ± 0.014 | 0.355 ± 0.020 |
| 2281 | 0.651 ± 0.041 | 0.914 ± 0.177 | 2375 | 0.305 ± 0.040 | 0.481 ± 0.062 |
| 2282 | 0.824 ± 0.155 | 1.209 ± 0.132 | 2376 | 0.228 ± 0.029 | 0.546 ± 0.115 |
| 2283 | 0.882 ± 0.026 | 1.175 ± 0.194 | 2377 | 0.958 ± 0.189 | 0.900 ± 0.189 |
| 2284 | 0.787 ± 0.062 | 1.227 ± 0.266 | 2378 | 0.734 ± 0.170 | 0.994 ± 0.246 |
| 2285 | 0.723 ± 0.088 | 1.109 ± 0.247 | 2379 | 0.939 ± 0.204 | 0.858 ± 0.098 |
| 2286 | 0.878 ± 0.078 | 1.291 ± 0.367 | 2380 | 1.722 ± 0.101 | 1.128 ± 0.285 |
| 2287 | 0.751 ± 0.011 | 0.871 ± 0.102 | 2381 | 1.063 ± 0.191 | 0.756 ± 0.109 |
| 2288 | 0.932 ± 0.118 | 0.943 ± 0.029 | 2382 | 1.151 ± 0.365 | 1.070 ± 0.064 |
| 2289 | 1.039 ± 0.146 | 0.992 ± 0.153 | 2383 | 1.060 ± 0.292 | 0.833 ± 0.082 |
| 2290 | 0.353 ± 0.036 | 0.698 ± 0.155 | 2384 | 0.439 ± 0.101 | 0.533 ± 0.067 |
| 2291 | 0.434 ± 0.046 | 0.911 ± 0.092 | 2385 | 0.515 ± 0.089 | 0.701 ± 0.178 |
| 2292 | 0.832 ± 0.000 | 1.135 ± 0.048 | 2386 | 0.274 ± 0.087 | 0.603 ± 0.032 |
| 2293 | 0.925 ± 0.126 | 1.010 ± 0.045 | 2387 | 0.201 ± 0.063 | 0.436 ± 0.028 |
| 2294 | 0.546 ± 0.033 | 0.743 ± 0.100 | 2388 | 0.436 ± 0.021 | 0.901 ± 0.318 |
| 2295 | 0.863 ± 0.122 | 1.047 ± 0.184 | 2389 | 0.820 ± 0.184 | 1.085 ± 0.307 |
| 2296 | 0.213 ± 0.028 | 0.411 ± 0.079 | 2390 | 0.568 ± 0.108 | 0.772 ± 0.175 |
| 2297 | 0.643 ± 0.028 | 0.704 ± 0.083 | 2391 | 0.129 ± 0.015 | 0.273 ± 0.006 |
| 2298 | 0.695 ± 0.037 | 0.729 ± 0.092 | 2392 | 0.283 ± 0.052 | 0.636 ± 0.039 |
| 2299 | 0.827 ± 0.067 | 0.907 ± 0.171 | 2393 | 1.049 ± 0.089 | 0.862 ± 0.388 |
| 2300 | 0.786 ± 0.181 | 1.090 ± 0.106 | 2394 | 0.254 ± 0.026 | 0.533 ± 0.076 |
| 2301 | 0.423 ± 0.102 | 0.558 ± 0.034 | 2395 | 0.218 ± 0.029 | 0.494 ± 0.104 |
| 2302 | 0.147 ± 0.028 | 0.414 ± 0.019 | 2396 | 0.939 ± 0.299 | 1.321 ± 0.070 |
| 2303 | 0.294 ± 0.034 | 0.414 ± 0.002 | 2397 | 0.119 ± 0.024 | 0.254 ± 0.048 |
| 2304 | 0.302 ± 0.025 | 0.528 ± 0.116 | 2398 | 0.534 ± 0.043 | 1.047 ± 0.047 |
| 2305 | 0.992 ± 0.217 | 0.961 ± 0.120 | 2399 | 0.418 ± 0.081 | 0.784 ± 0.071 |
| 2306 | 0.613 ± 0.031 | 0.596 ± 0.038 | 2400 | 0.165 ± 0.020 | 0.478 ± 0.028 |
| 2307 | 0.702 ± 0.142 | 0.800 ± 0.248 | 2401 | 0.174 ± 0.003 | 0.375 ± 0.062 |
| 2308 | 0.998 ± 0.059 | 0.799 ± 0.084 | 2402 | 0.128 ± 0.015 | 0.389 ± 0.060 |
| 2309 | 1.081 ± 0.135 | 0.823 ± 0.096 | 2403 | 0.568 ± 0.106 | 0.930 ± 0.132 |
| 2310 | 0.923 ± 0.101 | 0.785 ± 0.122 | 2404 | 0.104 ± 0.019 | 0.234 ± 0.045 |
| 2311 | 0.841 ± 0.130 | 0.888 ± 0.051 | 2405 | 0.138 ± 0.035 | 0.261 ± 0.044 |
| 2312 | 0.725 ± 0.173 | 0.899 ± 0.124 | 2406 | 0.168 ± 0.044 | 0.241 ± 0.022 |
| 2313 | 0.886 ± 0.243 | 0.853 ± 0.133 | 2407 | 0.124 ± 0.021 | 0.222 ± 0.027 |
| 2314 | 0.920 ± 0.150 | 0.692 ± 0.141 | 2408 | 0.282 ± 0.004 | 0.730 ± 0.045 |
| 2315 | 0.876 ± 0.099 | 0.781 ± 0.206 | 2409 | 0.104 ± 0.020 | 0.301 ± 0.085 |
| 2316 | 0.579 ± 0.055 | 0.797 ± 0.211 | 2410 | 0.154 ± 0.022 | 0.228 ± 0.033 |
| 2317 | 0.843 ± 0.157 | 0.842 ± 0.239 | 2411 | 0.410 ± 0.083 | 0.796 ± 0.110 |
| 2318 | 0.780 ± 0.103 | 0.885 ± 0.370 | 2412 | 0.291 ± 0.014 | 0.515 ± 0.037 |
| 2319 | 0.234 ± 0.055 | 0.454 ± 0.101 | 2413 | 0.317 ± 0.055 | 0.675 ± 0.104 |
| 2320 | 0.486 ± 0.059 | 0.770 ± 0.312 | 2414 | 0.167 ± 0.038 | 0.422 ± 0.070 |
| 2321 | 0.665 ± 0.033 | 0.561 ± 0.043 | 2415 | 0.119 ± 0.015 | 0.180 ± 0.097 |
| 2322 | 0.306 ± 0.059 | 0.468 ± 0.012 | 2416 | 0.166 ± 0.031 | 0.247 ± 0.031 |
| 2323 | 0.664 ± 0.166 | 0.631 ± 0.085 | 2417 | 0.253 ± 0.037 | 0.295 ± 0.057 |
| 2324 | 1.046 ± 0.208 | 1.081 ± 0.293 | | | |

Example 11. Hif2α RNAi Trigger $EC_{50}$ Determination

The eight best canonical sequences were further evaluated by determining the $EC_{50}$ concentration. Each trigger was assessed for knockdown under the same conditions and assays as above, but at 10 different concentrations ranging from 0.00051 nM to 10 nM. $EC_{50}$ were determined using GraphPad Prism software. Each of the top five canonical sequences were modified to contain UNA at sites 6 and 7. These triggers, along with their parent canonical sequences, were evaluated side-by-side for $EC_{50}$ concentration determination using the same conditions and assays as above, Table 6.

TABLE 6

EC$_{50}$ values (nM) determined in vitro for the indicated RNAi triggers.

| EC50 | | EC50 UNAs | | |
|---|---|---|---|---|
| ID number | EC50 (nM) | ID number | Mod. | EC50 |
| XD-02335 | 0.0593 | AD00988 | UNA6 | 0.8406 |
|  |  | AD00993 | UNA7 | 0.5504 |
| XD-02337 | 0.1010 |  |  |  |
| XD-02371 | 0.0592 | AD00989 | UNA6 | 0.3754 |
|  |  | AD00994 | UNA7 | 0.08068 |
| XD-02391 | 0.1554 |  |  |  |
| XD-02397 | 0.0858 |  |  |  |
| XD-02404 | 0.0570 | AD00990 | UNA6 | 0.1534 |
|  |  | AD00995 | UNA7 | 0.1689 |
| XD-02407 | 0.0287 | AD00991 | UNA6 | 0.3503 |
|  |  | AD00996 | UNA7 | 0.1176 |
| XD-02415 | 0.0892 | AD00992 | UNA6 | 0.1419 |
|  |  | AD00997 | UNA7 | 0.1827 |

Example 12. Creation of SEAP-Expressing Clear Cell Renal Cell Carcinoma (ccRCC) A498 Cells A pCR3.1 expression vector expressing the reporter gene secreted alkaline phosphatase (SEAP) under the CMV promoter was prepared by directional cloning of the SEAP coding sequence PCR amplified from Clontech's pSEAP2-basic vector. Convenient restriction sites were added onto primers used to amplify the SEAP coding sequence for cloning into the pCR3.1 vector (Invitrogen). The resultant construct pCR3-SEAP was used to create a SEAP-expressing A498 ccRCC cell line. Briefly, pCR3-SEAP plasmid was transfected into A498 ccRCC cells by electroporation following manufacturer's recommendation. Stable transfectants were selected by G418 resistance. Selected A498-SEAP clones were evaluated for SEAP expression and integration stability.

Example 13. Orthotopic RCC Tumor Bearing Mice with A498 Cell Stably Expressing SEAP Female athymic nude mice were anesthetized with ~3% isoflourane and placed in the right lateral decubitus position. A small, 0.5-1 cm, longitudinally abdominal incision in the left flank was made. Using a moist cotton swab, the left kidney was lifted out of the peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 µl aliquot of 2:1 (vol:vol) cell/matrigel mixture containing about 300,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Serum was collected every 7-14 days after implantation to monitor tumor growth using a commercial SEAP assay kit. For most studies, tumor mice were used 5-6 weeks after implantation, when tumor measurements were typically around 4-8 mm.

Example 14. Evaluation of HiF2α-RNAi Triggers Orthotopic RCC Tumor Bearing Mice RGD targeted HiF2α-RNAi trigger delivery conjugates. Delivery polymers were modified using RGD-PEG-HyNic, RGD-PEG-ACit-PNP, or RDG-PEG-FCitFP-TFP and PEG-dipeptide modifying agents. The indicated amount of polymer 126 or 100A polymer was modified with 8×PEG$_{12}$-ACit-PABC-PNP/0.5× aldehyde-PEG$_{24}$-FCit-PABC-PNP (with RGD mimic #1-PEG-HyNic using protocol #1) and the indicated amount of the indicated Hif2α RNAi trigger. Polymer 064 was modified according to protocol 7. Kidney RCC tumor-bearing mice were generated as described and treated with a single tail vein injection of isotonic glucose (G1) or the indicated Hif2α RNAi trigger-delivery polymer conjugate. Mice were euthanized at the indicated time after injection and total RNA was prepared from kidney tumor using Trizol reagent following manufacturer's recommendation. Relative Hif2α mRNA levels were determined by RT-qPCR as described below and compared to mice treated with delivery buffer (isotonic glucose) only.

TABLE 7

Hif2α knockdown in mice following Hif2α RNAi trigger delivery. RNAi triggers were conjugated to the indicated reversibly modified delivery polymer.

| RNAi trigger | | Polymer | | Relative Expression | |
|---|---|---|---|---|---|
| duplex number | µg | number | µg | day 4 | low error/ high error |
| isotonic glucose | 0 |  | 0 | 1.00 | 0.06/0.06 |
| AD01031 | 80 | 126 | 400 | 0.20 | 0.04/0.05 |
| AD01214 | 80 | 126 | 400 | 0.29 | 0.08/0.12 |
| AD01214 | 112.5 | 006 | 300 | 0.36 | 0.07/0.09 |
| AD01255 | 80 | 126 | 400 | 0.28 | 0.05/0.05 |
| AD01476 | 115 | 100A | 375 | 0.32 | 0.04/0.04 |
| AD01291 | 80 | 126 | 400 | 0.19 | 0.03/0.03 |
| AD01292 | 80 | 126 | 400 | 0.27 | 0.06/0.08 |
| AD01293 | 80 | 126 | 400 | 0.20 | 0.01/0.01 |
| AD01294 | 80 | 126 | 400 | 0.17 | 0.01/0.02 |
| AD01295 | 80 | 126 | 400 | 0.22 | 0.02/0.02 |
| AD01296 | 80 | 126 | 400 | 0.21 | 0.04/0.06 |
| AD01029 | 80 | 126 | 400 | 0.94 | 0.08/0.09 |
| AD01030 | 80 | 126 | 400 | 0.47 | 0.08/0.10 |
| AD01256 | 80 | 126 | 400 | 0.22 | 0.05/0.07 |
| AD01257 | 80 | 126 | 400 | 0.24 | 0.04/0.05 |
| AD01258 | 80 | 126 | 400 | 0.38 | 0.03/0.03 |
| AD01424 | 150 | 100A | 300 | 0.54 | 0.06/0.07 |
| AD01404 | 150 | 100A | 300 | 0.58 | 0.11/0.13 |
| AD01405 | 150 | 100A | 300 | 0.51 | 0.10/0.12 |
| AD01406 | 150 | 100A | 300 | 0.45 | 0.06/0.07 |
| AD01407 | 150 | 100A | 300 | 0.47 | 0.06/0.07 |
| AD01408 | 150 | 100A | 300 | 0.50 | 0.07/0.09 |
| AD01409 | 150 | 100A | 300 | 0.55 | 0.03/0.03 |
| AD01410 | 150 | 100A | 300 | 0.41 | 0.10/0.12 |
| AD01411 | 150 | 100A | 300 | 0.36 | 0.01/0.01 |
| AD01288 | 115 | 100A | 375 | 0.32 | 0.02/0.02 |
| AD01522 | 115 | 100A | 375 | 0.44 | 0.07/0.09 |
| AD01289 | 115 | 100A | 375 | 0.28 | 0.06/0.08 |
| AD01290 | 115 | 100A | 375 | 0.39 | 0.02/0.02 |
| AD01523 | 115 | 100A | 375 | 0.49 | 0.04/0.05 |
| AD01524 | 115 | 100A | 375 | 0.26 | 0.05/0.07 |
| AD01554 | 115 | 100A | 375 | 0.29 | 0.04/0.04 |
| AD01555 | 115 | 100A | 375 | 0.20 | 0.03/0.03 |
| AD01025 | 80 | 126 | 400 | 0.34 | 0.02/0.02 |
| AD01023 | 80 | 126 | 400 | 0.93 | 0.10/0.12 |
| AD01024 | 80 | 126 | 400 | 0.51 | 0.04/0.05 |
| AD01028 | 80 | 126 | 400 | 0.39 | 0.04/0.04 |
| AD01026 | 80 | 126 | 400 | 0.97 | 0.12/0.13 |

TABLE 7-continued

Hif2α knockdown in mice following Hif2α RNAi trigger delivery. RNAi triggers were conjugated to the indicated reversibly modified delivery polymer.

| RNAi trigger duplex number | µg | Polymer number | µg | day 4 | Relative Expression low error/ high error |
|---|---|---|---|---|---|
| AD01027 | 80 | 126 | 400 | 0.92 | 0.08/0.09 |
| AD01034 | 80 | 126 | 400 | 0.35 | 0.07/0.09 |
| AD01032 | 80 | 126 | 400 | 1.00 | 0.09/0.10 |
| AD01033 | 80 | 126 | 400 | 1.08 | 0.08/0.09 |
| AD01022 | 80 | 126 | 400 | 0.53 | 0.07/0.09 |
| AD01020 | 80 | 126 | 400 | 0.94 | 0.06/0.06 |
| AD01021 | 80 | 126 | 400 | 0.90 | 0.05/0.05 |
| AD01654 | 100 | 100A | 250 | 0.185 | 0.01/0.01 |
| AD01655 | 100 | 100A | 250 | 0.234 | 0.02/0.02 |
| AD01656 | 100 | 100A | 250 | 0.184 | 0.01/0.01 |
| AD01657 | 100 | 100A | 250 | 0.256 | 0.03/0.03 |
| AD01658 | 100 | 100A | 250 | 0.138 | 0.01/0.01 |
| AD01659 | 100 | 100A | 250 | 0.249 | 0.04/0.05 |
| AD01884 | 100 | 064 | 250 | 0.091 | 0.01/0.01 |
| AD01885 | 100 | 064 | 250 | 0.146 | 0.02/0.02 |
| AD01886 | 100 | 064 | 250 | 0.292 | 0.04/0.05 |
| AD01887 | 100 | 064 | 250 | 0.329 | 0.05/0.06 |
| AD01888 | 100 | 064 | 250 | 0.209 | 0.04/0.08 |
| AD01889 | 100 | 064 | 250 | 0.282 | 0.04/0.05 |
| AD01890 | 100 | 064 | 250 | 0.256 | 0.02/0.03 |
| AD01891 | 100 | 064 | 250 | 0.189 | 0.02/0.03 |
| AD01892 | 100 | 064 | 250 | 0.146 | 0.03/0.03 |
| AD01893 | 100 | 064 | 250 | 0.115 | 0.02/0.03 |
| AD02691 | 75 | 064 | 187.5 | 0.124 | 0.04/0.07 |
| AD02692 | 75 | 064 | 187.5 | 0.089 | 0.03/0.04 |
| AD02693 | 75 | 064 | 187.5 | 0.122 | 0.01/0.01 |
| AD02694 | 75 | 064 | 187.5 | 0.099 | 0.01/0.01 |
| AD02695 | 75 | 064 | 187.5 | 0.101 | 0.02/0.02 |
| AD02733 | 75 | 064 | 187.5 | 0.283 | 0.02/0.03 |
| AD02734 | 75 | 064 | 187.5 | 0.262 | 0.03/0.03 |
| AD02735 | 75 | 064 | 187.5 | 0.080 | 0.01/0.02 |
| AD01884 | 75 | 064 | 187.5 | 0.227 | 0.02/0.02 |
| AD01884 | 50 | 064 | 125 | 0.203 | 0.03/0.03 |
| AD02692 | 75 | 064 | 187.5 | 0.121 | 0.02/0.02 |
| AD02692 | 50 | 064 | 125 | 0.092 | 0.01/0.01 |
| AD02695 | 75 | 064 | 187.5 | 0.155 | 0.02/0.02 |
| AD02695 | 50 | 064 | 125 | 0.123 | 0.03/0.03 |
| AD02735 | 75 | 064 | 187.5 | 0.222 | 0.07/0.10 |
| AD02735 | 50 | 064 | 125 | 0.144 | 0.03/0.03 |
| AD02857 | 50 | 064 | 125 | 0.192 | 0.03/0.03 |
| AD02858 | 50 | 064 | 125 | 0.192 | 0.04/0.05 |
| AD02859 | 50 | 064 | 125 | 0.214 | 0.03/0.03 |
| AD02860 | 50 | 064 | 125 | 0.165 | 0.02/0.02 |
| AD02949 | 50 | 064 | 125 | 0.176 | 0.05/0.07 |
| AD02074 | 50 | 064 | 125 | 0.566 | 0.01/0.13 |
| AD02861 | 50 | 064 | 125 | 0.103 | 0.03/0.05 |
| AD02862 | 50 | 064 | 125 | 0.093 | 0.05/0.11 |
| AD02873 | 50 | 064 | 125 | 0.079 | 0.04/0.06 |
| AD02875 | 50 | 064 | 125 | 0.101 | 0.01/0.01 |
| AD03011 | 50 | 064 | 125 | 0.183 | 0.01/0.02 |
| AD02874 | 50 | 064 | 125 | 0.138 | 0.05/0.07 |
| AD03187 | 50 | 064 | 125 | 1.000 | 0.06/0.07 |
| AD03188 | 50 | 064 | 125 | 0.308 | 0.08/0.07 |
| AD03189 | 50 | 064 | 125 | 0.245 | 0.02/0.02 |
| AD03190 | 50 | 064 | 125 | 0.269 | 0.08/0.12 |
| AD03191 | 50 | 064 | 125 | 0.307 | 0.13/0.24 |
| AD03192 | 50 | 064 | 125 | 0.286 | 0.01/0.01 |
| AD03193 | 50 | 064 | 125 | 0.275 | 0.07/0.09 |
| AD03125 | 50 | 064 | 125 | 0.205 | 0.04/0.05 |
| AD03126 | 50 | 064 | 125 | 0.172 | 0.04/0.04 |
| AD03253 | 50 | 064 | 125 | 0.188 | 0.04/0.05 |
| AD03264 | 50 | 064 | 125 | 0.264 | 0.09/0.13 |
| AD03265 | 50 | 064 | 125 | 0.294 | 0.07/0.08 |
| AD03266 | 50 | 064 | 125 | 0.408 | 0.07/0.08 |
| AD03254 | 50 | 064 | 125 | 0.295 | 0.06/0.07 |
| AD03255 | 50 | 064 | 125 | 0.264 | 0.07/0.10 |
| AD03256 | 50 | 064 | 125 | 0.333 | 0.06/0.08 |
| AD03257 | 50 | 064 | 125 | 0.203 | 0.04/0.05 |
| AD03258 | 50 | 064 | 125 | 0.137 | 0.02/0.02 |
| AD03259 | 50 | 064 | 125 | 0.179 | 0.03/0.04 |
| AD03260 | 50 | 064 | 125 | 0.175 | 0.03/0.04 |
| AD03261 | 50 | 064 | 125 | 0.177 | 0.02/0.02 |
| AD03262 | 50 | 064 | 125 | 0.197 | 0.01/0.01 |
| AD03263 | 50 | 064 | 125 | 0.134 | 0.04/0.06 |

Quantitative Real-Time PCR assay. In preparation for quantitative PCR, total RNA was isolated from tissue samples homogenized in TriReagent (Molecular Research Center, Cincinnati, Ohio) following the manufacturer's protocol. Approximately 500 ng RNA was reverse-transcribed using the High Capacity cDNA Reverse Transcription Kit (Life Technologies). For human (tumor) Hif2α (EPAS1) expression, pre-manufactured TaqMan gene expression assays for human Hif2α (Catalog #4331182) and CycA (PPIA) Catalog #: 4326316E) were used in biplex reactions in triplicate using TaqMan Gene Expression Master Mix (Life Technologies) or VeriQuest Probe Master Mix (Affymetrix). For human (tumor) VegFa (VEGFA) expression, pre-manufactured TaqMan gene expression assays for human VegFa (Catalog #4331182, Assay ID: Hs00900055) and CycA (Part #: 4326316E) were used in biplex reactions in triplicate using TaqMan Gene Expression Master Mix (Life Technologies) or VeriQuest Probe Master Mix (Affymetrix). Quantitative PCR was performed by using a 7500 Fast or StepOnePlus Real-Time PCR system (Life Technologies). The ΔΔCs method was used to calculate relative gene expression.

Example 15. Multi-Dose Hif2α RNAi Trigger-Delivery Polymer Conjugate Inhibits Tumor Growth in Orthotopic RCC Tumor Bearing Mice Hif2α RNAi trigger-delivery polymer conjugate was prepared using protocol #1 with RNAi trigger duplex ID AD01031 and polymer Ant 126. The conjugate was then TFF purified and polymer concentration, RNAi trigger, RGD and modifying conjugation efficiency was determined as described above. Weekly doses of Hif2α RNAi trigger-delivery polymer conjugate containing either 400 µg (polymer weight) or 280 µg (polymer weight) were administered intravenously to 2 different groups of tumor bearing mice. Tumor bearing mice receiving isotonic glucose (IG) were used as treatment control. A total of 3 weekly doses were administered during the course of study. Tumor growth rates were evaluated by serum SEAP collected at 5-7 days interval during treatment. Tumor weight and volume was determined at necropsy. Gross tumor morphology and H&E histopathology were evaluated.

TABLE 8

Hif2α RNAi trigger-delivery polymer conjugate
knockdown HiF2α and VEGFa

| Treatment | Hif2α expression | | VEGFa expression | |
|---|---|---|---|---|
| | Relative Expression | low/high error | Relative Expression | low/high error |
| G1 - IG | 1.00 | 0.07/0.07 | 1.00 | 0.07/0.08 |
| G2 - 400 µg | 0.18 | 0.03/0.04 | 0.45 | 0.07/0.09 |
| G3 - 280 µg | 0.19 | 0.04/0.05 | 0.39 | 0.10/0.13 |

Expression of Hif2α in the 400 µg or 280 µg Hif2α RNAi trigger-delivery polymer conjugate group was 82% and 81% decreased, respectively, compared to control treatment (Table 8). Expression of VEGFa, a well characterized downstream Hif2α regulated gene, was also decreased by 55% and 61%, respectively (Table 8).

Figure 8:
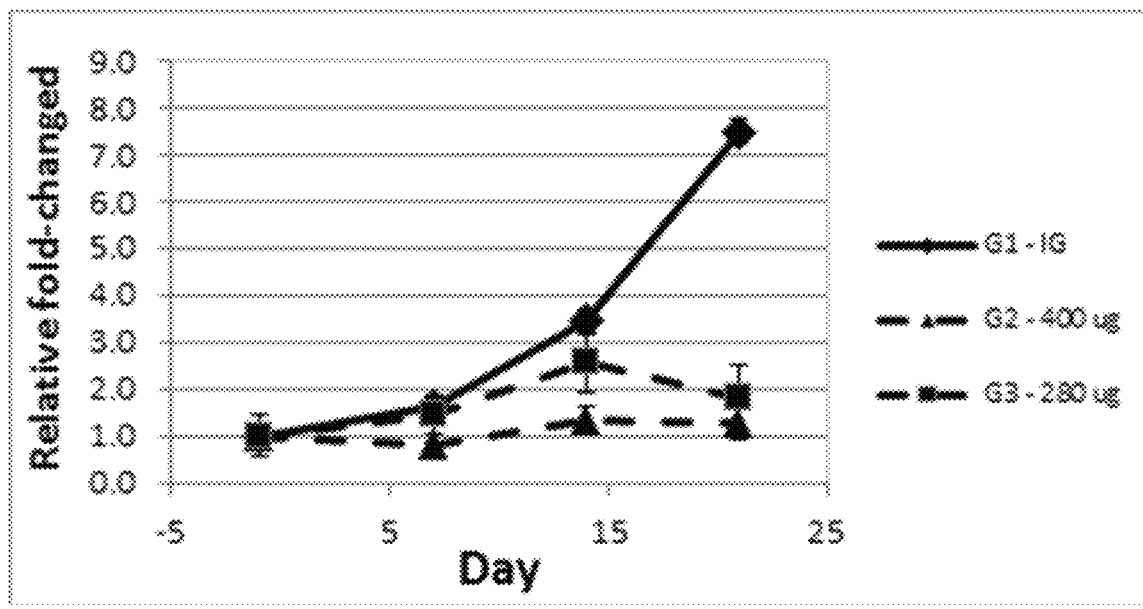
FIG. 8. Graph illustrating serum SEAP levels during treatment in mice. Fold-changed in serum SEAP levels relative to day (−1) pre-dose levels. For G1 and G2, n=4. For G3, n=3.
Figure 9:
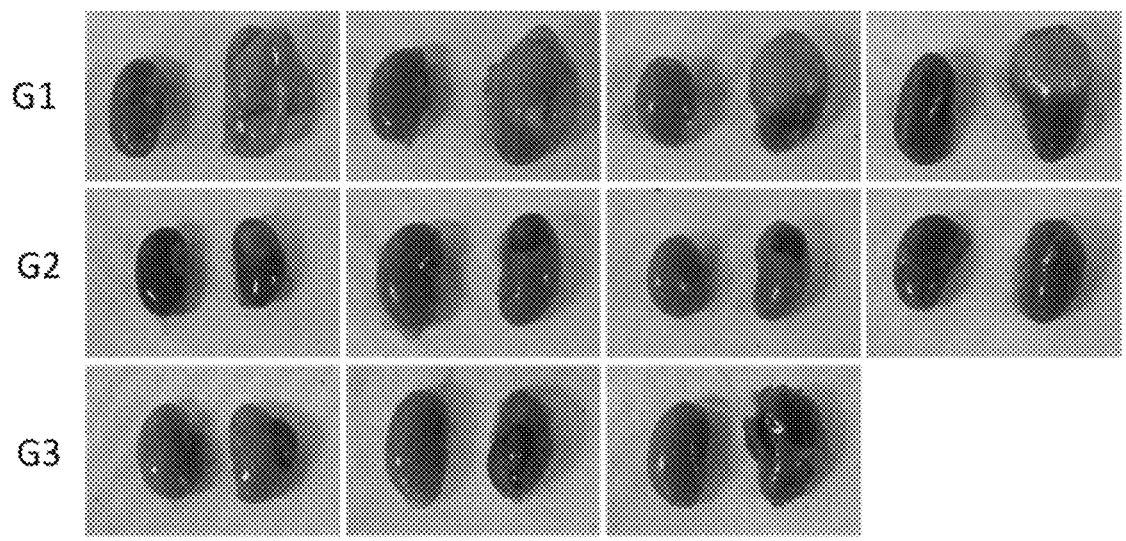
FIG. 9. Tumor gross morphology after 3 weekly treatments in mice G1, vehicle; G2 400 µg Hif2α-ITG-DPC; G3 280 µg Hif2α-ITG-DPC. Both kidneys from each animal are shown. Tumor was implanted into the kidney shown on the right. Tumor from treatment groups were all significantly smaller and showed some discoloration when compared to controls.
Figure 10:
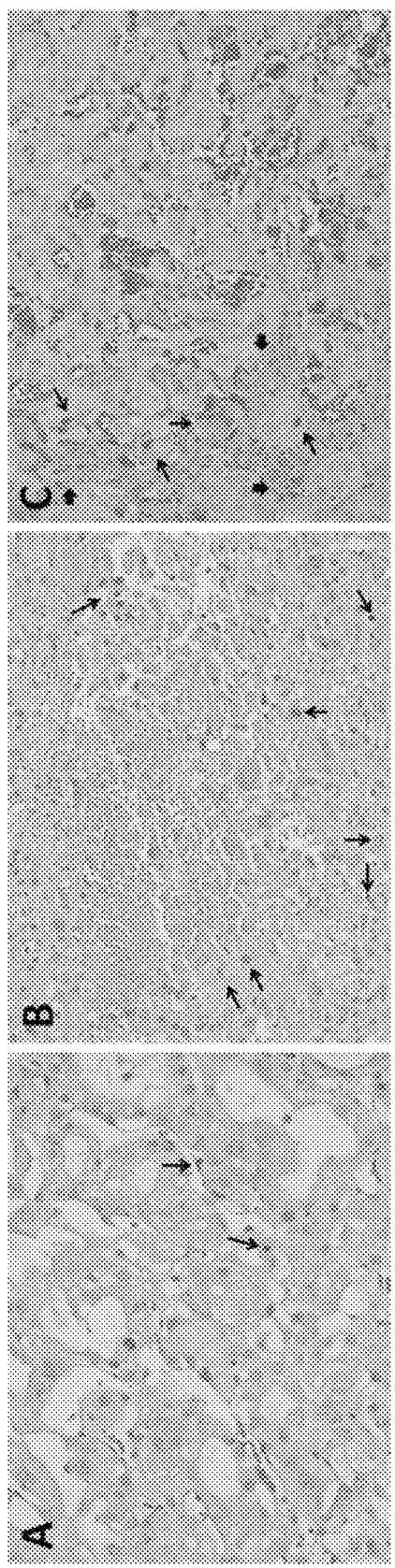
FIG. 10. H&E staining of tumor formalin fixed paraffin sections. Thin arrows indicate apoptotic cells. Thick arrows indicate macrophage infiltration. Panel A, G1 vehicle treated. Typical tubular type RCC morphology with rare apoptotic cells (thin arrows) Panel B, G2 400 µg Hif2α-ITG-DPC treated. Massive necrotic center with numerous apoptotic cells in surrounding areas and overall loss of tumor structure. Panel C, G3 280 µg Hif2α-ITG-DPC treated. Destruction of typical tubular tumor structures with macrophage infiltration and numerous apoptotic cells.

Collectively, after 3 weekly Hif2α RNAi trigger-delivery polymer conjugate injections, tumor growth was dramatically inhibited in both dosages evaluated. This is supported by the overall tumor sizes and serum SEAP levels (FIGS. 8-9 and 12, Table 9). A downward trend of the SEAP levels after the third injections suggest beginning of tumor regression. In addition, tumor histopathology examination from H&E stained formalin fixed paraffin sections showed destruction of typical RCC tubular structure. The number of apoptotic cells was increased in treatment groups. Some tumor sample contained large areas of tumor necrosis (FIG. 10).

TABLE 9

Serum SEAP levels during treatment, G1 and G2, n = 4; G3, n = 3

| Treatment | SEAP (fold-changed relative to day −1) | | | |
|---|---|---|---|---|
| | Day −1 | Day 7 | Day 14 | Day 21 |
| G1 - IG | 1.00 ± 0.19 | 1.65 ± 0.22 | 3.44 ± 0.23 | 7.48 ± 0.27 |
| G2- 400 µg | 1.00 ± 0.45 | 0.79 ± 0.43 | 1.36 ± 0.61 | 1.25 ± 0.68 |
| G3- 280 µg | 1.00 ± 0.14 | 1.46 ± 0.09 | 2.55 ± 0.29 | 1.82 ± 0.35 |

Example 16. Evaluation of HiF2α-RNAi Triggers in Orthotopic RCC Tumor Bearing Mice RGD targeted HiF2α-RNAi trigger delivery polymer conjugates were formed using polymer 126, 100A, or 006. The RNAi trigger, µg indicates the quantity of trigger reacted with polymer. The polymer was modified with the indicated RGD mimic and PEG modifying agents as described above. Kidney RCC tumor-bearing mice were generated as described and treated with a single tail vein injection of isotonic glucose (GI) or the indicated Hif2α RNAi trigger-delivery polymer conjugate. Mice were euthanized 72 h (day 4) after injection and total RNA was prepared from kidney tumor using Trizol reagent following manufacturer's recommendation. Relative Hif2α mRNA levels were determined by RT-qPCR as described and compared to mice treated with delivery buffer (isotonic glucose) only (Table 11).

Example 17. HiF2α RNAi Trigger/Second Therapeutic Combination Study

HiF2α RNAi trigger-delivery polymer conjugate (125 µg polymer) was prepared using protocol 7 Duplex ID No. AD1884 and polymer 064. HiF2α RNAi trigger-delivery polymer conjugate was dosed every 4 weeks by iv injection, 4 doses total. Sunitinib (Malate salt) obtained from LC laboratories was suspended in Ora-plus/Ora sweet (50:50, vol:vol). Sunitinib treatment started 2 weeks after the first HiF2α RNAi trigger dose was administered. Mice were dosed by oral gavage 5 days/week for 2 weeks, then off 2 weeks, 3 cycles total.

Tumor growth rates were evaluated by serum SEAP collected at 5-7 days interval during treatment. Tumor weight and volume was determined at necropsy. Gross tumor morphology and H&E histopathology were evaluated. Relative HiF2α expression levels were of were 11.4%, 73.8%, and 77.6% decreased in the sunitinib alone, DPC+sunitinib and DPC alone treated groups, respectively (Table 10A). Combined HiF2α RNAi trigger and sunitinib treatments resulted in increased tumor growth inhibition response. Overall smaller tumor sizes were smaller and lower overall growth (as measured by overall-fold increase in SEAP) was observed (Table 10B).

TABLE 10A

HiF2α expression in RCC tumors in animal models
treated with Sunitinib, HiF2α RNAi trigger,
or HiF2α RNAi trigger + Sunitinib.

| | HiF2α expression | | |
|---|---|---|---|
| Treatment | Relative expression | Low error | High error |
| isotonic glucose | 1.000 | 0.153 | 0.180 |
| Sunitinib | 0.886 | 0.070 | 0.076 |
| HiF2α RNAi trigger | 0.262 | 0.071 | 0.097 |
| HiF2α RNAi trigger + Sunitinib | 0.224 | 0.081 | 0.126 |

TABLE 10B

Tumor size and SEAP expression in RCC tumors in
animal models treated with Sunitinib, HiF2α
RNAi trigger, or HiF2α RNAi trigger + Sunitinib.

| Treatment | Tumor weight (mg) | Tumor volume (mm3) | Fold increase in SEAP |
|---|---|---|---|
| isotonic glucose | 4158.5 ± 865 | 3576.3 ± 279 | 21.8 ± 11 |
| Sunitinib | 2385.7 ± 845 | 2113.5 ± 368 | 18.1 ± 9.8 |
| HiF2α RNAi trigger | 2130.9 ± 1066 | 1537.4 ± 999 | 20.54 ± 20 |
| HiF2α RNAi trigger + Sunitinib | 1075.8 ± 600 | 1008.8 ± 650 | 5.7 ± 3.3 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 11

Hif2α expression in RCC cells in RCC tumor bearing mice following Hif2α RNAi trigger delivery.

| HiF2α RNAi trigger | | polymer | | | RGD | | PEG | | Relative Expression | |
|---|---|---|---|---|---|---|---|---|---|---|
| duplex ID | µg | ID | µg | purification | modifying agent | amt. | no. | modifying agent | day 4 | error low | high |

| duplex ID | µg | ID | µg | purification | modifying agent | amt. | no. | modifying agent | day 4 | low | high |
|---|---|---|---|---|---|---|---|---|---|---|---|
| isotonic glucose | | | | | | | | | 1.000 | 0.060 | 0.064 |
| AD01031 | 80 | 126 | 280 | | RGD-PEG$_8$-HyNic | 0.5x | | PEG$_{12}$-ACit-PABC-PNP | 0.300 | 0.074 | 0.098 |
| AD01031 | 80 | 126 | 280 | | RGD-PEG$_8$-ACit-PABC-PNP | 0.4x | | PEG$_6$-ACit-PABC-PNP | 0.311 | 0.055 | 0.067 |
| AD01214 | 80 | 126 | 280 | TFF | RGD-PEG$_8$-HyNic | 0.5x | | PEG$_{12}$-FCitFP-TFP | 0.489 | 0.022 | 0.023 |
| AD01214 | 80 | 126 | 280 | | RGD-PEG$_8$-HyNic | 0.5x | | PEG$_{12}$-FCitFP-TFP | 0.210 | 0.032 | 0.038 |
| AD01214 | 80 | 126 | 280 | | RGD-PEG$_8$-ACit-PABC-PNP | 0.4x | | PEG$_6$-ACit-PABC-PNP | 0.360 | 0.019 | 0.021 |
| AD01214 | 80 | 126 | 280 | | RGD-PEG$_8$-ACitFP-NHS | 1x | | PEG$_6$-ACit-PABC-PNP | 0.288 | 0.005 | 0.005 |
| AD01214 | 115 | 100A | 375 | | RGD-PEG$_8$-HyNic | 0.5x | | PEG$_{12}$-FCitFP-TFP | 0.258 | 0.033 | 0.038 |
| AD01214 | 112.5 | 100A | 375 | TFF | RGD-PEG$_{15}$-FCitFP-TFP | 0.5x | 10.8 | PEG$_{12}$-ACit-PABC-PNP | 0.193 | 0.046 | 0.061 |
| AD01214 | 112.5 | 100A | 375 | TFF | RGD-PEG$_{15}$-FCitFP-TFP | 1x | 16.1 | PEG$_{12}$-ACit-PABC-PNP | 0.182 | 0.007 | 0.008 |
| AD01214 | 112.5 | 100A | 375 | TFF | RGD-PEG$_{15}$-FCitFP-TFP | 2x | 29.0 | PEG$_{12}$-ACit-PABC-PNP | 0.182 | 0.031 | 0.038 |
| AD01214 | 112.5 | 100A | 375 | TFF | RGD-PEG$_{19}$-FCitFP-TFP | 0.5x | 10.7 | PEG$_{12}$-ACit-PABC-PNP | 0.163 | 0.023 | 0.027 |
| AD01214 | 112.5 | 100A | 375 | TFF | RGD-PEG$_{19}$-FCitFP-TFP | 1x | 18.5 | PEG$_{12}$-ACit-PABC-PNP | 0.114 | 0.011 | 0.012 |
| AD01214 | 112.5 | 100A | 375 | TFF | RGD-PEG$_{19}$-FCitFP-TFP | 2x | 31.1 | PEG$_{12}$-ACit-PABC-PNP | 0.182 | 0.047 | 0.063 |
| AD01214 | 112.5 | 100A | 375 | | RGD-PEG$_{19}$-FCitFP-TFP | 1x | | PEG$_{12}$-FCitFP-TFP | 0.148 | 0.079 | 0.169 |
| AD01214 | 112.5 | 100A | 375 | | RGD-PEG$_{19}$-FCitFP-TFP | 1x | | PEG$_{12}$-FCitFP-TFP | 0.188 | 0.026 | 0.03 |
| AD01214 | 112.5 | 100A | 375 | | RGD-PEG$_{19}$-FCitFP-TFP | 1x | | PEG$_{12}$-ACit-PABC-PNP | 0.195 | 0.043 | 0.055 |
| AD01214 | 112.5 | 006 | 300 | | RGD-PEG$_8$-HyNic | | | PEG$_{12}$-ACit-PABC-PNP | 0.357 | 0.069 | 0.086 |
| AD01214 | 112.5 | 100A | 375 | TFF | RGD-PEG$_{20}$-FCitFP-TFP | 0.125x | 1.9 | PEG$_{12}$-ACit-PABC-PNP | 0.169 | 0.052 | 0.075 |
| AD01214 | 112.5 | 100A | 375 | TFF | RGD-PEG$_{20}$-FCitFP-TFP | 0.25x | 3.4 | PEG$_{12}$-ACit-PABC-PNP | 0.168 | 0.029 | 0.035 |
| AD01214 | 112.5 | 100A | 375 | TFF | RGD-PEG$_{20}$-FCitFP-TFP | 0.5x | 6.6 | PEG$_{12}$-ACit-PABC-PNP | 0.130 | 0.004 | 0.005 |
| AD01214 | 112.5 | 100A | 375 | TFF | RGD-PEG$_{20}$-FCitFP-TFP | 1x | 12.7 | PEG$_{12}$-ACit-PABC-PNP | 0.121 | 0.016 | 0.018 |
| AD01214 | 112.5 | 100A | 375 | TFF | RGD-PEG$_{20}$-FCitFP-TFP | 1.5x | 20.3 | PEG$_{12}$-ACit-PABC-PNP | 0.135 | 0.018 | 0.020 |

The invention claimed is:

1. A composition comprising an RNA interference (RNAi) trigger for inhibiting the expression of an Hif2α gene, wherein the RNAi trigger comprises a sense strand and an antisense strand, wherein the antisense strand is 21 to 26 nucleotides in length and nucleotides 2-21 of the antisense strand (5'→3') comprise the base sequence of nucleotides 2-21 of SEQ ID NO. 4 (UU-CAUGAAAUCGUUACGUUG).

2. The composition of claim 1, wherein
the antisense strand comprises a nucleotide base sequence of nucleotides 2-21 of SEQ ID NO. 4 (UU-CAUGAAAUCGUUACGUUG) and the sense strand comprises a nucleotide base sequence of SEQ ID NO. 53 (ACGUAACGAUUUCAUGAAU).

3. The composition of claim 1, wherein the sense strand and/or the antisense strand further comprises a 3' and/or 5' extension of 1-6 nucleotides in length.

4. The composition of claim 1, wherein a targeting group is conjugated to the RNAi trigger.

5. The composition of claim 4, wherein the targeting group comprises a compound selected from the group consisting of: integrin-binding compound, $\alpha_v\beta_3$ integrin-binding ligand, RGD peptide ligand, and RGD mimic.

6. The composition of claim 1, wherein a delivery polymer is conjugated to the RNAi trigger.

7. The composition of claim 1, wherein a linking group is conjugated to the RNAi trigger.

8. The composition of claim 1, wherein the sense strand and/or antisense strand independently comprises one or more modified nucleotides or nucleotide mimics.

9. The composition of claim 8, wherein the sense strand contains one, two, or three 2'-deoxy-2'-fluoro modified nucleotides at positions 11, 12, and/or 13 from the 3' end.

10. The composition of claim 8, wherein the antisense strand contains a 2'-deoxy-2'-fluoro modified nucleotide at position 2 from the 5' end.

11. The composition of claim 8, wherein the antisense strand contains a 2'-deoxy-2'-fluoro modified nucleotide at position 14 from the 5' end.

12. The composition of claim 8, wherein the antisense strand contains one, two, three, or four 2' deoxy-2'-fluoro modified nucleotides at positions 4, 6, 8, 10, and 12 from the 5' end.

13. The composition of claim 1, wherein the RNAi trigger comprises one or more phosphorothioate internucleotide linkages.

14. The composition of claim 13, wherein the antisense strand contains one, two, three, or four phosphorothioate internucleotide linkages.

15. The composition of claim 1, further comprising one or more additional therapeutics or treatments.

16. The composition of claim 1 further comprising a pharmaceutically acceptable excipient.

17. The composition of claim 1, wherein said composition is packaged in a kit, container, pack, dispenser, pre-filled syringes, or vials.

18. A method for inhibiting Hif2α expression in a cell, tissue, or subject, the method comprising: administering to the subject a therapeutically effective amount of a composition of claim 1.

19. The method of claim 18, wherein the composition is administered via subcutaneous injection.

20. The method of claim 18, wherein the cell or tissue is a renal cell carcinoma cell.

* * * * *